US008604061B2

(12) United States Patent
Galley et al.

(10) Patent No.: US 8,604,061 B2
(45) Date of Patent: Dec. 10, 2013

(54) 2-AMINOOXAZOLINES AS TAAR1 LIGANDS

(75) Inventors: Guido Galley, Rheinfelden (DE); Katrin Groebke Zbinden, Liestal (CH); Roger Norcross, Olsberg (CH); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/426,736

(22) Filed: Mar. 22, 2012

(65) Prior Publication Data

US 2012/0196903 A1 Aug. 2, 2012

Related U.S. Application Data

(63) Continuation of application No. 12/639,076, filed on Dec. 16, 2009, now abandoned, which is a continuation of application No. 12/011,384, filed on Jan. 25, 2008, now abandoned.

(30) Foreign Application Priority Data

Feb. 2, 2007  (EP) .................................. 07101681

(51) Int. Cl.
*A01N 43/40* (2006.01)
*A61K 31/44* (2006.01)
*C07D 413/00* (2006.01)

(52) U.S. Cl.
USPC ......... 514/340; 514/337; 546/271.4; 548/233

(58) Field of Classification Search
None
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,377,247 A | 4/1968 | Elbe | |
| 3,577,428 A | 5/1971 | Suh et al. | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,146,647 A | 3/1979 | Lafon | |
| 4,311,840 A | 1/1982 | Condon | |
| 4,323,570 A | 4/1982 | Stenzel et al. | |
| 4,665,095 A | 5/1987 | Winn et al. | |
| 5,610,174 A | 3/1997 | Craig et al. | |
| 5,658,938 A | 8/1997 | Geerts et al. | |
| 6,268,389 B1 | 7/2001 | Esser et al. | |
| 2002/0019390 A1 | 2/2002 | Wong et al. | |
| 2003/0181354 A1 | 9/2003 | Abdulrazik | |
| 2003/0236274 A1 | 12/2003 | Tasaka et al. | |

FOREIGN PATENT DOCUMENTS

| | | |
|---|---|---|
| CA | 2246027 | 2/2000 |
| DE | 842065 | 6/1952 |
| DE | 1795517 | 2/1972 |
| DE | 2203373 | 8/1972 |
| DE | 2253555 | 11/1972 |
| DE | 2446758 | 4/1976 |
| DE | 2849537 | 5/1980 |
| EP | 0024829 | 3/1981 |
| EP | 0125410 | 11/1984 |
| EP | 0166937 | 1/1986 |
| EP | 0167459 | 1/1986 |
| EP | 0331374 | 9/1989 |
| EP | 0392929 | 10/1990 |
| EP | 0424059 | 4/1991 |
| EP | 0717037 | 6/1996 |
| EP | 0857483 | 8/1998 |
| EP | 0924209 | 6/1999 |
| EP | 1103243 | 5/2001 |
| EP | 1413576 | 4/2004 |
| ES | 323985 | 12/1966 |
| FR | 1355049 | 3/1964 |
| FR | 6551 | 12/1968 |

(Continued)

OTHER PUBLICATIONS

Branchek et al., "Curr Opin Pharmacol" 3:90-97 (2003).

(Continued)

*Primary Examiner* — Bong-Sook Baek

(57) ABSTRACT

The invention relates to compounds of formula I

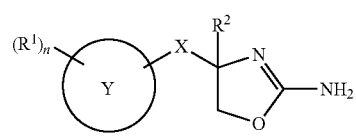

wherein
X, Y, $R^1$, $R^2$, and n are as defined herein
or to a pharmaceutically suitable acid addition salt thereof. The invention also relates to pharmaceutical compositions containing such compounds and methods for the treatment of diseases related to the biological function of the trace amine associated receptors, which diseases include depression, anxiety disorders, bipolar disorder, attention deficit hyperactivity disorder, stress-related disorders, psychotic disorders, schizophrenia, neurological diseases, Parkinson's disease, neurodegenerative disorders, Alzheimer's disease, epilepsy, migraine, substance abuse and metabolic disorders, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

2 Claims, No Drawings

(56) References Cited

FOREIGN PATENT DOCUMENTS

| | | |
|---|---|---|
| GB | 877306 | 9/1961 |
| GB | 1016514 | 1/1996 |
| WO | 96/22768 | 8/1996 |
| WO | 97/12874 | 4/1997 |
| WO | 98/12183 | 3/1998 |
| WO | 01/30762 | 5/2001 |
| WO | 01/81334 | 11/2001 |
| WO | 02/22801 | 3/2002 |
| WO | 02/40453 | 5/2002 |
| WO | 02/076950 | 10/2002 |
| WO | 03/092374 | 11/2003 |
| WO | 2004/014898 | 2/2004 |
| WO | 2006/119411 | 11/2006 |
| WO | 2007/024944 | 3/2007 |
| WO | 2007/085556 | 8/2007 |

OTHER PUBLICATIONS

Matsunaga et al., "Bioorganic & Medicinal Chemistry" (XP002444990),:4314-4336 ( 2004).
Russell et al., "Pharmacology Biochemistry and Behavior" 51:375-378 ( 1995).
Turner et al., J. Org. Chem. 56:5739-5740 ( 1981).
Usdin et al., "Psychopharmacology Series" (Trace Amines and the Brain), 1:1-281 ( 1976).
McLennan, P. L., "European Journal of Pharmacology" 69:477-482 ( 1981).
Carroll et al., "Med. Chem. Res." 13:134-148 ( 2004).
"Translation of Chinese Office Action for Corresponding Application 2008800003923.5" (Aug. 3, 2011).
Law et al., "J. Med. Chem." 41:2243-2251 ( 1998).
Premont et al., "Proc. Natl. Acad. Sci. USA" 98:9474-9475 ( 2001).
Nakamura et al., "J. Chem. Soc. Perkin Trans." 1:1061-1066 ( 2002).
Trani et al., Heterocycl. Chem. 11:257-262 ( 1974).
Mohammadpoor-Baltork, Synlett:2803-2805 ( 2004).
Ueda et al., Bioorganic & Medicinal Chem. Letters 14( Suppl 2):313-316 ( 2004).
Altenbach et al., "J. Med. Chem." 47:3220-3235 ( 2004).
Klapars et al., Journal of the Amer. Chem. Soc. 123:7727-7729 ( 2001).
Habib et al., Synthesis:825-827 ( 1984).
Ojida et al., Org. Letters:3051-3054 ( 2002).
"Translation Peruvian Technical Report for Appl 228" (Oct. 7, 2011).
Melloni et al., Eur. J. Med. Chem 26:207-213 ( 1991).
Tuite et al., "Expert Opin. Investig. Drugs" 12:1335-1352 ( 2003).
McCormack et al., "J. Neurosci." 6:94-101 ( 1986).
"Translated Russian Office Action in Corresponding Application 2009128619/04" (Oct. 3, 2011).
Olmos et al., "European Journal of Pharmacology" 262:41-48 ( 1994).
Cahiez et al., Synthesis:2138-2144 ( 1999).
Cordi et al., Journal of Med. Chem. 44(50):787-805 ( 2001).
Amemiya et al., Synth. Commun. 20:2483-2489 ( 1990).
Ohta, Chem. Pharm. Bull. 35:1058-1069 ( 1987).
Mosseau et al., "Prog. Brain res." 106:285-291 ( 1995).
Flippin et al., Tetrahedron Letters 34:3255-3258 ( 1993).
Touzeau et al., J. Med. Chem. 46:1962-1979 ( 2003).
"Australian Patent Office Written Opinion for SG 200904914-9" (Aug. 9, 2010).
Campos et al., Heterocycles 40:841-849 ( 1995).
Bagley et al., "Med. Chem. Res." 4(5):346-364 ( 1994).
Matsunaga et al., "Tetrahedron Asymmetry" 15:2021-2028 ( 2004).
Mohammadpoor-Baltork, Bull. Korean Chem. Sco. 24:1354-1356 ( 2003).
"Khimiya Geterotsiklicheskikh Soedinenii" (English language abstract attached),:77-79 ( 1988).
Katz et al., Tetrahedron 45:1801-1814 ( 1989).
Faust et al., "J. Org. Chem." 26:4044-4047 ( 1961).
"Abstract corresponding to EP 0 167 459", (1986).
Reimann et al., Arch. Pharm. 322:363-367 ( 1989).
Zhang et al., "Journal of Medicinal Chemistry" (XP002108693), 40:3014-3024 ( 1997).
Castellanos et al., "Nat. Rev. Neurosci." 3:617-628 ( 2002).
Turner et al., "J. Org. Chem." 56:5739-5740 ( 1991).
Olah, Synlett:647-650 ( 1992).
Agami et al., Tetrahedron 57:195-200 ( 2001).
Ohta, Synthesis:78-81 ( 1990).
Wentland et al., "J. Med. Chem." 30:1482-1489 ( 1987).
Parker et al., "J. Pharmacol. Exp. Ther." 245:199-210 ( 1988).
Wong et al., "Nat. Rev. Neurosci." 2:343-351 ( 2001).
Dyck, L. E., "Life Sci." 44:1149-1156 ( 1989).
Abdollahi-Alibeik et al., "Bioorg. Med. Chem. Lett." 14:6079-6082 ( 2004).
Mancuso et al., J. Org. Chem. 43:2480-2482 ( 1978).
Nathanson, J. A., "Amer. Soc. Pharmacology" 28:254-268 ( 1985).
Evans et al., "Tetrahedron Lett." 39:2937-2940 ( 1998).
Deutch et al. Neurotransmitters in Fundamental Neuroscience 2nd edition,Academic Press,:193-234 ( 1999).
Ojida et al., "Tetrahedron Asymmetry" 15:1555-1559 ( 2004).
Rascol et al., "Movement Disorders" 16(4):708-713 ( 2001).
Jetter et al., "Synthesis":829-831 ( 1998).
Debernardis et al., J. Med. Chem. 29:1413-1417 ( 1986).
Bunzow et al., "Molecular Pharmacology" 60:1181-1188 ( 2001).
Holt et al., "J. of Psychiatry & Neuroscience" (XP002438693), 28(6):409-414 ( 2003).
"Abstract corresponding to DE 842 065", (1952).
Huh et al., Tetrahedron 60:9857-9862 ( 2004).
Liebigs et al., Ann. Chem.:2061-2071 ( 1980).
Tanaka et al., "Journal of the Pharmaceutical Society of Japan" (Abstract on first page), 97(2):157-164 ( 1977).
Timmermans et al., "Life Sciences" 28:653-660 ( 1981).
Amemiya et al., "J. Med. Chem." 35:750-755 ( 1992).
Huh et al., Tetrahedron 58:9925-9932 ( 2002).
Schramm et al., "The Journal of Neuroscience" 21(13):4875-4882 ( 2001).
Lee et al., "Bull. Korean Chem. Soc." 25:619-628 ( 2005).
Prisinzano et al., "Bioorganic & Medicinal Chemistry Letter" 14:4697-4699 ( 2004).
Carlsson et al., "Annu. Rev. Pharmacol. Toxicol." 41:237-260 ( 2001).
Debernardis et al., J. Med. Chem. 30:1011-1017 ( 1987).
"Abstract corresponding to FR 6551", (1968).
Lindemann et al., "Trends in Pharmacol. Sci." 26:274-281 ( 2005).
Anderson et al., "Tetrahedron" 58:8475-8481 ( 2002).
Savola et al., "Drug Res." 38:29-35 ( 1988).
Akinori et al., "Bioorganic & Medicinal Chemistry" (XP002442520), 10:117-123 ( 2002).
Lindemann et al., "Genomics" 85:372-385 ( 2005).

2-AMINOOXAZOLINES AS TAAR1 LIGANDS

PRIORITY TO RELATED APPLICATION(S)

This application is a continuation of U.S. application Ser. No. 12/639,076, filed and Dec. 16, 2009, now pending, which is a continuation of 12/011,384, filed Jan. 25, 2008, now abandoned, which claims the benefit of European Patent Application No. 07101681.0, filed Feb. 2, 2007. The entire contents of the above-identified applications are hereby incorporated by reference.

BACKGROUND OF THE INVENTION

2-Aminooxazolines are described in the literature as hypertensive agents with good affinity to the adrenergic receptor or as intermediates in processes for preparation of pharmaceutical active agents, for example in EP 0 167 459, U.S. Pat. No. 4,311,840, DE 2,253, 555, Tetrahedron (2001), 57(1), 195-200 or in Bioorganic and Medicinal Chemistry Letters (2004), 14(2), 313-316.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. Nat. Rev. Neurosci. 2, 343-351;

Carlsson, A. et al. (2001) Interactions between monoamines, glutamate, and GABA in schizophrenia: new evidence. *Annu. Rev. Pharmacol. Toxicol.* 41, 237-260;

Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain. [Proceedings of a Study Group at the 14th Annual Meeting of the American College of Neuropsychoparmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S. A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

SUMMARY OF THE INVENTION

The invention provides compounds of formula I

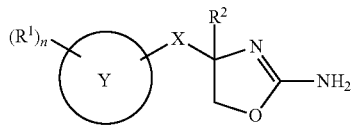

wherein
R' is hydrogen, deuterium, tritium, lower alkyl, lower alkoxy, lower alkyl substituted by halogen, lower alkoxy substituted by halogen, halogen, phenyl optionally substituted by halogen, phenyloxy, benzyl, benzyloxy, —COO-lower alkyl, —O—$(CH_2)_o$—O-lower alkyl, NH-cycloalkyl, cycloalkyl or tetrahydropyran-4-yloxy, wherein the substituents for n>1 are the same or different;
X is a bond, —CHR—, —CHRCHR'—, —$OCH_2$—, —$CH_2OCHR$—, —$CH_2CH_2CH_2$—, —$SCH_2$—, —$S(O)_2CH_2$—, —$CH_2SCH_2$—, —$CH_2N(R)CH_2$—, -cycloalkyl-$CH_2$— or SiRR'—$CH_2$—;
R and R' are each independently hydrogen, lower alkyl or lower alkyl substituted by halogen;
$R^2$ is hydrogen, phenyl or lower alkyl;
Y is phenyl, naphthyl, thiophenyl, pyridinyl, cycloalkyl, 1,2,3,4-tetrahydro-naphthalen-2-yl, 2,3-dihydrobenzo[1,4]dioxin-6-yl or benzo[1,3]dioxol-5-yl;
n is 0, 1, 2 or 3; and
o is 2 or 3;
and pharmaceutically suitable acid addition salts thereof.

The invention includes all racemic mixtures, all their corresponding enantiomers and/or optical isomers. In addition, all tautomeric forms of compounds of formula I are also encompassed by the present invention.

The invention also provides pharmaceutical compositions containing one or more compound of the invention and a pharmaceutically acceptable carrier. The invention further provides methods for the manufacture of the compounds and compositions of the invention. Compounds of formula I have a good affinity to the trace amine associated receptors (TAARs), especially for TAAR1. Thw invention provides a method for the treatment of diseases related to the biological function of trace amino associated receptors. Such diseases include depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety and attention deficit hyperactivity disorder (ADHD).

DETAILED DESCRIPTION OF THE INVENTION

Unless otherwise stated, the following terms used in the present description have the definitions given in the following. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

As used herein, the term "lower alkyl substituted by halogen" denotes an alkyl group as defined above, wherein at least one hydrogen atom is replaced by halogen, for example $CF_3$, CHF2, $CH_2F$, $CH_2CF_3$, $CH_2CH_2CF_3$, $CH_2CF_2CF_3$ and the like.

As used herein, the term "lower alkoxy substituted by halogen" denotes an alkoxy group as defined above, wherein at least one hydrogen atom is replaced by halogen, for example $OCF_3$, OCHF2, $OCH_2F$, $OCH_2CF_3$, $OCH_2CH_2CF_3$, $OCH_2CF_2CF_3$ and the like.

The term "halogen" denotes chlorine, iodine, fluorine and bromine.

The term "cycloalkyl" is an alkylene ring, containing from 3 to 6 carbon ring atoms.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The compounds mentioned below are specific novel and preferred for the uses as described above.

Preferred compounds of formula I are those, wherein X is a bond.

Preferred compounds of this group of formula I are those, wherein Y is phenyl, substituted by one or more halogen atoms:

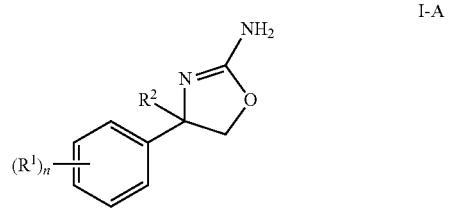

I-A $R^1$ is halogen, for n>1 the halogen atoms are the same or different;
$R^2$ is hydrogen, phenyl or lower alkyl; and
n is 1, 2 or 3;
or a pharmaceutically suitable acid addition salt, for example
(S)-4-(2-chloro-phenyl)-4,5-dihydro-oxazol-2-ylamine,
(RS)-4-(4-chloro-phenyl)-4,5-dihydro-oxazol-2-ylamine,
(RS)-4-(2,4-difluoro-phenyl)-4,5-dihydro-oxazol-2-ylamine,
(S)-4-(2,3-difluoro-phenyl)-4,5-dihydro-oxazol-2-ylamine, (RS)-4-(3,4-dichlorophenyl)-4,5-dihydro-oxazol-2-ylamine,
(RS)-4-(2,5-difluoro-phenyl)-4,5-dihydro-oxazol-2-ylamine,
(RS)-4-(2,3,4-trifluoro-phenyl)-4,5-dihydro-oxazol-2-ylamine,
(RS)-4-(3-chloro-2-fluoro-phenyl)-4,5-dihydro-oxazol-2-ylamine,
(RS)-4-(5-chloro-2-fluoro-phenyl)-4,5-dihydro-oxazol-2-ylamine,
(RS)-4-(4-bromo-phenyl)-4,5-dihydro-oxazol-2-ylamine,
(S)-4-(3-bromo-2,4-difluoro-phenyl)-4,5-dihydro-oxazol-2-ylamine,
(S)-4-(2,4-difluoro-phenyl)-4,5-dihydro-oxazol-2-ylamine,
(S)-4-(3,4-dichloro-phenyl)-4,5-dihydro-oxazol-2-ylamine,
(S)-4-(2,5-difluoro-phenyl)-4,5-dihydro-oxazol-2-ylamine,
(S)-4-(4-bromo-phenyl)-4,5-dihydro-oxazol-2-ylamine,
(S)-4-(2,4,5-trifluoro-phenyl)-4,5-dihydro-oxazol-2-ylamine,
(S)-4-(3-chloro-2-fluoro-phenyl)-4,5-dihydro-oxazol-2-ylamine,
(S)-4-(2,3,5-trifluoro-phenyl)-4,5-dihydro-oxazol-2-ylamine,
(S)-4-(3,4-dichloro-phenyl)-4-methyl-4,5-dihydro-oxazol-2-ylamine,
(S)-4-(4-chloro-phenyl)-4-methyl-4,5-dihydro-oxazol-2-ylamine,
(S)-4-(3,4-difluoro-phenyl)-4,5-dihydro-oxazol-2-ylamine,
(S)-4-(2,3-dichloro-phenyl)-4,5-dihydro-oxazol-2-ylamine,
(S)-4-(4-chloro-phenyl)-4,5-dihydro-oxazol-2-ylamine,
(S)-4-(3,4,5-trifluoro-phenyl)-4,5-dihydro-oxazol-2-ylamine,
(S)-4-(3-chloro-4-fluoro-phenyl)-4,5-dihydro-oxazol-2-ylamine,
(S)-4-(4-chloro-3-fluoro-phenyl)-4,5-dihydro-oxazol-2-ylamine,
(S)-4-(3,5-difluoro-phenyl)-4,5-dihydro-oxazol-2-ylamine,
(S)-4-(3-chloro-5-fluoro-phenyl)-4,5-dihydro-oxazol-2-ylamine,
(S)-4-(2-chloro-phenyl)-4-methyl-4,5-dihydro-oxazol-2-ylamine,
(RS)-4-(3-chloro-phenyl)-4,5-dihydro-oxazol-2-ylamine,
(RS)-4-(3-bromo-phenyl)-4,5-dihydro-oxazol-2-ylamine,
(S)-4-(2,5-difluoro-phenyl)-4-methyl-4,5-dihydro-oxazol-2-ylamine,
(RS)-4-(3-fluoro-phenyl)-4,5-dihydro-oxazol-2-ylamine,
(RS)-4-(3,5-dichloro-phenyl)-4,5-dihydro-oxazol-2-ylamine,
(+)-(S)-4-(5-chloro-2-fluoro-phenyl)-4,5-dihydro-oxazol-2-ylamine,
(+)-(S)-4-(3-chloro-phenyl)-4,5-dihydro-oxazol-2-ylamine,
(S)-4-(2-fluoro-phenyl)-4-methyl-4,5-dihydro-oxazol-2-ylamine,
(+)-(S)-4-(3-bromo-phenyl)-4,5-dihydro-oxazol-2-ylamine,
(+)-(S)-4-(3-fluoro-phenyl)-4,5-dihydro-oxazol-2-ylamine,
(+)-(S)-4-(3,5-dichloro-phenyl)-4,5-dihydro-oxazol-2-ylamine,
(S)-4-(2,4-difluoro-phenyl)-4-methyl-4,5-dihydro-oxazol-2-ylamine,
(RS)-4-methyl-4-(2,3,5-trifluoro-phenyl)-4,5-dihydro-oxazol-2-ylamine,
(S)-4-(4-bromo-phenyl)-4-methyl-4,5-dihydro-oxazol-2-ylamine,
(RS)-4-(2,4-dichloro-phenyl)-4,5-dihydro-oxazol-2-ylamine,
(S)-4-(4-chloro-3-fluoro-phenyl)-4-methyl-4,5-dihydro-oxazol-2-ylamine,
(RS)-4-(2-bromo-phenyl)-4,5-dihydro-oxazol-2-ylamine,
(RS)-4-methyl-4-(2,4,5-trifluoro-phenyl)-4,5-dihydro-oxazol-2-ylamine,
(RS)-4-(4-bromo-3-fluoro-phenyl)-4,5-dihydro-oxazol-2-ylamine,
(RS)-4-(2,5-dichloro-phenyl)-4,5-dihydro-oxazol-2-ylamine,
(+)-(S)-4-(2-bromo-phenyl)-4,5-dihydro-oxazol-2-ylamine,
(S)-4-(3-chloro-5-fluoro-phenyl)-4-methyl-4,5-dihydro-oxazol-2-ylamine,
(RS)-4-methyl-4-(2,3,4-trifluoro-phenyl)-4,5-dihydro-oxazol-2-ylamine,
(S)-4-(5-chloro-2-fluoro-phenyl)-4-methyl-4,5-dihydro-oxazol-2-ylamine,
(RS)-4-methyl-4-(4-chloro-2,5-difluoro-phenyl)-4,5-dihydro-oxazol-2-ylamine,
(RS)-4-methyl-4-(3,4,5-trifluoro-phenyl)-4,5-dihydro-oxazol-2-ylamine,
(S)-4-(3-chloro-4-fluoro-phenyl)-4-methyl-4,5-dihydro-oxazol-2-ylamine,
(S)-4-(4-chloro-2,5-difluoro-phenyl)-4-methyl-4,5-dihydro-oxazol-2-ylamine,
(RS)-4-(4-bromo-2-chloro-phenyl)-4,5-dihydro-oxazol-2-ylamine,
(RS)-4-(2,4-dichloro-phenyl)-4-methyl-4,5-dihydro-oxazol-2-ylamine,
(−)-(R)-4-(2,4-dichloro-phenyl)-4,5-dihydro-oxazol-2-ylamine,
(+)-(S)-4-(2,4-dichloro-phenyl)-4,5-dihydro-oxazol-2-ylamine,
(+)-(S)-4-(2,5-dichloro-phenyl)-4,5-dihydro-oxazol-2-ylamine,
(RS)-4-(2,5-dichloro-phenyl)-4-methyl-4,5-dihydro-oxazol-2-ylamine,
(+)-(S)-4-(2,3,4-trifluoro-phenyl)-4,5-dihydro-oxazol-2-ylamine,
(S)-4-methyl-4-(3,4,5-trifluoro-phenyl)-4,5-dihydro-oxazol-2-ylamine,
(RS)-4-(3-chloro-2-fluoro-phenyl)-4-methyl-4,5-dihydro-oxazol-2-ylamine,
(S)-4-(4-chloro-phenyl)-4-ethyl-4,5-dihydro-oxazol-2-ylamine,
(−)-(R)-4-(4-bromo-2-chloro-phenyl)-4,5-dihydro-oxazol-2-ylamine,
(+)-(S)-4-(4-bromo-2-chloro-phenyl)-4,5-dihydro-oxazol-2-ylamine,
(RS)-4-(2-chloro-4-fluoro-phenyl)-4-methyl-4,5-dihydro-oxazol-2-ylamine,
(+)-(S)-4-(4-bromo-3-fluoro-phenyl)-4,5-dihydro-oxazol-2-ylamine,
(RS)-4-(4-bromo-3-chloro-phenyl)-4,5-dihydro-oxazol-2-ylamine,
(S)-4-(3,4-dichloro-phenyl)-4-ethyl-4,5-dihydro-oxazol-2-ylamine,
(+)-(S)-4-(4-bromo-3-chloro-phenyl)-4,5-dihydro-oxazol-2-ylamine,
(RS)-4-(4-bromo-2-fluoro-phenyl)-4,5-dihydro-oxazol-2-ylamine, and
(S)-4-(4-bromo-2-fluoro-phenyl)-4,5-dihydro-oxazol-2-ylamine.

Further preferred compounds from this group are those, wherein Y is phenyl substituted by $CH_3$, $CF_3$, $OCH_3$, $OCF_3$ or $OCH_2$-phenyl,

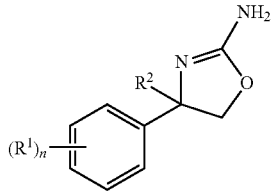

I-B $R^1$ is $CH_3$, $CF_3$, $OCH_3$, $OCF_3$ or $OCH_2$-phenyl; for n>1, each $R^1$ is the same or different;
$R^2$ is hydrogen, phenyl or lower alkyl; and
n is 1, 2 or 3;
or a pharmaceutically suitable acid addition salt, for example the following compounds
(RS)-4-(2-trifluoromethyl-phenyl)-4,5-dihydro-oxazol-2-ylamine,
(RS)-4-o-tolyl-4,5-dihydro-oxazol-2-ylamine,
(RS)-4-(4-trifluoromethoxy-phenyl)-4,5-dihydro-oxazol-2-ylamine,
(RS)-4-(4-methoxy-3-methyl-phenyl)-4,5-dihydro-oxazol-2-ylamine,
(S)-4-o-tolyl-4,5-dihydro-oxazol-2-ylamine,
(RS)-4-(4-benzyloxy-phenyl)-4,5-dihydro-oxazol-2-ylamine,
(S)-4-(2-trifluoromethyl-phenyl)-4,5-dihydro-oxazol-2-ylamine,
(S)-4-(4-methoxy-3-methyl-phenyl)-4,5-dihydro-oxazol-2-ylamine,
(S)-4-methyl-4-(4-trifluoromethyl-phenyl)-4,5-dihydro-oxazol-2-ylamine,
(S)-4-(3-trifluoromethyl-phenyl)-4,5-dihydro-oxazol-2-ylamine,
(S)-4-methyl-4-p-tolyl-4,5-dihydro-oxazol-2-ylamine,
(S)-4-methyl-4-(3-trifluoromethyl-phenyl)-4,5-dihydro-oxazol-2-ylamine,
(RS)-4-(4-methoxy-2-trifluoromethyl-phenyl)-4,5-dihydro-oxazol-2-ylamine, and
(+)-(S)-4-(4-methoxy-2-trifluoromethyl-phenyl)-4,5-dihydro-oxazol-2-ylamine.

Further preferred compounds from this group are those, wherein Y is phenyl substituted by phenyl, which is optionally substituted by halogen:

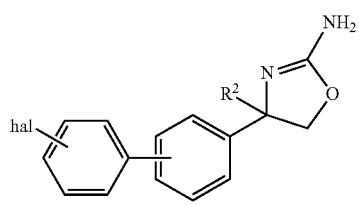

I-C $R^2$ is hydrogen, phenyl or lower alkyl;
or a pharmaceutically suitable acid addition salt, for example the following compounds
(RS)-4-biphenyl-4-yl-4,5-dihydro-oxazol-2-ylamine,
(S)-4-biphenyl-4-yl-4,5-dihydro-oxazol-2-ylamine, and
(RS)-4-(4'-chloro-biphenyl-4-yl)-4,5-dihydro-oxazol-2-ylamine.

Further preferred compounds from this group are those, wherein Y is phenyl substituted by halogen and $CF_3$, halogen and $CH_3$, halogen and cycloalkyl or by halogen and $OCH_3$,

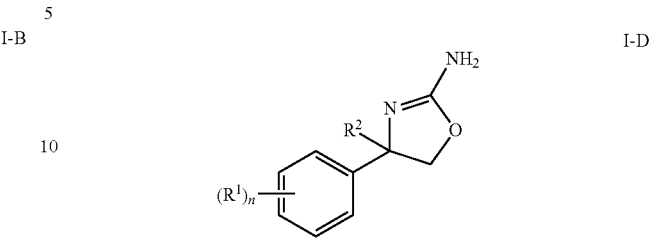

I-D $R^1$ is halogen and $CF_3$, or is halogen and $CH_3$, or is halogen and cycloalkyl, or is halogen and $OCH_3$; and
$R^2$ is hydrogen, phenyl or lower alkyl;
or a pharmaceutically suitable acid addition salt, for example the following compounds
(RS)-4-(3-chloro-4-methoxyphenyl)-4,5-dihydro-oxazol-2-ylamine,
(S)-4-(3-chloro-4-methoxy-phenyl)-4,5-dihydro-oxazol-2-ylamine,
(S)-4-(2-fluoro-4-trifluoromethyl-phenyl)-4-methyl-4,5-dihydro-oxazol-2-ylamine,
(RS)-4-(4-fluoro-2-trifluoromethyl-phenyl)-4,5-dihydro-oxazol-2-ylamine,
(RS)-4-(5-chloro-2-trifluoromethyl-phenyl)-4,5-dihydro-oxazol-2-ylamine,
(RS)-4-(4-chloro-2-trifluoromethyl-phenyl)-4,5-dihydro-oxazol-2-ylamine,
(RS)-4-(4,5-dichloro-2-trifluoromethyl-phenyl)-4,5-dihydro-oxazol-2-ylamine,
(+)-(S)-4-(4-chloro-2-trifluoromethyl-phenyl)-4,5-dihydro-oxazol-2-ylamine,
(+)-(S)-4-(4,5-dichloro-2-trifluoromethyl-phenyl)-4,5-dihydro-oxazol-2-ylamine,
(−)-(R)-4-(4,5-dichloro-2-trifluoromethyl-phenyl)-4,5-dihydro-oxazol-2-ylamine,
(+)-(S)-4-(4-fluoro-2-trifluoromethyl-phenyl)-4,5-dihydro-oxazol-2-ylamine,
(RS)-4-(5-fluoro-2-trifluoromethyl-phenyl)-4,5-dihydro-oxazol-2-ylamine,
(RS)-4-(5-fluoro-2-methyl-phenyl)-4,5-dihydro-oxazol-2-ylamine,
(+)-(S)-4-(5-fluoro-2-trifluoromethyl-phenyl)-4,5-dihydro-oxazol-2-ylamine,
(RS)-4-(4-chloro-3-methyl-phenyl)-4-methyl-4,5-dihydro-oxazol-2-ylamine,
(RS)-4-(5-chloro-2-methyl-phenyl)-4,5-dihydro-oxazol-2-ylamine,
(RS)-4-(4-chloro-2-fluoro-5-methyl-phenyl)-4-methyl-4,5-dihydro-oxazol-2-ylamine,
(S)-4-(4-chloro-3-methyl-phenyl)-4-methyl-4,5-dihydro-oxazol-2-ylamine,
(RS)-4-(4-bromo-2-trifluoromethyl-phenyl)-4,5-dihydro-oxazol-2-ylamine,
(S)-4-(4-chloro-2-fluoro-5-methyl-phenyl)-4-methyl-4,5-dihydro-oxazol-2-ylamine,
(+)-(S)-4-(5-chloro-2-methyl-phenyl)-4,5-dihydro-oxazol-2-ylamine,
(RS)-4-(4-fluoro-2-methyl-phenyl)-4,5-dihydro-oxazol-2-ylamine,
(+)-(S)-4-(4-bromo-2-trifluoromethyl-phenyl)-4,5-dihydro-oxazol-2-ylamine, (+)-(S)-4-(5-chloro-2-trifluoromethyl-phenyl)-4,5-dihydro-oxazol-2-ylamine,
(RS)-4-(4-chloro-2-ethyl-phenyl)-4,5-dihydro-oxazol-2-ylamine,
(+)-(S)-4-(4-fluoro-2-methyl-phenyl)-4,5-dihydro-oxazol-2-ylamine,
(RS)-4-(3-chloro-4-methyl-phenyl)-4,5-dihydro-oxazol-2-ylamine,
(RS)-4-(4-chloro-2-cyclopropyl-phenyl)-4,5-dihydro-oxazol-2-ylamine,
(S)-4-(4-chloro-2-ethyl-phenyl)-4,5-dihydro-oxazol-2-ylamine,
(RS)-4-(3-fluoro-2-methyl-phenyl)-4,5-dihydro-oxazol-2-ylamine,
(S)-4-(4-chloro-2-cyclopropyl-phenyl)-4,5-dihydro-oxazol-2-ylamine,
(RS)-4-(3-fluoro-2-trifluoromethyl-phenyl)-4,5-dihydro-oxazol-2-ylamine, and
(S)-4-(3-chloro-4-methyl-phenyl)-4,5-dihydro-oxazol-2-ylamine.

Preferred compounds of formula I are further those, wherein X is CHR.

Preferred compounds from this group are those, wherein Y is phenyl substituted by halogen, CF$_3$, or CH$_3$:

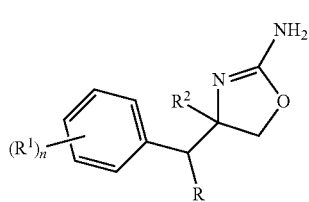

I-E

R$^1$ is halogen, CF$_3$ or CH$_3$, wherein substituents for n>1 are the same or different;
R$^2$ is hydrogen, phenyl or lower alkyl;
R is hydrogen, lower alkyl or lower alkyl substituted by halogen; and
n is 1 or 2;
or a pharmaceutically suitable acid addition salt, for example the following compounds
(S)-4-(2-chloro-benzyl)-4,5-dihydro-oxazol-2-ylamine,
(S)-4-(3-trifluoromethyl-benzyl)-4,5-dihydro-oxazol-2-ylamine, and
(RS)-4-(2-fluoro-5-methyl-benzyl)-4,5-dihydro-oxazol-2-ylamine.

Preferred compounds of formula I are further those, wherein X is CHRCHR'.

Preferred compounds from this group are those, wherein Y is optionally substituted phenyl,

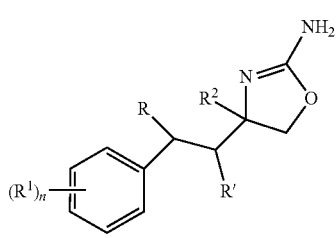

I-F

R$^1$ is hydrogen, lower alkyl, lower alkoxy, lower alkyl substituted by halogen, lower alkoxy substituted by halogen or is halogen, wherein the substituents for n>1 are the same or different;

R and R' are each independently hydrogen, lower alkyl or lower alkyl substituted by halogen;
R$^2$ is hydrogen, phenyl or lower alkyl; and
n is 0, 1, 2 or 3;
or a pharmaceutically suitable acid addition salt, for example the following compounds
(R)-4-phenethyl-4,5-dihydro-oxazol-2-ylamine,
(S)-4-phenethyl-4,5-dihydro-oxazol-2-ylamine,
(RS)-4-methyl-4-phenethyl-4,5-dihydro-oxazol-2-ylamine,
(S)-4-methyl-4-phenethyl-4,5-dihydro-oxazol-2-ylamine,
(S)-4-[2-(4-fluoro-phenyl)-ethyl]-4,5-dihydro-oxazol-2-ylamine,
(S)-4-[2-(4-fluoro-3-methoxy-phenyl)-ethyl]-4,5-dihydro-oxazol-2-ylamine,
((S)-4-[2-(2,4-difluoro-phenyl)-ethyl]-4,5-dihydro-oxazol-2-ylamine,
(S)-4-[2-(3,4-difluoro-phenyl)-ethyl]-4,5-dihydro-oxazol-2-ylamine,
(S)-4-[2-(2-trifluoromethyl-phenyl)-ethyl]-4,5-dihydro-oxazol-2-ylamine,
(S)-4-[2-(2-fluoro-phenyl)-ethyl]-4,5-dihydro-oxazol-2-ylamine,
(S)-4-[2-(3-fluoro-phenyl)-ethyl]-4,5-dihydro-oxazol-2-ylamine,
(S)-4-[2-(3,5-difluoro-phenyl)-ethyl]-4,5-dihydro-oxazol-2-ylamine,
(S)-4-(2-o-tolyl-ethyl)-4,5-dihydro-oxazol-2-ylamine,
(S)-4-(2-m-tolyl-ethyl)-4,5-dihydro-oxazol-2-ylamine,
(S)-4-(2-p-tolyl-ethyl)-4,5-dihydro-oxazol-2-ylamine,
(S)-4-[2-(4-trifluoromethyl-phenyl)-ethyl]-4,5-dihydro-oxazol-2-ylamine,
(S)-4-[2-(3-trifluoromethyl-phenyl)-ethyl]-4,5-dihydro-oxazol-2-ylamine,
(R)-4-[2-(3,4-dichloro-phenyl)-ethyl]-4,5-dihydro-oxazol-2-ylamine,
(S)-4-[2-(3,4-dichloro-phenyl)-ethyl]-4,5-dihydro-oxazol-2-ylamine,
(S)-4-[2-(4-chloro-2-fluoro-phenyl)-ethyl]-4,5-dihydro-oxazol-2-ylamine,
(S)-4-[2-(4-fluoro-3-trifluoromethyl-phenyl)-ethyl]-4,5-dihydro-oxazol-2-ylamine,
(S)-4-[2-(3-fluoro-4-trifluoromethyl-phenyl)-ethyl]-4,5-dihydro-oxazol-2-ylamine,
(S)-4-[2-(3,5-dichloro-phenyl)-ethyl]-4,5-dihydro-oxazol-2-ylamine,
(S)-4-[2-(2-chloro-4-fluoro-phenyl)-ethyl]-4,5-dihydro-oxazol-2-ylamine,
(S)-4-[2-(4-fluoro-3-methyl-phenyl)-ethyl]-4,5-dihydro-oxazol-2-ylamine,
(S)-4-{2-[3-(1,1,2,2-tetrafluoro-ethoxy)-phenyl]-ethyl}-4,5-dihydro-oxazol-2-ylamine,
(S)-4-[2-(2-fluoro-3-trifluoromethyl-phenyl)-ethyl]-4,5-dihydro-oxazol-2-ylamine,
(S)-4-[2-(3-bromo-phenyl)-ethyl]-4,5-dihydro-oxazol-2-ylamine,
(S)-4-[2-(4-chloro-3-trifluoromethyl-phenyl)-ethyl]-4,5-dihydro-oxazol-2-ylamine,
(S)-4-[2-(3-fluoro-4-trifluoromethoxy-phenyl)-ethyl]-4,5-dihydro-oxazol-2-ylamine,
(S)-4-[2-(4-fluoro-3-trifluoromethoxy-phenyl)-ethyl]-4,5-dihydro-oxazol-2-ylamine,
(S)-4-[2-(2,3-dichloro-phenyl)-ethyl]-4,5-dihydro-oxazol-2-ylamine,
(S)-4-[2-(3-chloro-4-trifluoromethoxy-phenyl)-ethyl]-4,5-dihydro-oxazol-2-ylamine,
(S)-4-[2-(2-chloro-3-trifluoromethyl-phenyl)-ethyl]-4,5-dihydro-oxazol-2-ylamine, (S)-4-(1-methyl-2-phenyl-ethyl)-4,5-dihydro-oxazol-2-ylamine,
(S)-4-[2-(2-fluoro-5-trifluoromethyl-phenyl)-ethyl]-4,5-dihydro-oxazol-2-ylamine,
(S)-4-[2-(3-fluoro-5-trifluoromethyl-phenyl)-ethyl]-4,5-dihydro-oxazol-2-ylamine,
(S)-4-[2-(2,5-bis-trifluoromethyl-phenyl)-ethyl]-4,5-dihydro-oxazol-2-ylamine,
(S)-4-[2-(4-chloro-phenyl)-butyl]-4,5-dihydro-oxazol-2-ylamine,
(S)-4-(2-phenyl-butyl)-4,5-dihydro-oxazol-2-ylamine,
(S)-4-[2-(4-trifluoromethyl-phenyl)-propyl]-4,5-dihydro-oxazol-2-ylamine,
(S)-4-[2-(4-trifluoromethyl-phenyl)-butyl]-4,5-dihydro-oxazol-2-ylamine,
(S)-4-[2-(3-trifluoromethyl-phenyl)-propyl]-4,5-dihydro-oxazol-2-ylamine,
(S)-4-[2-(3-trifluoromethyl-phenyl)-butyl]-4,5-dihydro-oxazol-2-ylamine,
(S)-4-[2-(3,5-difluoro-phenyl)-propyl]-4,5-dihydro-oxazol-2-ylamine,
(S)-4-[2-(3,5-difluoro-phenyl)-butyl]-4,5-dihydro-oxazol-2-ylamine,
(S)-4-[2-(4-fluoro-phenyl)-butyl]-4,5-dihydro-oxazol-2-ylamine,
(S)-4-[2-(3,4-difluoro-phenyl)-butyl]-4,5-dihydro-oxazol-2-ylamine,
(S)-4-[2-(2-fluoro-phenyl)-propyl]-4,5-dihydro-oxazol-2-ylamine,
(S)-4-[2-(3,4-dichloro-phenyl)-propyl]-4,5-dihydro-oxazol-2-ylamine,
(S)-4-[2-(3,4-dichloro-phenyl)-butyl]-4,5-dihydro-oxazol-2-ylamine,
(S)-4-[2-(2-fluoro-phenyl)-butyl]-4,5-dihydro-oxazol-2-ylamine,
(S)-4-[2-(2-chloro-phenyl)-ethyl]-4-methyl-4,5-dihydro-oxazol-2-ylamine,
(S)-4-[2-(3-chloro-phenyl)-ethyl]-4,5-dihydro-oxazol-2-ylamine,
(S)-4-[2-(4-chloro-phenyl)-ethyl]-4-methyl-4,5-dihydro-oxazol-2-ylamine,
(S)-4-[2-(3-chloro-phenyl)-ethyl]-4-methyl-4,5-dihydro-oxazol-2-ylamine,
(S)-4-[2-(4-fluoro-phenyl)-ethyl]-4-methyl-4,5-dihydro-oxazol-2-ylamine,
(S)-4-[2-(4-chloro-phenyl)-ethyl]-4,5-dihydro-oxazol-2-ylamine,
(S)-4-[2-(2-chloro-phenyl)-ethyl]-4,5-dihydro-oxazol-2-ylamine,
(S)-4-[2-(3-chloro-phenyl)-butyl]-4,5-dihydro-oxazol-2-ylamine,
(S)-4-((S)-2-phenyl-butyl)-4,5-dihydro-oxazol-2-ylamine,
(S)-4-((R)-2-phenyl-butyl)-4,5-dihydro-oxazol-2-ylamine,
(S)-4-[2-(2-chloro-6-fluoro-phenyl)-ethyl]-4,5-dihydro-oxazol-2-ylamine,
(S)-4-[2-(2,4-dichloro-phenyl)-ethyl]-4-methyl-4,5-dihydro-oxazol-2-ylamine,
(S)-4-[2-(2-bromo-phenyl)-ethyl]-4,5-dihydro-oxazol-2-ylamine,
(S)-4-[2-(2,5-dichloro-phenyl)-ethyl]-4,5-dihydro-oxazol-2-ylamine,
(S)-4-[2-(3-fluoro-phenyl)-butyl]-4,5-dihydro-oxazol-2-ylamine,
(S)-4-[2-(3-chloro-2-fluoro-phenyl)-butyl]-4,5-dihydro-oxazol-2-ylamine,
(S)-4-[2-(3-chloro-4-fluoro-phenyl)-butyl]-4,5-dihydro-oxazol-2-ylamine,
(S)-4-[2-(3-chloro-5-fluoro-phenyl)-butyl]-4,5-dihydro-oxazol-2-ylamine, and
(S)-4-[2-(5-chloro-2-fluoro-phenyl)-butyl]-4,5-dihydro-oxazol-2-ylamine.

Preferred compounds of formula I are further those, wherein X is $OCH_2$ and Y is optionally substituted phenyl.

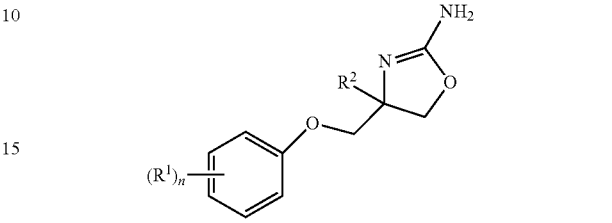

I-G $R^1$ is lower alkyl, lower alkyl substituted by halogen or halogen, wherein the substituents for n>1 are the same or different;
$R^2$ is hydrogen, phenyl or lower alkyl; and
n is 0, 1, 2 or 3;
or a pharmaceutically suitable acid addition salt, for example the following compounds
(S)-4-(4-fluoro-phenoxymethyl)-4,5-dihydro-oxazol-2-ylamine,
(S)-4-(4-chloro-phenoxymethyl)-4,5-dihydro-oxazol-2-ylamine,
(S)-4-(3,4-dichloro-phenoxymethyl)-4,5-dihydro-oxazol-2-ylamine,
(S)-4-(3,5-dichloro-phenoxymethyl)-4,5-dihydro-oxazol-2-ylamine,
(S)-4-(4-bromo-phenoxymethyl)-4,5-dihydro-oxazol-2-ylamine,
(S)-4-(3-chloro-phenoxymethyl)-4,5-dihydro-oxazol-2-ylamine,
(S)-4-(2,4-difluoro-phenoxymethyl)-4,5-dihydro-oxazol-2-ylamine, and
(S)-4-(2-fluoro-phenoxymethyl)-4,5-dihydro-oxazol-2-ylamine.

Preferred compounds of formula I are further those, wherein X is $CH_2OCHR$.

Preferred compounds from this group are those, wherein Y is phenyl optionally substituted by halogen:

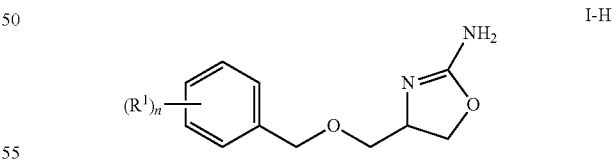

I-H $R^1$ is hydrogen or halogen; and
n is 0 or 1;
or a pharmaceutically suitable acid addition salt, for example the following compound
(S)-4-benzyloxymethyl-4,5-dihydro-oxazol-2-ylamine.

Preferred compounds of formula I are further those, wherein X is —$(CH_2)_3$

Preferred compounds from this group are those, wherein Y is phenyl, for example the following compounds
(S)-4-(3-Phenyl-propyl)-4,5-dihydro-oxazol-2-ylamine and
(R)-4-(3-Phenyl-propyl)-4,5-dihydro-oxazol-2-ylamine.

Preferred compounds of formula I are further those, wherein X is —SCH₂—, —S(O)₂CH₂—, or —CH₂SCH₂—.

Preferred compounds from this group are those, wherein Y is phenyl, for example the following compounds
(R)-4-phenylsulfanylmethyl-4,5-dihydro-oxazol-2-ylamine,
(R)-4-benzenesulfonylmethyl-4,5-dihydro-oxazol-2-ylamine,
(R)-4-benzylsulfanylmethyl-4,5-dihydro-oxazol-2-ylamine, and
(R)-4-(4-chloro-phenylsulfanylmethyl)-4,5-dihydro-oxazol-2-ylamine.

Preferred compounds of formula I are further those, wherein X is —CH₂N(R)CH₂—, cycloalkyl-CH₂— or SiRR'—CH₂—;

Preferred compounds from this group are those, wherein Y is optionally substituted phenyl, for example the following compounds
(S)-4-[1-(4-chloro-phenyl)-cyclopropylmethyl]-4,5-dihydro-oxazol-2-ylamine,
(S)-4-[1-(4-chloro-phenyl)-cyclobutylmethyl]-4,5-dihydro-oxazol-2-ylamine,
(S)-4-(1-phenyl-cyclopropylmethyl)-4,5-dihydro-oxazol-2-ylamine,
(S)-4-[(benzyl-ethyl-amino)-methyl]-4,5-dihydro-oxazol-2-ylamine, and
(R)-4-[(dimethyl-phenyl-silanyl)-methyl]-4,5-dihydro-oxazol-2-ylamine.

Preferred compounds of formula I are further those, wherein X is described above and Y is naphthyl, pyridyl, cyclohexyl, 2,3-dihydrobenzo[1,4]dioxin or 1,2,3,4-tetrahydronaphthalen.

Examples of such compounds are
(RS)-4-(2,3-dihydro-benzo[1,4]dioxin-6-yl)-4,5-dihydro-oxazol-2-ylamine,
(RS)-4-naphthalen-2-yl-4,5-dihydro-oxazol-2-ylamine,
(RS)-4-naphthalen-1-yl-4,5-dihydro-oxazol-2-ylamine,
(R)-4-naphthalen-1-ylmethyl-4,5-dihydro-oxazol-2-ylamine,
(S)-4-naphthalen-1-ylmethyl-4,5-dihydro-oxazol-2-ylamine,
(S)-4-naphthalen-2-ylmethyl-4,5-dihydro-oxazol-2-ylamine,
(RS)-4-(1,2,3,4-tetrahydro-naphthalen-2-yl)-4,5-dihydro-oxazol-2-ylamine,
(S)-4-naphthalen-2-yl-4,5-dihydro-oxazol-2-ylamine,
(S)-4-[2-(3-fluoro-pyridin-4-yl)-ethyl]-4,5-dihydro-oxazol-2-ylamine,
(S)-4-[2-(6-trifluoromethyl-pyridin-2-yl)-ethyl]-4,5-dihydro-oxazol-2-ylamine,
(S)-4-[2-(2-methyl-pyridin-4-yl)-ethyl]-4,5-dihydro-oxazol-2-ylamine, and
(S)-4-(2-cyclohexyl-ethyl)-4,5-dihydro-oxazol-2-ylamine.

A further embodiment of the invention is compounds of formula

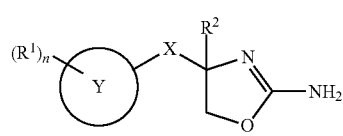

I wherein
$R^1$ is hydrogen, deuterium, tritium, lower alkyl, lower alkoxy, lower alkyl substituted by halogen, lower alkoxy substituted by halogen, halogen, phenyl optionally substituted by halogen, phenyloxy, benzyl, benzyloxy, or —COO-lower alkyl; wherein the substituents for n>1 are the same or different;
X is a bond, —CHR— or —CHRCH₂—;
R is hydrogen or lower alkyl;
$R^2$ is hydrogen or lower alkyl;
Y is aryl, heteroaryl, 1,2,3,4-tetrahydro-naphthalen-2-yl, 2,3-dihydrobenzo[1,4]dioxin-6-yl or benzo[1,3]dioxol-5-yl; and
n is 0, 1, 2 or 3;
or pharmaceutically suitable acid addition salt with the exception of
(S)-4-phenyl-4,5-dihydro-oxazol-2-ylamine,
(R)-4-phenyl-4,5-dihydro-oxazol-2-ylamine,
(S)-4-benzyl-4,5-dihydro-oxazol-2-ylamine, and
(RS)-4-phenethyl-4,5-dihydro-oxazol-2-ylamine.

The present compounds of formula I and their pharmaceutically acceptable salts can be prepared by methods known in the art, for example, by processes described below, which process comprises
a) Reacting a compound of formula

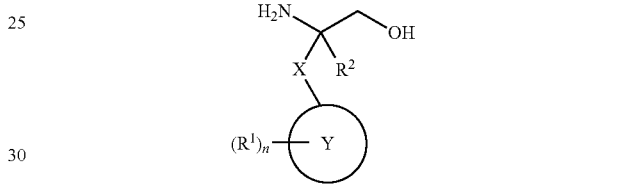

II with cyanogen bromide
to obtain a compound of formula

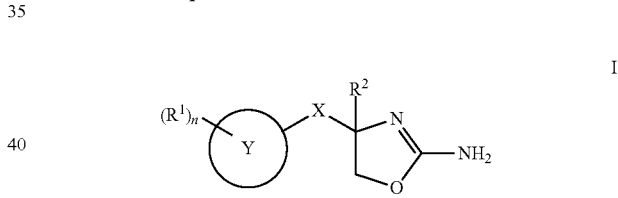

I wherein the definitions are as described above, or
if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following schemes 1-9. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 9, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

General Procedure

Scheme 1

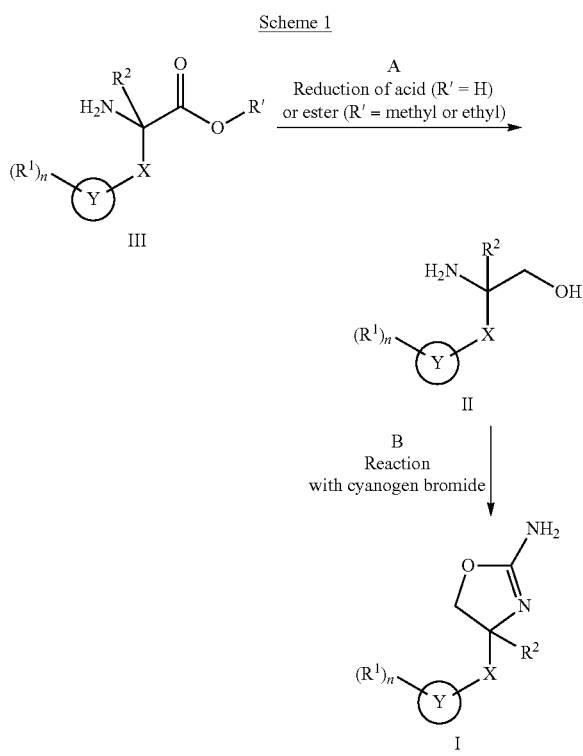

Step A: Reduction of an acid group (R'=H) can be effected by treatment with $LiAlH_4$, $BH_3$-THF, $BH_3$—$Me_2S$ complex in the presence of $BF_3$-etherate or Red-Al in a solvent such as 1,2-dimethoxyethane, THF, diethylether or toluene at r.t.->reflux for 1-24 hrs. Alternatively, reduction of an acid group (R'=H) can be effected by treatment with LiBH4 in the presence of $Me_3SiCl$ in a solvent such as methanol at 0° C.->r.t. for 1-24 hrs.

Reduction of an ester group (R'=methyl or ethyl) can be effected by treatment with $LiAlH_4$, $LiBH_4$, $NaBH_4$ or Red-Al in a suitable solvent such as 1,2-dimethoxyethane, THF, diethylether, toluene, MeOH or EtOH at −78° C.->reflux for 1-24 hrs.

Preferred conditions for acids and esters are $LiAlH_4$ in THF at r.t. overnight, or $LiBH_4$/$Me_3SiCl$ in methanol at 0° C.->r.t. overnight.

Step B: Cyclisation of the aminoalcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 2

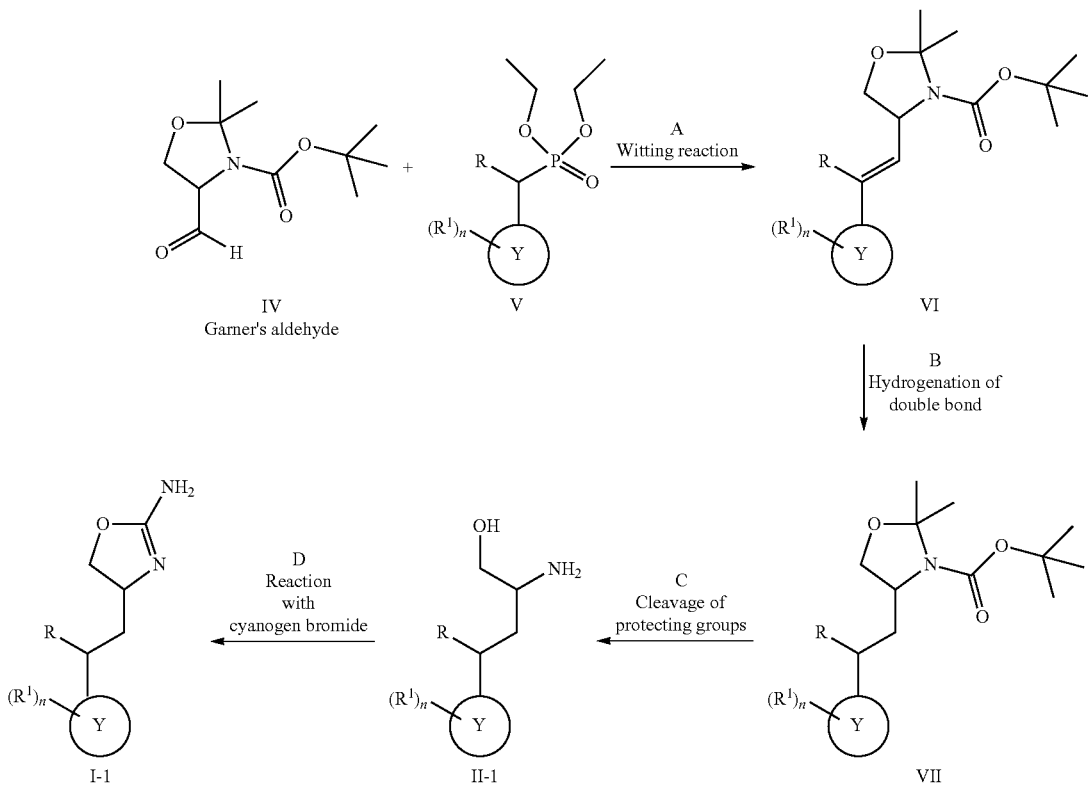

Step A: Wittig reaction between Garner's aldehyde IV and a benzyl-substituted phosphonic acid diethyl ester V can be accomplished by using a base such as NaH, KOtBu, NaOMe, NaOEt, n-BuLi, LiHMDS, NaHMDS, KHMDS, LDA in a solvent such as THF, dioxane, acetonitrile, 1,2-dimethoxyethan, DMF, benzene, toluene or mixtures thereof at temperatures from −78° C.-80° C. for 15 min-8 hrs and if appropriate optional addition of a crown ether for ylide generation and then condensing the ylide with the carbonyl compound in the same solvent at temperature between 0 and 80° C. for 1-24 hrs. Alternatively, the base, the carbonyl compound and the base and the optional crown ether can be added to the reaction mixture at the same time without preformation of the ylide at temperatures from −78° C.-80° C.

Preferred conditions are ylide formation at 0° C. using n-buthyl lithium solution in hexane as base and 1,2-dimethoxyethane as solvent, reacting the phosphonic acid ester for 5 min at 0° C., and then condensation with the carbonyl component at reflux overnight.

Step B: Reduction of the alkene can be effected by hydrogenation with hydrogen under normal or elevated pressure or by transfer hydrogenation using ammonium formiate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof. Alternatively, the reduction of the alkene can be effected by Mg in MeOH or by $LiAlH_4$ in THF or diethylether. Preferred conditions are hydrogenation in the presence of Pd/C as catalyst with EtOH as solvent.

Step C: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are 2N HCl in EtOH at reflux for 1-3 hrs or 4N HCl in dioxane at r.t. overnight.

Step D: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 3

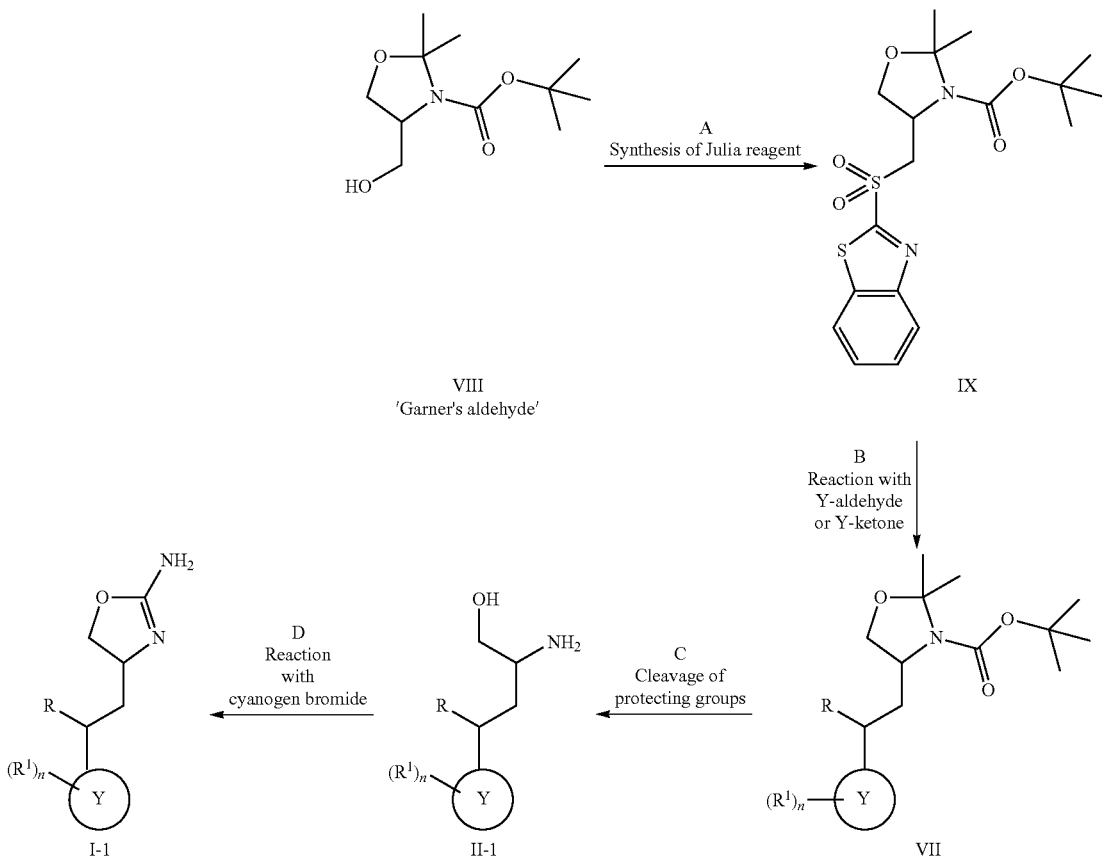

Step A: The synthesis of the Julia reagent (benzothiazole-2-sulfonyl derivative) IX from 'Garner's alcohol' VIII was accomplished as described in literature (Dandanpani, S. et al., *Journal of Organic Chemistry* 2005, 70(23), 9447).

Step B: Julia reaction between an Y-aldehyde or ketone and the benzothiazole sulfonyl compound can be accomplished by using a base such as LiHMDS, NaHMDS, KHMDS, LDA, KOtBu, DBU in a solvent such as THF, diethyl ether, 1,2-dimethoxyethane, dichloromethane, DMF or mixtures thereof at temperatures from −100° C.-r.t. for 15 min-8 hrs for anion generation and then condensing the ylide with the carbonyl compound in the same solvent at temperatures between −100° C. and r.t. for 1-24 hrs. Preferred conditions are anion generation with LiHMDS at −78° C. in THF and subsequent condensation with the carbonyl component under the same conditions.

Step C: Simultaneous cleavage of the amino alcohol protecting groups can be effected with a mineral acid such as HCl, H₂SO₄ or H₃PO₄ or a organic acid such as CF₃COOH, CHCl₂COOH, HOAc or p-toluonesulfonic acid in a solvent such as CH₂Cl₂, CHCl₃, THF, MeOH, EtOH or H₂O at 0 to 60° C.

Preferred conditions are 2N HCl in EtOH at reflux for 1-3 hrs or 4N HCl in dioxane at r.t. overnight.

Step D: Cyclisation of the amino alcohol to the corresponding 2-aminooxazoline can be accomplished by treatment with cyanogen bromide in THF as solvent and K₂CO₃ as base at r.t. overnight, or by treatment with cyanogen bromide in methanol as solvent and sodium acetate as base at 0° C. to r.t. overnight.

Scheme 4

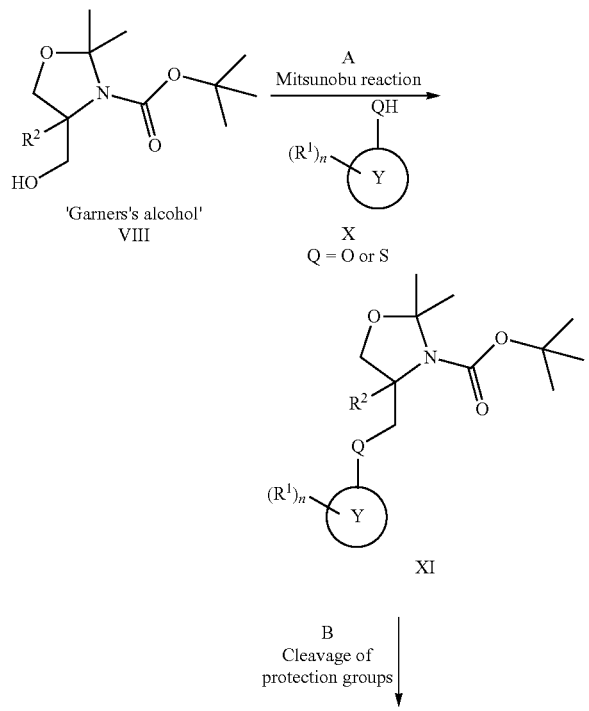

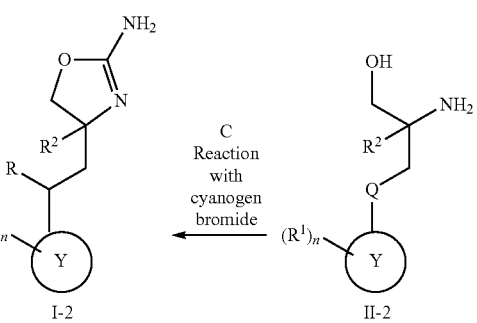

Step A: Mitsunobu reaction of 'Garner's alcohol' VIII with phenol derivatives X or thiophenol derivatives X can be accomplished by using a phosphine such as triphenylphosphine and an azodicarboxylate reagent such as diethylazodicarboxylate, diisopropylazodicarboxylate, or di-tert-butylazodicarboxylate in a solvent such as THF at temperatures from 50° C.-70° C. for 1-18 hrs. Preferred conditions are triphenylphosphine and di-tert-butylazodicarboxylate in THF at 60° C. for 16 h.

Step B: Simultaneous cleavage of the amino alcohol protecting groups can be effected with a mineral acid such as HCl, H₂SO₄ or H₃PO₄ or a organic acid such as CF₃COOH, CHCl₂COOH, HOAc or p-toluonesulfonic acid in a solvent such as CH₂Cl₂, CHCl₃, THF, MeOH, EtOH or H₂O at 0 to 60° C.

Preferred conditions are 2N HCl in EtOH at reflux for 1-3 hrs or 4N HCl in dioxane at r.t. overnight.

Step C: Cyclisation of the amino alcohol to the corresponding 2-aminooxazoline can be accomplished by treatment with cyanogen bromide in THF as solvent and K₂CO₃ as base at r.t. overnight, or by treatment with cyanogen bromide in methanol as solvent and sodium acetate as base at 0° C. to r.t. overnight.

Scheme 5

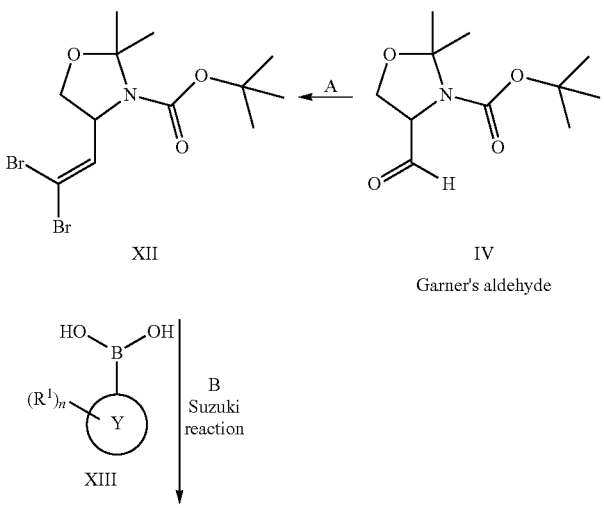

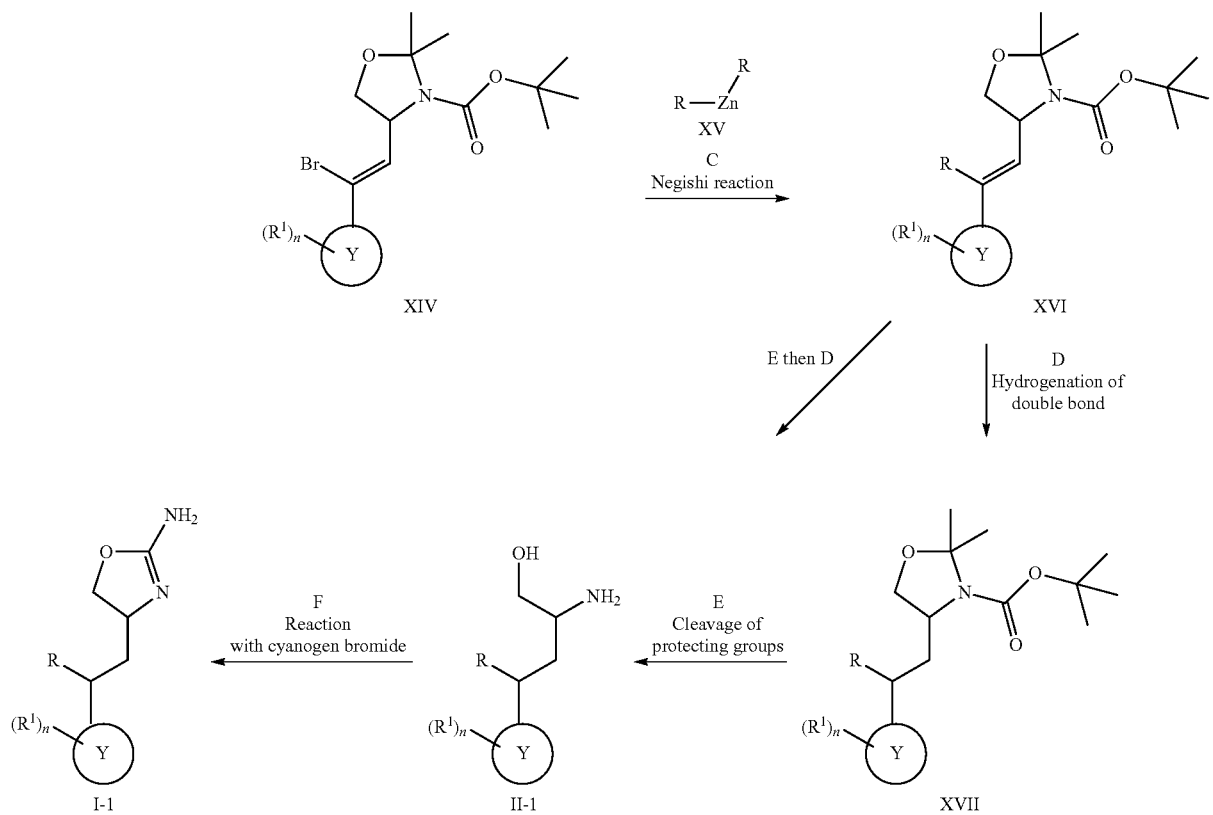

Step A: Conversion of Garner's aldehyde IV to the dibromo-alkene derivative XII can be accomplished by using a brominating agent such as carbon tetrabromide in the presence of a phosphine such as triphenylphosphine in a chlorinated solvent such as dichloromethane at temperatures between 0° C. and room temperature.

Step B: Suzuki reaction of dibromo-alkene derivative XII with an arylboronic acid XIII can be accomplished using a palladium catalyst such as tris(dibenzylideneacetone)dipalladium (0) in the presence of a phosphine such as tris(2-furyl) phosphine and a base such as aqueous sodium carbonate in a solvent such as THF, dioxane, 1,2-dimethoxyethan, DMF, benzene, toluene or mixtures thereof at temperatures from 50° C.-100° C. for 1-18 hrs.

Step C: Negishi reaction of bromo-alkene derivative XIV with a dialkylzinc reagent XV can be accomplished using a palladium catalyst such as bis(tri-tert-butylphosphine)dipalladium (0) in a solvent such as THF, dioxane, 1,2-dimethoxyethan, DMF, benzene, toluene or mixtures thereof at temperatures from 20° C.-100° C. for 1-18 hrs. Preferred conditions are a THF-toluene mixture at room temperature.

Step D: Reduction of the alkene can be effected by hydrogenation with hydrogen under normal or elevated pressure or by transfer hydrogenation using ammonium formiate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof. Alternatively, the reduction of the alkene can be effected by Mg in MeOH or by $LiAlH_4$ in THF or diethylether.

Preferred conditions for $R^1 \ne$ chlorine are hydrogenation in the presence of Pd/C as catalyst with EtOH as solvent.

Preferred conditions for $R^1$=chlorine are hydrogenation in the presence of Pt/C as catalyst with EtOH as solvent.

Step E: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C. Preferred conditions are 2N HCl in EtOH at reflux for 1-3 hrs or 4N HCl in dioxane at r.t. overnight.

Steps D and E can also be carried out in the opposite order, in which case the stereochemical preference of the hydrogenation step is typically reversed.

Step F: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 6

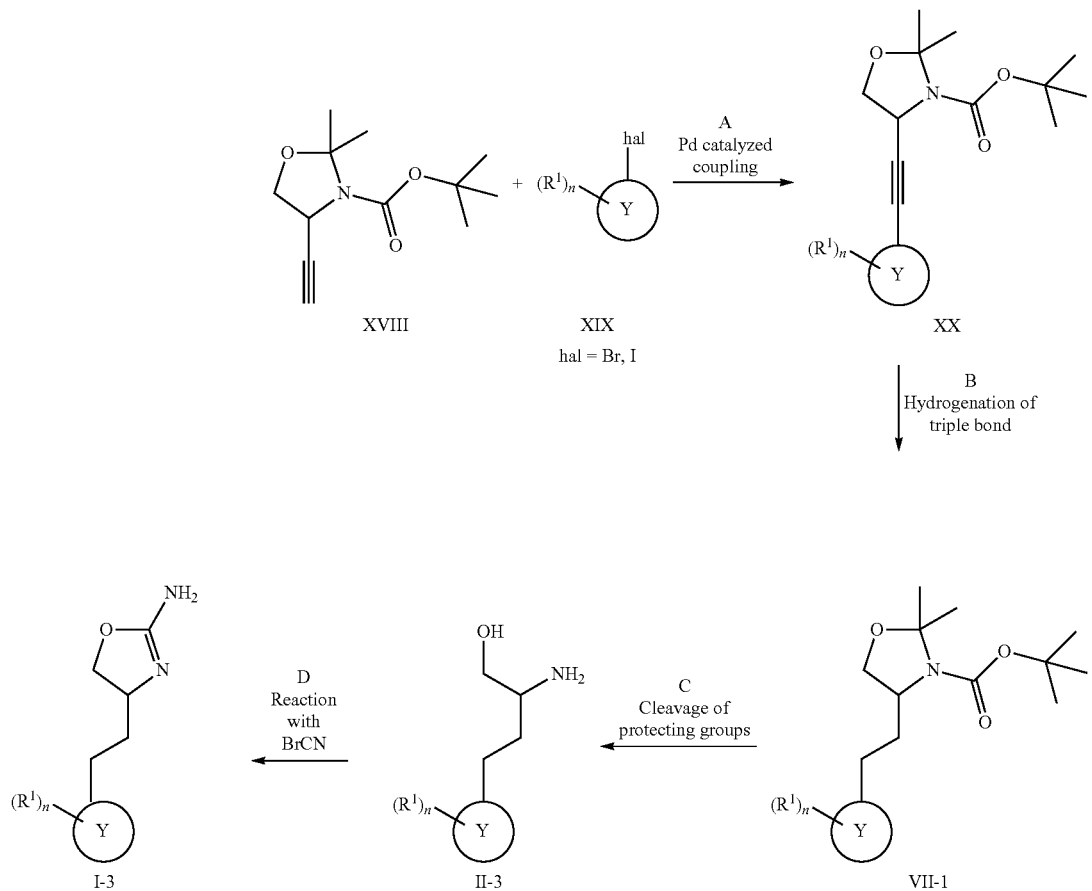

Step A: Coupling of 4-ethinyl-2,2-dimethyl-1,3-oxazolidine-3-carboxylate XVIII (Dickson, H. D. et al *Tetrahedron Lett.* 2004, 45 (29), 5597-5599; Pietruszka, J. et al *Eur. J. Org. Chem.* 2003, 3219-3229) with an aryl or hetaryl bromide or iodide XIX in the presence of a palladium and a copper(I) salt in a solvent such as dioxane, tetrahydrofurane, benzene, triethylamine or the like.

Preferred conditions are the use of copper(I)-iodide and bis(triphenylphosphine)palladium(II) chloride with triethylamine as solvent at room temperature.

Step B: Reduction of the alkyne XX can be effected by hydrogenation with hydrogen under normal or elevated pressure or by transfer hydrogenation using ammonium formiate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof. Alternatively, the reduction of the alkyne can be effected by Mg in MeOH or by $LiAlH_4$ in THF or diethylether. Preferred conditions are transfer hydrogenation using ammonium formiate in the presence of Pd/C as catalyst with MeOH as solvent.

Step C: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are 2N HCl in EtOH at reflux for 1-3 hrs or 4N HCl in dioxane at r.t. overnight.

Step D: Cyclisation of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 7

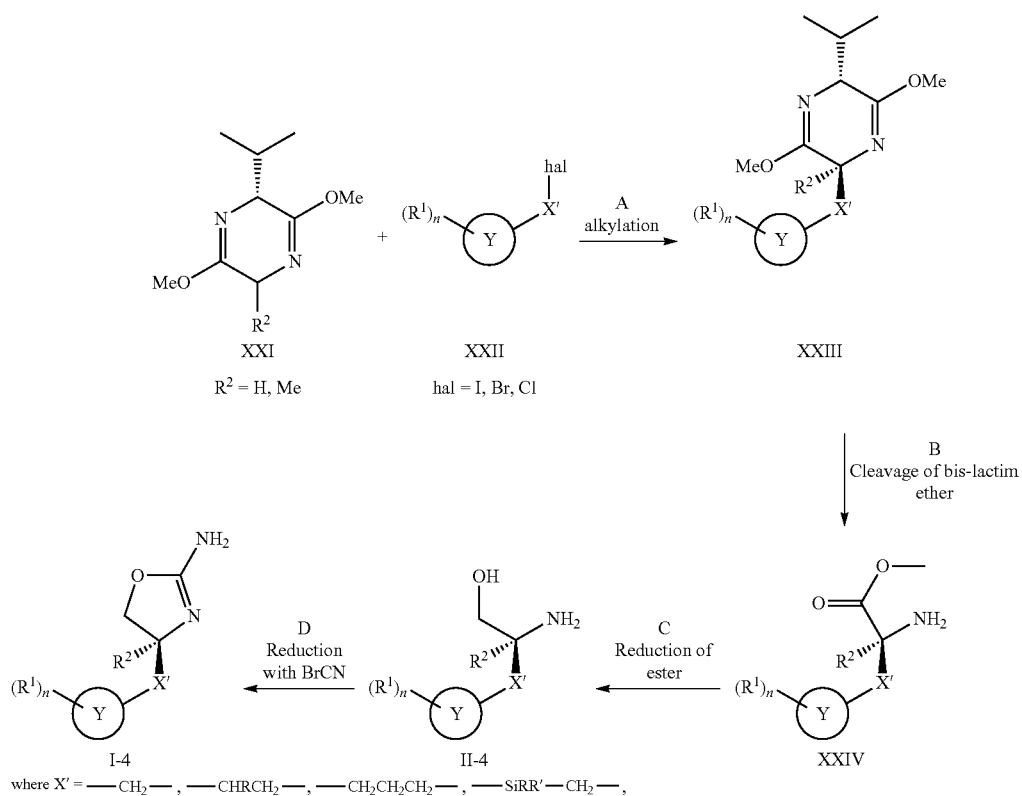

where X' = —CH₂—, —CHRCH₂—, —CH₂CH₂CH₂—, —SiRR'—CH₂—,

Step A: Deprotonation of bis-lactimether XXI (also called "Schöllkopf's chiral auxiliary") with a suitable base such as n-butyl-lithium or tert-butyl-lithium in an appropriate organic solvent such as tetrahydrofuran at a low temperature followed by addition of the organic halide XXII and reaction for several hours leads to product XXIII (Vassiliou, S. et al *Synlett* 2003, 2398-2400; Schöllkopf, U. *Topics Curr. Chem.* 1983, 109, 65). Preferred conditions are the use of tert-butyllithium and an organic iodide in tetrahydrofuran at −78° C. and allowing the mixture to reach room temperature overnight.

Step B: Cleavage of bis-lactim ether product XXIII under acidic conditions using a mineral acid such as HCl, $H_2SO_4$ or $H_3PO_4$ or an organic acid such as $CF_3COOH$, $CHCl_2COOH$, HOAc or p-toluonesulfonic acid in a solvent such as acetonitrile, $CH_2Cl_2$, $CHCl_3$, THF, MeOH, EtOH or $H_2O$ at 0 to 60° C.

Preferred conditions are a 10% trifluoroacetic acid in a mixture of water and acetonitrile (1:3) at 40° C. overnight.

Step C: Reduction of the ester XXIV can be effected by treatment with $LiAlH_4$, LiBH4, $NaBH_4$ or Red-Al in a suitable solvent such as 1,2-dimethoxyethane, THF, diethylether, toluene, MeOH or EtOH at −78° C.->reflux for 1-24 hrs.

Preferred conditions for acids and esters are $LiAlH_4$ in THF at r.t. overnight.

Step D: Cyclisation of the amino alcohol II-4 to the corresponding 2-aminooxazoline I-4 can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 8

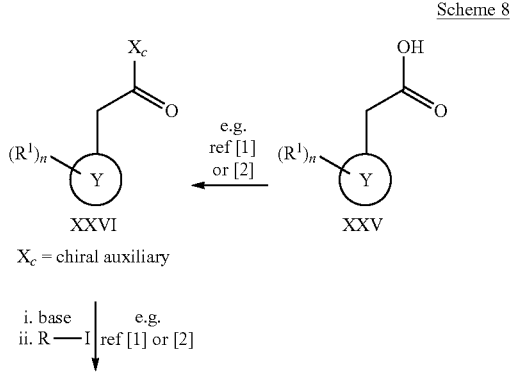

$X_c$ = chiral auxiliary

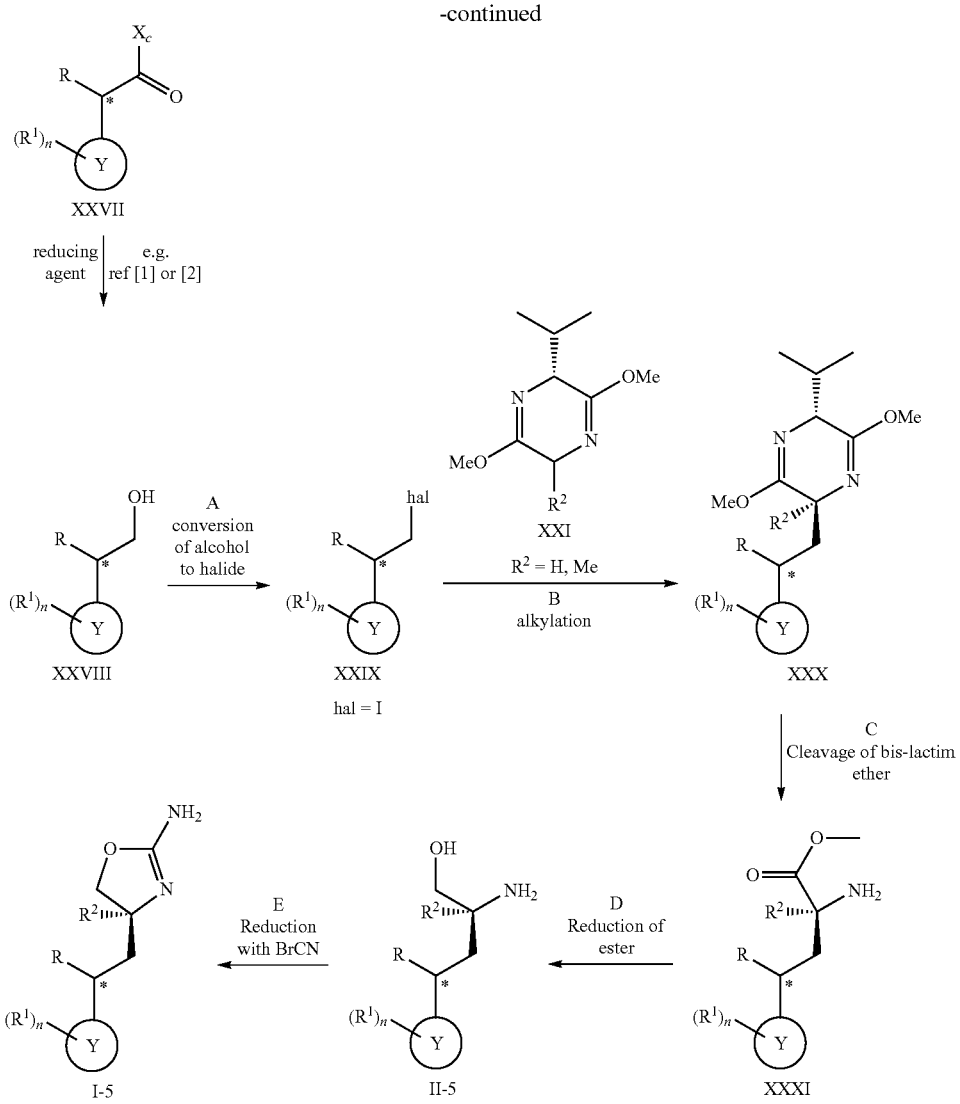

Homochiral alcohols of formula XXVIII may be prepared by a variety of methods reported in the chemical literature, for instance starting from carboxylic acids of formula XXV and using the methodologies of Evans et al. (ref [1]) or Meyers et al. (ref [2]). According to these procedures, introduction of a chiral auxilliary, such as the Evans oxazolidinone auxiliary (ref [1]) or the Meyers pseudoephedrine-derived auxiliary (ref [2]) affords a homochiral acyl compound of formula XXVI. Enolisation of the acyl compound XX with a suitable base followed by treatment with an alkyl halide affords compounds of formula XXVII. Reductive removal of the chiral auxiliary then affords the homochiral alcohols of formula XXVIII.

[1] Evans, D. A. et al. *J. Am. Chem. Soc.* 1982, 104, 1737-1739.

[2] Meyers, A. G. et al. *J. Am. Chem. Soc.* 1997, 119, 6496-5611.

Step A: Homochiral alcohol XXVIII may be converted to the corresponding alkyl iodide XXIX using a reagent system comprising imidazole, triphenylphosphine and iodine in dichloromethane (Müller, P. & Boléa, C. *Helv. Chim. Acta* 2002, 85, 483-494) or sequential treatment with p-toluensulphonyl chloride/pyridine and sodium iodide in acetone (Taber, D. F. et al. *J. Am. Chem. Soc.* 1985, 107, 196-199). Preferred conditions are the use of imidazole, triphenylphosphine and iodine in dichloromethane.

Step B: Deprotonation of bis-lactimether XXI (also called "Schöllkopf's chiral auxiliary") with a suitable base such as n-butyl-lithium or tert-butyl-lithium in an appropriate organic solvent such as tetrahydrofuran at a low temperature followed by addition of the homochiral alkyl iodide XXIX and reaction for several hours leads to product XXX(Vassiliou, S. et al *Synlett* 2003, 2398-2400; Schöllkopf, U. *Topics Curr. Chem.* 1983, 109, 65). Preferred conditions are the use of n-butyl-lithium at −78° C. and allowing the mixture to reach room temperature overnight.

Step C: Cleavage of bis-lactim ether product XXX under acidic conditions using a mineral acid such as HCl, $H_2SO_4$ or $H_3PO_4$ or an organic acid such as $CF_3COOH$, $CHCl_2COOH$, HOAc or p-toluonesulfonic acid in a solvent such as acetonitrile, $CH_2Cl_2$, $CHCl_3$, THF, MeOH, EtOH or $H_2O$ at 0 to 60°

C. Preferred conditions are a 10% trifluoroacetic acid in a mixture of water and acetonitrile (1:3) at room temperature overnight.

Step D: Reduction of the ester XXXI can be effected by treatment with LiAlH$_4$, LiBH4, NaBH$_4$ or Red-Al in a suitable solvent such as 1,2-dimethoxyethane, THF, diethylether, toluene, MeOH or EtOH at −78° C.->reflux for 1-24 hrs. Preferred conditions for acids and esters are LiAlH$_4$ in THF at r.t. overnight.

Step E: Cyclisation of the amino alcohol II-5 to the corresponding 2-aminooxazoline 1-5 can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight.

aldehyde (R$^2$=methyl; from L- or D-α-methylserine; Avenoza, A. et al. *Tetrahedron Asymm.* 2001, 12, 949) with a primary amine compound of formula XXXII-1 can be accomplished by a reducing agent such as NaBH$_4$, LiBH$_4$, NaBH(OAc)$_3$ or Na(CN)BH$_3$ in a solvent such as MeOH, EtOH, dichloromethane, 1,2-dichloroethane, THF, dioxane or mixtures thereof in the presence of an activating protic acid such as HCl or a carboxylic acid or an activating Lewis acid such as ZnC12 or Ti(OiPr)$_4$ at a temperature of −10 to 60° C. for 1-40 h. Preferred conditions are heating of compound XXXII-1 and compound IV in MeOH at 60° C. overnight, followed by treatment with NaBH$_4$ in MeOH at room temperature.

Step B: Alkylation of the compound of formula XXXIII-1 to compound of formula XXXIII-2 can by accomplished by treatment with a suitable aldehyde RCHO in the presence of

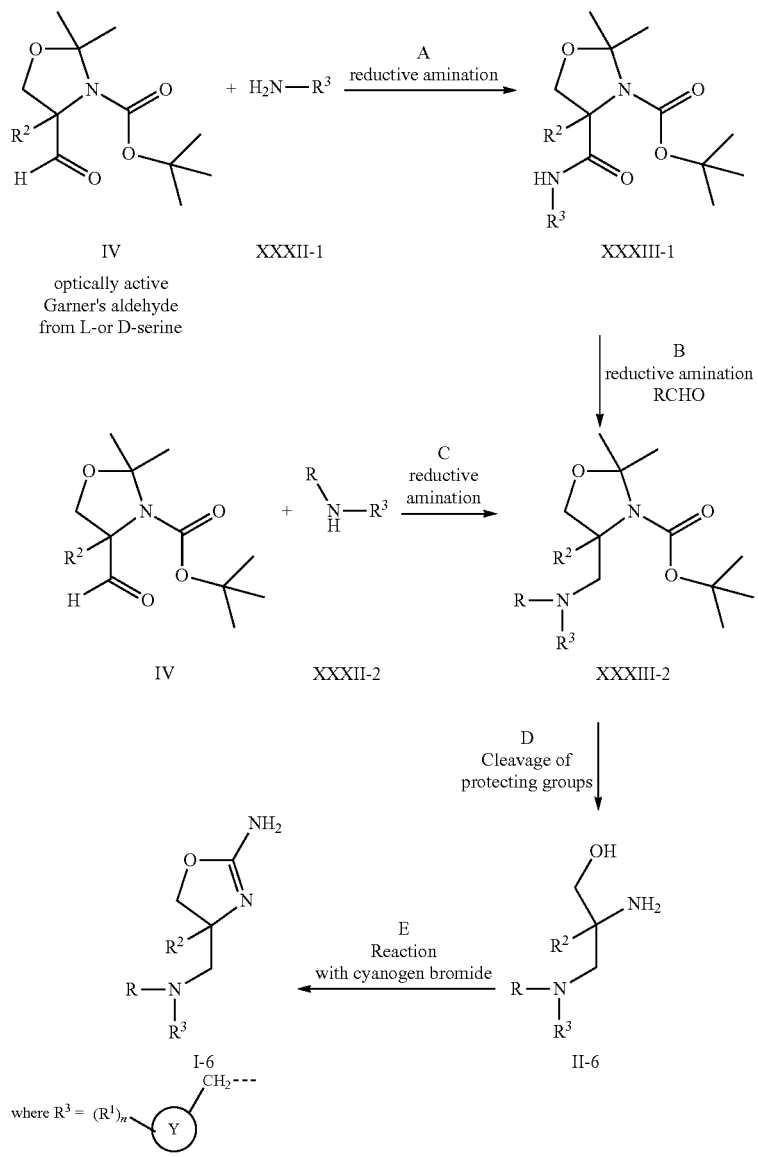

Scheme 9

Step A: Reductive amination of optically active Garner's aldehyde (R$^2$=H; from L- or D-serine; Garner, P.; Park, J. M. *Org. Synth.* 1998, IX, 300) or α-methyl-substituted Garner's a reducing agent such as NaBH$_4$, LiBH$_4$, NaBH(OAc)$_3$ or Na(CN)BH$_3$ in a solvent such as MeOH, EtOH, dichloromethane, 1,2-dichloroethane, THF, dioxane or mixtures thereof in the presence of an activating protic acid such as HCl or a carboxylic acid or an activating Lewis acid such as ZnC12 or Ti(OiPr)$_4$ at a temperature of −10 to 60° C. for 1-40 h.

Step C: Preparation of a compound of formula XXXIII-2 may alternatively be accomplished by reductive amination of a secondary amine compound of formula XXXIII-2 and Garner's aldehyde (from L- or D-serine; Garner, P.; Park, J. M. Org. Synth. 1998, IX, 300) in the presence of a reducing agent such as NaBH$_4$, LiBH$_4$, NaBH(OAc)$_3$ or Na(CN)BH$_3$ in a solvent such as MeOH, EtOH, dichloromethane, 1,2-dichloroethane, THF, dioxane or mixtures thereof in the presence of an activating protic acid such as HCl or a carboxylic acid or an activating Lewis acid such as ZnC12 or Ti(OiPr)$_4$ at a temperature of −10 to 60° C. for 1-40 h. Preferred conditions are NaBH$_3$CN and ZnC12 in MeOH at r.t.−40° C. overnight.

Step D: Simultaneous cleavage of the amino alcohol protecting groups of the compound of formula XXXIII-2 can be effected with a mineral acid such as HCl, H$_2$SO$_4$ or H$_3$PO$_4$ or a organic acid such as CF$_3$COOH, CHCl$_2$COOH, HOAc or p-toluonesulfonic acid in a solvent such as CH$_2$Cl$_2$, CHCl$_3$, THF, MeOH, EtOH or H$_2$O at 0 to 60° C. Preferred conditions are 2N HCl in EtOH at reflux for 1-3 hrs or 4N HCl in dioxane at r.t. overnight.

Step E: Cyclisation of the amino alcohol II-6 to the corresponding 2-aminooxazoline 1-6 can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC #CRL-1573) were cultured essentially as described Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

Membrane Preparation and Radioligand Binding

Cells at confluence were rinsed with ice-cold phosphate buffered saline without Ca$^{2+}$ and Mg$^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. Cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including MgCl$_2$ (10 mM) and CaCl$_2$ g protein per ml and (2 mM) (buffer B) at 200 homogenized with a Polytron at 10,000 rpm for 10 s.

Binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated K$_d$ value of 60 nM to give a bound at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 µM). Competing ligands were tested in a wide range of concentrations (10 pM-30 µM). The final dimethylsulphoxide concentration in the assay was 2%, and it did not affect radioligand binding. Each experiment was performed in duplicate. All incubations were terminated by rapid filtration through UniFilter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 µl/well, Packard Instrument Company) and bound radioactivity was counted by a TopCount Microplate Scintillation Counter (Packard Instrument Company).

The preferred compounds show a Ki value (µM) in mouse or rat on TAAR1 in the range of <0.01 µM. The values for representative compounds are shown in the table below.

| Example | Ki (µM) mouse/rat |
|---|---|
| 4 | 0.0012 |
| 5 | 0.0021 |
| 6 | 0.0038 |
| 7 | 0.0083 |
| 8 | 0.0058 |
| 9 | 0.0034 |
| 10 | 0.0025 |
| 12 | 0.008 |
| 14 | 0.0005 |
| 16 | 0.0048 |
| 17 | 0.0057 |
| 18 | 0.0022 |
| 19 | 0.0018 |
| 20 | 0.0009 |
| 21 (S) | 0.0008 |
| 22 | 0.0011 |
| 29 (S) | 0.0054 |
| 31 | 0.0022 |
| 32 | 0.0029 |
| 33 | 0.0007 |
| 34 | 0.0011 |
| 35 | 0.0033 |
| 36 | 0.0034 |
| 37b (S) | 0.0087 |
| 39a (S) | 0.0025 |
| 48 | 0.0002 |
| 49 | 0.0054 |
| 60 | 0.0047 |
| 63 | 0.0086 |
| 73 | 0.0089 |
| 78 | 0.0064 |
| 80 (S) | 0.0008 |
| 80 (R) | 0.0083 |
| 81 (S) | 0.0064 |
| 82 (S, S) | 0.0080 |
| 82 (S, R) | 0.0016 |
| 84 | 0.0017 |
| 85 | 0.0011 |
| 86 | 0.0008 |
| 88 | 0.001 |
| 89 | 0.0013 |
| 91 | 0.0006 |
| 101 | 0.0034 |
| 103 | 0.0004 |
| 105 | 0.0007 |
| 107 | 0.004 |
| 109 | 0.0014 |
| 110 | 0.0018 |
| 111 | 0.0011 |
| 112 | 0.0012 |
| 113 | 0.0016 |
| 114 | 0.0021 |
| 115 | 0.001 |
| 116 | 0.0012 |
| 118 | 0.003 |
| 119 | 0.0026 |
| 120 | 0.0014 |
| 122 | 0.0034 |
| 124 | 0.0044 |
| 127 | 0.0003 |
| 129 | 0.0029 |
| 131 | 0.0024 |
| 132 | 0.0007 |
| 133 | 0.0022 |
| 135 | 0.0009 |
| 136 | 0.0038 |
| 137 | 0.0025 |
| 138 | 0.0012 |
| 139 | 0.0019 |
| 140 | 0.001 |
| 141 | 0.0027 |
| 142 | 0.0018 |
| 143 | 0.0007 |
| 144 | 0.0012 |
| 145 | 0.0026 |
| 146 | 0.0041 |
| 147 | 0.0041 |
| 149 | 0.0019 |
| 150 | 0.0009 |
| 151 | 0.001 |
| 153 | 0.0083 |
| 154 | 0.0034 |
| 156 | 0.0064 |
| 158 | 0.0068 |
| 159 | 0.001 |
| 160 | 0.0028 |
| 161 | 0.0062 |
| 162 | 0.0025 |
| 163 | 0.0037 |
| 165 | 0.0012 |
| 166 | 0.0047 |
| 168 | 0.0006 |
| 169 | 0.0014 |
| 170 | 0.0011 |
| 172 | 0.0019 |
| 174 | 0.0006 |
| 176 | 0.002 |
| 178 | 0.0004 |
| 180 | 0.0088 |
| 184 | 0.0063 |
| 185 | 0.005 |
| 186 | 0.0045 |
| 187 | 0.0021 |
| 188 | 0.0038 |
| 189 | 0.0008 |
| 190 | 0.0008 |
| 192 | 0.0019 |
| 193 | 0.0043 |
| 194 | 0.0073 |
| 195 | 0.0018 |
| 196 | 0.0066 |
| 198 | 0.002 |
| 199 | 0.0093 |
| 201 | 0.0002 |
| 202 | 0.0017 |
| 203 | 0.0039 |
| 206 | 0.0032 |
| 210 | 0.0014 |
| 211 | 0.0024 |
| 212 | 0.0068 |
| 213 | 0.003 |
| 215 | 0.0024 |
| 216 | 0.002 |
| 217 | 0.0015 |
| 219 | 0.0009 |
| 220 | 0.0084 |

| Example | Ki (μM) mouse/rat |
|---|---|
| 221 | 0.0022 |
| 222 | 0.0048 |
| 223 | 0.0059 |
| 224 | 0.0063 |
| 225 | 0.0062 |
| 226 | 0.0054 |
| 227 | 0.0081 |
| 228 | 0.004 |
| 229 | 0-003 |
| 231 | 0.0025 |
| 232 | 0.0006 |
| 234 | 0.0093 |
| 235 | 0.001 |
| 236 | 0.002 |
| 237 | 0.0025 |
| 238 | 0.003 |
| 240 | 0.0032 |
| 242 | 0.0072 |
| 243 | 0.0094 |
| 244 | 0.0057 |
| 246 | 0.0055 |
| 248 | 0.0029 |
| 249 | 0.0075 |
| 250 | 0.0022 |
| 251 | 0.0086 |
| 252 | 0.0008 |
| 255 | 0.0074 |
| 256 | 0.0006 |
| 257 | 0.0074 |
| 259 | 0.0088 |
| 260 | 0.0013 |
| 263 | 0.0023 |
| 265 | 0.0009 |
| 266 | 0.0016 |
| 267 | 0.0011 |
| 269 | 0.0083 |
| 270 | 0.0016 |
| 271 | 0.0013 |
| 272 | 0.0013 |
| 273 | 0.0095 |
| 274 | 0.0011 |
| 277 | 0.0016 |
| 281 | 0.0019 rat |
| 284 | 0.0028 rat |
| 285 | 0.0045 rat |
| 287 | 0.0027 rat |
| 289 | 0.0017 |
| 291 | 0.0008 |
| 292 | 0.0035 |
| 293 | 0.0062 |
| 294 | 0.0038 |
| 295 | 0.0082 |
| 296 | 0.0004 |
| 298 | 0.0004 |
| 299 | 0.0042 |
| 301 | 0.0023 |
| 302 | 0.0017 |
| 303 | 0.0011 |
| 304 | 0.0033 |
| 306 | 0.0027 |
| 308 | 0.0009 |
| 310 | 0.009 rat |
| 311 | 0.0042 rat |
| 313 | 0.005 rat |
| 314 | 0.003 rat |
| 315 | 0.0016 rat |
| 316 | 0.0003 rat |
| 318 | 0.002 rat |
| 321 | 0.0014 rat |
| 322 | 0.002 rat |
| 326 | 0.001 |
| 328 | 0.0052 |
| 330 | 0.0008 |
| 332 | 0.0061 |
| 333 | 0.0021 |
| 337 | 0.0034 |
| 338 | 0.0031 |
| 340 | 0.002 |
| 341 | 0.0046 |
| 342 | 0.0045 |
| 343 | 0.0028 |
| 344 | 0.0025 |
| 348 | 0.0036 |
| 349 | 0.0023 |
| 350 | 0.0064 |
| 351 | 0.0024 |
| 353 | 0.0014 |
| 354 | 0.0003 |
| 355 | 0.0043 |
| 356 | 0.0043 |
| 357 | 0.0068 |
| 358 | 0.0084 |
| 359 | 0.0021 |
| 364 | 0.0020 |
| 365 | 0.0029 |
| 367 | 0.001 |
| 369 | 0.0009 |
| 370 | 0.0037 |
| 371 | 0.0096 |
| 374 | 0.0006 |
| D | 0.001 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment or prevention of depression, psychosis, Parkinson's disease, anxiety and attention deficit hyperactivity disorder (ADHD). Thus, the present invention provides methods of the treatment of depression, psychosis, Parkinson's disease, anxiety and attention deficit hyperactivity disorder (ADHD) which comprises administering a therapeutically effective amount of a compound of formula I or a pharmaceutically acceptable acid addition salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 2 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXPERIMENTAL

The following examples illustrate the invention but are not intended to limit its scope.

Example 1

(RS)-4-Methyl-4-phenyl-4,5-dihydro-oxazol-2-ylamine

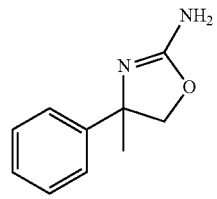

a) (RS)-2-Amino-2-phenyl-propan-1-ol

To a stirred, cooled suspension of 2-amino-2-phenyl-propionic acid (488 mg) at r.t. in THF (10 ml) under an argon atmosphere was added portionwise LiAlH$_4$ (244 mg). The ice bath was removed and stirring at r.t. was then continued for 20 h. The mixture was cooled in an ice bath, diluted with 5 ml THF and H$_2$O (0.23 ml), 4 N NaOH (0.23 ml) and H$_2$O (0.92 ml) were added successively and carefully. After 30 min stirring at r.t., the mixture was filtered and the cake was washed with THF. The filtrate was concentrated. The crude product was purified by column chromatography (silica gel; gradient: CH$_2$Cl$_2$->CH$_2$Cl$_2$/MeOH 9:1) to give 2-amino-2-phenyl-propan-1-ol (266 mg) as colorless viscous oil. MS (ISP): 152.3 ([M+H]$^+$)

b) (RS)-4-Methyl-4-phenyl-4,5-dihydro-oxazol-2-ylamine

To a stirred, cooled (0° C.) mixture of 2-amino-2-phenyl-propan-1-ol (266 mg) and K$_2$CO$_3$ (292 mg) in THF (5 ml) under an argon atmosphere was added a solution of cyanogen bromide (292 mg) in THF (5 ml). The ice bath was removed and stirring at r.t. was continued for 18 h. The mixture (white suspension) was taken up in EtOAc/H$_2$O 1:1. The aqueous phase was back extracted with EtOAc. The combined organics were washed with brine, dried over MgSO$_4$, filtered and concentrated. The crude product was purified by column chromatography (silica gel; gradient: CH$_2$Cl$_2$->CH$_2$Cl$_2$/MeOH 9:1) to give 4-methyl-4-phenyl-4,5-dihydro-oxazol-2-ylamine (204 mg) as white solid. MS (ISP): 177.1 ([M+H]$^+$)

In analogy to example 1 and starting from the respective amino acid or amino acid derivative were prepared:

Example 2

(S)-4-(4-Trifluoromethyl-phenyl)-4,5-dihydro-oxazol-2-ylamine

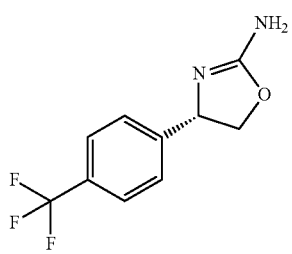 [SMILES: NC1=N[C@@H](c2ccc(C(F)(F)F)cc2)CO1]

From L-4-(trifluoromethyl)phenylglycine. Off-white solid.

MS (ISP): 231.3 ([M+H]$^+$)

Example 3

(S)-4-(4-Fluoro-phenyl)-4,5-dihydro-oxazol-2-ylamine

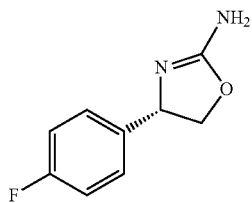 [SMILES: NC1=N[C@@H](c2ccc(F)cc2)CO1]

From L-4-fluorophenylglycine. Off-white solid.
MS (ISP): 180.9 ([M+H]$^+$)

Example 4

(S)-4-(2-Chloro-phenyl)-4,5-dihydro-oxazol-2-ylamine

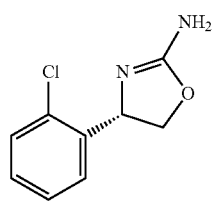 [SMILES: NC1=N[C@@H](c2ccccc2Cl)CO1]

From L-2-chlorophenylglycine. Light yellow solid.
MS (ISP): 197.3 ([M+H]$^+$)

Example 5

(RS)-4-(4-Chloro-phenyl)-4,5-dihydro-oxazol-2-ylamine

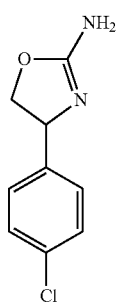 [SMILES: NC1=NC(c2ccc(Cl)cc2)CO1]

From DL-4-chlorophenylglycine. Light yellow solid.
MS (ISP): 197.1 ([M+H]$^+$)

Example 6

(RS)-4-(2-Trifluoromethyl-phenyl)-4,5-dihydro-oxazol-2-ylamine

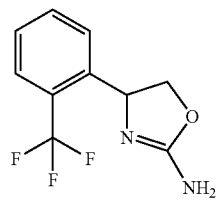 [SMILES: NC1=NC(c2ccccc2C(F)(F)F)CO1]

From DL-2-(trifluoromethyl)phenylglycine. Off-white solid.
MS (ISP): 231.3 ([M+H]$^+$)

Example 7

(RS)-4-(2,4-Difluoro-phenyl)-4,5-dihydro-oxazol-2-ylamine

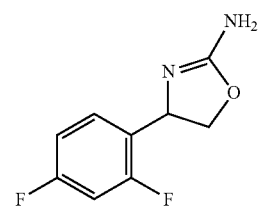 [SMILES: NC1=NC(c2ccc(F)cc2F)CO1]

From DL-2,4-difluorophenylglycine. Off-white solid. MS (ISP): 198.9 ([M+H]$^+$)

Example 8

(RS)-4-o-Tolyl-4,5-dihydro-oxazol-2-ylamine

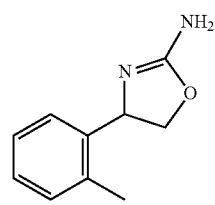

From (RS)-α-amino-(2-methylphenyl)acetic acid. Off-white solid.
MS (ISP): 177.3 ([M+H]$^+$)

Example 9

(S)-4-(2,3-Difluoro-phenyl)-4,5-dihydro-oxazol-2-ylamine

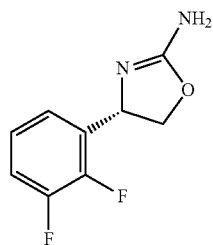 [SMILES: NC1=N[C@@H](c2cccc(F)c2F)CO1]

From L-2,3-difluorophenylglycine. Off-white solid.
MS (ISP): 199.3 ([M+H]$^+$)

Example 10

(RS)-4-Biphenyl-4-yl-4,5-dihydro-oxazol-2-ylamine

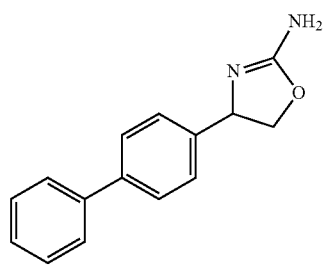 [SMILES: NC1=NC(c2ccc(-c3ccccc3)cc2)CO1]

From (RS)-amino-biphenyl-4-yl-acetic acid. Off-white solid.
MS (ISP): 239.1 ([M+H]$^+$)

Example 11

(RS)-4-(2-Fluoro-phenyl)-4,5-dihydro-oxazol-2-ylamine

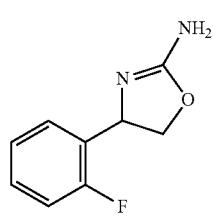 [SMILES: NC1=NC(c2ccccc2F)CO1]

From DL-2-fluorophenylglycine. Off-white solid.
MS (ISP): 180.9 ([M+H]$^+$)

Example 12

(RS)-4-(4-Trifluoromethoxy-phenyl)-4,5-dihydro-oxazol-2-ylamine

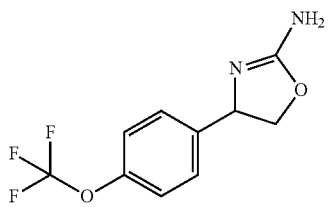 [SMILES: NC1=NC(c2ccc(OC(F)(F)F)cc2)CO1]

From DL-4-(trifluoromethoxy)phenylglycine. Off-white solid.
MS (ISP): 247.3 ([M+H]$^+$)

Example 13

(RS)-4-(3-Trifluoromethoxy-phenyl)-4,5-dihydro-oxazol-2-ylamine

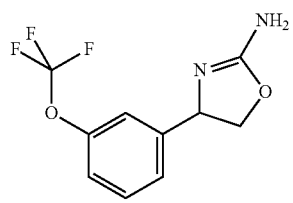 [SMILES: NC1=NC(c2cccc(OC(F)(F)F)c2)CO1]

From DL-3-(trifluoromethoxy)phenylglycine. Off-white solid.
MS (ISP): 247.3 ([M+H]$^+$)

Example 14

(RS)-4-(3,4-Dichlorophenyl)-4,5-dihydro-oxazol-2-ylamine

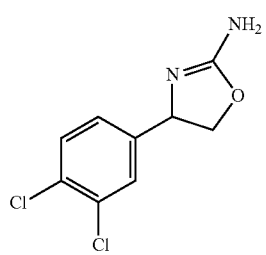 [SMILES: NC1=NC(c2ccc(Cl)c(Cl)c2)CO1]

From DL-3,4-dichlorophenylglycine. Off-white solid. MS (ISP): 231.1 ([M+H]$^+$)

Example 15

(RS)-4-(2-Methoxy-phenyl)-4,5-dihydro-oxazol-2-ylamine

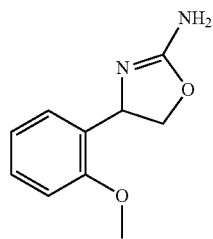

From DL-2-methoxyphenylglycine. Off-white solid. MS (ISP): 193.4 ([M+H]$^+$)

Example 16

(RS)-4-(2,5-Difluoro-phenyl)-4,5-dihydro-oxazol-2-ylamine

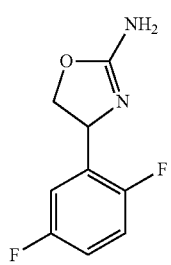 [SMILES: NC1=NC(c2cc(F)ccc2F)CO1]

From DL-2,5-difluorophenylglycine. Off-white solid. MS (ISP): 199.1 ([M+H]$^+$)

Example 17

(RS)-4-(2,3,4-Trifluoro-phenyl)-4,5-dihydro-oxazol-2-ylamine

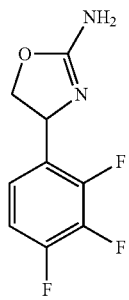

From DL-2,3,4-trifluorophenylglycine. Off-white solid. MS (ISP): 217.3 ([M+H]$^+$)

Example 18

(RS)-4-(3-Chloro-2-fluoro-phenyl)-4,5-dihydro-oxazol-2-ylamine

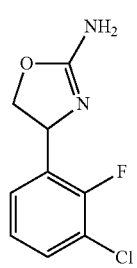 [SMILES: NC1=NC(c2cccc(Cl)c2F)CO1]

From DL-3-chloro-2-fluorophenylglycine. Off-white solid.

MS (ISP): 215.1 ([M+H]$^+$)

Example 19

(RS)-4-(5-Chloro-2-fluoro-phenyl)-4,5-dihydro-oxazol-2-ylamine

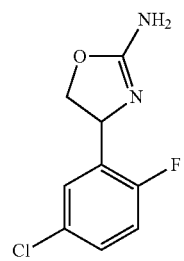 [SMILES: NC1=NC(c2cc(Cl)ccc2F)CO1]

From DL-5-chloro-2-fluorophenylglycine. Off-white solid.

MS (ISP): 215.1 ([M+H]$^+$)

Example 20

(RS)-4-(4-Bromo-phenyl)-4,5-dihydro-oxazol-2-ylamine

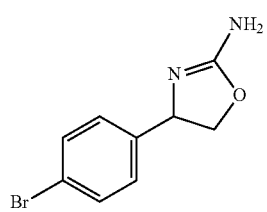 [SMILES: NC1=NC(c2ccc(Br)cc2)CO1]

From DL-4-bromophenylglycine. Off-white solid. MS (ISP): 243.1 ([M+H]$^+$)

Example 21

(S)-4-Biphenyl-4-yl-4,5-dihydro-oxazol-2-ylamine and (R)-4-biphenyl-4-yl-4,5-dihydro-oxazol-2-ylamine

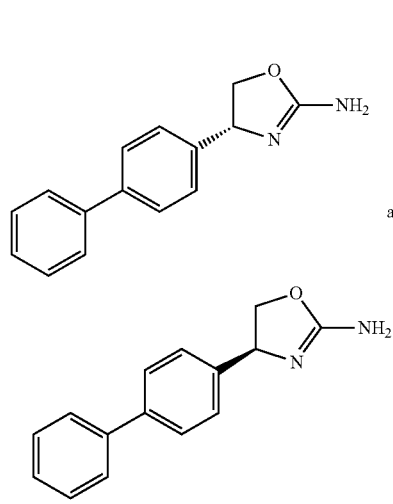

and (RS)-4-Biphenyl-4-yl-4,5-dihydro-oxazol-2-ylamine (example 10) was separated by chiral HPLC (Chiralpak AD, EtOH/heptane=15:85) to yield (S)-4-biphenyl-4-yl-4,5-dihydro-oxazol-2-ylamine (off-white solid; MS (ISP): 239.3 ([M+H]$^+$)) and (R)-4-biphenyl-4-yl-4,5-dihydro-oxazol-2-ylamine (off-white solid; MS (ISP): 239.3 ([M+H]$^+$))

In analogy to example 1 and starting from the respective amino acid or amino acid derivative were prepared:

Example 22

(RS)-4-(4-Benzyloxy-phenyl)-4,5-dihydro-oxazol-2-ylamine

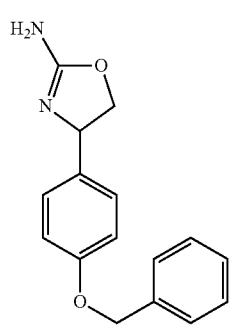 [SMILES: NC1=NC(c2ccc(OCc3ccccc3)cc2)CO1]

From (RS)-amino-(4-benzyloxy-phenyl)-acetic acid methyl ester. White solid.
MS (ISP): 269.4 ([M+H]$^+$)

Example 23

(RS)-4-(4-Phenoxy-phenyl)-4,5-dihydro-oxazol-2-ylamine

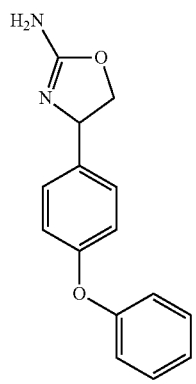 [SMILES: NC1=NC(c2ccc(Oc3ccccc3)cc2)CO1]

From (RS)-amino-(4-phenoxy-phenyl)-acetic acid methyl ester. White solid.
MS (ISP): 255.4 ([M+H]$^+$)

Example 24

(RS)-4-(3-Benzyloxy-phenyl)-4,5-dihydro-oxazol-2-ylamine

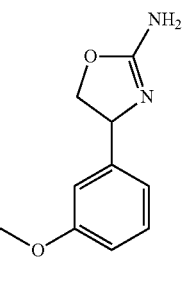

From (RS)-amino-(3-benzyloxy-phenyl)-acetic acid methyl ester. White solid. MS (ISP): 269.3 ([M+H]$^+$)

Example 25

(RS)-4-(3-Phenoxy-phenyl)-4,5-dihydro-oxazol-2-ylamine

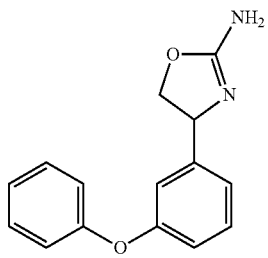 [SMILES: NC1=NC(c2cccc(Oc3ccccc3)c2)CO1]

From (RS)-amino-(3-phenoxy-phenyl)-acetic acid methyl ester. White solid.
MS (ISP): 255.4 ([M+H]$^+$)

Example 26

(S)-4-Methyl-4-phenyl-4,5-dihydro-oxazol-2-ylamine and (R)-4-methyl-4-phenyl-4,5-dihydro-oxazol-2-ylamine

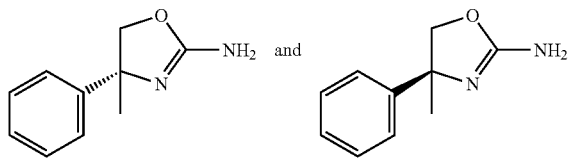

(RS)-4-Methyl-4-phenyl-4,5-dihydro-oxazol-2-ylamine (example 1) was separated by chiral HPLC (Chiralpak AD, EtOH/heptane=15:85) to yield (S)-4-methyl-4-phenyl-4,5-dihydro-oxazol-2-ylamine (off-white solid; MS (ISP): 177.3 ([M+H]$^+$)) and (R)-4-methyl-4-phenyl-4,5-dihydro-oxazol-2-ylamine (off-white solid; MS (ISP): 177.4 ([M+H]$^+$))

In analogy to example 1 and starting from the respective amino acid or amino acid derivative were prepared:

Example 27

(RS)-4-Biphenyl-3-yl-4,5-dihydro-oxazol-2-ylamine

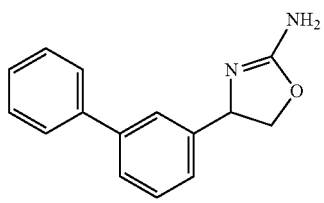 [SMILES: NC1=NC(c2cccc(-c3ccccc3)c2)CO1]

From (RS)-amino-biphenyl-3-yl-acetic acid. Off-white solid. MS (ISP): 239.1 ([M+H]$^+$)

Example 28

(RS)-4-Ethyl-4-phenyl-4,5-dihydro-oxazol-2-ylamine

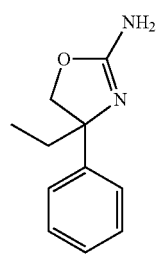

From (RS)-2-amino-2-phenylbutyric acid. Off-white solid.
MS (ISP): 191.3 ([M+H]$^+$)

Example 29

(S)-4-(3-Bromo-2,4-difluoro-phenyl)-4,5-dihydro-oxazol-2-ylamine and (R)-4-(3-bromo-2,4-difluoro-phenyl)-4,5-dihydro-oxazol-2-ylamine

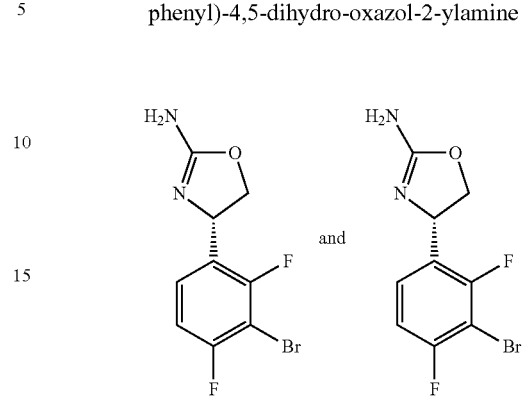

a) (RS)-4-(3-Bromo-2,4-difluoro-phenyl)-4,5-dihydro-oxazol-2-ylamine

A solution of lithium diisopropylamide in THF (2 M, 5.05 ml) was cooled to −55° C. and treated with (RS)-4-(2,4-difluoro-phenyl)-4,5-dihydro-oxazol-2-ylamine (667 mg, example 7) in THF (6 ml). The reaction mixture was stirred at −55° C. for 2 hrs, then treated dropwise with 1,2-dibromoethane (0.58 ml). The reaction mixture was warmed to r.t., then stirred overnight at r.t. It was quenched with H$_2$O and extracted with EtOAc. The organic layer was dried over MgSO$_4$, filtrated and concentrated. The crude product was purified by column chromatography (SiO$_2$; gradient: CH$_2$Cl$_2$->CH$_2$Cl$_2$/MeOH 95:5) to give (RS)-4-(3-bromo-2,4-difluoro-phenyl)-4,5-dihydro-oxazol-2-ylamine (61 mg) as light yellow solid.
MS (ISP): 279.1 ([M+H]$^+$)

b) (S)-4-(3-Bromo-2,4-difluoro-phenyl)-4,5-dihydro-oxazol-2-ylamine and (R)-4-(3-bromo-2,4-difluoro-phenyl)-4,5-dihydro-oxazol-2-ylamine (RS)-4-(3-Bromo-2,4-difluoro-phenyl)-4,5-dihydro-oxazol-2-ylamine was separated by chiral HPLC (Chiralpak AD, EtOH/heptane=10:90) to yield (S)-4-(3-bromo-2,4-difluoro-phenyl)-4,5-dihydro-oxazol-2-ylamine (off-white solid; MS (ISP): 279.1 ([M+H]$^+$)) and (R)-4-(3-bromo-2,4-difluoro-phenyl)-4,5-dihydro-oxazol-2-ylamine (off-white solid; MS (ISP): 279.1 ([M+H]$^+$)

Example 30

(RS)-4-(4'-Fluoro-biphenyl-4-yl)-4,5-dihydro-oxazol-2-ylamine

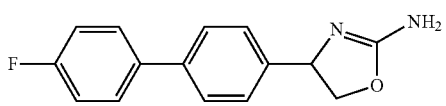

To a stirred solution of (RS)-4-(4-bromo-phenyl)-4,5-dihydro-oxazol-2-ylamine (80 mg; example 20) at r.t. in 1,2-dimethoxyethane (4 ml) under an argon atmosphere were added PdCl$_2$(dppf) (24 mg), 10% aq. Na$_2$CO$_3$ (1 ml) and 4-fluorophenylboronic acid (186 mg). The mixture was heated to 85° C. and stirring at that temperature was continued for 18 h. The dark brown mixture was cooled to r.t., diluted with EtOAc and washed with H₂O. The aqueous phase was back extracted with EtOAc. The combined organics were washed with H₂O and brine, dried over MgSO₄, filtered and concentrated. The crude product was purified by column chromatography (SiO₂; gradient: CH₂Cl₂->CH₂Cl₂/MeOH 9:1) to give (RS)-4-(4'-fluoro-biphenyl-4-yl)-4,5-dihydro-oxazol-2-ylamine (46 mg) as off-white solid. MS (ISP): 257.0 ([M+H]⁺)

Example 31

(RS)-4-(4'-Chloro-biphenyl-4-yl)-4,5-dihydro-oxazol-2-ylamine

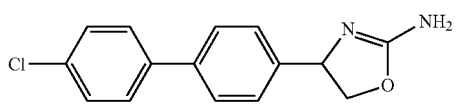 [SMILES: NC1=NC(c2ccc(-c3ccc(Cl)cc3)cc2)CO1]

In analogy to example 30, (RS)-4-(4-bromo-phenyl)-4,5-dihydro-oxazol-2-ylamine was reacted with 4-chlorophenyl-boronic acid to give (RS)-4-(4'-chloro-biphenyl-4-yl)-4,5-dihydro-oxazol-2-ylamine. Off-white solid. MS (ISP): 273.1 ([M+H]⁺)

In analogy to example 1 and starting from the respective amino acid or amino acid derivative were prepared:

Example 32

(RS)-4-(2,3-Dihydro-benzo[1,4]dioxin-6-yl)-4,5-dihydro-oxazol-2-ylamine

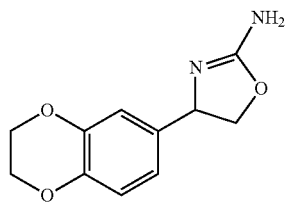 [SMILES: NC1=NC(c2ccc3c(c2)OCCO3)CO1]

From (RS)-amino-(2,3-dihydro-benzo[1,4]dioxin-6-yl)-acetic acid. Off-white solid.
MS (ISP): 221.1 ([M+H]⁺)

Example 33

(RS)-4-Naphthalen-2-yl-4,5-dihydro-oxazol-2-ylamine

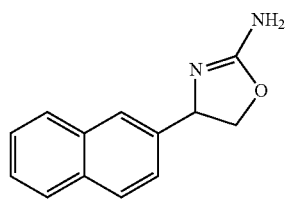

From (RS)-amino-naphtalen-2-yl-acetic acid. Light yellow solid.
MS (ISP): 213.1 ([M+H]9

Example 34

(RS)-4-Naphthalen-1-yl-4,5-dihydro-oxazol-2-ylamine

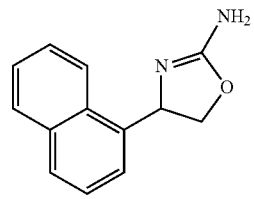 [SMILES: NC1=NC(c2cccc3ccccc23)CO1]

From (RS)-amino-naphtalen-1-yl-acetic acid. Light yellow solid.
MS (ISP): 213.1 ([M+H]⁺)

Example 35

(RS)-4-(4-Methoxy-3-methyl-phenyl)-4,5-dihydro-oxazol-2-ylamine

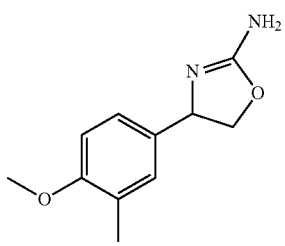

From (RS)-amino-(4-methoxy-3-methylphenyl)-acetic acid. Off-white solid.
MS (ISP): 207.1 ([M+H]⁺)

Example 36

(RS)-4-(3-Chloro-4-methoxyphenyl)-4,5-dihydro-oxazol-2-ylamine

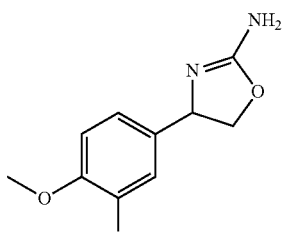

From (RS)-amino-(3-chloro-4-methoxyphenyl)acetic acid. Off-white solid.
MS (ISP): 227.3 ([M+H]⁺)

Example 37

(S)-4-(2,4-Difluoro-phenyl)-4,5-dihydro-oxazol-2-ylamine and (R)-4-(2,4-difluoro-phenyl)-4,5-dihydro-oxazol-2-ylamine

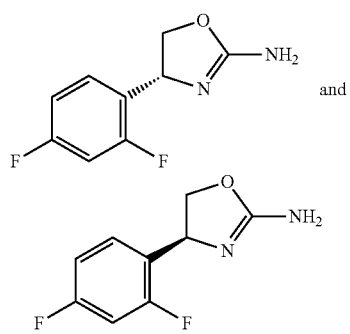

(RS)-4-(2,4-Difluoro-phenyl)-4,5-dihydro-oxazol-2-ylamine (example 7) was separated by chiral HPLC (Chiralpak AD, EtOH/heptane=10:90) to yield (S)-4-(2,4-difluoro-phenyl)-4,5-dihydro-oxazol-2-ylamine (light yellow solid; MS (ISP): 199.1 ([M+H]$^+$) and (R)-4-(2,4-difluoro-phenyl)-4,5-dihydro-oxazol-2-ylamine (off-white solid; MS (ISP): 199.1 ([M+H]$^+$)

Example 38

(S)-4-(2,4-Difluoro-3-[$^3$H]-phenyl)-4,5-dihydro-oxazol-2-ylamine

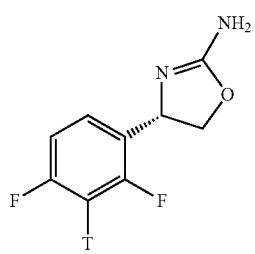

A solution of (S)-4-(3-bromo-2,4-difluoro-phenyl)-4,5-dihydro-oxazol-2-ylamine (3.5 mg; example 29.b) in EtOAc (1 ml) was treated with 1.2 mg of 10% palladium on charcoal (1.2 mg) and triethylamine (20 µml) was stirred for 1 h at room temperature under tritium gas. The volatiles were removed by vacuum transfer and 5 ml of ethanol/water 9:1 were added in three portions to the reaction flask. After brief stirring the volatiles were removed by vacuum transfer.

The reaction flask was removed from the tritiation apparatus and the residue was suspended in ethanol. The suspension was filtered through a 0.45 µm PTFE filter cartouche (Ø=13 mm) and the filter was rinsed 5× with ethanol, the filtrate was evaporated to about 0.5 ml and then partitioned between dichloromethane and water plus 10% sodium carbonate. After a second extraction with dichloromethane the organic phase was dried over potassium carbonate. Filtration, evaporation, dissolution in toluene and evaporation to remove residual triethylamin furnished the crude product, which was dissolved in 50 ml of ethanol. The total activity was 229 mCi. Half of the crude product was purified by HPLC (column: XTerra RP-18 5 µm 10×150 mm; mobile phase: A/B=65 : 35; A: 100 mM ammonium-carbonate pH=10+5% acetonitrile; B: acetonitrile; flow rate: 5 ml/min; UV: 220 nm). The HPLC-eluate was evaporated to about half of its volume and then partitioned between dichloromethane and water plus 10% sodium carbonate as described above. Finally the purified product was dissolved in 25 ml of ethanol. The total activity was 98.29 mCi and the radiochemical purity was 100% and 98% according to radio-HPLC and radio-TLC respectively. The specific activity was 17.5 Ci/mole according to mass spectrometry. The enantiomeric purity was over 99% according to HPLC (column: Chiralpak AD 10 µm 4.6×250 mm; mobile phase: 10% ethanol in n-heptane; flow rate: 1 ml/min; UV: 220 nm).

Example 39

(S)-4-o-Tolyl-4,5-dihydro-oxazol-2-ylamine and (R)-4-o-tolyl-4,5-dihydro-oxazol-2-ylamine

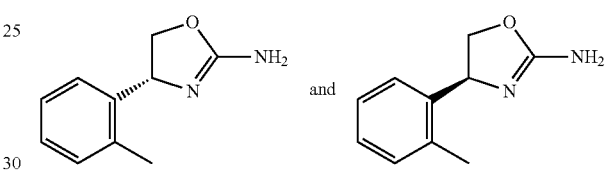

(RS)-4-o-Tolyl-4,5-dihydro-oxazol-2-ylamine (example 8) was separated by chiral HPLC (Chiralpak AD, EtOH/heptane=10:90) to yield (S)-4-o-tolyl-4,5-dihydro-oxazol-2-ylamine (light yellow solid; MS (ISP): 177.1 ([M+H]$^+$) and (R)-4-o-tolyl-4,5-dihydro-oxazol-2-ylamine (light yellow solid; MS (ISP): 177.1 ([M+H]$^+$)

In analogy to example 1 and starting from the respective amino acid or amino acid derivative were prepared:

Example 40

(RS)-4-(2,3,5-Trifluoro-phenyl)-4,5-dihydro-oxazol-2-ylamine

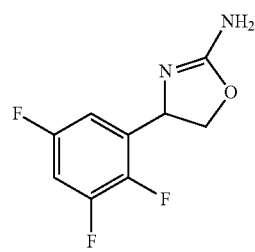 [SMILES: NC1=NC(c2cc(F)cc(F)c2F)CO1]

From 2,4,5-trifluoro-DL-phenylglycine. White solid.
MS (ISP): 217.3 ([M+H]$^+$)

Example 41

(RS)-4-(2-Amino-4,5-dihydro-oxazol-4-yl)-benzoic acid methyl ester

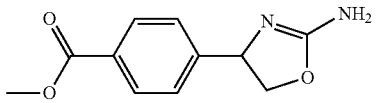 [SMILES: COC(=O)c1ccc(C2COC(N)=N2)cc1]

From (RS)-4-(amino-methoxycarbonyl-methyl)-benzoic acid methyl ester. White solid.
MS (ISP): 221.13 ([M+H]$^+$)

Example 42

(RS)-4-Thiophen-2-yl-4,5-dihydro-oxazol-2-ylamine

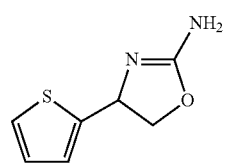 [SMILES: NC1=NC(c2cccs2)CO1]

From DL-α-aminothiophene-2-acetic acid methyl ester hydrochloride. Off-white solid.
MS (ISP): 169.1 ([M+H]$^+$)

Example 43

(RS)-(4-(5-Chloro-thiophen-2-yl)-4,5-dihydro-oxazol-2-ylamine

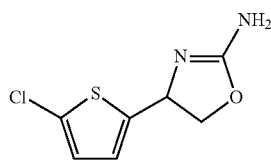 [SMILES: NC1=NC(c2ccc(Cl)s2)CO1]

From (RS)-amino-(5-chloro-thiophen-2-yl)-acetic acid methyl ester hydrochloride. Off-white solid. MS (ISP): 203.3 ([M+H]9

Example 44

(RS)-4-Pyridin-3-yl-4,5-dihydro-oxazol-2-ylamine

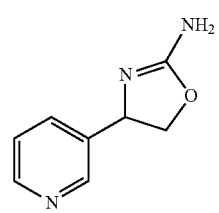 [SMILES: NC1=NC(c2cccnc2)CO1]

From (RS)-3-pyridyl-aminoacetic acid hydrochloride. Light yellow solid. In analogy to example 1 and starting from the respective amino acid or amino acid derivative were prepared:

Example 45

(R)-4-Naphthalen-2-ylmethyl-4,5-dihydro-oxazol-2-ylamine

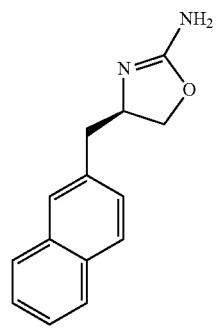 [SMILES: NC1=N[C@H](Cc2ccc3ccccc3c2)CO1]

From (R)-2-amino-3-naphthalen-2-yl-propionic acid. Light yellow viscous oil.
MS (ISP): 227.4 ([M+H]$^+$)

Example 46

(R)-4-Naphthalen-1-ylmethyl-4,5-dihydro-oxazol-2-ylamine

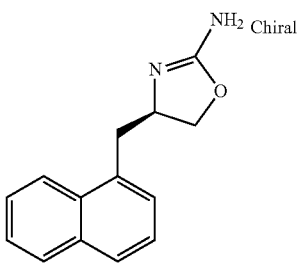 [SMILES: NC1=N[C@H](Cc2cccc3ccccc23)CO1]

From (R)-2-amino-3-naphthalen-1-yl-propionic acid. Light yellow viscous oil.
MS (ISP): 227.4 ([M+H]$^+$)

Example 47

(R)-4-Benzyl-4,5-dihydro-oxazol-2-ylamine

From D-phenylalanine. Light yellow solid.
MS (ISP): 177.1 ([M+H]$^+$)

Example 48

(S)-4-Naphthalen-1-ylmethyl-4,5-dihydro-oxazol-2-ylamine

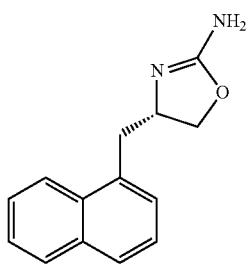 [SMILES: NC1=N[C@@H](Cc2cccc3ccccc23)CO1]

From (S)-2-amino-3-naphthalen-1-yl-propionic acid. Off-white solid.

MS (ISP): 227.4 ([M+H]$^+$)

Example 49

(S)-4-Naphthalen-2-ylmethyl-4,5-dihydro-oxazol-2-ylamine

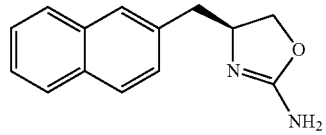

From (S)-2-amino-3-naphthalen-2-yl-propionic acid. Light yellow amorphous solid.

MS (ISP): 227.1 ([M+H]$^+$)

Example 50

(RS)-4-Benzyl-4-methyl-4,5-dihydro-oxazol-2-ylamine

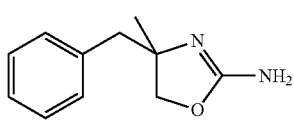

From α-methyl-DL-phenylalanine. Colorless viscous oil.
MS (ISP): 191.1 ([M+H]$^+$)

Example 51

(S)-4-(4-Chloro-benzyl)-4,5-dihydro-oxazol-2-ylamine

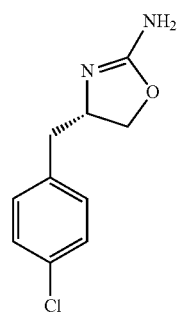 [SMILES: NC1=N[C@@H](Cc2ccc(Cl)cc2)CO1]

From L-4-chlorophenylalanine. Light yellow viscous oil.
MS (ISP): 211.1 ([M+H]$^+$)

Example 52

(S)-4-(4-Methoxy-benzyl)-4,5-dihydro-oxazol-2-ylamine

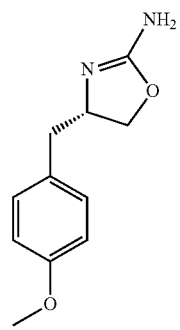

From L-4-methoxyphenylalanine. Off-white solid.
MS (ISP): 207.1 ([M+H]$^+$)

Example 53

(S)-4-(4-Benzyloxy-benzyl)-4,5-dihydro-oxazol-2-ylamine

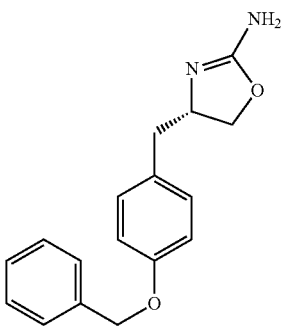 [SMILES: NC1=N[C@@H](Cc2ccc(OCc3ccccc3)cc2)CO1]

From L-4-benzyloxyphenylalanine. Off-white solid.
MS (ISP): 283.3 ([M+]$^+$)

Example 54

(S)-4-(3-Fluoro-benzyl)-4,5-dihydro-oxazol-2-ylamine

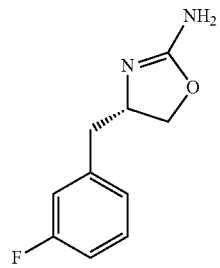 [SMILES: NC1=N[C@@H](Cc2cccc(F)c2)CO1]

From L-3-fluorophenylalanine. Light yellow amorphous solid.
MS (ISP): 195.1 [M+H]⁺

Example 55

(S)-4-(2-Fluoro-benzyl)-4,5-dihydro-oxazol-2-ylamine

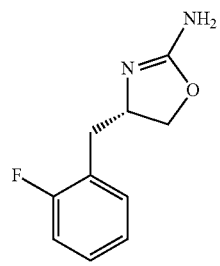 [SMILES: NC1=N[C@@H](Cc2ccccc2F)CO1]

From L-2-fluorophenylalanine. Light yellow amorphous solid.
MS (ISP): 195.1 ([M+H]⁺)

Example 56

(S)-4-(2-Trifluoromethyl-benzyl)-4,5-dihydro-oxazol-2-ylamine

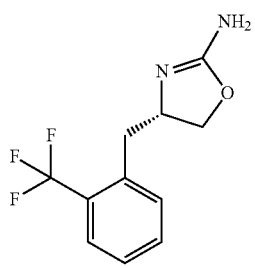 [SMILES: NC1=N[C@@H](Cc2ccccc2C(F)(F)F)CO1]

From L-2-trifluoromethylphenylalanine. Light yellow solid.
MS (ISP): 245.1 ([M+H]⁺)

Example 57

(S)-4-Benzo[1,3]dioxol-5-ylmethyl-4,5-dihydro-oxazol-2-ylamine

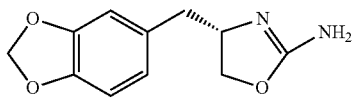 [SMILES: NC1=N[C@@H](Cc2ccc3c(c2)OCO3)CO1]

From (S)-2-amino-3-benzo[1,3]dioxol-5-yl-propionic acid. Light yellow amorphous solid. MS (ISP): 221.3 ([M+H]⁺)

Example 58

(S)-4-(3-Methyl-benzyl)-4,5-dihydro-oxazol-2-ylamine

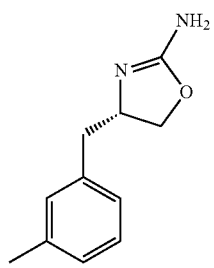

From L-3-methylphenylalanine. Yellow amorphous solid.
MS (ISP): 191.4 ([M+H]⁺)

Example 59

(S)-4-(4-Methyl-benzyl)-4,5-dihydro-oxazol-2-ylamine

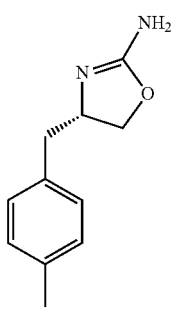

From L-4-methylphenylalanine. Light yellow solid.
MS (ISP): 191.4 ([M+H]⁺)

Example 60

(S)-4-(2-Chloro-benzyl)-4,5-dihydro-oxazol-2-ylamine

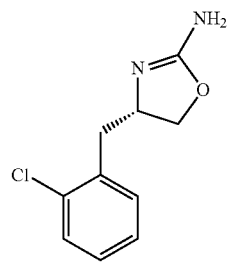 [SMILES: NC1=N[C@@H](Cc2ccccc2Cl)CO1]

From L-2-chlorophenylalanine. Light yellow oil.
MS (ISP): 211.1 ([M+H]$^+$)

Example 61

(S)-4-(3-Chloro-benzyl)-4,5-dihydro-oxazol-2-ylamine

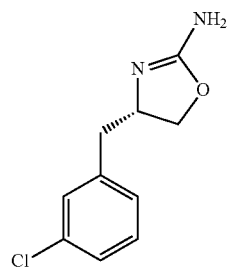 [SMILES: NC1=N[C@@H](Cc2cccc(Cl)c2)CO1]

From L-3-chlorophenylalanine. Light yellow oil.
MS (ISP): 210.9 ([M+H]$^+$)

Example 62

(S)-4-(2-Methyl-benzyl)-4,5-dihydro-oxazol-2-ylamine

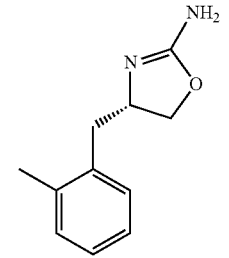

From L-2-methylphenylalanine. Yellow oil.
MS (ISP): 191.4 ([M+H]$^+$)

Example 63

(S)-4-(3-Trifluoromethyl-benzyl)-4,5-dihydro-oxazol-2-ylamine

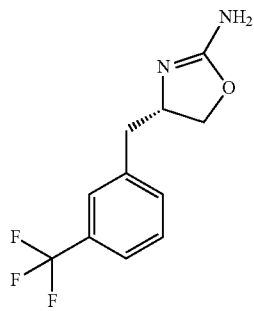 [SMILES: NC1=N[C@@H](Cc2cccc(C(F)(F)F)c2)CO1]

From L-3-trifluoromethylphenylalanine. Yellow oil.
MS (ISP): 245.3 ([M+H]$^+$)

Example 64

(S)-4-(4-Trifluoromethyl-benzyl)-4,5-dihydro-oxazol-2-ylamine

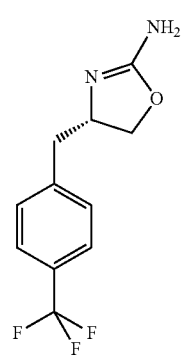

From L-4-trifluoromethylphenylalanine. Yellow oil.
MS (ISP): 245.3 ([M+H]$^+$)

Example 65

(S)-4-(4-Fluoro-benzyl)-4,5-dihydro-oxazol-2-ylamine

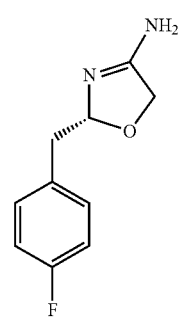 [SMILES: NC1=N[C@@H](Cc2ccc(F)cc2)OC1]

From L-4-fluorophenylalanine. Yellow oil. MS (ISP): 195.1 ([M+H]$^+$)

Example 66

(RS)-4-(2,6-Dimethyl-benzyl)-4-methyl-4,5-dihydro-oxazol-2-ylamine

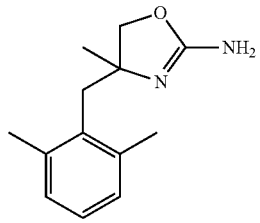 [SMILES: Cc1cccc(C)c1CC1(C)COC(N)=N1]

From (RS)-2-amino-3-(2,6-dimethyl-phenyl)-2-methyl-propionic acid hydrochloride. White solid.
MS (ISP): 219.4 ([M+H]$^+$)

Example 67

(S)-4-(4-tert-Butoxy-benzyl)-4,5-dihydro-oxazol-2-ylamine

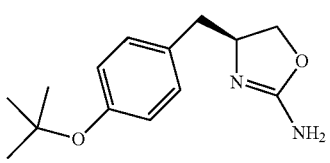 [SMILES: CC(C)(C)Oc1ccc(C[C@H]2COC(N)=N2)cc1]

From L-4-tert-butoxyphenylalanine. Light yellow solid.
MS (ISP): 249.4 ([M+H]$^+$)

Example 68

4-(1-Phenyl-ethyl)-4,5-dihydro-oxazol-2-ylamine

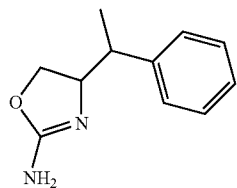

From 2-amino-3-phenylbutanoic acid hydrochloride. Off-white solid.
MS (ISP): 191.4 ([M+H]$^+$)

Example 69

(RS)-4-(2-Chloro-6-fluoro-benzyl)-4,5-dihydro-oxazol-2-ylamine

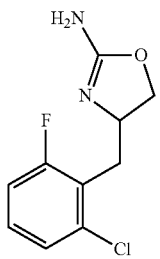 [SMILES: NC1=NC(Cc2c(F)cccc2Cl)CO1]

From DL-2-chloro-6-fluorophenylalanine. Off-white solid.
MS (ISP): 229.4 ([M+H]$^+$)

Example 70

(S)-4-(3,4-Difluoro-benzyl)-4,5-dihydro-oxazol-2-ylamine

From L-3,4-difluorophenylalanine. Off-white solid.
MS (ISP): 213.1 ([M+H]$^+$)

Example 71

(S)-4-(3,4-Dimethoxy-benzyl)-4,5-dihydro-oxazol-2-ylamine

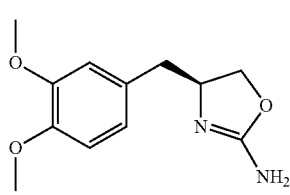 [SMILES: COc1ccc(C[C@H]2COC(N)=N2)cc1OC]

From L-3,4-dimethoxyphenylalanine. Light yellow gum.
MS (ISP): 237.1 ([M+H]$^+$)

Example 72

(RS)-4-(2-Phenoxy-benzyl)-4,5-dihydro-oxazol-2-ylamine

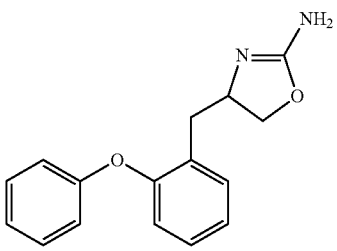 [SMILES: NC1=NC(Cc2ccccc2Oc2ccccc2)CO1]

From DL-2-phenoxyphenylalanine. Colorless oil.
MS (ISP): 269.4 ([M+H]$^+$)

Example 73

(RS)-4-(2-Fluoro-5-methyl-benzyl)-4,5-dihydro-oxazol-2-ylamine

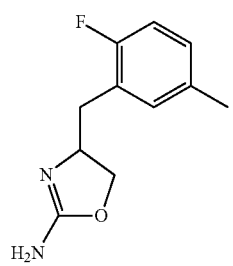

From DL-2-fluoro-5-methylphenylalanine. Light yellow viscous oil.
MS (ISP): 209.1 ([M+H]$^+$)

Example 74

(RS)-4-(2,6-Difluoro-3-methyl-benzyl)-4,5-dihydro-oxazol-2-ylamine

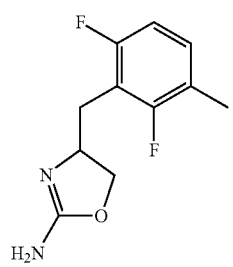

From DL-2,6-difluoro-3-methylphenylalanine. Off-white solid.
MS (ISP): 227.1 ([M+H]$^+$)

Example 75

(RS)-4-(2-Fluoro-6-trifluoromethyl-benzyl)-4,5-dihydro-oxazol-2-ylamine

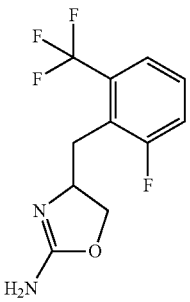 [SMILES: NC1=NC(Cc2c(F)cccc2C(F)(F)F)CO1]

From DL-2-fluoro-6-trifluoromethylphenylalanine. Light yellow viscous oil.
MS (ISP): 263.0 ([M+H]$^+$)

Example 76

(RS)-4-(2,6-Dimethyl-benzyl)-4,5-dihydro-oxazol-2-ylamine

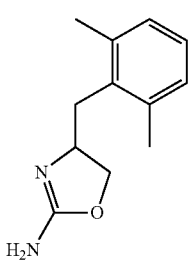

From DL-2,6-dimethylphenylalanine. White solid.
MS (ISP): 205.1 ([M+H]$^+$)

Example 77

(RS)-4-(2,6-Diethyl-benzyl)-4,5-dihydro-oxazol-2-ylamine

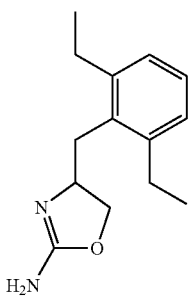

From DL-2,6-diethylphenylalanine. Off-white amorphous solid.
MS (ISP): 233.3 ([M+H]$^+$)

In analogy to example 1 and starting from the respective amino acid or amino acid derivative were prepared:

Example 78

(RS)-4-Methyl-4-phenethyl-4,5-dihydro-oxazol-2-ylamine

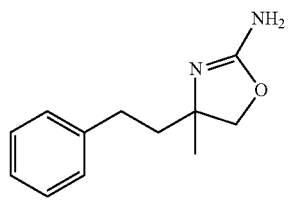

From (RS)-2-amino-2-methyl-4-phenyl-butyric acid. Off-white solid.
MS (ISP): 205.1 ([M+H]$^+$)

Example 79

(S)-4-(2-Phenyl-propyl)-4,5-dihydro-oxazol-2-ylamine

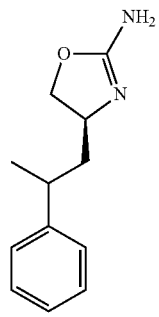

a) (S)-2,2-dimethyl-4-((E)-2-phenyl-propenyl)-oxazolidine-3-carboxylic acid tert-butyl ester A solution of diethyl 1-phenylethyl phosphonate (2.35 ml) in 1,2-dimethoxyethane (15 ml) was cooled under an argon atmosphere to 0° C. and treated dropwise with an n-butyl-lithium solution (5.9 ml; 1.6 M in hexane). The reaction mixture was stirred for 5 min at 0° C., then treated dropwise with a solution of (R)-4-formyl-2,2-dimethyl-oxazolidine-3-carboxylic acid tert-butyl ester (1.5 g) in 1,2-dimethoxyethane (15 ml). The solution was warmed to r.t., then refluxed overnight. After cooling to r.t., the mixture was quenched with water and extracted with EtOAc. The organic layer was dried over MgSO$_4$, filtrated and concentrated. The crude product was isolated by column chromatography (SiO$_2$; gradient: cyclohexane ->cyclohexane/EtOAc 1:1) to give (S)-2,2-dimethyl-4-((E)-2-phenyl-propenyl)-oxazolidine-3-carboxylic acid tert-butyl ester (720 mg) as light yellow viscous oil.
MS (ISP): 318.3 ([M+H]$^+$)

b) (S)-2-amino-4-phenyl-pentan-1-ol

A solution of (S)-2,2-dimethyl-4-((E)-2-phenyl-propenyl)-oxazolidine-3-carboxylic acid tert-butyl ester (700 mg) in EtOH (30 ml) and CHCl$_3$ (15 ml) was treated with 10% Pd/C (200 mg) and hydrogenated with a balloon overnight. The catalyst was filtered off, washed with EtOH and concentrated. The residue was dissolved in EtOH (10 ml) and treated with 2N HCl (15 ml). The mixture was heated for 90 min to 100° C., then concentrated. The residue was taken up in 1N NaOH and extracted with CH$_2$Cl$_2$/MeOH 4:1. The organic layer was dried over MgSO$_4$, filtrated and concentrated. The crude product was purified by column chromatography (SiO$_2$; gradient: CH$_2$Cl$_2$->CH$_2$Cl$_2$/MeOH 9:1) to give (S)-2-amino-4-phenyl-pentan-1-ol (342 mg) as off-white waxy solid.
MS (ISP): 180.3 ([M+H]$^+$))

c) (S)-4-(2-Phenyl-propyl)-4,5-dihydro-oxazol-2-ylamine

In analogy to example 1b (S)-2-amino-4-phenyl-pentan-1-ol was reacted with cyanogen bromide to give (S)-4-(2-phenyl-propyl)-4,5-dihydro-oxazol-2-ylamine. Off-white waxy solid.
MS (ISP): 205.1 ([M+H]$^+$))

Example 80

(S)-4-Phenethyl-4,5-dihydro-oxazol-2-ylamine and (R)-4-phenethyl-4,5-dihydro-oxazol-2-ylamine

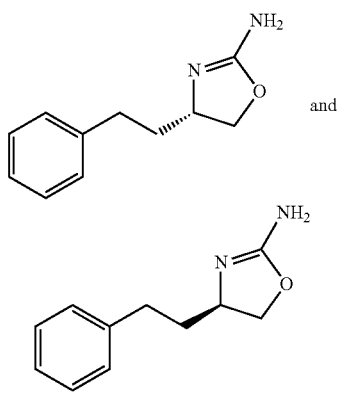

(RS)-4-Phenethyl-4,5-dihydro-oxazol-2-ylamine was separated by chiral HPLC (Chiralpak AD, EtOH/heptane=15:85) to yield (S)-4-phenethyl-4,5-dihydro-oxazol-2-ylamine (off-white solid; MS (ISP): 191.3 ([M+H]$^+$)) and (R)-4-phenethyl-4,5-dihydro-oxazol-2-ylamine (off-white solid; MS (ISP): 191.3 ([M+H]$^+$))

Example 81

(S)-4-Methyl-4-phenethyl-4,5-dihydro-oxazol-2-ylamine and (R)-4-methyl-4-phenethyl-4,5-dihydro-oxazol-2-ylamine

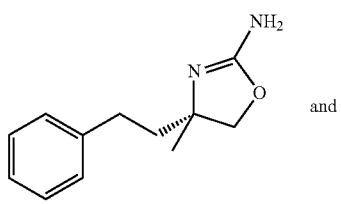

-continued

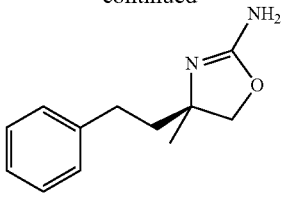

(RS)-4-Methyl-4-phenethyl-4,5-dihydro-oxazol-2-ylamine (example 75) was separated by chiral HPLC (Chiralpak AD, EtOH/heptane=10:90) to yield (S)-4-methyl-4-phenethyl-4,5-dihydro-oxazol-2-ylamine (off-white solid; MS (ISP): 205.3 ([M+H]$^+$)) and (R)-4-methyl-4-phenethyl-4,5-dihydro-oxazol-2-ylamine (off-white solid; MS (ISP): 205.1 ([M+H]$^+$))

Example 82

(S)-4-((R)-2-Phenyl-propyl)-4,5-dihydro-oxazol-2-ylamine and (S)-4-((S)-2-phenyl-propyl)-4,5-dihydro-oxazol-2-ylamine

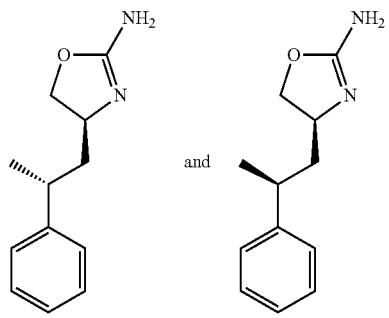

(S)-4-(2-Phenyl-propyl)-4,5-dihydro-oxazol-2-ylamine (example 79.c) was separated by chiral HPLC (Chiralpak AD, EtOH/heptane=15:85) to yield (S)-4-((R)-2-phenyl-propyl)-4,5-dihydro-oxazol-2-ylamine (off-white solid; MS (ISP): 205.1 ([M+H]$^+$)) and (R)-4-((S)-2-phenyl-propyl)-4,5-dihydro-oxazol-2-ylamine (off-white solid; MS (ISP): 205.3 ([M+H]$^+$))

Example 83

(R)-4-[2-(4-Fluoro-phenyl)-ethyl]-4,5-dihydro-oxazol-2-ylamine

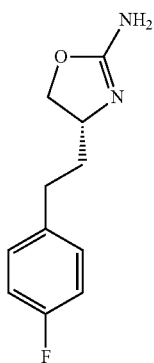 [SMILES: NC1=N[C@H](CCc2ccc(F)cc2)CO1]

a) (S)-4-(Benzothiazol-2-ylsulfanyl-methyl)-2,2-dimethyl-oxazolidine-3-carboxylic acid tert-butyl ester To a stirred, cooled (0° C.) solution of (R)-4-hydroxymethyl-2,2-dimethyl-oxazolidine-3-carboxylic acid tert-butyl ester (1.36 g; CAS 108149-65-1), 2-mercaptobenzothiazole (1.48 g) and triphenylphosphine (2.32 g) in THF (80 ml) under an argon atmosphere was added diethyl azodicarboxylate (4.1 ml; 40% solution in toluene). The mixture (soon turning to a yellow suspension, slowly warming up to r.t.) was stirred for 18 h overnight, then diluted with EtOAc and washed with sat. aq. Na$_2$CO$_3$. The aqueous phase was back extracted with EtOAc. The combined organics were washed with brine, dried over MgSO$_4$, filtered and concentrated. The crude product was purified by column chromatography (SiO$_2$; gradient: cyclohexane ->cyclohexane/EtOAc 85:15) to give (S)-4-(benzothiazol-2-ylsulfanyl-methyl)-2,2-dimethyl-oxazolidine-3-carboxylic acid tert-butyl ester (2.0 g) as light yellow viscous oil.

b) (S)-4-(Benzothiazole-2-sulfonylmethyl)-2,2-dimethyl-oxazolidine-3-carboxylic acid tert-butyl ester To a stirred solution of (S)-4-(benzothiazol-2-ylsulfanyl-methyl)-2,2-dimethyl-oxazolidine-3-carboxylic acid tert-butyl ester (2.0 g) at 0° C. in dichloromethane (80 ml) under an argon atmosphere was added 3-chloroperbenzoic acid (2.29 g) in one portion. The mixture (slowly warming up to r.t.) was stirred overnight. The mixture was washed with 10% aq. sodium bisulfite (80 ml), sat. aq. Na$_2$CO$_3$ and brine, dried over MgSO$_4$, filtered and concentrated. The crude product was isolated by column chromatography (SiO$_2$; gradient: cyclohexane ->cyclohexane/EtOAc 3:2) to give (S)-4-(benzothiazole-2-sulfonylmethyl)-2,2-dimethyl-oxazolidine-3-carboxylic acid tert-butyl ester (1.64 g) as white solid. MS (ISP): 413.3 ([M+H]$^+$))

c) ((R)-4-[(E)-2-(4-Fluoro-phenyl)-vinyl]-2,2-dimethyl-oxazolidine-3-carboxylic acid tert-butyl ester To a stirred, cooled (−78° C.) solution of (S)-4-(benzothiazole-2-sulfonylmethyl)-2,2-dimethyl-oxazolidine-3-carboxylic acid tert-butyl ester (0.484 mg) in THF (12 ml) under an argon atmosphere was added slowly a 1 M solution of LiHMDS in THF (1.1 ml). The mixture was warmed to −40° C. and stirring at that temperature was continued for 30 min. The mixture was cooled again to −78° C. and a solution of 4-fluorobenzaldehyde (0.112 g) in THF (3 ml) was then added slowly via a syringe. Stirring at −78° C. was continued for 2 h, and then the reaction mixture was slowly allowed to warm to 0° C. The mixture was quenched by the addition of sat. aq. NH$_4$Cl (15 ml) and H$_2$O (15 ml) and extracted with EtOAc. The aqueous phase was back extracted with EtOAc. The combined organics were washed with brine, dried over MgSO$_4$, filtered and concentrated. The crude product was purified by column chromatography (SiO$_2$; gradient: cyclohexane ->cyclohexane/EtOAc 85:15) to give (R)-4-[(E)-2-(4-fluoro-phenyl)-vinyl]-2,2-dimethyl-oxazolidine-3-carboxylic acid tert-butyl ester (0.201 g) as colorless viscous oil. MS (ISP): 322.4 ([M+H]$^+$))

d) (R)-4-[2-(4-Fluoro-phenyl)-ethyl]-2,2-dimethyl-oxazolidine-3-carboxylic acid tert-butyl ester To a stirred solution of (R)-4-[(E)-2-(4-fluoro-phenyl)-vinyl]-2,2-dimethyl-oxazolidine-3-carboxylic acid tert-butyl ester (0.205 g) at r.t. in ethanol (5 ml) under an argon atmosphere was added 10% Pd/C (20 mg). The mixture was stirred at r.t. under a hydrogen atmosphere for 3 hrs. The catalyst was filtered off and the filtrate was concentrated to give (R)-4-[2-(4-fluoro-phenyl)-ethyl]-2,2-dimethyl-oxazolidine-3-carboxylic acid tert-butyl ester (0.195 g) as light brown viscous oil. MS (ISP): 324.5 ([M+H]$^+$))

e) (R)-2-Amino-4-(4-fluoro-phenyl)-butan-1-ol

To a stirred solution of (R)-4-[2-(4-fluoro-phenyl)-ethyl]-2,2-dimethyl-oxazolidine-3-carboxylic acid tert-butyl ester (190 mg) at r.t. in dioxane (3.5 ml) under an argon atmosphere was added 4 M HCl solution in dioxane (1.47 ml). The mixture was stirred for 16 h. The mixture was concentrated. The crude product was purified by column (SiO₂; gradient: CH₂Cl₂->CH₂Cl₂/MeOH 9:1) to give (R)-2-amino-4-(4-fluoro-phenyl)-butan-1-ol (78 mg) as off-white solid. MS (ISP): 184.1 ([M+H]⁺))

f) (R)-4-[2-(4-Fluoro-phenyl)-ethyl]-4,5-dihydro-oxazol-2-ylamine

In analogy to example 1b (R)-2-amino-4-(4-fluoro-phenyl)-butan-1-ol was reacted with cyanogen bromide to give (R)-4-[2-(4-fluoro-phenyl)-ethyl]-4,5-dihydro-oxazol-2-ylamine. White solid. MS (ISP): 209.3 ([M+H]⁺))

In analogy to example 1 and starting from the respective amino acid or amino acid derivative was prepared:

Example 84

(RS)-4-(1,2,3,4-Tetrahydro-naphthalen-2-yl)-4,5-dihydro-oxazol-2-ylamine

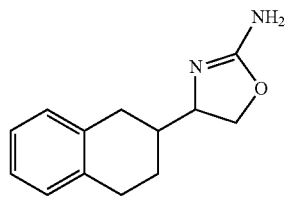 [SMILES: NC1=NC(C2CCc3ccccc3C2)CO1]

From (RS)-amino-(1,2,3,4-tetrahydro-naphthalen-2-yl)-acetic acid. Off-white solid.

MS (ISP): 217.3 ([M+H]⁺)

In analogy to example 83, starting from (S)-4-hydroxymethyl-2,2-dimethyl-oxazolidine-3-carboxylic acid tert-butyl ester and using the respective benzaldehyde were prepared:

Example 85

(S)-4-[2-(4-Fluoro-phenyl)-ethyl]-4,5-dihydro-oxazol-2-ylamine

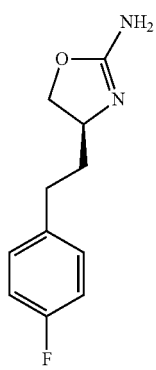

From 4-fluorobenzaldehyde. White solid. MS (ISP): 209.3 ([M+H]⁺)

Example 86

(S)-4-[2-(4-Fluoro-3-methoxy-phenyl)-ethyl]-4,5-dihydro-oxazol-2-ylamine

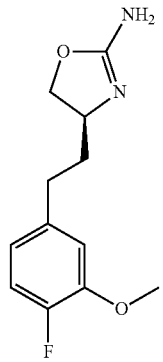 [SMILES: COc1cc(CC[C@H]2COC(N)=N2)ccc1F]

From 4-fluoro-3-methoxybenzaldehyde. Off-white solid. MS (ISP): 239.3 ([M+H]⁺)

Example 87

(R)-4-Phenoxymethyl-4,5-dihydro-oxazol-2-ylamine

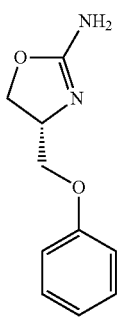 [SMILES: NC1=N[C@H](COc2ccccc2)CO1]

a) (R)-2,2-Dimethyl-4-phenoxymethyl-oxazolidine-3-carboxylic acid tert-butyl ester To a stirred solution of tert-butyl (R)-4-(hydroxymethyl)-2,2-dimethyl-3-oxazolidinecarboxylate (400 mg; CAS 108149-63-9) in THF (20 ml) were added phenol (197 mg), triphenylphosphine (573 mg) and di-tert-butyl azodicarboxylate (488 mg). The resulting yellow solution was stirred at 70° C. for 18 h overnight, then concentrated in vacuo. The crude product was purified by column chromatography (SiO₂; gradient: heptane/EtOAc 100:0->70:30) to give (R)-2,2-dimethyl-4-phenoxymethyl-oxazolidine-3-carboxylic acid tert-butyl ester (336 mg, 63%) as a colourless viscous oil. MS (ISP): 308.3 ([M+H]⁺)).

b) (S)-2-Amino-3-phenoxy-propan-1-ol

To a stirred solution of (R)-2,2-dimethyl-4-phenoxymethyl-oxazolidine-3-carboxylic acid tert-butyl ester (300 mg) at r.t. in dioxane (5 ml) under an argon atmosphere was added 4 M HCl solution in dioxane (2.44 ml). The mixture was stirred for 16 h. The mixture was concentrated. The residue was resuspended in saturated aq sodium carbonate solution and the mixture was extracted twice with ethyl acetate. The combined organic phases were dried over sodium sulphate and concentrated in vacuo. The crude product was purified by column chromatography (SiO$_2$; gradient: CH$_2$Cl$_2$->CH$_2$Cl$_2$/MeOH 9:1) to give (S)-2-amino-3-phenoxy-propan-1-ol (108 mg, 66%) as a white solid. MS (ISP): 168.3 ([M+H]$^+$)).

c) (R)-4-Phenoxymethyl-4,5-dihydro-oxazol-2-ylamine

In analogy to example 1b (S)-2-amino-3-phenoxy-propan-1-ol was reacted with cyanogen bromide to give (R)-4-phenoxymethyl-4,5-dihydro-oxazol-2-ylamine. Colourless gum. MS (ISP): 193.1 ([M+H]$^+$))

In analogy to example 83, starting from (S)-4-hydroxymethyl-2,2-dimethyl-oxazolidine-3-carboxylic acid tert-butyl ester and using the respective benzaldehyde were prepared:

Example 88

((S)-4-[2-(2,4-Difluoro-phenyl)-ethyl]-4,5-dihydro-oxazol-2-ylamine

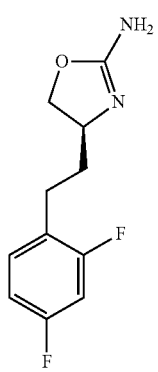

From 2,4-difluoro-benzaldehyde. Off-white solid. MS (ISP): 227.1 ([M+H]$^+$)

Example 89

(S)-4-[2-(3,4-Difluoro-phenyl)-ethyl]-4,5-dihydro-oxazol-2-ylamine

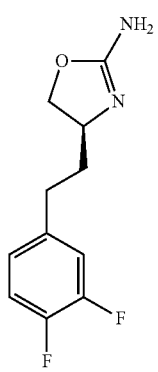

From 3,4-difluoro-benzaldehyde. Off-white solid. MS (ISP): 227.1 ([M+H]$^+$)

Example 90

(R)-4-(3,4-Dichloro-phenyl)-4,5-dihydro-oxazol-2-ylamine

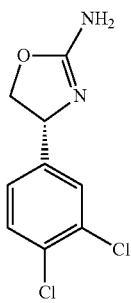 [SMILES: NC1=N[C@H](c2ccc(Cl)c(Cl)c2)CO1]

(RS)-4-(3,4-Dichloro-phenyl)-4,5-dihydro-oxazol-2-ylamine (example 14) was separated by chiral HPLC (Chiralpak AD, EtOH/heptane=20:80) to give (R)-4-(3,4-dichloro-phenyl)-4,5-dihydro-oxazol-2-ylamine. (−)-Enantiomer. Off-white solid. MS (ISP): 231.1 ([M+H]$^+$))

Example 91

(S)-4-(3,4-Dichloro-phenyl)-4,5-dihydro-oxazol-2-ylamine

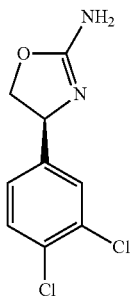 [SMILES: NC1=N[C@@H](c2ccc(Cl)c(Cl)c2)CO1]

(RS)-4-(3,4-Dichloro-phenyl)-4,5-dihydro-oxazol-2-ylamine (example 14) was separated by chiral HPLC (Chiralpak AD, EtOH/heptane=20:80) to give (S)-4-(3,4-dichloro-phenyl)-4,5-dihydro-oxazol-2-ylamine. (+)-Enantiomer. Off-white solid. MS (ISP): 231.1 ([M+H]$^+$)

Example 92

(RS)-4-(3-Cyclohexylamino-phenyl)-4,5-dihydro-oxazol-2-ylamine

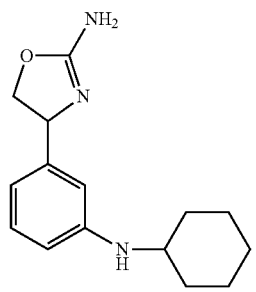 [SMILES: NC1=NC(c2cccc(NC3CCCCC3)c2)CO1]

a) (RS)-tert-Butoxycarbonylamino-(3-cyclohexylamino-phenyl)-acetic acid methyl ester A solution of (3-amino-phenyl)-tert-butoxycarbonylamino-acetic acid methyl ester (165 mg, CAS 180081-34-9) in MeOH (5 ml) was treated under an argon atmosphere with cyclohexanone (0.07 ml), zinc chloride (321 mg) and NaBH$_3$CN (111 mg) and stirred overnight at 40° C. The MeOH was distilled off. The residue was taken up in EtOAc and H$_2$O. The aqueous phase was back extracted with EtOAc. The combined organics were washed with water, dried over MgSO$_4$, filtered and concentrated. The crude product was purified by column chromatography (silica gel; gradient: cyclohexane ->cyclohexane/EtOAc 14:1) to give (RS)-tert-butoxycarbonylamino-(3-cyclohexylamino-phenyl)-acetic acid methyl ester (200 mg, 94%) as viscous colorless oil.

MS (ISP): 363.4 ([M+H]$^+$)

b) (RS)-Amino-(3-cyclohexylamino-phenyl)-acetic acid methyl ester

A solution of (RS)-tert-butoxycarbonylamino-(3-cyclohexylamino-phenyl)-acetic acid methyl ester (200 mg) in dioxane (5 ml) was treated with 4M HCl in dioxane (2.76 ml) and stirred at r.t. overnight, then concentrated. The crude product was purified by column chromatography (silica gel; gradient: CH$_2$Cl$_2$->CH$_2$Cl$_2$/MeOH 9:1) to give (RS)-amino-(3-cyclohexylamino-phenyl)-acetic acid methyl ester (126 mg, 87%) as light yellow viscous oil.

MS (ISP): 263.0 ([M+H]$^+$))

c) (RS)-2-Amino-2-(3-cyclohexylamino-phenyl)-ethanol

A solution of (RS)-amino-(3-cyclohexylamino-phenyl)-acetic acid methyl ester (120 mg) in THF (1 ml) was treated under an argon atmosphere with lithium chloride (78 mg), sodium borohydride (68 mg) and EtOH (1.8 ml) and stirred at r.t. overnight. The mixture was filtrated. The residue was washed with EtOH. The filtrate was concentrated. The residue was taken up in CH$_2$Cl$_2$. The solids were removed by filtration. The filtrate was concentrated. The crude product was isolated by column chromatography (silica gel; gradient: CH$_2$Cl$_2$->CH$_2$Cl$_2$/MeOH 9:1) to give (RS)-2-amino-2-(3-cyclohexylamino-phenyl)-ethanol (87 mg, 65%) as colorless viscous oil.

MS (ISP): 235.3 ([M+H]$^+$))

d) (RS)-4-(3-Cyclohexylamino-phenyl)-4,5-dihydro-oxazol-2-ylamine

In analogy to example 1.b (RS)-2-amino-2-(3-cyclohexylamino-phenyl)-ethanol was converted to the title compound. Colorless viscous oil.

MS (ISP): 235.3 ([M+H]$^+$))

Example 93

(R)-4-[2-(3,5-Difluoro-phenyl)-ethyl]-4,5-dihydro-oxazol-2-ylamine

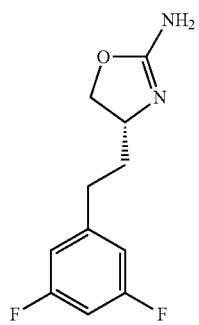 [SMILES: NC1=N[C@H](CCc2cc(F)cc(F)c2)CO1]

In analogy to example 83, the title compound was prepared starting from (R)-4-hydroxymethyl-2,2-dimethyl-oxazolidine-3-carboxylic acid tert-butyl ester and 3,5-difluorobenzaldehyde. Off-white solid. MS (ISP): 227.4 ([M+H]$^+$)

Example 94

(RS)-4-[3-(Tetrahydro-pyran-4-yloxy)-phenyl]-4,5-dihydro-oxazol-2-ylamine

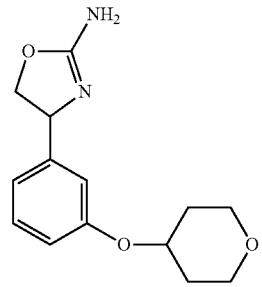 [SMILES: NC1=NC(c2cccc(OC3CCOCC3)c2)CO1]

a) (RS)-(tert-Butoxycarbonylamino-[3-(tetrahydro-pyran-4-yloxy)-phenyl]-acetic acid methyl ester A solution of (RS)-tert-butoxycarbonylamino-(3-hydroxy-phenyl)-acetic acid methyl ester (CAS 526217-60-7) in THF (10 ml) was treated under an argon atmosphere with tetrahydro-pyran-4-ol (0.24 ml), triphenylphosphine (649 mg) and di-tert-butyl azodicarboxylate (570 mg) and stirred at r.t. overnight. The reaction mixture was concentrated. The crude product was purified by column chromatography (silical gel; gradient: cyclohexane ->cyclohexane/EtOAc 1:1) to give (RS)-tert-butoxycarbonylamino-[3-(tetrahydro-pyran-4-yloxy)-phenyl]-acetic acid methyl ester (884 mg, 82%) as viscous light yellow oil.

MS (ISP): 366.3 ([M+H]$^+$)

b) (RS)-4-[3-(Tetrahydro-pyran-4-yloxy)-phenyl]-4,5-dihydro-oxazol-2-ylamine

In analogy to examples 92.b, 1.a and 92.d, (RS)-tert-butoxycarbonylamino-[3-(tetrahydro-pyran-4-yloxy)-phenyl]-acetic acid methyl ester was converted to the title compound. Light yellow solid.

MS (ISP): 263.0 ([M+H]$^+$))

In analogy to example 87 were prepared:

Example 95

(R)-4-(4-Chloro-phenoxymethyl)-4,5-dihydro-oxazol-2-ylamine

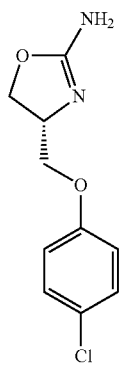 [SMILES: NC1=N[C@H](COc2ccc(Cl)cc2)CO1]

From tert-butyl (R)-4-(hydroxymethyl)-2,2-dimethyl-3-oxazolidinecarboxylate and 4-chlorophenol. White solid.

MS (ISP): 229.2 ([{$^{37}$Cl}M+H]$^+$), 227.2 ([{$^{35}$Cl}M+H]$^+$).

Example 96

(R)-4-(4-Trifluoromethyl-phenoxymethyl)-4,5-dihydro-oxazol-2-ylamine

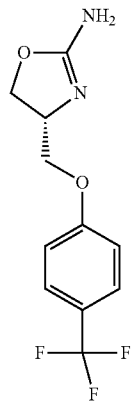 [SMILES: NC1=N[C@H](COc2ccc(C(F)(F)F)cc2)CO1]

From tert-butyl (R)-4-(hydroxymethyl)-2,2-dimethyl-3-oxazolidinecarboxylate and 4-(trifluoromethyl)-phenol. White solid.
MS (ISP): 261.0 ([M+H]$^+$).

Example 97

(R)-4-(4-Fluoro-phenoxymethyl)-4,5-dihydro-oxazol-2-ylamine

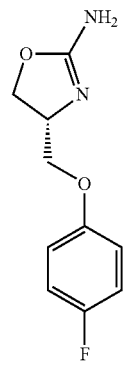

From tert-butyl (R)-4-(hydroxymethyl)-2,2-dimethyl-3-oxazolidinecarboxylate and 4-fluorophenol. White solid.
MS (ISP): 211.1 ([M+H]$^+$).

Example 98

(R)-4-(4-Bromo-phenoxymethyl)-4,5-dihydro-oxazol-2-ylamine

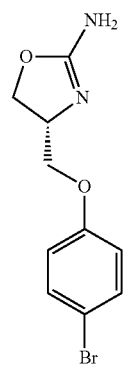

From tert-butyl (R)-4-(hydroxymethyl)-2,2-dimethyl-3-oxazolidinecarboxylate and 4-bromophenol. White solid.
MS (ISP): 273.0 ([{$^{81}$Br}M+H]$^+$), 271.0 ([{$^{79}$Br}M+H]$^+$).

Example 99

(RS)-4-[4-(2-Methoxy-ethoxy)-phenyl]-4,5-dihydro-oxazol-2-ylamine

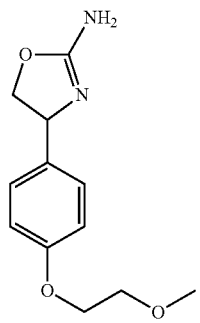 [SMILES: COCCOc1ccc(C2COC(N)=N2)cc1]

a) (RS)-tert-Butoxycarbonylamino-[4-(2-methoxy-ethoxy)-phenyl]-acetic acid methyl ester A solution of (RS)-tert-butoxycarbonylamino-(4-hydroxy-phenyl)-acetic acid methyl ester (500 mg, CAS 143323-49-3) in DMF (4 ml) was treated under an argon atmosphere with 2-bromoethyl methyl ether (0.34 ml), cesium carbonate (695 mg) and tetrabutylammonium iodide (66 mg) and stirred at r.t. overnight. Then it was quenched with H$_2$O and extracted with EtOAc. The organics were washed with water, dried over MgSO$_4$, filtrated and concentrated. The crude product was purified by column chromatography (silica gel; gradient: cyclohexane ->cyclohexane/EtOAc 4:1) to give (RS)-tert-butoxycarbonylamino-[4-(2-methoxy-ethoxy)-phenyl]-acetic acid methyl ester (434 mg, 72%) as viscous colorless oil.
MS (ISP): 340.4 ([M+H]$^+$)

b) (RS)-4-[4-(2-Methoxy-ethoxy)-phenyl]-4,5-dihydro-oxazol-2-ylamine

In analogy to examples 92.b, 1.a and 92.d, (RS)-tert-butoxycarbonylamino-[4-(2-methoxy-ethoxy)-phenyl]-acetic acid methyl ester was converted to the title compound. White solid.
MS (ISP): 237.1 ([M+H]$^+$))

Example 100

(R)-4-(2,5-Difluoro-phenyl)-4,5-dihydro-oxazol-2-ylamine

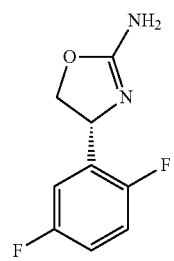

(RS)-4-(2,5-Difluoro-phenyl)-4,5-dihydro-oxazol-2-ylamine (example 16) was separated by chiral HPLC (Chiralpak AD, EtOH/heptane=15:85) to give (R)-4-(2,5-difluoro-phenyl)-4,5-dihydro-oxazol-2-ylamine. (−)-Enantiomer. Light yellow solid.
MS (ISP): 199.1 ([M+H]⁺))

Example 101

(S)-4-(2,5-Difluoro-phenyl)-4,5-dihydro-oxazol-2-ylamine

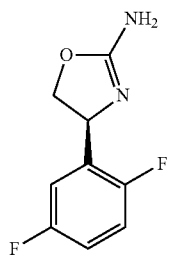 [SMILES: NC1=N[C@@H](c2cc(F)ccc2F)CO1]

(RS)-4-(2,5-Difluoro-phenyl)-4,5-dihydro-oxazol-2-ylamine (example 16) was separated by chiral HPLC (Chiralpak AD, EtOH/heptane=15:85) to give (S)-4-(2,5-difluoro-phenyl)-4,5-dihydro-oxazol-2-ylamine. (+)-Enantiomer. Light yellow solid. MS (ISP): 199.1 ([M+H]⁺))

Example 102

(R)-4-Naphthalen-2-yl-4,5-dihydro-oxazol-2-ylamine

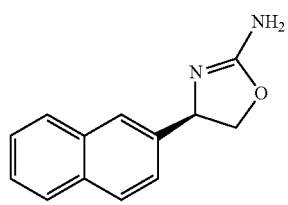 [SMILES: NC1=N[C@H](c2ccc3ccccc3c2)CO1]

(RS)-4-Naphthalen-2-yl-4,5-dihydro-oxazol-2-ylamine (example 33) was separated by chiral HPLC (Chiralpak AD, EtOH/heptane=20:80) to give (R)-4-naphthalen-2-yl-4,5-dihydro-oxazol-2-ylamine. (+)-Enantiomer. Off-white solid. MS (ISP): 213.3 ([M+H]⁺))

Example 103

(S)-4-Naphthalen-2-yl-4,5-dihydro-oxazol-2-ylamine

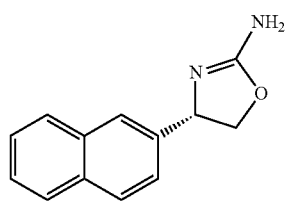 [SMILES: NC1=N[C@@H](c2ccc3ccccc3c2)CO1]

(RS)-4-Naphthalen-2-yl-4,5-dihydro-oxazol-2-ylamine (example 33) was separated by chiral HPLC (Chiralpak AD, EtOH/heptane=20:80) to give (S)-4-naphthalen-2-yl-4,5-dihydro-oxazol-2-ylamine. (−)-Enantiomer. Off-white solid.
MS (ISP): 213.3 ([M+H]⁺))

Example 104

(R)-4-(4-Bromo-phenyl)-4,5-dihydro-oxazol-2-ylamine

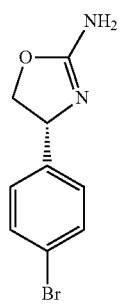 [SMILES: NC1=N[C@H](c2ccc(Br)cc2)CO1]

(RS)-4-(4-Bromo-phenyl)-4,5-dihydro-oxazol-2-ylamine (example 20) was separated by chiral HPLC (Chiralpak AD, EtOH/heptane=20:80) to give (R)-4-(4-bromo-phenyl)-4,5-dihydro-oxazol-2-ylamine. (−)-Enantiomer. Off-white solid.
MS (ISP): 241.1 ([M+H]⁺))

Example 105

(S)-4-(4-Bromo-phenyl)-4,5-dihydro-oxazol-2-ylamine

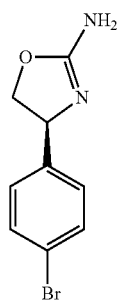 [SMILES: NC1=N[C@@H](c2ccc(Br)cc2)CO1]

(RS)-4-(4-Bromo-phenyl)-4,5-dihydro-oxazol-2-ylamine (example 20) was separated by chiral HPLC (Chiralpak AD, EtOH/heptane=20:80) to give (S)-4-(4-bromo-phenyl)-4,5-dihydro-oxazol-2-ylamine. (+)-Enantiomer. Off-white solid.
MS (ISP): 241.1 ([M+H]⁺))

Example 106

(R)-4-(2,4,5-Trifluoro-phenyl)-4,5-dihydro-oxazol-2-ylamine

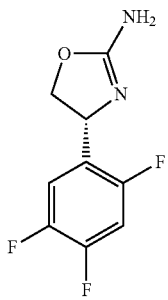 [SMILES: NC1=N[C@H](c2cc(F)c(F)cc2F)CO1]

a) (RS)-4-(2,4,5-Trifluoro-phenyl)-4,5-dihydro-oxazol-2-ylamine

In analogy to example 1, the title compound was obtained from 2,4,5-trifluoro-DL-phenylglycine. Off-white solid.
MS (ISP): 217.1 ([M+H]$^+$)

b) ((R)-4-(2,4,5-Trifluoro-phenyl)-4,5-dihydro-oxazol-2-ylamine (RS)-4-(2,4,5-Trifluoro-phenyl)-4,5-dihydro-oxazol-2-ylamine (example 20) was separated by chiral HPLC (Chiralpak AD, isopropanol/heptane=10:90) to give (R)-4-(2,4,5-trifluoro-phenyl)-4,5-dihydro-oxazol-2-ylamine. (−)-Enantiomer. White solid.
MS (ISP): 217.1 ([M+H]$^+$))

Example 107

(S)-4-(2,4,5-Trifluoro-phenyl)-4,5-dihydro-oxazol-2-ylamine

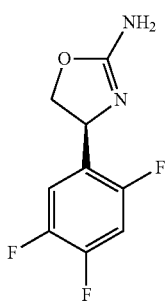 [SMILES: NC1=N[C@@H](c2cc(F)c(F)cc2F)CO1]

(RS)-4-(2,4,5-Trifluoro-phenyl)-4,5-dihydro-oxazol-2-ylamine (example 106) was separated by chiral HPLC (Chiralpak AD, isopropanol/heptane=10:90) to give (S)-4-(2,4,5-trifluoro-phenyl)-4,5-dihydro-oxazol-2-ylamine. (+)-Enantiomer. White solid.
MS (ISP): 217.4 ([M+H]$^+$))

Example 108

(R)-4-(3-Chloro-2-fluoro-phenyl)-4,5-dihydro-oxazol-2-ylamine

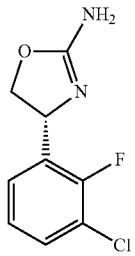 [SMILES: NC1=N[C@H](c2cccc(Cl)c2F)CO1]

(RS)-4-(3-Chloro-2-fluoro-phenyl)-4,5-dihydro-oxazol-2-ylamine (example 18) was separated by chiral HPLC (Chiralpak AD, isopropanol/heptane=1:9) to give (R)-4-(3-chloro-2-fluoro-phenyl)-4,5-dihydro-oxazol-2-ylamine. (−)-Enantiomer. Off-white solid.
MS (ISP): 215.3 ([M+H]$^+$))

Example 109

(S)-4-(3-Chloro-2-fluoro-phenyl)-4,5-dihydro-oxazol-2-ylamine

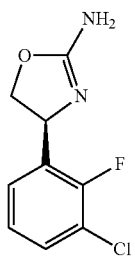 [SMILES: NC1=N[C@@H](c2cccc(Cl)c2F)CO1]

(RS)-4-(3-Chloro-2-fluoro-phenyl)-4,5-dihydro-oxazol-2-ylamine (example 18) was separated by chiral HPLC (Chiralpak AD, isopropanol/heptane=1:9) to give (S)-4-(3-chloro-2-fluoro-phenyl)-4,5-dihydro-oxazol-2-ylamine. (+)-Enantiomer. Off-white solid.
MS (ISP): 215.1 ([M+H]$^+$))

In analogy to example 83, starting from (S)-4-hydroxymethyl-2,2-dimethyl-oxazolidine-3-carboxylic acid tert-butyl ester and using the respective benzaldehyde were prepared:

Example 110

(S)-4-[2-(2-Trifluoromethyl-phenyl)-ethyl]-4,5-dihydro-oxazol-2-ylamine

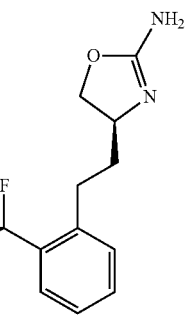

From 2-trifluoromethylbenzaldehyde. White solid. MS (ISP): 259.0 ([M+H]$^+$)

Example 111

(S)-4-[2-(2-Fluoro-phenyl)-ethyl]-4,5-dihydro-oxazol-2-ylamine

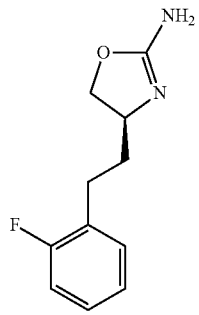 [SMILES: NC1=N[C@@H](CCc2ccccc2F)CO1]

From 2-fluorobenzaldehyde. White solid. MS (ISP): 209.3 ([M+H]$^+$)

Example 112

(S)-4-[2-(3-Fluoro-phenyl)-ethyl]-4,5-dihydro-oxazol-2-ylamine

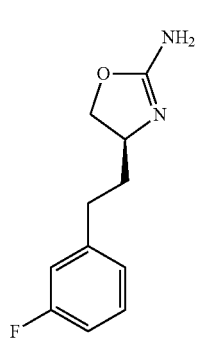 [SMILES: NC1=N[C@@H](CCc2cccc(F)c2)CO1]

From 3-fluorobenzaldehyde. White solid. MS (ISP): 209.1 ([M+H]$^+$)

Example 113

(S)-4-[2-(3,5-Difluoro-phenyl)-ethyl]-4,5-dihydro-oxazol-2-ylamine

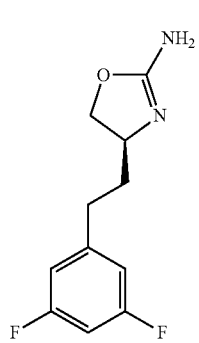 [SMILES: NC1=N[C@@H](CCc2cc(F)cc(F)c2)CO1]

From 3,5-difluorobenzaldehyde. White solid. MS (ISP): 227.1 ([M+H]$^+$)

Example 114

(S)-4-(2-o-Tolyl-ethyl)-4,5-dihydro-oxazol-2-ylamine

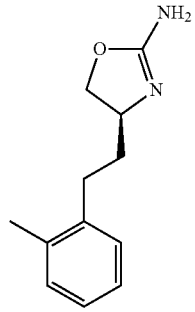

From o-tolylaldehyde. Off-white solid. MS (ISP): 205.3 ([M+H]$^+$)

Example 115

(S)-4-(2-m-Tolyl-ethyl)-4,5-dihydro-oxazol-2-ylamine

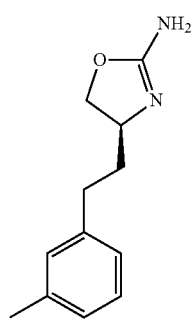

From m-tolylaldehyde. Off-white solid. MS (ISP): 205.3 ([M+H]$^+$)

Example 116

(S)-4-(2-p-Tolyl-ethyl)-4,5-dihydro-oxazol-2-ylamine

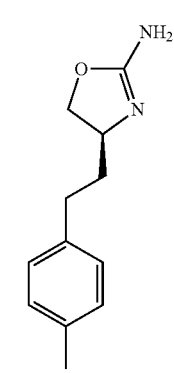

From p-tolylaldehyde. Off-white solid. MS (ISP): 205.3 ([M+H]$^+$)

Example 117

(R)-4-(2,3,5-Trifluoro-phenyl)-4,5-dihydro-oxazol-2-ylamine

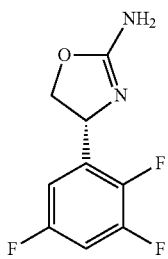 [SMILES: NC1=N[C@H](c2cc(F)cc(F)c2F)CO1]

(RS)-4-(2,3,5-Trifluoro-phenyl)-4,5-dihydro-oxazol-2-ylamine (example 40) was separated by chiral HPLC (Chiralpak AD, isopropanol/heptane=10:90) to give (R)-4-(2,3,5-trifluoro-phenyl)-4,5-dihydro-oxazol-2-ylamine. (−)-Enantiomer. Off-white solid.
MS (ISP): 217.4 ([M+H]$^+$))

Example 118

(S)-4-(2,3,5-Trifluoro-phenyl)-4,5-dihydro-oxazol-2-ylamine

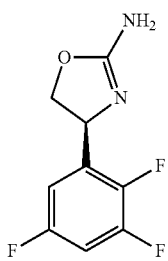 [SMILES: NC1=N[C@@H](c2cc(F)cc(F)c2F)CO1]

(RS)-4-(2,3,5-Trifluoro-phenyl)-4,5-dihydro-oxazol-2-ylamine (example 40) was separated by chiral HPLC (Chiralpak AD, isopropanol/heptane=10:90) to give (S)-4-(2,3,5-trifluoro-phenyl)-4,5-dihydro-oxazol-2-ylamine. (+)-Enantiomer. Off-white solid.
MS (ISP): 217.4 ([M+H]$^+$))

In analogy to example 83, starting from (S)-4-hydroxymethyl-2,2-dimethyl-oxazolidine-3-carboxylic acid tert-butyl ester and using the respective benzaldehyde were prepared:

Example 119

(S)-4-[2-(4-Trifluoromethyl-phenyl)-ethyl]-4,5-dihydro-oxazol-2-ylamine

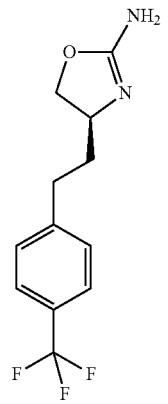 [SMILES: NC1=N[C@@H](CCc2ccc(C(F)(F)F)cc2)CO1]

From 4-trifluoromethylbenzaldehyde. Off-white solid. MS (ISP): 259.1 ([M+H]$^+$)

Example 120

(S)-4-[2-(3-Trifluoromethyl-phenyl)-ethyl]-4,5-dihydro-oxazol-2-ylamine

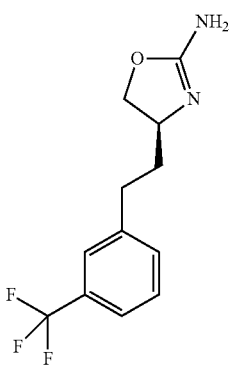 [SMILES: NC1=N[C@@H](CCc2cccc(C(F)(F)F)c2)CO1]

From 3-trifluoromethylbenzaldehyde. White solid. MS (ISP): 259.1 ([M+H]$^+$)

Example 121

(R)-4-(2-Trifluoromethyl-phenyl)-4,5-dihydro-oxazol-2-ylamine

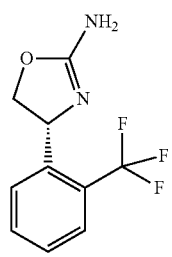 [SMILES: NC1=N[C@H](c2ccccc2C(F)(F)F)CO1]

(RS)-4-(2-Trifluoromethyl-phenyl)-4,5-dihydro-oxazol-2-ylamine (example 40) was separated by chiral HPLC (Chiralpak AD, isopropanol/heptane=5:95) to give (R)-4-(2-trifluoromethyl-phenyl)-4,5-dihydro-oxazol-2-ylamine. (−)-Enantiomer. Off-white solid.
MS (ISP): 231.4 ([M+H]$^+$))

Example 122

(S)-4-(2-Trifluoromethyl-phenyl)-4,5-dihydro-oxazol-2-ylamine

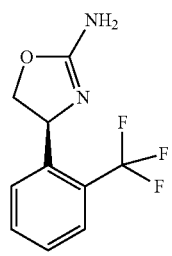 [SMILES: NC1=N[C@@H](c2ccccc2C(F)(F)F)CO1]

(RS)-4-(2-Trifluoromethyl-phenyl)-4,5-dihydro-oxazol-2-ylamine (example 40) was separated by chiral HPLC (Chiralpak AD, isopropanol/heptane=5:95) to give (S)-4-(2-trifluoromethyl-phenyl)-4,5-dihydro-oxazol-2-ylamine. (+)-Enantiomer. Off-white solid.

MS (ISP): 231.4 ([M+H]+))

In analogy to example 87 was prepared:

Example 123

(R)-4-p-Tolyloxymethyl-4,5-dihydro-oxazol-2-ylamine

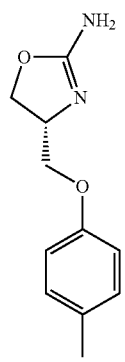

From tert-butyl (R)-4-(hydroxymethyl)-2,2-dimethyl-3-oxazolidinecarboxylate and 4-methylphenol. White solid.

MS (ISP): 207.1 ([M+H]+).

In analogy to example 83, starting from the respective benzaldehyde was prepared:

Example 124

(R)-4-[2-(3,4-Dichloro-phenyl)-ethyl]-4,5-dihydro-oxazol-2-ylamine

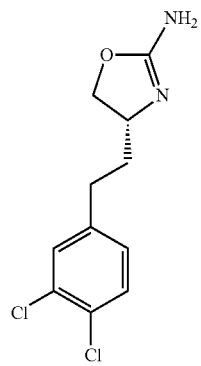 [SMILES: NC1=N[C@H](CCc2ccc(Cl)c(Cl)c2)CO1]

From 3,4-dichlorobenzaldehyde. Colorless gum. MS (ISP): 259.0 ([M+H]+) In analogy to example 1 and starting from the respective amino acid were prepared:

Example 125

(S)-4-Biphenyl-4-ylmethyl-4,5-dihydro-oxazol-2-ylamine

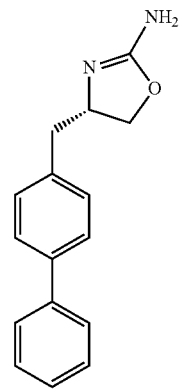 [SMILES: NC1=N[C@@H](Cc2ccc(-c3ccccc3)cc2)CO1]

From (S)-2-amino-3-phenyl-propionic acid. Off-white solid. MS (ISP): 253.1 ([M+H]+)

Example 126

(S)-4-(4-Fluoro-phenyl)-4-methyl-4,5-dihydro-oxazol-2-ylamine

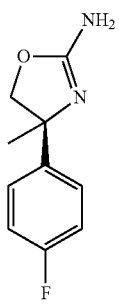

a) ((RS)-4-(4-Fluoro-phenyl)-4-methyl-4,5-dihydro-oxazol-2-ylamine

In analogy to example 1, the title compound was obtained from 2-(4-fluorophenyl)alanine. White solid.

MS (ISP): 195.3 ([M+H]+)

b) (S)-4-(4-Fluoro-phenyl)-4-methyl-4,5-dihydro-oxazol-2-ylamine (RS)-4-(4-Fluoro-phenyl)-4-methyl-4,5-dihydro-oxazol-2-ylamine was separated by chiral HPLC (Chiralpak AD, EtOH/heptane 2:8) to give (S)-4-(4-fluoro-phenyl)-4-methyl-4,5-dihydro-oxazol-2-ylamine. (+)-Enantiomer. Off-white solid.

MS (ISP): 195.3 ([M+H]+))

In analogy to example 83 and starting from (S)-4-hydroxymethyl-2,2-dimethyl-oxazolidine-3-carboxylic acid tert-butyl ester and the respective benzaldehyde was prepared:

Example 127

(S)-4-[2-(3,4-Dichloro-phenyl)-ethyl]-4,5-dihydro-oxazol-2-ylamine

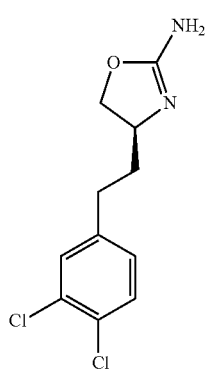 [SMILES: NC1=N[C@@H](CCc2ccc(Cl)c(Cl)c2)CO1]

From 3,4-dichlorobenzaldehyde. Viscous colorless oil. MS (ISP): 259.0 ([M+H]⁺)

Example 128

(R)-4-(4-Methoxy-3-methyl-phenyl)-4,5-dihydro-oxazol-2-ylamine

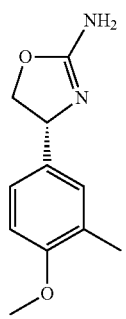

(RS)-4-(4-Methoxy-3-methyl-phenyl)-4,5-dihydro-oxazol-2-ylamine (example 35) was separated by chiral HPLC (Chiralpak AD, EtOH/heptane=20:80) to give (R)-4-(4-methoxy-3-methyl-phenyl)-4,5-dihydro-oxazol-2-ylamine. (−)-Enantiomer. Off-white solid.
MS (ISP): 206.9 ([M+H]⁺))

Example 129

(S)-4-(4-Methoxy-3-methyl-phenyl)-4,5-dihydro-oxazol-2-ylamine

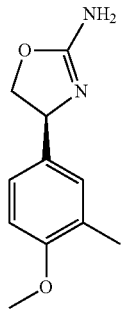

(RS)-4-(4-Methoxy-3-methyl-phenyl)-4,5-dihydro-oxazol-2-ylamine (example 35) was separated by chiral HPLC (Chiralpak AD, EtOH/heptane=20:80) to give (S)-4-(4-methoxy-3-methyl-phenyl)-4,5-dihydro-oxazol-2-ylamine. (+)-Enantiomer. Off-white solid. MS (ISP): 207.1 ([M+H]⁺))

Example 130

(R)-4-(3-Chloro-4-methoxy-phenyl)-4,5-dihydro-oxazol-2-ylamine

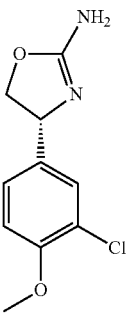

(RS)-4-(3-Chloro-4-methoxy-phenyl)-4,5-dihydro-oxazol-2-ylamine (example 36) was separated by chiral HPLC (Chiralpak AD, EtOH/heptane=20:80) to give (R)-4-(3-chloro-4-methoxy-phenyl)-4,5-dihydro-oxazol-2-ylamine. (−)-Enantiomer. Off-white solid.
MS (ISP): 227.1 ([M+H]⁺))

Example 131

(S)-4-(3-Chloro-4-methoxy-phenyl)-4,5-dihydro-oxazol-2-ylamine

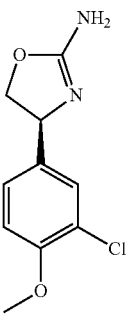

(RS)-4-(3-Chloro-4-methoxy-phenyl)-4,5-dihydro-oxazol-2-ylamine (example 36) was separated by chiral HPLC (Chiralpak AD, EtOH/heptane=20:80) to give (S)-4-(3-chloro-4-methoxy-phenyl)-4,5-dihydro-oxazol-2-ylamine. (+)-Enantiomer. Off-white solid.

MS (ISP): 227.1 ([M+H]+))

In analogy to example 83, starting from (S)-4-hydroxymethyl-2,2-dimethyl-oxazolidine-3-carboxylic acid tert-butyl ester and using the respective benzaldehyde were prepared:

Example 132

(S)-4-[2-(4-Chloro-2-fluoro-phenyl)-ethyl]-4,5-dihydro-oxazol-2-ylamine

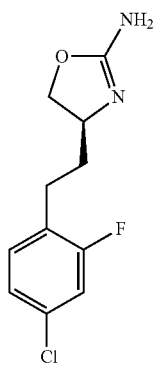 [SMILES: NC1=N[C@@H](CCc2ccc(Cl)cc2F)CO1]

From 4-chloro-2-fluorobenzaldehyde. White solid. MS (ISP): 243.3 ([M+H]+)

Example 133

(S)-4-[2-(4-Fluoro-3-trifluoromethyl-phenyl)-ethyl]-4,5-dihydro-oxazol-2-ylamine

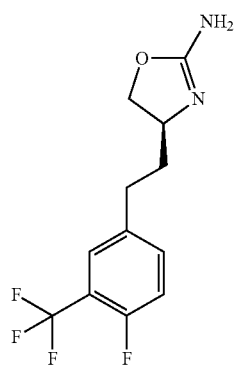 [SMILES: NC1=N[C@@H](CCc2ccc(F)c(C(F)(F)F)c2)CO1]

From 4-fluoro-3-trifluoromethyl-benzaldehyde. Off-white solid. MS (ISP): 277.0 ([M+H]+)

Example 134

(R)-4-(3,4-Dichloro-phenyl)-4-methyl-4,5-dihydro-oxazol-2-ylamine

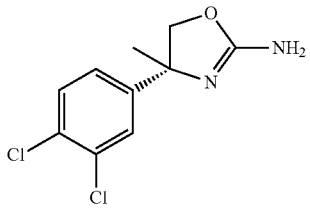

a) (RS)-2-Amino-2-(3,4-dichloro-phenyl)-propionic acid hydrochloride

A solution of 5-(3,4-dichloro-phenyl)-5-methyl-imidazolidine-2,4-dione (3.0 g; CAS 52715-57-8) in 3N NaOH (30 ml) was refluxed overnight. The reaction mixture was cooled to 0°, then brought to pH 1 by dropwise addition of concentrated HCl. The resulting white slurry was filtered. The solid was washed extensively with H$_2$O, dried in the vacuum, resuspended in EtOH (25 ml), collected by filtration, washed with EtOH and diethylether and dried in the vacuum to give (RS)-2-amino-2-(3,4-dichloro-phenyl)-propionic acid hydrochloride (1.35 g, 27%) as off white solid.

MS (ISP): 266.9 ([M+Na]+)

b) (RS)-4-(3,4-Dichloro-phenyl)-4-methyl-4,5-dihydro-oxazol-2-ylamine

In analogy to example 1 (RS)-2-amino-2-(3,4-dichlorophenyl)-propionic acid hydrochloride was converted to the title compound. Off-white solid.

MS (ISP): 244.9 ([M+H]+))

c) (R)-4-(3,4-Dichloro-phenyl)-4-methyl-4,5-dihydro-oxazol-2-ylamine ((RS)-4-(3,4-Dichloro-phenyl)-4-methyl-4,5-dihydro-oxazol-2-ylamine was separated by chiral HPLC (Chiralpak AD, EtOH/heptane=15:85) to give (R)-4-(3,4-dichloro-phenyl)-4-methyl-4,5-dihydro-oxazol-2-ylamine. (−)-Enantiomer. Off-white solid.

MS (ISP): 245.3 ([M+H]+))

Example 135

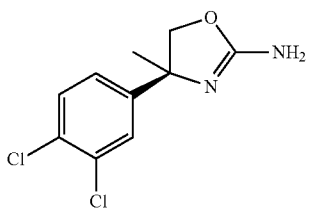

(S)-4-(3,4-Dichloro-phenyl)-4-methyl-4,5-dihydro-oxazol-2-ylamine ((RS)-4-(3,4-Dichloro-phenyl)-4-methyl-4,5-dihydro-oxazol-2-ylamine was separated by chiral HPLC (Chiralpak AD, EtOH/heptane=15:85) to give (S)-4-(3,4-dichloro-phenyl)-4-methyl-4,5-dihydro-oxazol-2-ylamine. (+)-Enantiomer. Off-white solid.

MS (ISP): 245.3 ([M+H]+))

Example 136

(S)-4-(4-Chloro-phenyl)-4-methyl-4,5-dihydro-oxazol-2-ylamine

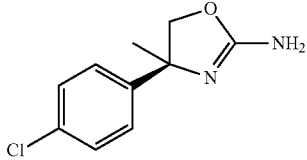

In analogy to example 126 (RS)-2-amino-2-(4-chloro-phenyl)-propionic acid was converted to (RS)-4-(4-chloro-phenyl)-4-methyl-4,5-dihydro-oxazol-2-ylamine which was subsequently separated by chiral HPLC (Chiralpak AD, EtOH/heptane 15:85) to give (S)-4-(4-chloro-phenyl)-4-methyl-4,5-dihydro-oxazol-2-ylamine. Off-white solid.
MS (ISP): 211.1 ([M+H]$^+$))

In analogy to example 83, starting from (S)-4-hydroxymethyl-2,2-dimethyl-oxazolidine-3-carboxylic acid tert-butyl ester and using the respective benzaldehyde were prepared:

Example 137

(S)-4-[2-(3-Fluoro-4-trifluoromethyl-phenyl)-ethyl]-4,5-dihydro-oxazol-2-ylamine

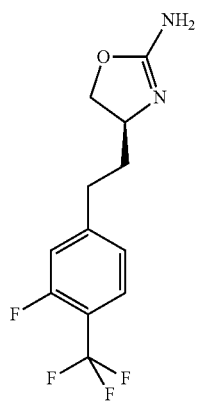 [SMILES: NC1=N[C@@H](CCc2ccc(C(F)(F)F)c(F)c2)CO1]

From 3-fluoro-4-trifluoromethyl-benzaldehyde. Off-white solid. MS (ISP): 277.0 ([M+H]$^+$)

Example 138

(S)-4-[2-(3,5-Dichloro-phenyl)-ethyl]-4,5-dihydro-oxazol-2-ylamine

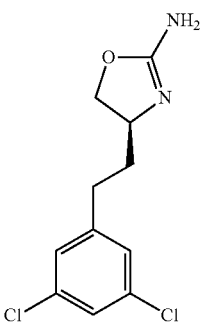 [SMILES: NC1=N[C@@H](CCc2cc(Cl)cc(Cl)c2)CO1]

From 3,5-dichloro-benzaldehyde. Light yellow solid. MS (ISP): 259.0 ([M+H]$^+$)

Example 139

(S)-4-[2-(2-Chloro-4-fluoro-phenyl)-ethyl]-4,5-dihydro-oxazol-2-ylamine

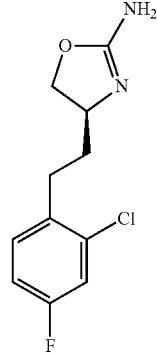

From 2-chloro-4-fluoro-benzaldehyde. Off-white solid. MS (ISP): 243.3 ([M+H]$^+$)

Example 140

(S)-4-[2-(4-Fluoro-3-methyl-phenyl)-ethyl]-4,5-dihydro-oxazol-2-ylamine

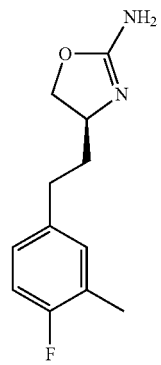 [SMILES: Cc1cc(CC[C@H]2COC(N)=N2)ccc1F]

From 4-fluoro-3-methyl-benzaldehyde. White solid. MS (ISP): 223.3 ([M+H]$^+$)

Example 141

(S)-4-{2-[3-(1,1,2,2-Tetrafluoro-ethoxy)-phenyl]-ethyl}-4,5-dihydro-oxazol-2-ylamine

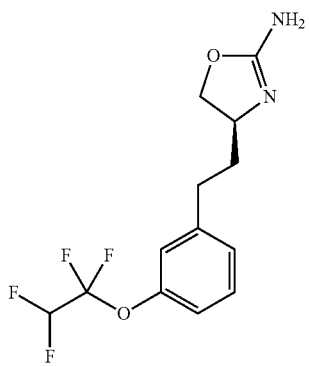 [SMILES: NC1=N[C@@H](CCc2cccc(OC(F)(F)C(F)F)c2)CO1]

From 3-(1,1,2,2-tetrafluoro-ethoxy)-benzaldehyde. Colorless oil. MS (ISP): 307.0 ([M+H]$^+$)

Example 142

(S)-4-[2-(2-Fluoro-3-trifluoromethyl-phenyl)-ethyl]-4,5-dihydro-oxazol-2-ylamine

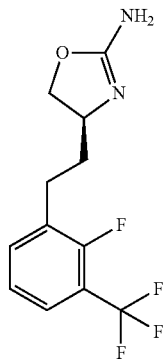 [SMILES: NC1=N[C@@H](CCc2cccc(C(F)(F)F)c2F)CO1]

From 2-fluoro-3-trifluoromethyl-benzaldehyde. Off-white solid. MS (ISP): 277.0 ([M+H]$^+$)

Example 143

(S)-4-[2-(3-Bromo-phenyl)-ethyl]-4,5-dihydro-oxazol-2-ylamine

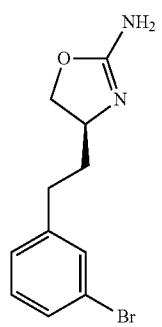

From 3-bromo-benzaldehyde. Off-white waxy solid. MS (ISP): 269.0 ([M+H]$^+$)

Example 144

(S)-4-[2-(4-Chloro-3-trifluoromethyl-phenyl)-ethyl]-4,5-dihydro-oxazol-2-ylamine

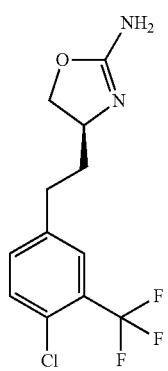 [SMILES: NC1=N[C@@H](CCc2ccc(Cl)c(C(F)(F)F)c2)CO1]

From 4-chloro-3-trifluoromethyl-benzaldehyde. Colorless viscous oil. MS (ISP): 293.0 ([M+H]$^+$)

Example 145

(S)-4-[2-(3-Fluoro-4-trifluoromethoxy-phenyl)-ethyl]-4,5-dihydro-oxazol-2-ylamine

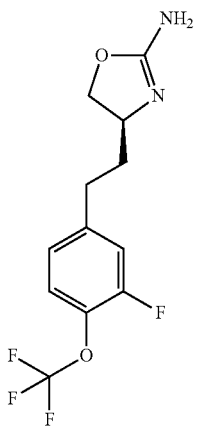 [SMILES: NC1=N[C@@H](CCc2ccc(OC(F)(F)F)c(F)c2)CO1]

From 3-fluoro-4-trifluoromethoxy-benzaldehyde. Off-white solid. MS (ISP): 293.0 ([M+H]$^+$)

Example 146

(S)-4-[2-(4-Fluoro-3-trifluoromethoxy-phenyl)-ethyl]-4,5-dihydro-oxazol-2-ylamine

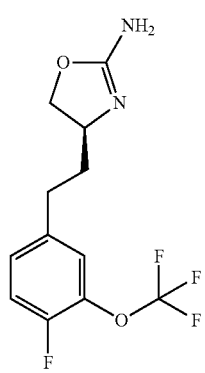 [SMILES: NC1=N[C@@H](CCc2ccc(F)c(OC(F)(F)F)c2)CO1]

From 4-fluoro-3-trifluoromethoxy-benzaldehyde. Viscous colorless oil. MS (ISP): 293.0 ([M+H]$^+$)

Example 147

(S)-4-Methyl-4-(4-trifluoromethyl-phenyl)-4,5-dihydro-oxazol-2-ylamine

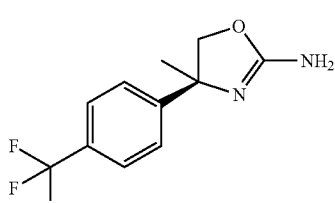

a) (RS)-(5-Methyl-5-(4-trifluoromethyl-phenyl)-imidazolidine-2,4-dione

A solution of 2-(trifluoremethyl)acetophenone (4.0 g) in EtOH/H$_2$O 1:1 (60 ml) were treated under an argon atmosphere with ammoniumcarbonate (10.21 g) and NaCN (1.25 g). The reaction mixture was heated to 60° C. and stirred for 3 hours. It was cooled to 0° C. and the solution was brought to acidic pH by dropwise addition of 3N HCl (ca. 80 ml). Then, $N_2$ was bubbled through the solution for 90 minutes to remove the remaining HCN.

EtOH and part of the water were removed by distillation. The remaining aqueous solution was extracted with EtOAc. The crude product was purified by column chromatography (silica gel; gradient: cyclohexane ->cyclohexane/EtOAc 3:7) to give 5-methyl-5-(4-trifluoromethyl-phenyl)-imidazolidine-2,4-dione (3.14 g, 57%) as off-white solid.

MS (ISP): 276.3 ([M+H]$^+$)

b) (RS)-2-Amino-2-(4-trifluoromethyl-phenyl)-propionic acid

In analogy to example 134.a 5-methyl-5-(4-tri-fluoromethyl-phenyl)-imidazolidine-2,4-dione was converted to (RS)-2-amino-2-(4-trifluoromethyl-phenyl)-propionic acid.

MS (ISP): 234.1 ([M+H]$^+$))

c) (RS)-4-Methyl-4-(4-trifluoromethyl-phenyl)-4,5-dihydro-oxazol-2-ylamine

In analogy to example 1 (RS)-2-amino-2-(4-trifluoromethyl-phenyl)-propionic acid was converted to the title compound. Off-white solid.

MS (ISP): 245.3 ([M+H]$^+$))

c) (S)-4-Methyl-4-(4-trifluoromethyl-phenyl)-4,5-dihydro-oxazol-2-ylamine (RS)-4-Methyl-4-(4-trifluoromethyl-phenyl)-4,5-dihydro-oxazol-2-ylamine was separated by chiral HPLC (Chiralpak AD, EtOH/heptane=10:90) to give (S)-4-methyl-4-(4-trifluoromethyl-phenyl)-4,5-dihydro-oxazol-2-ylamine. (−)-Enantio-mer. Light yellow solid.

MS (ISP): 245.3 ([M+H]$^+$))

Example 148

(R)-4-methyl-4-(4-trifluoromethyl-phenyl)-4,5-dihydro-oxazol-2-ylamine

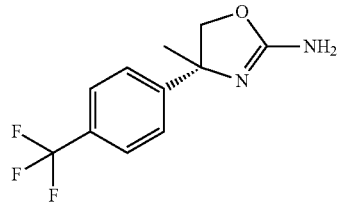 [SMILES: C[C@@]1(c2ccc(C(F)(F)F)cc2)COC(N)=N1]

(RS)-4-Methyl-4-(4-trifluoromethyl-phenyl)-4,5-dihydro-oxazol-2-ylamine (example 147) was separated by chiral HPLC (Chiralpak AD, EtOH/heptane=10:90) to give (R)-4-methyl-4-(4-trifluoromethyl-phenyl)-4,5-dihydro-oxazol-2-ylamine. (+)-Enantiomer. Off-white solid.

MS (ISP): 245.3 ([M+H]$^+$))

In analogy to example 83, starting from (S)-4-hydroxymethyl-2,2-dimethyl-oxazolidine-3-carboxylic acid tert-butyl ester and using the respective benzaldehyde were prepared:

Example 149

(S)-4-[2-(2,3-Dichloro-phenyl)-ethyl]-4,5-dihydro-oxazol-2-ylamine

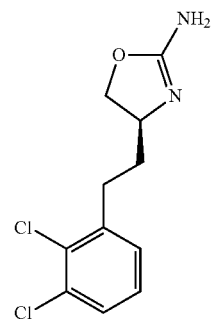 [SMILES: NC1=N[C@@H](CCc2cccc(Cl)c2Cl)CO1]

From 2,3-dichloro-benzaldehyde. Light yellow solid. MS (ISP): 259.0 ([M+H]$^+$)

Example 150

(S)-4-[2-(3-Chloro-4-trifluoromethoxy-phenyl)-ethyl]-4,5-dihydro-oxazol-2-ylamine

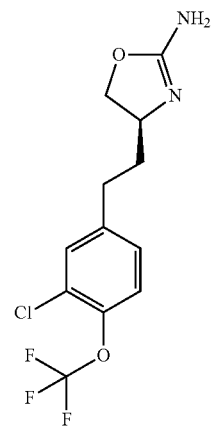 [SMILES: NC1=N[C@@H](CCc2ccc(OC(F)(F)F)c(Cl)c2)CO1]

From 3-chloro-4-trifluoromethoxy-benzaldehyde. Light yellow viscous oil. MS (ISP): 309.3 ([M+H]$^+$)

Example 151

(S)-4-[2-(2-Chloro-3-trifluoromethyl-phenyl)-ethyl]-4,5-dihydro-oxazol-2-ylamine

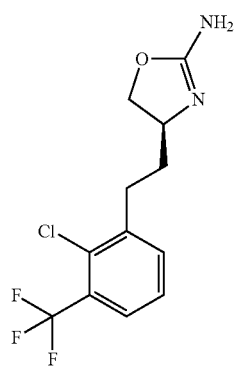 [SMILES: NC1=N[C@@H](CCc2cccc(C(F)(F)F)c2Cl)CO1]

From 2-chloro-3-trifluoromethyl-benzaldehyde. Off-white solid. MS (ISP): 293.1 ([M+H]$^+$)

Example 152

(R)-4-(3-Trifluoromethyl-phenyl)-4,5-dihydro-oxazol-2-ylamine

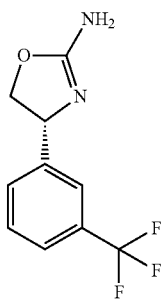 [SMILES: NC1=N[C@H](c2cccc(C(F)(F)F)c2)CO1]

a) (RS)-4-(3-Trifluoromethyl-phenyl)-4,5-dihydro-oxazol-2-ylamine

In analogy to example 1, the title compound was obtained from 2-(3-trifluoromethyl-phenyl)-DL-glycine. Off-white solid.

MS (ISP): 231.3 ([M+H]$^+$)

b) (R)-4-(3-Trifluoromethyl-phenyl)-4,5-dihydro-oxazol-2-ylamine (RS)-4-(3-Trifluoromethyl-phenyl)-4,5-dihydro-oxazol-2-ylamine was separated by chiral HPLC (Chiralpak AD, EtOH/heptane 15:85) to give (R)-4-(3-trifluoromethyl-phenyl)-4,5-dihydro-oxazol-2-ylamine. (−)-Enantiomer. Off-white solid.

MS (ISP): 231.4 ([M+H]$^+$))

Example 153

(S)-4-(3-Trifluoromethyl-phenyl)-4,5-dihydro-oxazol-2-ylamine

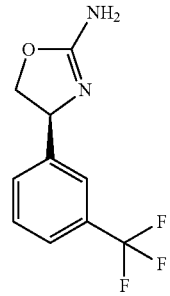 [SMILES: NC1=N[C@@H](c2cccc(C(F)(F)F)c2)CO1]

((RS)-4-(3-Trifluoromethyl-phenyl)-4,5-dihydro-oxazol-2-ylamine was separated by chiral HPLC (Chiralpak AD, EtOH/heptane 15:85) to give (S)-4-(3-trifluoromethyl-phenyl)-4,5-dihydro-oxazol-2-ylamine. (+)-Enantiomer. Off-white solid.

MS (ISP): 231.1 ([M+H]$^+$))

Example 154

(S)-4-(1-Methyl-2-phenyl-ethyl)-4,5-dihydro-oxazol-2-ylamine

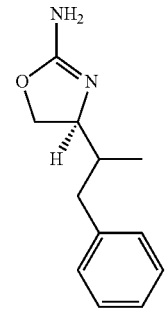

a) (R)-4-(1-Hydroxy-1-methyl-2-phenyl-ethyl)-2,2-dimethyl-oxazolidine-3-carboxylic acid tert-butyl ester A solution of (R)-4-acetyl-2,2-dimethyl-oxazolidine-3-carboxylic acid tert-butyl ester (2.80 g, CAS 167102-63-8) in THF (40 ml) was cooled under an argon atmosphere to 0° C. and treated dropwise with benzylmagnesium chloride solution (1 M in diethylether, 34.5 ml). The reaction mixture was stirred at r.t. overnight, then quenched with saturated aqueous NH$_4$Cl (50 ml) and extracted with EtOAc. The organic layer was washed with H$_2$O and brine, dried over MgSO$_4$, filtered and concentrated. The crude product was purified by column chromatography (silica gel; gradient: cyclohexane ->cyclohexane/EtOAc 3:1) to give (R)-4-(1-hydroxy-1-methyl-2-phenyl-ethyl)-2,2-dimethyl-oxazolidine-3-carboxylic acid tert-butyl ester (3.45 g, 89%) as off-white waxy solid.

MS (ISP): 336.4 ([M+H]$^+$)

b) (S)-2-Amino-3-methyl-4-phenyl-butan-1-ol

A stirred solution of (R)-4-(1-hydroxy-1-methyl-2-phenyl-ethyl)-2,2-dimethyl-oxazolidine-3-carboxylic acid tert-butyl ester (0.50 g) in THF (25 ml) was cooled under an argon atmosphere to −78° C. and treated dropwise with 1 M lithium-bis-(trimethylsilyl)amide in THF (1.79 ml). The solution was allowed to warm to r.t. Then, phenyl chlorothionoformate (0.3 ml) was added. After stirring at r.t. for 2 hrs, the reaction mixture was quenched with saturated aqueous NH₄Cl solution and extracted with EtOAc. The organic layer was washed with brine, dried over MgSO₄ and concentrated to give crude (R)-2,2-dimethyl-4-(1-methyl-1-phenoxythiocarbonyloxy-2-phenyl-ethyl)-oxazoli-dine-3-carboxylic acid tert-butyl ester as pale yellow oil which was used in the next reaction step without further purification.

A solution of crude (R)-2,2-dimethyl-4-(1-methyl-1-phenoxythiocarbonyloxy-2-phenyl-ethyl)-oxazolidine-3-carboxylic acid tert-butyl ester (700 mg) in toluene (5 ml) was treated under an argon atmosphere with 2,2' azobis(2-methylpropionitrile) (122 mg) and tri-N-butyltin hydride (0.79 ml). The reaction mixture was refluxed for 30 min, then cooled to r.t. and then directly purified by column chromatography (silica gel, gradient: cyclohexane ->cyclohexane/EtOAc 10:1) to give (S)-2,2-dimethyl-4-(1-methyl-2-phenyl-vinyl)-oxazo-lidine-3-carboxylic acid tert-butyl ester (279 mg, 59%) as light yellow waxy solid. MS (ISP): 318.3 ([M+H]⁺))

A solution of (S)-2,2-dimethyl-4-(1-methyl-2-phenyl-vinyl)-oxazolidine-3-carboxylic acid tert-butyl ester (250 mg) in 4M HCl in dioxane (2 ml) was stirred at r.t. overnight. The reaction mixture was concentrated. The crude product was purified by column chromatography (silica gel; gradient: CH₂Cl₂->CH₂Cl₂/MeOH 9:1) to give (S)-2-amino-3-methyl-4-phenyl-but-3-en-1-ol (122 mg, 87%) as light yellow oil. MS (ISP): 177.9 ([M+H]⁺))

A solution of (S)-2-amino-3-methyl-4-phenyl-but-3-en-1-ol (115 mg) in EtOH (5 ml) was hydrogenated at normal pressure (balloon) overnight in the presence of 10% Pd/C (10 mg). The reaction mixture was filtered and concentrated. The crude product was purified by column chromatography (silica gel; gradient: CH₂Cl₂->CH₂Cl₂/MeOH 9:1) to give (S)-2-amino-3-methyl-4-phenyl-butan-1-ol (57 mg, 49%) as light yellow oil. MS (ISP): 180.3 ([M+H]⁺))

c) (S)-4-(1-Methyl-2-phenyl-ethyl)-4,5-dihydro-oxazol-2-ylamine

In analogy to example 1b (S)-2-amino-3-methyl-4-phenyl-butan-1-ol was reacted with cyanogen bromide to give (S)-4-(1-methyl-2-phenyl-ethyl)-4,5-dihydro-oxazol-2-ylamine. Off-white amorphous solid.

MS (ISP): 205.1 ([M+H]⁺))

In analogy to example 83, starting from (S)-4-hydroxymethyl-2,2-dimethyl-oxazolidine-3-carboxylic acid tert-butyl ester and using the respective benzaldehyde were prepared:

Example 155

(S)-4-[2-(3,5-Bis-trifluoromethyl-phenyl)-ethyl]-4,5-dihydro-oxazol-2-ylamine

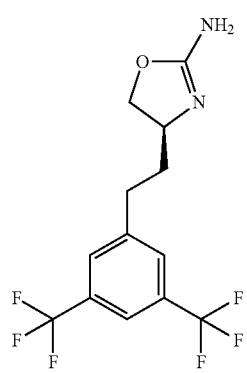 [SMILES: NC1=N[C@@H](CCc2cc(C(F)(F)F)cc(C(F)(F)F)c2)CO1]

From 3,5-bis-trifluoromethyl-benzaldehyde. Off-white solid. MS (ISP): 327.3 ([M+H]⁺)

Example 156

(S)-4-[2-(2-Fluoro-5-trifluoromethyl-phenyl)-ethyl]-4,5-dihydro-oxazol-2-ylamine

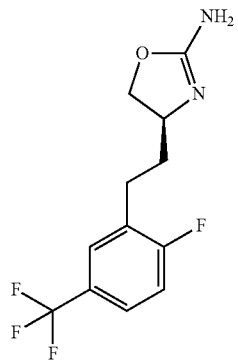 [SMILES: NC1=N[C@@H](CCc2cc(C(F)(F)F)ccc2F)CO1]

From 2-fluoro-5-trifluoromethyl-benzaldehyde. White solid. MS (ISP): 277.0 ([M+H]⁺)

Example 157

(S)-4-[2-(6-Trifluoromethyl-pyridin-3-yl)-ethyl]-4,5-dihydro-oxazol-2-ylamine

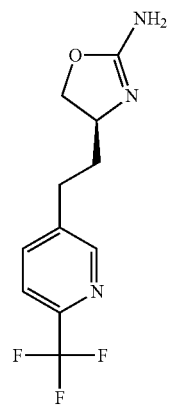

From 6-(trifluoromethyl)pyridine-3-carboxaldehyde. Colorless gum. MS (ISP): 260.3 ([M+H]⁺)

Example 158

(S)-4-[2-(3-Fluoro-pyridin-4-yl)-ethyl]-4,5-dihydro-oxazol-2-ylamine

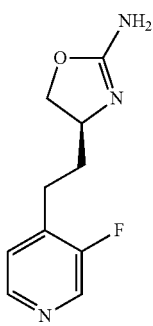 [SMILES: NC1=N[C@@H](CCc2ccncc2F)CO1]

From 3-fluoro-isonicotinaldehyde. Light yellow solid. MS (ISP): 210.1 ([M+H]⁺)

Example 159

(S)-4-[2-(3-Fluoro-5-trifluoromethyl-phenyl)-ethyl]-4,5-dihydro-oxazol-2-ylamine

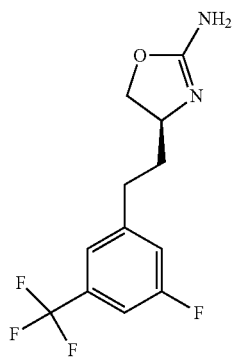 [SMILES: NC1=N[C@@H](CCc2cc(F)cc(C(F)(F)F)c2)CO1]

From 3-fluoro-5-trifluoromethyl-benzaldehyde. Colorless viscous oil. MS (ISP): 277.1 ([M+H]$^+$)

Example 160

(S)-4-[2-(2,5-Bis-trifluoromethyl-phenyl)-ethyl]-4,5-dihydro-oxazol-2-ylamine

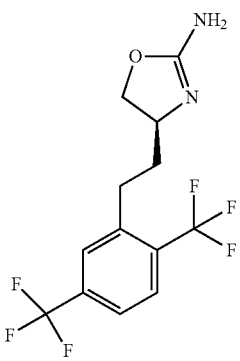 [SMILES: NC1=N[C@@H](CCc2cc(C(F)(F)F)ccc2C(F)(F)F)CO1]

From 2,5-bis-trifluoromethyl-benzaldehyde. Colorless viscous oil. MS (ISP): 327.1 ([M+H]$^+$)

Example 161

(S)-4-Methyl-4-p-tolyl-4,5-dihydro-oxazol-2-ylamine

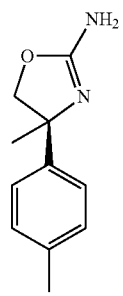

a) (RS)-4-Methyl-4-p-tolyl-4,5-dihydro-oxazol-2-ylamine

In analogy to example 1, the title compound was obtained from DL-2-(4-methylphenyl)alanine. White solid. MS (ISP): 191.3 ([M+H]$^+$)

b) (s)-4-Methyl-4-p-tolyl-4,5-dihydro-oxazol-2-ylamine (RS)-4-Methyl-4-p-tolyl-4,5-dihydro-oxazol-2-ylamine was separated by chiral HPLC (Chiralpak AD, EtOH/heptane 15:85) to give (S)-4-methyl-4-p-tolyl-4,5-dihydro-oxazol-2-ylamine. (+)-Enantiomer. Off-white solid. MS (ISP): 191.3 ([M+H]$^+$)

Example 162

(S)-4-[2-(4-Chloro-phenyl)-butyl]-4,5-dihydro-oxazol-2-ylamine

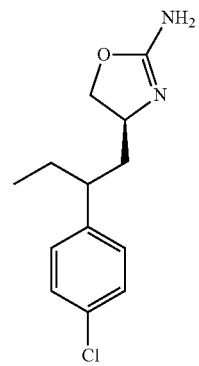 [SMILES: CCC(C[C@H]1COC(N)=N1)c1ccc(Cl)cc1]

a) (S)-4-(2,2-Dibromo-vinyl)-2,2-dimethyl-oxazolidine-3-carboxylic acid tert-butyl ester To a stirred, cooled (0° C.) solution of (R)-4-formyl-2,2-dimethyl-oxazolidine-3-carboxylic acid tert-butyl ester (4.30 g; CAS 95715-87-0 and triphenylphosphine (9.15 g) in dichloromethane (100 ml) was added portionwise carbon tetrabromide (6.94 g). The mixture was stirred at 0° C. for 20 min and then at r.t. for 2 h. The mixture was concentrated in vacuo to ca 20 ml, then diluted with hexane (100 ml) and concentrated in vacuo to half-volume. The residue was stirred at 0° C. for 15 min, then the mixture was filtered and the filtrate was concentrated in vacuo to afford (S)-4-(2,2-dibromo-vinyl)-2,2-dimethyl-oxazolidine-3-carboxylic acid tert-butyl ester (6.18 g, 92%) as a colourless oil. MS (EI): 330.9 ([{$^{81}$Br}M—C$_4$H$_8$]$^+$), 328.9 ([{$^{81}$ Br$^{79}$ Br}M—C$_4$H$_8$]$^+$), 326.9 ([{$^{79}$ Br}M—C$_4$H$_8$]$^+$).

b) (S)-4-[(Z)-2-Bromo-2-(4-chloro-phenyl)-vinyl]-2,2-dimethyl-oxazolidine-3-carboxylic acid tert-butyl ester To a stirred solution of (S)-4-(2,2-dibromo-vinyl)-2,2-dimethyl-oxazolidine-3-carboxylic acid tert-butyl ester (3.6 g) in dioxane (48 ml) were added 4-chlorophenylboronic acid (1.75 g), tris(dibenzylideneacetone)dipalladium (0) (290 mg), tris(2-furyl)phosphine (326 mg) and aqueous sodium carbonate solution (18.7 ml, 1 M solution). The mixture was stirred at 50° C. for 90 min. The mixture was diluted with ethyl acetate and washed with saturated brine, dried over MgSO$_4$, filtered and concentrated in vacuo. The residue was purified by column chromatography (SiO$_2$; gradient: heptane/EtOAc) to give (S)-4-(benzothiazole-2-sulfonylmethyl)-2,2-dimethyl-oxazolidine-3-carboxylic acid tert-butyl ester (1.77 g, 45%) as a light yellow oil. MS (ISP): 420.0 ([{$^{37}$Cl$^{81}$Br}M+H]$^+$), 418.0 ([{$^{37}$Cl$^{79}$Br, $^{35}$Cl$^{81}$Br}M+H]$^+$), 416.0 ([{$^{35}$Cl$^{79}$Cl}M+H]$^+$).

c) (S)-4-[(E)-2-(4-Chloro-phenyl)-but-1-enyl]-2,2-dimethyl-oxazolidine-3-carboxylic acid tert-butyl ester To a stirred solution of (S)-4-[(Z)-2-bromo-2-(4-chloro-phenyl)-vinyl]-2,2-dimethyl-oxazolidine-3-carboxylic acid tert-butyl ester (1.04 g) in THF (8 ml) were added bis(tri-tert-butylphosphine)dipalladium (0) (64 mg) and diethylzinc (4.99 ml, 1.1 M solution in toluene). The mixture was stirred at r.t. for 90 min then was diluted with ethyl acetate and washed with saturated brine, dried over MgSO$_4$, filtered and concentrated in vacuo. The residue was purified by column chromatography (SiO$_2$; gradient: heptane/EtOAc) to give (S)-4-[(E)-2-(4-chloro-phenyl)-but-1-enyl]-2,2-dimethyl-oxazolidine-3-carboxylic acid tert-butyl ester (824 mg, 90%) as a colourless oil. MS (ISP): 368.5 ([{$^{37}$Cl}M+H]$^+$), 366.5 ([{$^{35}$Cl}M+H]$^+$).

d) (E)-(S)-2-Amino-4-(4-chloro-phenyl)-hex-3-en-1-ol

To a stirred solution of (S)-4-[(E)-2-(4-chloro-phenyl)-but-1-enyl]-2,2-dimethyl-oxazolidine-3-carboxylic acid tert-butyl ester (820 mg) at r.t. in dioxane (8 ml) was added 4 M HCl solution in dioxane (11.2 ml). The mixture was stirred at 35° C. for 3.5 h. The mixture was then diluted with ethyl acetate and made basic by addition of 2 N aq sodium hydroxide solution. The phases were separated and the organic phase was washed with saturated brine, dried over sodium sulphate and concentrated in vacuo to give (E)-(S)-2-amino-4-(4-chloro-phenyl)-hex-3-en-1-ol (524 mg, quant.) as a yellow oil. MS (ISP): 228.2 ([{$^{37}$Cl}M+H]$^+$), 226.2 ([{$^{35}$Cl}M+H]$^{3o}$).

e) (S)-2-Amino-4-(4-chloro-phenyl)-hexan-1-ol

To a stirred solution of (E)-(S)-2-amino-4-(4-chloro-phenyl)-hex-3-en-1-ol (0.52 g) at r.t. in ethanol (30 ml) under an argon atmosphere was added 5% Pt/C (180 mg). The mixture was stirred at r.t. under a hydrogen atmosphere for 16 hrs. The catalyst was filtered off and the filtrate was concentrated in vacuo. The residue was purified by column chromatography (SiO$_2$; gradient: heptane/EtOAc) to give (S)-2-amino-4-(4-chloro-phenyl)-hexan-1-ol (mainly one epimer) (0.157 g, 30%) as colourless oil. MS (ISP): 230.3 ([{$^{37}$Cl}M+H]$^+$), 228.2 ([{$^{35}$Cl}M+H]$^+$).

f) (S)-4-[2-(4-Chloro-phenyl)-butyl]-4,5-dihydro-oxazol-2-ylamine

In analogy to example 1b (S)-2-amino-4-(4-chloro-phenyl)-hexan-1-ol was reacted with cyanogen bromide to give (S)-4-[2-(4-chloro-phenyl)-butyl]-4,5-dihydro-oxazol-2-ylamine (mainly one epimer). Colourless oil. MS (ISP): 255.2 ([{$^{37}$Cl}M+H]$^+$), 253.2 ([{$^{35}$Cl}M+H]$^+$).

Example 163

(S)-4-(2-Phenyl-butyl)-4,5-dihydro-oxazol-2-ylamine

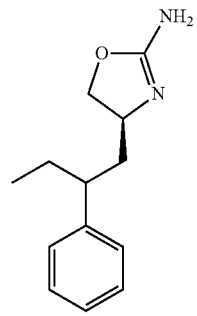 [SMILES: CCC(C[C@H]1COC(N)=N1)c1ccccc1]

a) (S)-4-((Z)-2-Bromo-2-phenyl-vinyl)-2,2-dimethyl-oxazolidine-3-carboxylic acid tert-butyl ester In analogy to example 162b (S)-4-(2,2-dibromo-vinyl)-2,2-dimethyl-oxazolidine-3-carboxylic acid tert-butyl ester was reacted with phenylboronic acid to give (S)-4-((Z)-2-bromo-2-phenyl-vinyl)-2,2-dimethyl-oxazolidine-3-carboxylic acid tert-butyl ester. Light yellow crystalline solid.

b) (S)-2,2-Dimethyl-4-((E)-2-phenyl-but-1-enyl)-oxazolidine-3-carboxylic acid tert-butyl ester In analogy to example 162c (S)-4-((Z)-2-bromo-2-phenyl-vinyl)-2,2-dimethyl-oxazolidine-3-carboxylic acid tert-butyl ester was reacted with diethylzinc to give (S)-2,2-dimethyl-4-((E)-2-phenyl-but-1-enyl)-oxazolidine-3-carboxylic acid tert-butyl ester. Colourless oil. MS (ISP): 332.3 ([M+H]$^+$).

c) (E)-(S)-2-Amino-4-phenyl-hex-3-en-1-ol

In analogy to example 162d (S)-2,2-dimethyl-4-((E)-2-phenyl-but-1-enyl)-oxazolidine-3-carboxylic acid tert-butyl ester was reacted with hydrogen chloride to give (E)-(S)-2-amino-4-phenyl-hex-3-en-1-ol. Yellow crystalline solid.

d) (S)-2-Amino-4-phenyl-hexan-1-ol

To a stirred solution of (E)-(S)-2-amino-4-phenyl-hex-3-en-1-ol (1.0 g) at r.t. in methanol (50 ml) under an argon atmosphere was added 10% Pd/C (278 mg). The mixture was stirred at r.t. under a hydrogen atmosphere for 30 min. The catalyst was filtered off and the filtrate was concentrated in vacuo. The residue was purified by column chromatography (SiO$_2$; gradient: dichloromethane/methanol) to give (S)-2-amino-4-phenyl-hexan-1-ol (mainly one epimer) (0.81 g, 80%) as a colourless oil. MS (ISP): 194.4 ([M+H]$^+$).

e) (S)-4-(2-Phenyl-butyl)-4,5-dihydro-oxazol-2-ylamine

In analogy to example 1b (S)-2-amino-4-phenyl-hexan-1-ol was reacted with cyanogen bromide to give (S)-4-(2-phe nyl-butyl)-4,5-dihydro-oxazol-2-ylamine (mainly one epimer). White crystalline solid. MS (ISP): 219.4 ([M+H]⁺).

In analogy to example 163 were prepared:

Example 164

(R)-4-[2-(4-Trifluoromethyl-phenyl)-propyl]-4,5-dihydro-oxazol-2-ylamine

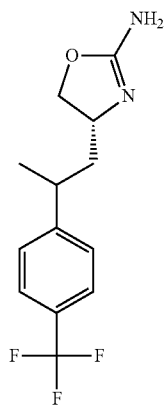 [SMILES: CC(C[C@@H]1COC(N)=N1)c1ccc(C(F)(F)F)cc1]

From (R)-4-(2,2-dibromo-vinyl)-2,2-dimethyl-oxazolidine-3-carboxylic acid tert-butyl ester by sequential treatment with 4-(trifluoromethyl)phenyl boronic acid and dimethylzinc. Mainly one epimer. Colourless oil. MS (ISP): 273.3 ([M+H]⁺).

Example 165

(S)-4-[2-(4-Trifluoromethyl-phenyl)-propyl]-4,5-dihydro-oxazol-2-ylamine

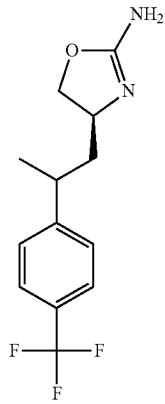 [SMILES: CC(C[C@H]1COC(N)=N1)c1ccc(C(F)(F)F)cc1]

From (S)-4-(2,2-dibromo-vinyl)-2,2-dimethyl-oxazolidine-3-carboxylic acid tert-butyl ester by sequential treatment with 4-(trifluoromethyl)phenyl boronic acid and dimethylzinc. Mainly one epimer. Colourless oil. MS (ISP): 273.3 ([M+H]⁺).

Example 166

(S)-4-(3,4-Difluoro-phenyl)-4,5-dihydro-oxazol-2-ylamine

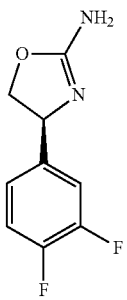 [SMILES: NC1=N[C@@H](c2ccc(F)c(F)c2)CO1]

a) (RS)-4-(3,4-Difluoro-phenyl)-4,5-dihydro-oxazol-2-ylamine

In analogy to example 1, the title compound was obtained from DL-3,4-difluorophenylglycine. Off-white solid.

MS (ISP): 199.3 ([M+H]⁺)

b) (S)-4-(3,4-Difluoro-phenyl)-4,5-dihydro-oxazol-2-ylamine (RS)-4-(3,4-Difluoro-phenyl)-4,5-dihydro-oxazol-2-ylamine was separated by chiral HPLC (Chiralpak AD, EtOH/heptane 15:85) to give (S)-4-(3,4-difluoro-phenyl)-4,5-dihydro-oxazol-2-ylamine. (+)-Enantiomer. Off-white solid.

MS (ISP): 199.1 ([M+H]⁺))

Example 167

(R)-4-(2,3-Dichloro-phenyl)-4,5-dihydro-oxazol-2-ylamine

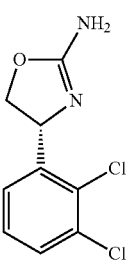 [SMILES: NC1=N[C@H](c2cccc(Cl)c2Cl)CO1]

a) (RS)-4-(2,3-Dichloro-phenyl)-4,5-dihydro-oxazol-2-ylamine

In analogy to example 1, the title compound was obtained from DL-amino-(2,3-dichloro-phenyl)-acetic acid. Light yellow solid.

MS (ISP): 231.1 ([M+H]⁺)

b) (R)-4-(2,3-Dichloro-phenyl)-4,5-dihydro-oxazol-2-ylamine (RS)-4-(2,3-Dichloro-phenyl)-4,5-dihydro-oxazol-2-ylamine was separated by chiral HPLC (Chiralpak AD, EtOH/heptane 1:9) to give (R)-4-(2,3-dichloro-phenyl)-4,5-dihydro-oxazol-2-ylamine. (−)-Enantiomer. White solid.
MS (ISP): 231.1 ([M+H]+)

Example 168

(S)-4-(2,3-Dichloro-phenyl)-4,5-dihydro-oxazol-2-ylamine

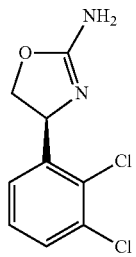 [SMILES: NC1=N[C@@H](c2cccc(Cl)c2Cl)CO1]

(RS)-4-(2,3-Dichloro-phenyl)-4,5-dihydro-oxazol-2-ylamine was separated by chiral HPLC (Chiralpak AD, EtOH/heptane 1:9) to give (S)-4-(2,3-dichloro-phenyl)-4,5-dihydro-oxazol-2-ylamine. (+)-Enantiomer. White solid.
MS (ISP): 231.3 ([M+H]+)

Example 169

(S)-4-(4-Chloro-phenyl)-4,5-dihydro-oxazol-2-ylamine

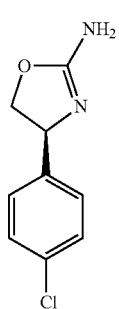 [SMILES: NC1=N[C@@H](c2ccc(Cl)cc2)CO1]

In analogy to example 1, the title compound was obtained from (S)-4-chlorophenyl glycine. Light yellow solid.
MS (ISP): 197.3 ([M+H]+)

Example 170

(S)-4-(3,4,5-Trifluoro-phenyl)-4,5-dihydro-oxazol-2-ylamine

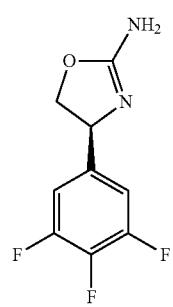 [SMILES: NC1=N[C@@H](c2cc(F)c(F)c(F)c2)CO1]

a) (RS)-4-(3,4,5-Trifluoro-phenyl)-4,5-dihydro-oxazol-2-ylamine

In analogy to example 1, the title compound was obtained from 3,4,5-trifluoro-DL-phenylglycine. Light yellow solid.
MS (ISP): 217.4 ([M+H]+)

b) (S)-4-(3,4,5-Trifluoro-phenyl)-4,5-dihydro-oxazol-2-ylamine (RS)-4-(3,4,5-Trifluoro-phenyl)-4,5-dihydro-oxazol-2-ylamine was separated by chiral HPLC (Chiralpak AD, EtOH/heptane 15:85) to give (S)-4-(3,4,5-trifluoro-phenyl)-4,5-dihydro-oxazol-2-ylamine. (+)-Enantiomer. Colorless viscous oil. MS (ISP): 217.3 ([M+H]+))

Example 171

(R)-4-(3-Chloro-4-fluoro-phenyl)-4,5-dihydro-oxazol-2-ylamine

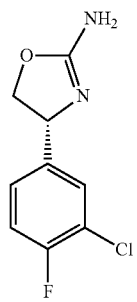 [SMILES: NC1=N[C@H](c2ccc(F)c(Cl)c2)CO1]

a) (RS)-4-(3-Chloro-4-fluoro-phenyl)-4,5-dihydro-oxazol-2-ylamine

In analogy to example 1, the title compound was obtained from 3-chloro-4-fluoro-DL-phenylglycine. Light yellow waxy solid.
MS (ISP): 215.1 ([M+H]+)

b) (R)-4-(3-Chloro-4-fluoro-phenyl)-4,5-dihydro-oxazol-2-ylamine (RS)-4-(3-Chloro-4-fluoro-phenyl)-4,5-dihydro-oxazol-2-ylamine was separated by chiral HPLC (Chiralpak AD, EtOH/heptane 15:85) to give (R)-4-(3-chloro-4-fluoro-phenyl)-4,5-dihydro-oxazol-2-ylamine. (−)-Enantiomer. White solid.
MS (ISP): 215.4 ([M+H]+)

Example 172

(R)-4-(3-Chloro-4-fluoro-phenyl)-4,5-dihydro-oxazol-2-ylamine

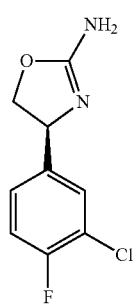 [SMILES: NC1=N[C@@H](c2ccc(F)c(Cl)c2)CO1]

(RS)-4-(3-Chloro-4-fluoro-phenyl)-4,5-dihydro-oxazol-2-ylamine was separated by chiral HPLC (Chiralpak AD, EtOH/heptane 15:85) to give (S)-4-(3-chloro-4-fluoro-phenyl)-4,5-dihydro-oxazol-2-ylamine. (+)-Enantiomer. White solid.
MS (ISP): 215.1 ([M+H]$^+$))

Example 173

(R)-4-(4-Chloro-3-fluoro-phenyl)-4,5-dihydro-oxazol-2-ylamine

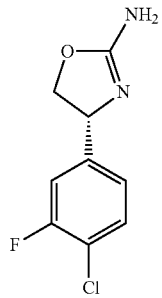 [SMILES: NC1=N[C@H](c2ccc(Cl)c(F)c2)CO1]

a) (RS)-4-(4-Chloro-3-fluoro-phenyl)-4,5-dihydro-oxazol-2-ylamine

In analogy to example 1, the title compound was obtained from 4-chloro-3-fluoro-DL-phenylglycine. Yellow waxy solid.
MS (ISP): 215.1 ([M+H]$^+$)

b) (R)-4-(4-Chloro-3-fluoro-phenyl)-4,5-dihydro-oxazol-2-ylamine (RS)-4-(4-Chloro-3-fluoro-phenyl)-4,5-dihydro-oxazol-2-ylamine was separated by chiral HPLC (Chiralpak AD, EtOH/heptane 15:85) to give (R)-4-(4-chloro-3-fluoro-phenyl)-4,5-dihydro-oxazol-2-ylamine. (−)-Enantiomer. Off-white solid.
MS (ISP): 215.1 ([M+H]$^+$)

Example 174

(S)-4-(4-Chloro-3-fluoro-phenyl)-4,5-dihydro-oxazol-2-ylamine

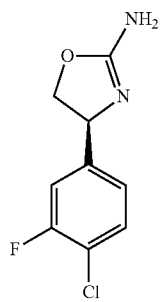 [SMILES: NC1=N[C@@H](c2ccc(Cl)c(F)c2)CO1]

(RS)-4-(4-Chloro-3-fluoro-phenyl)-4,5-dihydro-oxazol-2-ylamine was separated by chiral HPLC (Chiralpak AD, EtOH/heptane 15:85) to give (S)-4-(4-chloro-3-fluoro-phenyl)-4,5-dihydro-oxazol-2-ylamine. (+)-Enantiomer. Off-white solid.
MS (ISP): 215.3 ([M+H]$^+$))

Example 175

(R)-4-(3,5-Difluoro-phenyl)-4,5-dihydro-oxazol-2-ylamine

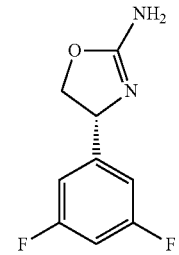 [SMILES: NC1=N[C@H](c2cc(F)cc(F)c2)CO1]

a) ((RS)-4-(3,5-Difluoro-phenyl)-4,5-dihydro-oxazol-2-ylamine

In analogy to example 1, the title compound was obtained from 3,5-difluoro-DL-phenylglycine. Yellow solid.
MS (ISP): 199.1 ([M+H]$^+$)

b) (R)-4-(3,5-Difluoro-phenyl)-4,5-dihydro-oxazol-2-ylamine (RS)-4-(3,5-Difluoro-phenyl)-4,5-dihydro-oxazol-2-ylamine was separated by chiral HPLC (Chiralpak AD, EtOH/heptane 15:85) to give (R)-4-(3,5-difluoro-phenyl)-4,5-dihydro-oxazol-2-ylamine. (−)-Enantiomer. Light yellow solid.
MS (ISP): 199.1 ([M+H]$^+$))

Example 176

(S)-4-(3,5-Difluoro-phenyl)-4,5-dihydro-oxazol-2-ylamine

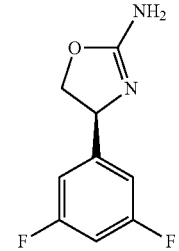 [SMILES: NC1=N[C@@H](c2cc(F)cc(F)c2)CO1]

(RS)-4-(3,5-Difluoro-phenyl)-4,5-dihydro-oxazol-2-ylamine was separated by chiral HPLC (Chiralpak AD, EtOH/heptane 15:85) to give (S)-4-(3,5-difluoro-phenyl)-4,5-dihydro-oxazol-2-ylamine. (+)-Enantiomer. White solid.
MS (ISP): 199.3 ([M+H]$^+$)

Example 177

(R)-4-(3-Chloro-5-fluoro-phenyl)-4,5-dihydro-oxazol-2-ylamine

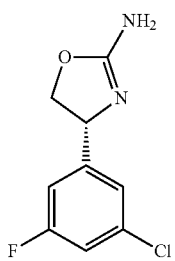 [SMILES: NC1=N[C@H](c2cc(F)cc(Cl)c2)CO1]

a) (RS)-4-(3-Chloro-5-fluoro-phenyl)-4,5-dihydro-oxazol-2-ylamine

In analogy to example 1, the title compound was obtained from 3-chloro-5-fluoro-DL-phenylglycine. Waxy yellow solid.

MS (ISP): 215.3 ([M+H]$^+$)

b) (R)-4-(3-Chloro-5-fluoro-phenyl)-4,5-dihydro-oxazol-2-ylamine (RS)-4-(3-Chloro-5-fluoro-phenyl)-4,5-dihydro-oxazol-2-ylamine was separated by chiral HPLC (Chiralpak AD, EtOH/heptane 15:85) to give (R)-4-(3-chloro-5-fluoro-phenyl)-4,5-dihydro-oxazol-2-ylamine. (−)-Enantiomer. Light yellow solid.

MS (ISP): 215.3 ([M+H]$^+$))

Example 178

(S)-4-(3-Chloro-5-fluoro-phenyl)-4,5-dihydro-oxazol-2-ylamine

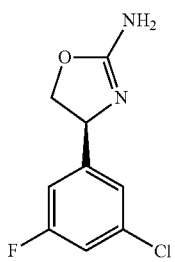 [SMILES: NC1=N[C@@H](c2cc(F)cc(Cl)c2)CO1]

(RS)-4-(3-Chloro-5-fluoro-phenyl)-4,5-dihydro-oxazol-2-ylamine was separated by chiral HPLC (Chiralpak AD, EtOH/heptane 15:85) to give (S)-4-(3-chloro-5-fluoro-phenyl)-4,5-dihydro-oxazol-2-ylamine. (+)-Enantiomer. Light yellow solid.

MS (ISP): 215.1 ([M+H]$^+$))

Example 179

(R)-4-(2-Chloro-phenyl)-4-methyl-4,5-dihydro-oxazol-2-ylamine

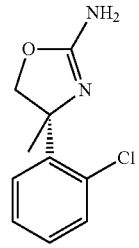

a) (RS)-4-(2-Chloro-phenyl)-4-methyl-4,5-dihydro-oxazol-2-ylamine

In analogy to example 147, the title compound was obtained starting from 2'-chloro-acetophenone. White solid.

MS (ISP): 211.1 ([M+H]$^+$)

b) (R)-4-(2-Chloro-phenyl)-4-methyl-4,5-dihydro-oxazol-2-ylamine (RS)-4-(2-Chloro-phenyl)-4-methyl-4,5-dihydro-oxazol-2-ylamine was separated by chiral HPLC (Chiralpak AD, EtOH/heptane 1:9) to give (R)-4-(2-chloro-phenyl)-4-methyl-4,5-dihydro-oxazol-2-ylamine. (−)-Enantiomer. White solid.

MS (ISP): 211.1 ([M+H]$^+$))

Example 180

(S)-4-(2-Chloro-phenyl)-4-methyl-4,5-dihydro-oxazol-2-ylamine

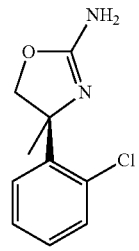

(RS)-4-(2-Chloro-phenyl)-4-methyl-4,5-dihydro-oxazol-2-ylamine was separated by chiral HPLC (Chiralpak AD, EtOH/heptane 1:9) to give (S)-4-(2-chloro-phenyl)-4-methyl-4,5-dihydro-oxazol-2-ylamine. (+)-Enantiomer. White solid.

MS (ISP): 211.1 ([M+H]$^+$))

113

In analogy to example 165, except that the order of the hydrogenation and deprotection steps was reversed, was prepared:

Example 181

(S)-4-[2-(4-Trifluoromethyl-phenyl)-propyl]-4,5-dihydro-oxazol-2-ylamine

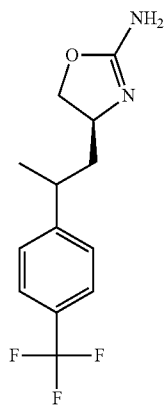 [SMILES: CC(C[C@H]1COC(N)=N1)c1ccc(C(F)(F)F)cc1]

From (S)-4-(2,2-dibromo-vinyl)-2,2-dimethyl-oxazolidine-3-carboxylic acid tert-butyl ester by sequential treatment with 4-(trifluoromethyl)phenyl boronic acid and dimethylzinc. Mainly one epimer, which is different from the major epimer produced in example 165. Colourless amorphous solid. MS (ISP): 273.4 ([M+H]$^+$).

In analogy to example 164, except that the order of the hydrogenation and deprotection steps was reversed, was prepared:

Example 182

(R)-4-[2-(4-Trifluoromethyl-phenyl)-propyl]-4,5-dihydro-oxazol-2-ylamine

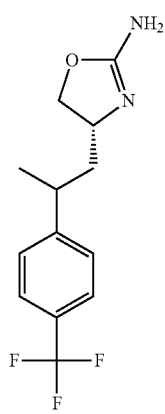

From (R)-4-(2,2-dibromo-vinyl)-2,2-dimethyl-oxazolidine-3-carboxylic acid tert-butyl ester by sequential treatment with 4-(trifluoromethyl)phenyl boronic acid and dimethylzinc. Mainly one epimer, which is different from the major epimer produced in example 164. Colourless oil. MS (ISP): 273.1 ([M+H]$^+$).

114

In analogy to example 184, except that the order of the hydrogenation and deprotection steps was reversed, was prepared:

Example 183

(S)-4-[2-(4-Trifluoromethyl-phenyl)-butyl]-4,5-dihydro-oxazol-2-ylamine

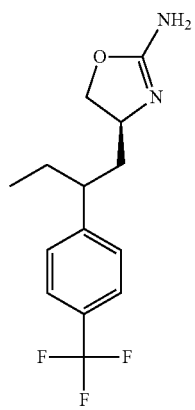 [SMILES: CCC(C[C@H]1COC(N)=N1)c1ccc(C(F)(F)F)cc1]

From (S)-4-(2,2-dibromo-vinyl)-2,2-dimethyl-oxazolidine-3-carboxylic acid tert-butyl ester by sequential treatment with 4-(trifluoromethyl)phenyl boronic acid and diethylzinc. Mainly one epimer, which is different from the major epimer produced in example 184.

Colourless oil. MS (ISP): 287.1 ([M+H]$^+$).

In analogy to example 163 was prepared:

Example 184

(S)-4-[2-(4-Trifluoromethyl-phenyl)-butyl]-4,5-dihydro-oxazol-2-ylamine

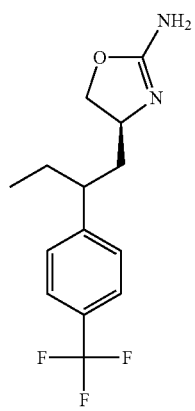 [SMILES: CCC(C[C@H]1COC(N)=N1)c1ccc(C(F)(F)F)cc1]

From (S)-4-(2,2-dibromo-vinyl)-2,2-dimethyl-oxazolidine-3-carboxylic acid tert-butyl ester by sequential treatment with 4-(trifluoromethyl)phenyl boronic acid and diethylzinc. Mainly one epimer. Colourless oil. MS (ISP): 287.1 ([M+H]$^+$).

Example 185

(RS)-4-(3-Chloro-phenyl)-4,5-dihydro-oxazol-2-ylamine

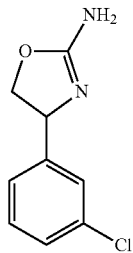 [SMILES: NC1=NC(c2cccc(Cl)c2)CO1]

a) (RS)-2-Amino-2-(3-chloro-phenyl)-ethanol

To a stirred solution of lithium borohydride in THF (10.5 ml, 2 M solution) under an argon atmosphere was added dropwise chlorotrimethylsilane (5.34 ml). The resulting suspension was cooled to 0° C. and amino-(3-chlorophenyl)-acetic acid (2.0 g) was added portionwise. The ice bath was removed and stirring at r.t. was then continued for 16 h. The mixture was quenched by dropwise addition of methanol (15 ml) and then concentrated in vacuo. The residue was suspended in ethyl acetate and washed with 2 N aq NaOH. The phases were separated and the aqueous phase was extracted with ethyl acetate. The combined organic phases were dried over sodium sulphate and concentrated in vacuo to afford (RS)-2-amino-2-(3-chloro-phenyl)-ethanol (1.84 g, quant.) as a yellow viscous oil. MS (ISP): 174.2 ($[\{^{37}Cl\}M+H]^+$), 172.2 ($[\{^{35}Cl\}M+H]^+$).

b) (RS)-4-(3-Chloro-phenyl)-4,5-dihydro-oxazol-2-ylamine

In analogy to example 1.b (RS)-2-amino-2-(3-chloro-phenyl)-ethanol was converted to (RS)-4-(3-chloro-phenyl)-4,5-dihydro-oxazol-2-ylamine by treatment with cyanogen bromide and potassium carbonate. White solid. MS (ISP): 199.0 ($[\{^{37}Cl\}M+H]^+$), 197.0 ($[\{^{35}Cl\}M+H]^+$). In analogy to example 185 and starting from the respective amino acid or amino acid derivative was prepared:

Example 186

(RS)-4-(3-Bromo-phenyl)-4,5-dihydro-oxazol-2-ylamine

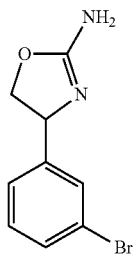 [SMILES: NC1=NC(c2cccc(Br)c2)CO1]

From (RS)-2-amino-2-(3-bromophenyl)-acetic acid. White solid.
MS (ISP): 243.2 ($[\{^{81}Br\}M+H]^+$), 241.1 ($[\{^{79}Br\}M+H]^+$).

Example 187

(S)-4-(2,5-Difluoro-phenyl)-4-methyl-4,5-dihydro-oxazol-2-ylamine

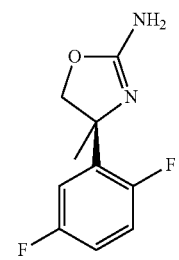

a) (RS)-4-(2,5-Difluoro-phenyl)-4-methyl-4,5-dihydro-oxazol-2-ylamine

In analogy to example 147, the title compound was obtained starting from 2',3',6'-trifluoroacetophenone (one of the ortho fluorine atoms gets lost during the lithium aluminium hydride reduction). White solid.

MS (ISP): 213.3 ($[M+H]^+$)

b) (S)-4-(2,5-Difluoro-phenyl)-4-methyl-4,5-dihydro-oxazol-2-ylamine (RS)-4-(2,5-Difluoro-phenyl)-4-methyl-4,5-dihydro-oxazol-2-ylamine was separated by chiral HPLC (Chiralpak AD, EtOH/heptane 1:9) to give (S)-4-(2,5-difluoro-phenyl)-4-methyl-4,5-dihydro-oxazol-2-ylamine. (+)-Enantiomer. White solid.

MS (ISP): 213.3 ($[M+H]^+$)

In analogy to example 186 and starting from the respective amino acid or amino acid derivative were prepared:

Example 188

(RS)-4-(3-Fluoro-phenyl)-4,5-dihydro-oxazol-2-ylamine

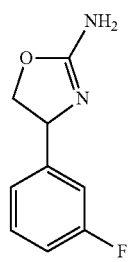

From (RS)-2-amino-2-(3-fluorophenyl)-acetic acid. White solid.
MS (ISP): 181.1 ($[M+H]^+$).

Example 189

(RS)-4-(3,5-Dichloro-phenyl)-4,5-dihydro-oxazol-2-ylamine

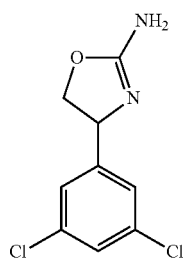 [SMILES: NC1=NC(c2cc(Cl)cc(Cl)c2)CO1]

From (RS)-2-amino-2-(3,5-dichlorophenyl)-acetic acid. White solid.
MS (ISP): 235.1 ([{$^{37}$Cl}M+H]$^+$), 233.1 ([{$^{37}$Cl$^{35}$Cl}M+H]$^+$), 231.2 ([{$^{35}$Cl}M+H]$^+$.

Example 190

(+)-(S)-4-(5-Chloro-2-fluoro-phenyl)-4,5-dihydro-oxazol-2-ylamine

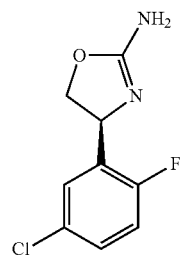 [SMILES: NC1=N[C@@H](c2cc(Cl)ccc2F)CO1]

(RS)-4-(5-chloro-2-fluoro-phenyl)-4,5-dihydro-oxazol-2-ylamine (example 19) was separated by chiral HPLC (Chiralpak AD, EtOH/heptane=10:90) to yield (+)-(S)-4-(5-chloro-2-fluoro-phenyl)-4,5-dihydro-oxazol-2-ylamine (white solid; MS (ISP): 217.1 ([{$^{37}$Cl}M+H]$^+$), 215.1 ([{$^{35}$Cl}M+H]$^+$)).

Examples 191 & 192

(−)-(R)-4-(3-Chloro-phenyl)-4,5-dihydro-oxazol-2-ylamine & (+)-(S)-4-(3-Chloro-phenyl)-4,5-dihydro-oxazol-2-ylamine

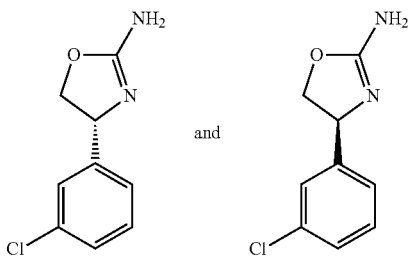 [SMILES: NC1=N[C@H](c2cccc(Cl)c2)CO1 ; NC1=N[C@@H](c2cccc(Cl)c2)CO1]

(RS)-4-(3-Chloro-phenyl)-4,5-dihydro-oxazol-2-ylamine (example 185) was separated by chiral HPLC (Chiralpak AD, EtOH/heptane=15:85) to yield (−)-(R)-4-(3-chloro-phenyl)-4,5-dihydro-oxazol-2-ylamine (light yellow solid; MS (ISP): 199.0 ([{$^{37}$Cl}M+H]$^+$), 197.0 ([{$^{35}$Cl}M+H]$^+$)) and (+)-(S)-4-(3-chloro-phenyl)-4,5-dihydro-oxazol-2-ylamine (light yellow solid; MS (ISP): 199.0 ([{$^{37}$Cl}M+H]$^+$), 197.0 ([{$^{35}$Cl}M+H]$^+$)).

In analogy to example 163 were prepared:

Example 193

(S)-4-[2-(3-Trifluoromethyl-phenyl)-propyl]-4,5-dihydro-oxazol-2-ylamine

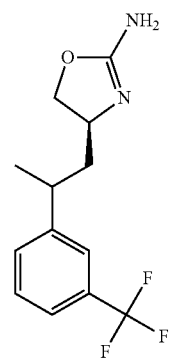 [SMILES: CC(C[C@H]1COC(N)=N1)c1cccc(C(F)(F)F)c1]

From (S)-4-(2,2-dibromo-vinyl)-2,2-dimethyl-oxazolidine-3-carboxylic acid tert-butyl ester by sequential treatment with 3-(trifluoromethyl)phenyl boronic acid and dimethylzinc. Mainly one epimer. Colourless oil. MS (ISP): 273.3 ([M+H]$^+$).

Example 194

(S)-4-[2-(3-Trifluoromethyl-phenyl)-butyl]-4,5-dihydro-oxazol-2-ylamine

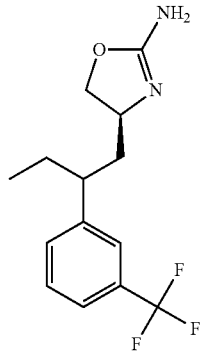 [SMILES: CCC(C[C@H]1COC(N)=N1)c1cccc(C(F)(F)F)c1]

From (S)-4-(2,2-dibromo-vinyl)-2,2-dimethyl-oxazolidine-3-carboxylic acid tert-butyl ester by sequential treatment with 3-(trifluoromethyl)phenyl boronic acid and diethylzinc. Mainly one epimer. Colourless oil. MS (ISP): 287.1 ([M+H]$^+$).

Example 195

(R)-4-Phenylsulfanylmethyl-4,5-dihydro-oxazol-2-ylamine

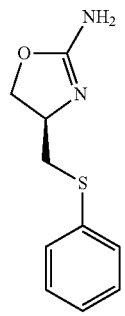 [SMILES: NC1=N[C@@H](CSc2ccccc2)CO1]

a) (R)-2-Amino-3-phenylsulfanyl-propionic acid methyl ester hydrochloride

To a solution of S-phenyl-L-cysteine (5.0 g, 25.4 mmol) in methanol (50 ml) was added acetylchloride (2.7 ml, 38 mmol) and the mixture was refluxed overnight. The solvent was evaporated and the residue was recrystallised from ethyl acetate/methanol (3:1) to yield a white solid (3.81 g, 61%). MS (ISP): 211.9 ([M+H]$^+$).

b) (R)-2-Amino-3-phenylsulfanyl-propan-1-ol

To a stirred suspension of (R)-2-amino-3-phenylsulfanyl-propionic acid methyl ester hydrochloride (0.50 g, 2.0 mmol) in tetrahydrofuran (10 ml) under an argon atmosphere was added slowly lithium aluminum hydride (0.153 g, 4.0 mmol) and the mixture was stirred overnight at room temperature. For work-up water (1.5 ml) and 2N sodium hydroxide solution (0.5 ml) were added and the mixture was stirred for 30 min. After filtration the solvent was evaporated and the residue was purified by column chromatography (column: Isolute® Flash-NH$_2$ from Separtis; eluent: heptane/EtOAc=1:1 to yield a light yellow oil, (0.095 g, 26%); MS (ISP): 183.9 ((M+H)$^{+\cdot}$).

c) (R)-4-Phenylsulfanylmethyl-4,5-dihydro-oxazol-2-ylamine

To a stirred mixture of (R)-2-amino-3-phenylsulfanyl-propan-1-ol (0.09 g, 0.49 mmol) and K$_2$CO$_3$ (0.081 g, 0.59 mmol) in THF (3 ml) under an argon atmosphere was added a solution of cyanogen bromide (0.062 g, 0.59 mmol) in THF (1 ml). The mixture was stirred overnight, then ethyl acetate and water were added. The aqueous phase was back-extracted with EtOAc. The combined organics were dried over MgSO$_4$, filtered and concentrated. The crude product was purified by column chromatography (column: Isolute® Flash-NH$_2$ from Separtis; eluent: EtOAc/MeOH=95:5) to yield a light yellow solid, (0.026 g, 26%); MS (ISP): 209.1 ((M+H)$^{+\cdot}$).

Example 196

(R)-4-(2-Fluoro-phenyl)-4-methyl-4,5-dihydro-oxazol-2-ylamine

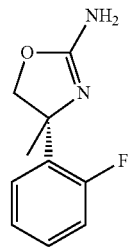

a) (RS)-4-(2-Fluoro-phenyl)-4-methyl-4,5-dihydro-oxazol-2-ylamine

In analogy to example 147, the title compound was obtained starting from 2'-fluoro-acetophenone. Viscous colorless oil.

MS (ISP): 195.1 ([M+H]$^+$)

b) (R)-4-(2-Fluoro-phenyl)-4-methyl-4,5-dihydro-oxazol-2-ylamine (RS)-4-(2-Fluoro-phenyl)-4-methyl-4,5-dihydro-oxazol-2-ylamine was separated by chiral HPLC (Chiralpak AD, EtOH/heptane 1:9) to give (R)-4-(2-fluoro-phenyl)-4-methyl-4,5-dihydro-oxazol-2-ylamine. (−)-Enantiomer. White solid.

MS (ISP): 195.1 ([M+H]$^+$))

Example 197

(S)-4-(2-Fluoro-phenyl)-4-methyl-4,5-dihydro-oxazol-2-ylamine

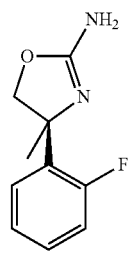

(RS)-4-(2-Fluoro-phenyl)-4-methyl-4,5-dihydro-oxazol-2-ylamine was separated by chiral HPLC (Chiralpak AD, EtOH/heptane 1:9) to give (S)-4-(2-fluoro-phenyl)-4-methyl-4,5-dihydro-oxazol-2-ylamine. (+)-Enantiomer. Off-white solid.

MS (ISP): 195.1 ([M+H]$^+$))

Example 198

(+)-(S)-4-(3-Bromo-phenyl)-4,5-dihydro-oxazol-2-ylamine

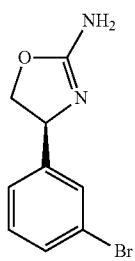 [SMILES: NC1=N[C@@H](c2cccc(Br)c2)CO1]

(RS)-4-(3-Bromo-phenyl)-4,5-dihydro-oxazol-2-ylamine (example 186) was separated by chiral HPLC (Chiralpak AD, EtOH/heptane=15:85) to yield (+)-(S)-4-(3-bromo-phenyl)-4,5-dihydro-oxazol-2-ylamine (white solid; MS (ISP): 243.2 ([{$^{81}$Br}M+H]$^+$), 241.1 ([{$^{79}$Br}M+H]$^+$)).

Example 199

(+)-(S)-4-(3-Fluoro-phenyl)-4,5-dihydro-oxazol-2-ylamine

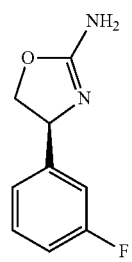

(RS)-4-(3-Fluoro-phenyl)-4,5-dihydro-oxazol-2-ylamine (example 188) was separated by chiral HPLC (Chiralpak AD, EtOH/heptane=15:85) to yield (+)-(S)-4-(3-fluoro-phenyl)-4,5-dihydro-oxazol-2-ylamine (white solid; MS (ISP): 181.1 ([M+H]$^+$)).

Examples 200 & 201

(−)-(R)-4-(3,5-Dichloro-phenyl)-4,5-dihydro-oxazol-2-ylamine & (+)-(S)-4-(3,5-Dichloro-phenyl)-4,5-dihydro-oxazol-2-ylamine

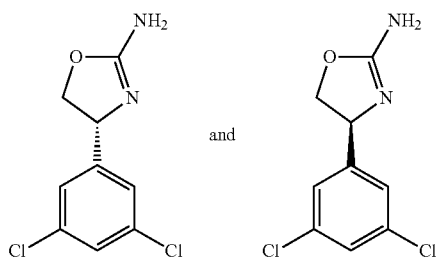 [SMILES: NC1=N[C@H](c2cc(Cl)cc(Cl)c2)CO1 ; NC1=N[C@@H](c2cc(Cl)cc(Cl)c2)CO1]

(RS)-4-(3,5-Dichloro-phenyl)-4,5-dihydro-oxazol-2-ylamine (example 189) was separated by chiral HPLC (Chiralpak AD, EtOH/heptane=15:85) to yield (−)-(R)-4-(3,5-dichloro-phenyl)-4,5-dihydro-oxazol-2-ylamine (white solid; MS (ISP): 235.1 ([{$^{37}$Cl}M+H]$^+$), 233.1 ([{$^{37}$Cl$^{35}$Cl}M+H]$^+$), 231.2 ([{$^{35}$Cl}M+H]$^+$)) and (+)-(S)-4-(3,5-dichloro-phenyl)-4,5-dihydro-oxazol-2-ylamine (white solid; MS (ISP): 235.1 ([{$^{37}$Cl}M+H]$^+$), 233.1 ([{$^{37}$Cl$^{35}$Cl}M+H]$^+$), 231.2 ([{$^{35}$Cl}M+H]$^+$)).

In analogy to example 163 were prepared:

Example 202

(S)-4-[2-(3,5-Difluoro-phenyl)-propyl]-4,5-dihydro-oxazol-2-ylamine

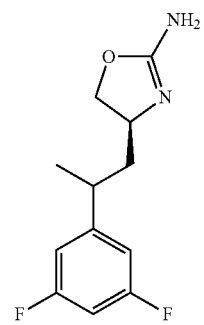 [SMILES: CC(C[C@H]1COC(N)=N1)c1cc(F)cc(F)c1]

From (S)-4-(2,2-dibromo-vinyl)-2,2-dimethyl-oxazolidine-3-carboxylic acid tert-butyl ester by sequential treatment with 3,5-difluorophenyl boronic acid and dimethylzinc. Mainly one epimer. Colourless oil. MS (ISP): 241.4 ([M+H]$^+$).

Example 203

(S)-4-[2-(3,5-Difluoro-phenyl)-butyl]-4,5-dihydro-oxazol-2-ylamine

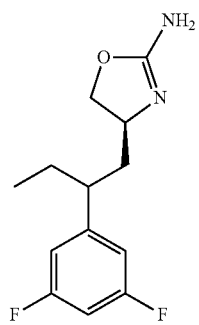 [SMILES: CCC(C[C@H]1COC(N)=N1)c1cc(F)cc(F)c1]

From (S)-4-(2,2-dibromo-vinyl)-2,2-dimethyl-oxazolidine-3-carboxylic acid tert-butyl ester by sequential treatment with 3,5-difluorophenyl boronic acid and diethylzinc. Mainly one epimer. Colourless oil. MS (ISP): 255.3 ([M+H]$^+$).

Example 204

(S)-4-(2,6-Difluoro-phenyl)-4-methyl-4,5-dihydro-oxazol-2-ylamine

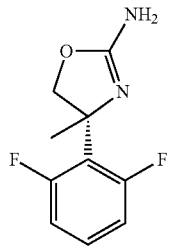

a) (RS)-4-(2,6-Difluoro-phenyl)-4-methyl-4,5-dihydro-oxazol-2-ylamine

In analogy to example 147, the title compound was obtained starting from 2',6'-difluoroacetophenone. White solid.

MS (ISP): 213.3 ([M+H]$^+$)

b) (S)-4-(2,6-Difluoro-phenyl)-4-methyl-4,5-dihydro-oxazol-2-ylamine (RS)-4-(2,6-Difluoro-phenyl)-4-methyl-4,5-dihydro-oxazol-2-ylamine was separated by chiral HPLC (Chiralpak AD, EtOH/heptane 1:9) to give (S)-4-(2,6-difluoro-phenyl)-4-methyl-4,5-dihydro-oxazol-2-ylamine. (−)-Enantiomer. White solid.

MS (ISP): 213.3 ([M+H]$^+$)

Example 205

(R)-4-(2,6-Difluoro-phenyl)-4-methyl-4,5-dihydro-oxazol-2-ylamine

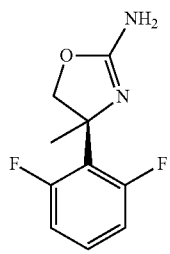

(RS)-4-(2,6-Difluoro-phenyl)-4-methyl-4,5-dihydro-oxazol-2-ylamine was separated by chiral HPLC (Chiralpak AD, EtOH/heptane 1:9) to give (R)-4-(2,6-difluoro-phenyl)-4-methyl-4,5-dihydrooxazol-2-ylamine. (+)-Enantiomer. White solid.

MS (ISP): 213.3 ([M+H]$^+$)

Example 206

(S)-4-(2,4-Difluoro-phenyl)-4-methyl-4,5-dihydro-oxazol-2-ylamine

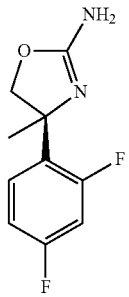

a) (RS)-(2-Amino-2-(2,4-difluoro-phenyl)-propionic acid hydrochloride

In analogy to example 147.a and 147.b, the title compound was obtained starting from 2',4'-difluoroacetophenone. White solid.

MS b) (RS)-2-Amino-2-(2,4-difluoro-phenyl)-propan-1-ol

To a stirred 2 M LiBH$_4$ solution (16.22 ml) at r.t. in THF under an argon atmosphere was added chlorotrimethylsilane (5.47 ml) over 2 min. The white suspension was cooled to 0° C. and (RS)-(2-amino-2-(2,4-difluoro-phenyl)-propionic acid hydrochloride (2.57 g) was added portionwise over 5 min. The ice bath was removed and the compact off-white suspension was stirred at r.t. for 20 h. The mixture was cooled again to 0° C. and treated carefully with methanol (15 ml). The mixture was stirred at r.t. for 30 min, filtered and the cake was washed with MeOH. The filtrate was concentrated. The crude product was purified by column chromatography (silica gel; gradient: CH$_2$Cl$_2$->CH$_2$Cl$_2$/MeOH 9:1) to give (RS)-2-amino-2-(2,4-difluoro-phenyl)-propan-1-ol (1.47 g, 73%) as colorless viscous oil.

MS (ISP): 188.3 ([M+H]$^+$)

c) (RS)-4-(2,4-Difluoro-phenyl)-4-methyl-4,5-dihydro-oxazol-2-ylamine

In analogy to example 1.b (RS)-2-amino-2-(2,4-difluoro-phenyl)-propan-1-ol was converted to the title compound. White solid.

MS (ISP): 213.3 ([M+H]$^+$)

d) (S)-4-(2,4-Difluoro-phenyl)-4-methyl-4,5-dihydro-oxazol-2-ylamine (RS)-4-(2,4-Difluoro-phenyl)-4-methyl-4,5-dihydro-oxazol-2-ylamine was separated by chiral HPLC (Chiralpak AD, EtOH/heptane 1:9) to give (S)-4-(2,4-difluoro-phenyl)-4-methyl-4,5-dihydro-oxazol-2-ylamine. (+)-Enantiomer. White solid.

MS (ISP): 213.1 ([M+H]$^+$)

Example 207

(R)-4-Benzenesulfonylmethyl-4,5-dihydro-oxazol-2-ylamine

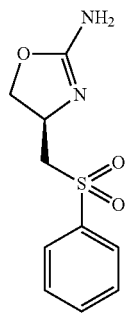

a) (R)-3-Benzenesulfonyl-2-tert-butoxycarbonylamino-propionic acid methyl ester To a stirred suspension of (R)-2-amino-3-phenylsulfanyl-propionic acid methyl ester hydrochloride (1.0 g, 4.0 mmol, Example 195a) in 1 M bicarbonate solution (10 ml) was added a solution of di-tert.-butyl dicarbonate (0.969 g, 4.4 mmol) in dioxane (10 ml) and the mixture was stirred at room temperature overnight. The solvents were evaporated and the residue was partitioned between water and ethyl acetate. The combined organic layers were dried (MgSO$_4$) and filtered and cooled to 0° C. Then meta-chloroperbenzoic acid (1.38 g, 10 mmol) was added slowly at 0° C. and the mixture was stirred for an additional 4 hours at room temperature. For work-up saturated sodium sulfite solution (6 ml) and saturated sodium bicarbonate solution (6 ml) were added. After stirring the mixture for additional 30 min it was extracted three times with ethyl acetate. The combined organic layers were dried (MgSO4), filtered and evaporated. The residue was purified by column chromatography (SiO$_2$, heptane/EtOAc=1:1) to yield a white solid, (1.068 g, 78%); MS (ISP): 344.0 ((M+H)$^{+/-}$); 244.0 ((M+H—BOC)$^{+\cdot}$).

b) ((R)-2-Benzenesulfonyl-1-hydroxymethyl-ethyl)-carbamic acid tert-butyl ester To a solution of lithium borohydride in tetrahydrofuran (2M, 1.14 ml, 2.28 mmol) was added slowly at 0° C. a solution of (R)-3-benzenesulfonyl-2-tert-butoxycarbonylamino-propionic acid methyl ester (0.52 g, 1.51 mmol) in tetrahydrofuran (3 ml). After stirring at room temperature for 2.5 hours methanol was added (0.5 ml). The mixture was partitioned between ethyl acetate and saturated ammoniumchloride solution. The combined organic layers were dried (MgSO$_4$), filtered and evaporated. The residue was purified by column chromatography (SiO$_2$, heptane/EtOAc=1:1 to yield a white solid, (0.292 g, 61%); MS (ISP): 316.0 ((M+H)$^{+/}$); 216.1 ((M+H—BOC)$^{+\cdot}$).

c) (R)-4-Benzenesulfonylmethyl-4,5-dihydro-oxazol-2-ylamine ((R)-2-Benzenesulfonyl-1-hydroxymethyl-ethyl)-carbamic acid tert-butyl ester (0.29 g, 0.92 mmol) was dissolved in ethanol (2 ml), hydrochloric acid in ethanol (5M, 5 ml) was added and the mixture was stirred at 60° C. for 3 hours. The solvent was evaporated and the residue was taken up in tetrahydrofuran (5 ml). K$_2$CO$_3$ (0.326 g, 2.36 mmol) and cyanogen bromide (0.136 g, 1.29 mmol) were added. The mixture was stirred overnight and afterwards partitioned between ethyl acetate and water. The combined organic layers were dried (MgSO$_4$), filtered and evaporated. The residue was purified by column chromatography (SiO$_2$, EtOAc/MeOH=95:5 to yield a white solid, (0.062 g, 28%); MS (ISP): 241.1 ((M+H)$^{+\cdot}$).

In analogy to example 163 were prepared:

Example 208

(S)-4-[3-Methyl-2-(3-trifluoromethyl-phenyl)-butyl]-4,5-dihydro-oxazol-2-ylamine

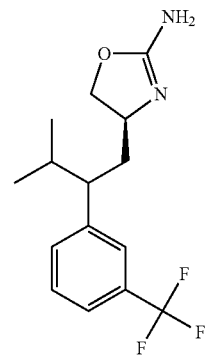 [SMILES: CC(C)C(C[C@H]1COC(N)=N1)c1cccc(C(F)(F)F)c1]

From (S)-4-(2,2-dibromo-vinyl)-2,2-dimethyl-oxazolidine-3-carboxylic acid tert-butyl ester by sequential treatment with 3-(trifluoromethyl)phenyl boronic acid and diisopropylzinc. Mainly one epimer. Colourless oil. MS (ISP): 301.5 ([M+H]$^+$).

Example 209

(S)-4-[2-(3,5-Difluoro-phenyl)-3-methyl-butyl]-4,5-dihydro-oxazol-2-ylamine

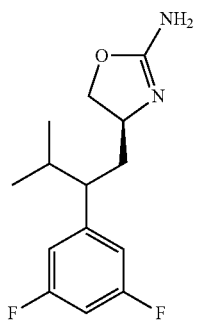 [SMILES: CC(C)C(C[C@H]1COC(N)=N1)c1cc(F)cc(F)c1]

From (S)-4-(2,2-dibromo-vinyl)-2,2-dimethyl-oxazolidine-3-carboxylic acid tert-butyl ester by sequential treatment with 3,5-difluorophenyl boronic acid and diisopropylzinc. Mainly one epimer. Colourless oil. MS (ISP): 269.5 ([M+H]$^+$).

Example 210

(S)-4-[2-(4-Fluoro-phenyl)-butyl]-4,5-dihydro-oxazol-2-ylamine

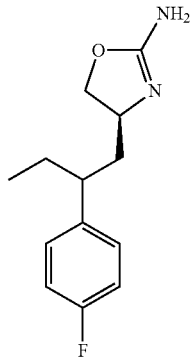 [SMILES: CCC(C[C@H]1COC(N)=N1)c1ccc(F)cc1]

From (S)-4-(2,2-dibromo-vinyl)-2,2-dimethyl-oxazolidine-3-carboxylic acid tert-butyl ester by sequential treatment with 4-fluorophenyl boronic acid and diethylzinc. Mainly one epimer. Colourless oil. MS (ISP): 237.1 ([M+H]$^+$).

Example 211

(S)-4-[2-(3,4-Difluoro-phenyl)-butyl]-4,5-dihydro-oxazol-2-ylamine

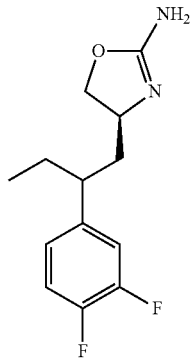 [SMILES: CCC(C[C@H]1COC(N)=N1)c1ccc(F)c(F)c1]

From (S)-4-(2,2-dibromo-vinyl)-2,2-dimethyl-oxazolidine-3-carboxylic acid tert-butyl ester by sequential treatment with 3,4-difluorophenyl boronic acid and diethylzinc. Mainly one epimer. Colourless oil. MS (ISP): 255.4 ([M+H]$^+$).

Example 212

(S)-4-[2-(6-Trifluoromethyl-pyridin-2-yl)-ethyl]-4,5-dihydro-oxazol-2-ylamine

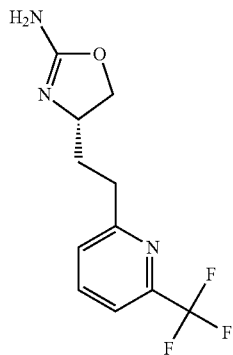 [SMILES: NC1=N[C@@H](CCc2cccc(C(F)(F)F)n2)CO1]

a) (S)-2,2-Dimethyl-4-(6-trifluoromethyl-pyridin-2-ylethynyl)-oxazolidine-3-carboxylic acid tert-butyl ester To a solution of tert.-butyl (4S)-4-ethinyl-2,2-dimethyl-1,3-oxazolidine-3-carboxylate (0.9 g, 4.0 mmol) in triethylamine (8 ml) were added 2-bromo-6-trifluoromethyl)pyridine (0.9 g, 4.0 mmol), copper(I) iodide (0.076 g, 0.4 mmol) and bis(triphenylphosphine)palladium(II) chloride (0.281 g, 0.4 mmol) and the mixture was stirred for 1 hour at room temperature. The solvent was evaporated, ether was added and the brown suspension was filtered through Celite. The filtrate was evaporated and purified by column chromatography (SiO$_2$, heptane/EtOAc=1:1 to yield an orange solid, (1.0 g, 67.5%); MS (ISP): 371.4 ((M+H)$^+$).

b) (S)-2,2-Dimethyl-4-[2-(6-trifluoromethyl-pyridin-2-yl)-ethyl]-oxazolidine-3-carboxylic acid tert-butyl ester To a solution of (S)-2,2-dimethyl-4-(6-trifluoromethyl-pyridin-2-ylethynyl)-oxazolidine-3-carboxylic acid tert-butyl ester (0.58 g, 1.56 mmol) in methanol (8 ml) were added ammonium formate (0.983 g, 15.6 mmol) and palladium on charcoal (10% Pd, 0.58 g). The mixture was refluxed for 1 hour. After cooling the solid was filtered off, the filtrate was evaporated and the residue was purified by column chromatography (SiO$_2$, heptane/EtOAc=7:3 to yield a light colourless liquid, (0.538 g, 92%); MS (ISP): 375.5 ((M+H)$^+$).

c) (S)-2-Amino-4-(6-trifluoromethyl-pyridin-2-yl)-butan-1-ol (S)-2,2-Dimethyl-4-[2-(6-trifluoromethyl-pyridin-2-yl)-ethyl]-oxazolidine-3-carboxylic acid tert-butyl ester (0.522 g, 1.39 mmol) was dissolved in ethanol (2.5 ml), hydrochloric acid in ethanol (5N, 2.5 ml) was added and the mixture was stirred at 60° C. for 2 hours. The solvent was evaporated and the residue was dissolved in dichloromethane. A solution of ammonia in methanol (2N, 2 ml) was added and the mixture was evaporated over Isolute® Flash-NH$_2$ silicagel. Chromatography (column: Isolute® Flash-NH$_2$ from Separtis; eluent: ethyl acetate/MeOH=90:10) yielded a colourless liquid, (0.237 g, 73%); MS (ISP): 235.1 ((M+H)$^+$).

d) (S)-4-[2-(6-Trifluoromethyl-pyridin-2-yl)-ethyl]-4,5-dihydro-oxazol-2-ylamine To a stirred mixture of (S)-2-amino-4-(6-trifluoromethyl-pyridin-2-yl)-butan-1-ol (0.224 g, 0.96 mmol) and K$_2$CO$_3$ (0.198 g, 1.43 mmol) in THF (7 ml) under an argon atmosphere was added a solution of cyanogen bromide (0.152 g, 1.05 mmol) in THF (1 ml). The mixture was stirred for 18 hours, then water and ethyl acetate were added. The organic layer was washed with water, dried over MgSO$_4$ and evaporated over Isolute® Flash-NH$_2$ silicagel. Chromatography (column: Isolute® Flash-NH$_2$ from Separtis; eluent: ethyl acetate/MeOH=90:10) yielded the title compound as off-white solid, (0.096 g, 39%); MS (ISP): 260.0 ((M+H)$^+$).
In analogy to example 87 was prepared:

Example 213

(S)-4-(4-Fluoro-phenoxymethyl)-4,5-dihydro-oxazol-2-ylamine

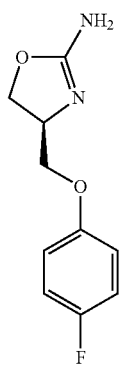 [SMILES: NC1=N[C@@H](COc2ccc(F)cc2)CO1]

From tert-butyl (S)-4-(hydroxymethyl)-2,2-dimethyl-3-oxazolidinecarboxylate and 4-fluorophenol. Colourless viscous oil.
MS (ISP): 211.1 ([M+H]$^+$).

Example 214

(R)-4-(2-Fluoro-4-trifluoromethyl-phenyl)-4-methyl-4,5-dihydro-oxazol-2-ylamine

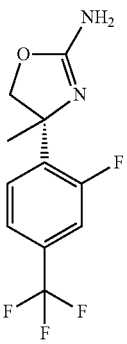 [SMILES: C[C@@]1(c2ccc(C(F)(F)F)cc2F)COC(N)=N1]

a) (RS)-4-(2-Fluoro-4-trifluoromethyl-phenyl)-4-methyl-4,5-dihydro-oxazol-2-ylamine In analogy to example 206, the title compound was obtained starting from 2'-fluoro-4'-(trifluoromethyl)acetophenone. White solid.
MS (ISP): 263.3 ([M+H]$^+$)

b) (R)-4-(2-Fluoro-4-trifluoromethyl-phenyl)-4-methyl-4,5-dihydro-oxazol-2-ylamine (RS)-4-(2-Fluoro-4-trifluoromethyl-phenyl)-4-methyl-4,5-dihydro-oxazol-2-ylamine was separated by chiral HPLC (Chiralpak AD, EtOH/heptane 5:95) to give (R)-4-(2-fluoro-4-trifluoromethyl-phenyl)-4-methyl-4,5-dihydro-oxazol-2-ylamine. (−)-Enantiomer. Colorless viscous oil.
MS (ISP): 263.0 ([M+H]$^+$)

Example 215

(S)-4-(2-Fluoro-4-trifluoromethyl-phenyl)-4-methyl-4,5-dihydro-oxazol-2-ylamine

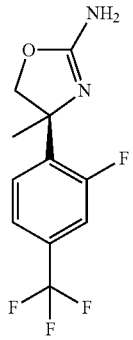

(RS)-4-(2-Fluoro-4-trifluoromethyl-phenyl)-4-methyl-4,5-dihydro-oxazol-2-ylamine was separated by chiral HPLC (Chiralpak AD, EtOH/heptane 5:95) to give (S)-4-(2-fluoro-4-trifluoromethyl-phenyl)-4-methyl-4,5-dihydro-oxazol-2-ylamine. (+)-Enantiomer. Colorless viscous oil.
MS (ISP): 263.0 ([M+H]$^+$)
In analogy to example 87 was prepared:

Example 216

(S)-4-(4-Chloro-phenoxymethyl)-4,5-dihydro-oxazol-2-ylamine

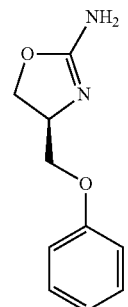

From tert-butyl (S)-4-(hydroxymethyl)-2,2-dimethyl-3-oxazolidinecarboxylate and 4-chlorophenol. White solid.
MS (ISP): 229.3 ([{$^{37}$Cl}M+H]$^+$), 227.1 ([{$^{35}$Cl}M+H]$^+$).
In analogy to example 163 was prepared:

Example 217

(S)-4-[2-(2-Fluoro-phenyl)-propyl]-4,5-dihydro-oxazol-2-ylamine

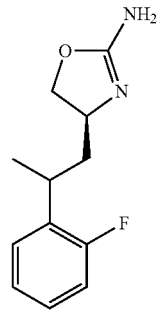 [SMILES: CC(C[C@H]1COC(N)=N1)c1ccccc1F]

From (S)-4-(2,2-dibromo-vinyl)-2,2-dimethyl-oxazolidine-3-carboxylic acid tert-butyl ester by sequential treatment with 2-fluorophenyl boronic acid and dimethylzinc. Mainly one epimer. White crystalline solid. MS (ISP): 223.3 ([M+H]+).

Example 218

(R)-4-Methyl-4-(3-trifluoromethyl-phenyl)-4,5-dihydro-oxazol-2-ylamine

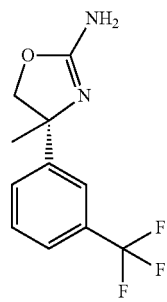 [SMILES: C[C@@]1(c2cccc(C(F)(F)F)c2)COC(N)=N1]

a) ((RS)-4-Methyl-4-(3-trifluoromethyl-phenyl)-4,5-dihydro-oxazol-2-ylamine

In analogy to example 206, the title compound was obtained starting from 2'-fluoro-4'-(trifluoromethyl)acetophenone. Viscous colorless oil.

MS (ISP): 245.1 ([M+H]+)

b) (R)-4-Methyl-4-(3-trifluoromethyl-phenyl)-4,5-dihydro-oxazol-2-ylamine (RS)-4-Methyl-4-(3-trifluoromethyl-phenyl)-4,5-dihydro-oxazol-2-ylamine was separated by chiral HPLC (Chiralpak AD, EtOH/heptane 5:95) to give (R)-4-methyl-4-(3-trifluoromethyl-phenyl)-4,5-dihydro-oxazol-2-ylamine. (−)-Enantiomer. Colorless viscous oil.

MS (ISP): 245.1 ([M+H]+)

Example 219

(S)-4-Methyl-4-(3-trifluoromethyl-phenyl)-4,5-dihydro-oxazol-2-ylamine

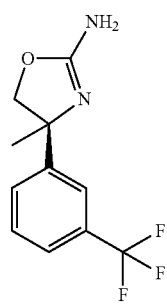 [SMILES: C[C@]1(c2cccc(C(F)(F)F)c2)COC(N)=N1]

(RS)-4-Methyl-4-(3-trifluoromethyl-phenyl)-4,5-dihydro-oxazol-2-ylamine was separated by chiral HPLC (Chiralpak AD, EtOH/heptane 5:95) to give (S)-4-methyl-4-(3-trifluoromethyl-phenyl)-4,5-dihydro-oxazol-2-ylamine. (+)-Enantiomer. Colorless viscous oil.

MS (ISP): 245.1 ([M+H]+)

Example 220

(S)-4-[2-(2-Methyl-pyridin-4-yl)-ethyl]-4,5-dihydro-oxazol-2-ylamine

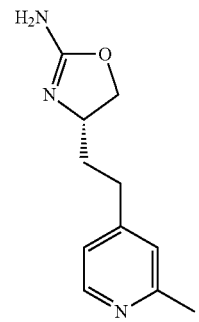

The title compound, MS (ISP): 206.1 ((M+H)+·) was obtained in comparable yield analogous to the procedure described for Example 212 using 4-bromo-2-methylpyridine instead of 2-bromo-6-trifluoromethyl)pyridine in step a).

Example 221

(S)-4-[2-(3,4-Dichloro-phenyl)-propyl]-4,5-dihydro-oxazol-2-ylamine

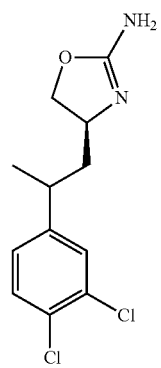 [SMILES: CC(C[C@H]1COC(N)=N1)c1ccc(Cl)c(Cl)c1]

a) (E)-(S)-2-Amino-4-phenyl-hex-3-en-1-ol

In analogy to example 162a-d (R)-4-formyl-2,2-dimethyl-oxazolidine-3-carboxylic acid tert-butyl ester was treated sequentially with triphenylphosphine/carbon tetrabromide, 3,4-dichlorophenylboronic acid, dimethyl zinc and hydrogen chloride to give (E)-(S)-2-amino-4-phenyl-hex-3-en-1-ol. Yellow oil.

b) (S)-2-Amino-4-(3,4-dichloro-phenyl)-pentan-1-ol

To a stirred solution of (E)-(S)-2-amino-4-phenyl-hex-3-en-1-ol (390 mg) at r.t. in THF (50 ml) under an argon atmosphere were added 10% Pd/C (280 mg) and zinc bromide (36 mg). The mixture was stirred at r.t. under a hydrogen atmosphere for 16. The catalyst was filtered off and the filtrate was concentrated in vacuo. The residue was purified by column chromatography (SiO$_2$; gradient: dichloromethane/methanol) to give (S)-2-amino-4-(3,4-dichloro-phenyl)-pentan-1-ol (mainly one epimer) (69 mg, 18%) as a colourless oil. MS (ISP): 252.2 ([{$^{37}$Cl}M+H]+), 250.2 ([{$^{37}$Cl$^{35}$Cl}M+H]+), 248.1 ([{$^{35}$Cl}M+H]+).

c) (S)-4-[2-(3,4-Dichloro-phenyl)-propyl]-4,5-dihydro-oxazol-2-ylamine

In analogy to example 1b (S)-2-amino-4-(3,4-dichlorophenyl)-pentan-1-ol was reacted with cyanogen bromide to give (5)-4-[2-(3,4-dichloro-phenyl)-propyl]-4,5-dihydro-oxazol-2-ylamine (mainly one epimer). Colourless oil. MS (ISP): 277.1 ([{$^{37}$Cl}M+H]$^+$), 275.0 ([{$^{37}$Cl$^{35}$Cl}M+H]$^+$), 273.1 ([{$^{35}$Cl}M+H]$^+$).

In analogy to example 221 was prepared:

Example 222

(S)-4-[2-(3,4-Dichloro-phenyl)-butyl]-4,5-dihydro-oxazol-2-ylamine

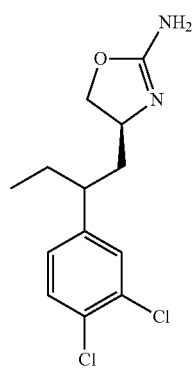

From (S)-4-(2,2-dibromo-vinyl)-2,2-dimethyl-oxazolidine-3-carboxylic acid tert-butyl ester by sequential treatment with 3,4-dichlorophenyl boronic acid and diethylzinc. Mainly one epimer. Colourless oil. MS (ISP): 291.1 ([{$^{37}$Cl}M+H]$^+$), 289.0 ([{$^{37}$Cl$^{35}$Cl}M+H]$^+$), 287.1 ([{$^{35}$Cl}M+H]$^+$).

In analogy to example 163 was prepared:

Example 223

(S)-4-[2-(2-Fluoro-phenyl)-butyl]-4,5-dihydro-oxazol-2-ylamine

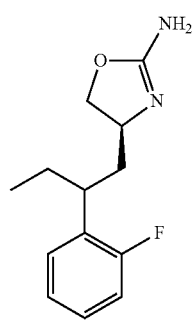 [SMILES: CCC(C[C@H]1COC(N)=N1)c1ccccc1F]

From (S)-4-(2,2-dibromo-vinyl)-2,2-dimethyl-oxazolidine-3-carboxylic acid tert-butyl ester by sequential treatment with 2-fluorophenyl boronic acid and diethylzinc. Mainly one epimer. Courless oil. MS (ISP): 237.1 ([M+H]$^+$).

Example 224

(RS)-4-(4-Fluoro-2-trifluoromethyl-phenyl)-4,5-dihydro-oxazol-2-ylamine

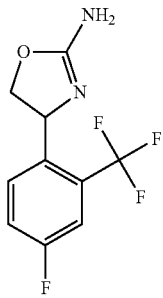 [SMILES: NC1=NC(c2ccc(F)cc2C(F)(F)F)CO1]

a) (RS)-Amino-(4-fluoro-2-trifluoromethyl-phenyl)-acetonitrile

To a stirred solution of 4-fluoro-2-(trifluoromethyl)benzaldehyde (5.0 g) in methanol (20 ml) were added sequentially ammonia solution (28.9 ml, 7 M solution in methanol) and tetraisopropyl orthotitanate (9.0 ml) and the resulting mixture was stirred at r.t. for 1 h. Trimethylsilylcyanide (3.3 ml) was then added dropwise and stirring continued at r.t. overnight. The reaction mixture was poured onto ice-water (400 ml) and the mixture was then extracted twice with ethyl acetate. The combined organic phases were washed with brine and then dried over sodium sulphate and concentrated in vacuo to afford (RS)-amino-(4-fluoro-2-trifluoromethyl-phenyl)-acetonitrile (4.48 g, 81%) as an orange viscous oil. MS (ISP): 219.1 ([M+H]$^+$).

b) (RS)-2-Amino-2-(4-fluoro-2-trifluoromethyl-phenyl)-acetamide hydrochloride

A solution of (RS)-amino-(4-fluoro-2-trifluoromethyl-phenyl)-acetonitrile (4.47 g) in formic acid (15 ml) saturated with hydrogen chloride was stirred at room temperature for 90 min. The mixture was then concentrated in vacuo and the residue was resuspended in acetone whereby white crystals formed The crystals were collected by filtration, washed with acetone and dried in vacuo to afford (RS)-2-amino-2-(4-fluoro-2-trifluoromethyl-phenyl)-acetamide hydrochloride (1.40 g, 25%) as a white solid. MS (ISP): 273.1 ([M+H]$^+$).

c) (RS)-Amino-(4-fluoro-2-trifluoromethyl-phenyl)-acetic acid 2-amino-2-(4-fluoro-2-trifluoromethyl-phenyl)-acetamide hydrochloride (1.39 g) was suspended in 5 N aq hydrochloric acid (15 ml) and the mixture was heated at reflux for 3 h. The mixture was then concentrated in vacuo, and the residue was resuspended in isopropanol and concentrated in vacuo again. The residue was taken up in water and neutralised by dropwise addition of 1 N aq NaOH, whereby white crystals slowly formed. The crystals were collected by filtration and dried in vacuo at 50° C. to afford (RS)-amino-(4-fluoro-2-trifluoromethyl-phenyl)-acetic acid (0.75 g, 62%) as a white solid. MS (ISP): 237.9 ([M+H]$^+$).

d) (RS)-2-Amino-2-(4-fluoro-2-trifluoromethyl-phenyl)-ethanol

In analogy to example 185.a (RS)-amino-(4-fluoro-2-trifluoromethyl-phenyl)-acetic acid was converted to (RS)-2-amino-2-(4-fluoro-2-trifluoromethyl-phenyl)-ethanol by treatment with lithium borohydride and chlorotrimethylsilane. Light yellow oil. MS (ISP): 224.3 ([M+H]$^+$).

e) (RS)-4-(4-Fluoro-2-trifluoromethyl-phenyl)-4,5-dihydro-oxazol-2-ylamine

In analogy to example 1.b (RS)-2-amino-2-(4-fluoro-2-trifluoromethyl-phenyl)-ethanol was converted to (RS)-4-(4-fluoro-2-trifluoromethyl-phenyl)-4,5-dihydro-oxazol-2-ylamine by treatment with cyanogen bromide and potassium carbonate. White solid. MS (ISP): 249.1 ([M+H]+).

In analogy to example 224 and starting from the respective aldehyde were prepared:

Example 225

(RS)-4-(5-Chloro-2-trifluoromethyl-phenyl)-4,5-dihydro-oxazol-2-ylamine

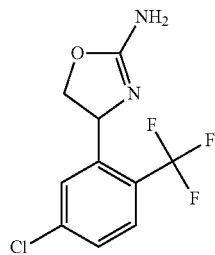 [SMILES: NC1=NC(c2cc(Cl)ccc2C(F)(F)F)CO1]

From 5-chloro-2-(trifluoromethyl)benzaldehyde. Off-white solid.
MS (ISP): 267.1 ([{37Cl}M+H]+), 265.0 ([{35Cl}M+H]+).

Example 226

(RS)-4-(4-Chloro-2-trifluoromethyl-phenyl)-4,5-dihydro-oxazol-2-ylamine

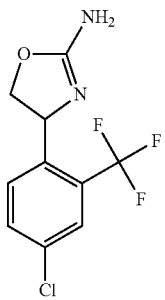 [SMILES: NC1=NC(c2ccc(Cl)cc2C(F)(F)F)CO1]

From 4-chloro-2-(trifluoromethyl)benzaldehyde. White solid.
MS (ISP): 267.1 ([{37Cl}M+H]+), 265.0 ([{35Cl}M+H]+).

Example 227

(RS)-4-Methyl-4-(2,3,5-trifluoro-phenyl)-4,5-dihydro-oxazol-2-ylamine

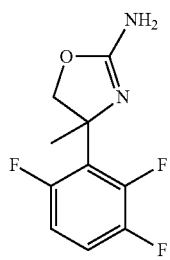 [SMILES: CC1(c2c(F)ccc(F)c2F)COC(N)=N1]

In analogy to example 206, the title compound was obtained starting from 2,3,5-trifluoroacetophenone. White solid.
MS (ISP): 231.1 ([M+H]+)

Example 228

(S)-4-[2-(2-Chloro-phenyl)-ethyl]-4-methyl-4,5-dihydro-oxazol-2-ylamine

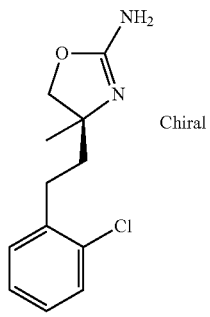 [SMILES: C[C@]1(CCc2ccccc2Cl)COC(N)=N1]

a) (2S,5R)-2-[2-(2-Chloro-phenyl)-ethyl]-5-isopropyl-3,6-dimethoxy-2-methyl-2,5-dihydro-pyrazine A solution of (R)-(−)-2,5-dihydro-3,6-dimethoxy-2-isopropyl-5-methylpyrazine (1.0 g, 5.0 mmol) in tetrahydrofuran (23 ml) was cooled to −70° C., then tert.butyllithium (1.7 M in pentane, 3.26 ml, 5.55 mmol) was added and the mixture was stirred for 1 hour. A solution of 1-(2-bromo-ethyl)-2-chlorobenzene (1.44 g, 6.56 mmol) in tetrahydrofuran (10 ml) was added slowly and the mixture was stirred overnight at −70° C. At room temperature saturated ammonium chloride solution was added and the mixture was extracted three times with ether. The combined organic layers were dried (MgSO4), filtered and evaporated. The residue was purified by column chromatography (SiO2, heptane/EtOAc=1:1 to yield an orange solid, (1.22 g, 72%); MS (ISP): 337.1; 339.1 ((M+H)+·).

b) (S)-2-Amino-4-(2-chloro-phenyl)-2-methyl-butyric acid methyl ester

To a solution of (2S,5R)-2-[2-(2-chloro-phenyl)-ethyl]-5-isopropyl-3,6-dimethoxy-2-methyl-2,5-dihydro-pyrazine (1.22 g, 3.62 mmol) in acetonitrile (12 ml) were added water (4 ml) and trifluoroacetic acid (2 ml). The mixture was stirred overnight at 40° C. Saturated ammonium chloride solution was added and the mixture was extracted with dichloromethane three times. The combined organic layers were dried (MgSO4), filtered and evaporated. The residue was purified by column chromatography (SiO2, EtOAc/MeOH=95:5 to yield a colorless oil, (0.46 g, 52%); MS (ISP): 242.1; 244.1 ((M+H)+·).

c) (S)-2-Amino-4-(2-chloro-phenyl)-2-methyl-butan-1-ol

To a suspension of lithium aluminum hydride (0.072 g, 1.9 mmol) in tetrahydrofuran (10 ml) was added a solution of (S)-2-amino-4-(2-chloro-phenyl)-2-methyl-butyric acid methyl ester (0.23 g, 0.95 mmol) in tetrahydrofuran (3 ml) and the mixture was stirred for 2 hours. Sodium sulphate solution (2M, 0.3 ml) was added and the mixture was filtered through Celite. The solvent was evaporated and the residue was purified by chromatography (column: Isolute® Flash- NH₂ from Separtis; eluent: ethyl acetate/MeOH=95:5) to yield a colourless oil, (0.190 g, 93%);
MS (ISP): 214.0; 216.0 ((M+H)⁺·).

d) (S)-4-[2-(2-Chloro-phenyl)-ethyl]-4-methyl-4,5-dihydro-oxazol-2-ylamine

To a stirred mixture of (S)-2-amino-4-(2-chloro-phenyl)-2-methyl-butan-1-ol (0.190 g, 0.89 mmol) and K₂CO₃ (0.155 g, 1.12 mmol) in THF (10 ml) under an argon atmosphere was added a solution of cyanogen bromide (0.119 g, 1.12 mmol) in THF (1 ml). The mixture was stirred for 18 hours, then water and ethyl acetate were added. The organic layer was washed with water, dried over MgSO₄ and evaporated over Isolute® Flash-NH₂ silica gel. Chromatography (column: Isolute® Flash-NH₂ from Separtis; eluent: ethyl acetate/MeOH=90:10) yielded the title compound as off-white solid, (0.070 g, 33%); MS (ISP): 239.2; 241.2 ((M+H)⁺·).
In analogy to example 224 and starting from the respective aldehyde was prepared:

Example 229

(RS)-4-(4-Methoxy-2-trifluoromethyl-phenyl)-4,5-dihydro-oxazol-2-ylamine

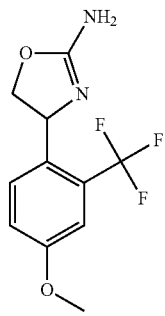 [SMILES: COc1ccc(C2COC(N)=N2)c(C(F)(F)F)c1]

From 4-methoxy-2-(trifluoromethyl)benzaldehyde. White solid.
MS (ISP): 261.1 ([M+H]⁺).

Example 230

(R)-4-(4-Bromo-phenyl)-4-methyl-4,5-dihydro-oxazol-2-ylamine

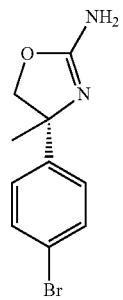

a) (RS)-4-(4-Bromo-phenyl)-4-methyl-4,5-dihydro-oxazol-2-ylamine

In analogy to example 147, the title compound was obtained starting from 4-bromoacetophenone. White solid.
MS (ISP): 255.1 ([M+H]⁺)

b) (R)-4-(4-Bromo-phenyl)-4-methyl-4,5-dihydro-oxazol-2-ylamine (RS)-4-(4-Bromo-phenyl)-4-methyl-4,5-dihydro-oxazol-2-ylamine was separated by chiral HPLC (Chiralpak AD, EtOH/heptane 20:80) to give (R)-4-(4-bromo-phenyl)-4-methyl-4,5-dihydro-oxazol-2-ylamine. (−)-Enantiomer. White solid.
MS (ISP): 255.1 ([M+H]⁺)

Example 231

(S)-4-(4-Bromo-phenyl)-4-methyl-4,5-dihydro-oxazol-2-ylamine

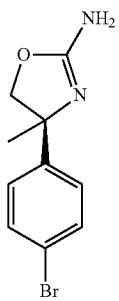

(RS)-4-(4-Bromo-phenyl)-4-methyl-4,5-dihydro-oxazol-2-ylamine was separated by chiral HPLC (Chiralpak AD, EtOH/heptane 20:80) to give (S)-4-(4-bromo-phenyl)-4-methyl-4,5-dihydro-oxazol-2-ylamine. (+)-Enantiomer. White solid.
MS (ISP): 255.2 ([M+H]⁺)

Example 232

(S)-4-[2-(3-Chloro-phenyl)-ethyl]-4,5-dihydro-oxazol-2-ylamine

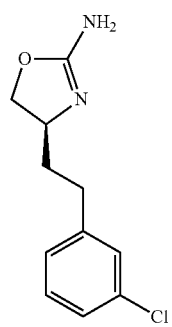 [SMILES: NC1=N[C@@H](CCc2cccc(Cl)c2)CO1]

a) (R)-4-(Benzothiazol-2-ylsulfanyl-methyl)-2,2-dimethyl-oxazolidine-3-carboxylic acid tert-butyl ester In analogy to example 83a. from (R)-4-hydroxymethyl-2,2-dimethyl-oxazolidine-3-carboxylic acid tert-butyl ester. Yellow viscous oil.

b) (R)-4-(Benzothiazole-2-sulfonylmethyl)-2,2-dimethyl-oxazolidine-3-carboxylic acid tert-butyl ester In analogy to example 83b. from (R)-4-(benzothiazol-2-ylsulfanyl-methyl)-2,2-dimethyl-oxazolidine-3-carboxylic acid tert-butyl ester. Off-white solid. MS (ISP): 413.3 ([M+H]⁺)).

c) (S)-4-[(E)-2-(3-Chloro-phenyl)-vinyl]-2,2-dimethyl-oxazolidine-3-carboxylic acid tert-butyl ester In analogy to example 83c. from (R)-4-(benzothiazole-2-sulfonylmethyl)-2,2-dimethyl-oxazolidine-3-carboxylic acid tert-butyl ester and 3-chloro-benzaldehyde. Off-white solid. MS (ISP): 340.2 ([{$^{37}$Cl}M+H]$^+$), 338.2 ([{$^{35}$Cl}M+H]$^+$).

d) (E)-(S)-2-Amino-4-(3-chloro-phenyl)-but-3-en-1-ol

In analogy to example 83e. from (S)-4-[(E)-2-(3-chloro-phenyl)-vinyl]-2,2-dimethyl-oxazolidine-3-carboxylic acid tert-butyl ester. Off-white solid.

e) (S)-2-Amino-4-(3-chloro-phenyl)-butan-1-ol

To a stirred solution of (E)-(S)-2-amino-4-(3-chloro-phenyl)-but-3-en-1-ol (155 mg) at r.t. in ethanol (5 ml) under an argon atmosphere was added 5% Pt/C (16 mg). The mixture was stirred at r.t. under a hydrogen atmosphere for 20 hrs. The catalyst was filtered off and the filtrate was concentrated to give (S)-2-amino-4-(3-chloro-phenyl)-butan-1-ol (102 mg, 65%) as light yellow oil. MS (ISP): 202.2 ([{$^{37}$Cl}M+H]$^+$), 200.2 ([{$^{35}$Cl}M+H]$^+$).

f) (S)-4-[2-(3-Chloro-phenyl)-ethyl]-4,5-dihydro-oxazol-2-ylamine

In analogy to example 1b (S)-2-amino-4-(3-chloro-phenyl)-butan-1-ol was reacted with cyanogen bromide to give (S)-4-[2-(3-chloro-phenyl)-ethyl]-4,5-dihydro-oxazol-2-ylamine. Light yellow viscous oil. MS (ISP): 227.2 ([{$^{37}$Cl}M+H]$^+$), 225.1 ([{$^{35}$Cl}M+H]$^+$).

In analogy to example 224 and starting from the respective aldehyde were prepared:

Example 233

(RS)-4-(3-Chloro-2-fluoro-6-trifluoromethyl-phenyl)-4,5-dihydro-oxazol-2-ylamine

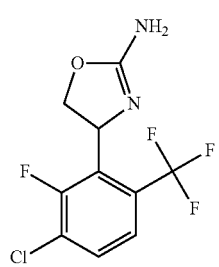 [SMILES: NC1=NC(c2c(C(F)(F)F)ccc(Cl)c2F)CO1]

From 3-chloro-2-fluoro-6-(trifluoromethyl)benzaldehyde. White solid.
MS (ISP): 284.9 ([{$^{37}$Cl}M+H]$^+$), 283.1 ([{$^{35}$Cl}M+H]$^+$).

Example 234

(RS)-4-(4,5-Dichloro-2-trifluoromethyl-phenyl)-4,5-dihydro-oxazol-2-ylamine

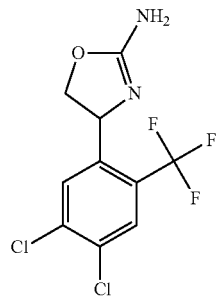 [SMILES: NC1=NC(c2cc(Cl)c(Cl)cc2C(F)(F)F)CO1]

From 4,5-dichloro-2-(trifluoromethyl)benzaldehyde. Orange solid.
MS (ISP): 303.0 ([{$^{37}$Cl}M+H]$^+$), 301.0 ([{$^{37}$Cl$^{35}$Cl}M+H]$^+$), 299.0 ([{$^{35}$Cl}M+H]$^+$).

In analogy to example 185 and starting from the respective amino acid or amino acid derivative was prepared:

Example 235

(RS)-4-(2,4-Dichloro-phenyl)-4,5-dihydro-oxazol-2-ylamine

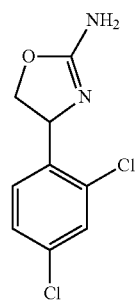 [SMILES: NC1=NC(c2ccc(Cl)cc2Cl)CO1]

From amino-(2,4-dichloro-phenyl)-acetic acid. White solid.
MS (ISP): 235.1 ([{$^{37}$Cl}M+H]$^+$), 233.1 ([{$^{37}$Cl$^{35}$Cl}M+H]$^+$), 231.2 ([{$^{35}$Cl}M+H]$^+$).

Example 236

(S)-4-(4-Chloro-3-fluoro-phenyl)-4-methyl-4,5-dihydro-oxazol-2-ylamine

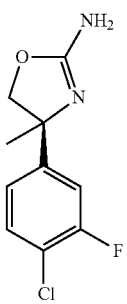

a) (RS)-4-(4-Chloro-3-fluoro-phenyl)-4-methyl-4,5-dihydro-oxazol-2-ylamine

In analogy to example 206, the title compound was obtained starting from 4-bromoacetophenone. White solid.
MS (ISP): 229.4 ([M+H]$^+$)

b) (S)-4-(4-Chloro-3-fluoro-phenyl)-4-methyl-4,5-dihydro-oxazol-2-ylamine (RS)-4-(4-Chloro-3-fluoro-phenyl)-4-methyl-4,5-dihydro-oxazol-2-ylamine was separated by chiral HPLC (Chiralpak AD, EtOH/heptane 5:95) to give (S)-4-(4-chloro-3-fluoro-phenyl)-4-methyl-4,5-dihydro-oxazol-2-ylamine. (+)-Enantiomer. Off-white solid.
MS (ISP): 229.1 ([M+H]$^+$)

In analogy to example 185 and starting from the respective amino acid or amino acid derivative was prepared:

Example 237

(RS)-4-(2-Bromo-phenyl)-4,5-dihydro-oxazol-2-ylamine

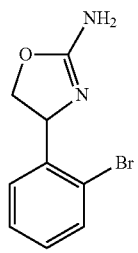 [SMILES: NC1=NC(c2ccccc2Br)CO1]

From amino-(2-bromo-phenyl)-acetic acid. White solid.
MS (ISP): 243.1 ([$^{81}$Br]M+H]$^+$), 241.1 ([$^{79}$Br]M+H]$^+$).

Examples 238 & 239

(+)-(S)-4-(4-Chloro-2-trifluoromethyl-phenyl)-4,5-dihydro-oxazol-2-ylamine & (−)-(R)-4-(4-Chloro-2-trifluoromethyl-phenyl)-4,5-dihydro-oxazol-2-ylamine

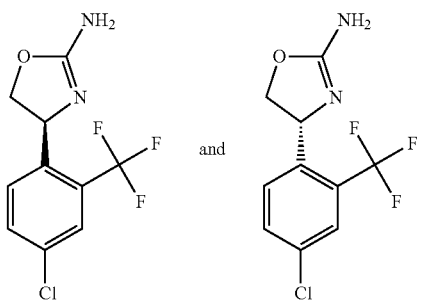 [SMILES: NC1=N[C@@H](c2ccc(Cl)cc2C(F)(F)F)CO1 ; NC1=N[C@H](c2ccc(Cl)cc2C(F)(F)F)CO1]

(RS)-4-(4-Chloro-2-trifluoromethyl-phenyl)-4,5-dihydro-oxazol-2-ylamine (example 226) was separated by chiral HPLC (Chiralpak AD, EtOH/heptane=5:95) to yield (+)-(S)-4-(4-chloro-2-trifluoromethyl-phenyl)-4,5-dihydro-oxazol-2-ylamine (white solid; MS (ISP): 267.1 ([$^{37}$Cl]M+H]$^+$), 265.0 ([$^{35}$Cl]M+H]$^+$) and (−)-(R)-4-(4-chloro-2-trifluoromethyl-phenyl)-4,5-dihydro-oxazol-2-ylamine (white solid; MS (ISP): 267.1 ([$^{37}$Cl]M+H]$^+$), 265.0 ([$^{35}$Cl]M+H]$^+$)).

Examples 240 & 241

(+)-(S)-4-(4-Methoxy-2-trifluoromethyl-phenyl)-4,5-dihydro-oxazol-2-ylamine & (−)-(R)-4-(4-Methoxy-2-trifluoromethyl-phenyl)-4,5-dihydro-oxazol-2-ylamine

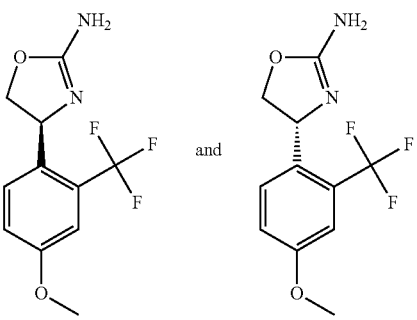 [SMILES: COc1ccc([C@H]2COC(N)=N2)c(C(F)(F)F)c1 ; COc1ccc([C@@H]2COC(N)=N2)c(C(F)(F)F)c1]

(RS)-4-(4-Methoxy-2-trifluoromethyl-phenyl)-4,5-dihydro-oxazol-2-ylamine (example 229) was separated by chiral HPLC (Chiralpak AD, EtOH/heptane=5:95) to yield (+)-(S)-4-(4-methoxy-2-trifluoromethyl-phenyl)-4,5-dihydro-oxazol-2-ylamine (colourless gum; MS (ISP): 261.1 ([M+H]$^+$)) and (−)-(R)-4-(4-methoxy-2-trifluoromethyl-phenyl)-4,5-dihydro-oxazol-2-ylamine (colourless gum; MS (ISP): 261.1 ([M+H]$^+$)).

Examples 242 & 243

(+)-(S)-4-(4,5-Dichloro-2-trifluoromethyl-phenyl)-4,5-dihydro-oxazol-2-ylamine & (−)-(R)-4-(4,5-Dichloro-2-trifluoromethyl-phenyl)-4,5-dihydro-oxazol-2-ylamine

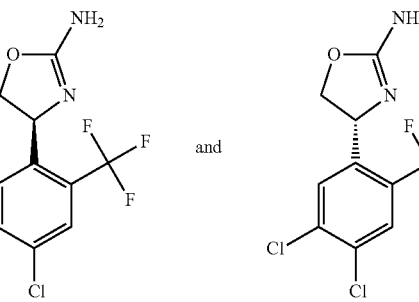

(RS)-4-(4,5-Dichloro-2-trifluoromethyl-phenyl)-4,5-dihydro-oxazol-2-ylamine (example 234) was separated by chiral HPLC (Chiralpak AD, EtOH/heptane=5:95) to yield (+)-(S)-4-(4,5-dichloro-2-trifluoromethyl-phenyl)-4,5-dihydro-oxazol-2-ylamine (white solid; MS (ISP): 303.0 ([$^{37}$Cl]M+H]$^+$), 301.0 ([$^{37}$Cl$^{35}$Cl]M+H]$^+$), 299.0 ([$^{35}$Cl]M+H]$^+$)) and (−)-(R)-4-(4,5-dichloro-2-trifluoromethyl-phenyl)-4,5-dihydro-oxazol-2-ylamine (white solid; MS (ISP): 303.0 ([$^{37}$Cl]M+H]$^+$), 301.0 ([$^{37}$Cl$^{35}$Cl]M+H]$^+$), 299.0 ([$^{35}$Cl]M+H]$^+$)).

Example 244

(S)-4-[2-(4-Chloro-phenyl)-ethyl]-4-methyl-4,5-dihydro-oxazol-2-ylamine

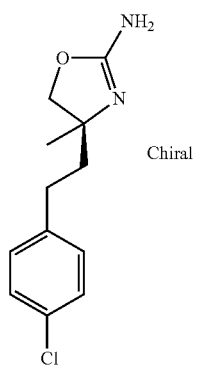 [SMILES: C[C@]1(CCc2ccc(Cl)cc2)COC(N)=N1]

The title compound, MS (ISP): 239.1; 241.2 ((M+H)$^{+\cdot}$) was obtained in comparable yield analogous to the procedure described for Example 228 using 1-(2-bromo-ethyl)-4-chlorobenzene instead of 1-(2-bromo-ethyl)-2-chlorobenzene in step a).

Example 245

(S)-4-Methyl-4-[2-(3-trifluoromethyl-phenyl)-ethyl]-4,5-dihydro-oxazol-2-ylamine

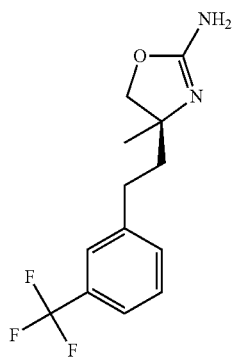 [SMILES: C[C@]1(CCc2cccc(C(F)(F)F)c2)COC(N)=N1]

The title compound, MS (ISP): 273.0 ((M+H)$^{+\cdot}$) was obtained in comparable yield analogous to the procedure described for Example 228 using 1-(2-iodo-ethyl)-3-trifluoromethyl-benzene instead of 1-(2-bromo-ethyl)-2-chlorobenzene in step a).

Example 246

(S)-4-[2-(3-Chloro-phenyl)-ethyl]-4-methyl-4,5-dihydro-oxazol-2-ylamine

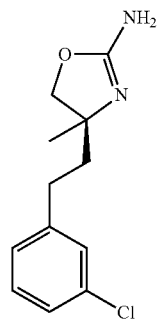 [SMILES: C[C@]1(CCc2cccc(Cl)c2)COC(N)=N1]

The title compound, MS (ISP): 239.1; 241.2 ((M+H)$^{+\cdot}$) was obtained in comparable yield analogous to the procedure described for Example 228 using 1-(2-bromo-ethyl)-3-chlorobenzene instead of 1-(2-bromo-ethyl)-2-chlorobenzene in step a).

Examples 247 & 248

(−)-(R)-4-(4-Fluoro-2-trifluoromethyl-phenyl)-4,5-dihydro-oxazol-2-ylamine & (+)-(S)-4-(4-Fluoro-2-trifluoromethyl-phenyl)-4,5-dihydro-oxazol-2-ylamine

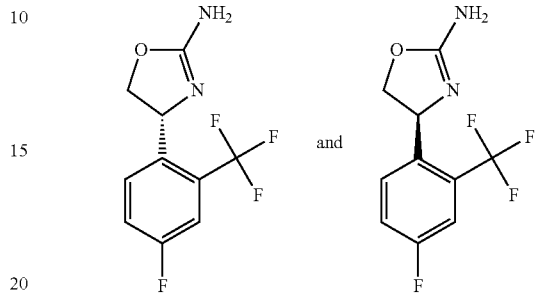

(RS)-4-(4-Fluoro-2-trifluoromethyl-phenyl)-4,5-dihydro-oxazol-2-ylamine (example 224) was separated by chiral HPLC (Chiralpak AD, EtOH/heptane=5:95) to yield (−)-(R)-4-(4-fluoro-2-trifluoromethyl-phenyl)-4,5-dihydro-oxazol-2-ylamine (colourless oil; MS (ISP): 249.1 ([M+H]$^+$) and (+)-(S)-4-(4-fluoro-2-trifluoromethyl-phenyl)-4,5-dihydro-oxazol-2-ylamine (colourless oil; MS (ISP): 249.1 ([M+H]$^+$).

In analogy to example 224 and starting from the respective aldehyde were prepared:

Example 249

(RS)-4-(5-Fluoro-2-trifluoromethyl-phenyl)-4,5-dihydro-oxazol-2-ylamine

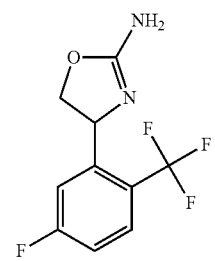 [SMILES: NC1=NC(c2cc(F)ccc2C(F)(F)F)CO1]

From 5-fluoro-2-(trifluoromethyl)benzaldehyde. Light yellow solid.
MS (ISP): 249.1 ([M+H]$^+$).

Example 250

(RS)-4-(5-Fluoro-2-methyl-phenyl)-4,5-dihydro-oxazol-2-ylamine

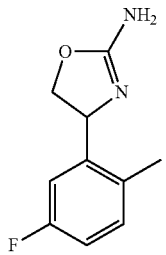

From 5-fluoro-2-methyl-benzaldehyde. White solid.
MS (ISP): 195.1 ([M+H]$^+$).

Example 251

(RS)-4-Methyl-4-(2,4,5-trifluoro-phenyl)-4,5-dihydro-oxazol-2-ylamine

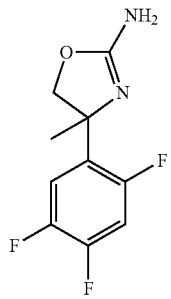 [SMILES: CC1(c2cc(F)c(F)cc2F)COC(N)=N1]

In analogy to example 206, the title compound was obtained starting from 2,4,5-trifluoroacetophenone. Viscous colorless oil.
MS (ISP): 231.3 ([M+H]$^+$)

Example 252

(RS)-4-(4-Bromo-3-fluoro-phenyl)-4,5-dihydro-oxazol-2-ylamine

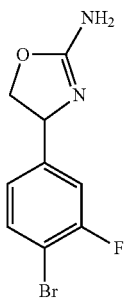

a) (RS)-2-Amino-2-(4-bromo-3-fluoro-phenyl)-ethanol

In analogy to example 224a-d 4-bromo-3-fluorobenzaldehyde was treated sequentially with ammonia/tetraisopropyl orthotitanate/trimethylsilyl cyanide, hydrogen chloride in formic acid, hydrochloric acid, and lithium borohydride/chlorotrimethylsilane to give (RS)-2-amino-2-(4-bromo-3-fluoro-phenyl)-ethanol. Yellow viscous oil. MS (ISP): 236.1 ([{$^{81}$Br}M+H]$^+$), 234.1 ([{$^{79}$Br}M+H]$^+$).

b) (RS)-4-(4-Bromo-3-fluoro-phenyl)-4,5-dihydro-oxazol-2-ylamine

To a stirred, cooled (0° C.) solution of (RS)-2-amino-2-(4-bromo-3-fluoro-phenyl)-ethanol (3.26 g) and sodium acetate (2.22 g) in methanol (25 ml) was added dropwise a solution of cyanogen bromide (1.52 g) in methanol (10 ml) over 10 min. The mixture was then allowed to warm to at r.t. and stirring continued for 16 h. The mixture was concentrated in vacuo and the residue was resuspended in water and made basic by addition of 1 M aq sodium hydroxide solution. The mixture was then extracted twice with dichloromethane and the combined organic phases were dried over sodium sulphate and concentrated in vacuo. The residue was triturated in dichloromethane and the resultign crystals washed with ether to give (RS)-4-(4-bromo-3-fluoro-phenyl)-4,5-dihydro-oxazol-2-ylamine (1.09 g, 30%) as a white solid. MS (ISP): 261.0 ([{$^{81}$Br}M+H]$^+$), 258.9 ([{$^{79}$Br}M+H]$^+$).

Example 253

(−)-(S)-4-(3-Chloro-2-fluoro-6-trifluoromethyl-phenyl)-4,5-dihydro-oxazol-2-ylamine

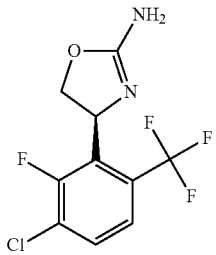 [SMILES: NC1=N[C@@H](c2c(C(F)(F)F)ccc(Cl)c2F)CO1]

(RS)-4-(3-Chloro-2-fluoro-6-trifluoromethyl-phenyl)-4,5-dihydro-oxazol-2-ylamine (example 233) was separated by chiral HPLC (Chiralpak AD, iPrOH/heptane=5:95) to yield (−)-(S)-4-(3-chloro-2-fluoro-6-trifluoromethyl-phenyl)-4,5-dihydro-oxazol-2-ylamine (white solid; MS (ISP): 284.9 ([{$^{37}$Cl}M+H]$^+$), 283.1 ([{$^{35}$Cl}M+H]$^+$).

Example 254

(S)-4-Methyl-4-(4-trifluoromethoxy-phenyl)-4,5-dihydro-oxazol-2-ylamine

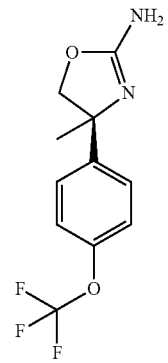 [SMILES: C[C@]1(c2ccc(OC(F)(F)F)cc2)COC(N)=N1]

a) (RS)-4-Methyl-4-(4-trifluoromethoxy-phenyl)-4,5-dihydro-oxazol-2-ylamine

In analogy to example 147, the title compound was obtained starting from 4'-(trifluoromethoxy)acetophenone. Viscous colorless oil.
MS (ISP): 261.0 ([M+H]$^+$)

b) (S)-4-Methyl-4-(4-trifluoromethoxy-phenyl)-4,5-dihydro-oxazol-2-ylamine ((RS)-4-Methyl-4-(4-trifluoromethoxy-phenyl)-4,5-dihydro-oxazol-2-ylamine was sepa-rated by chiral HPLC (Chiralpak AD, EtOH/heptane 10:90) to give (S)-4-methyl-4-(4-trifluoromethoxy-phenyl)-4,5-dihydro-oxazol-2-ylamine. (+)-Enantiomer. Viscous colorless oil.
MS (ISP): 261.0 ([M+H]$^+$)

Example 255

(S)-4-[2-(4-Fluoro-phenyl)-ethyl]-4-methyl-4,5-dihydro-oxazol-2-ylamine

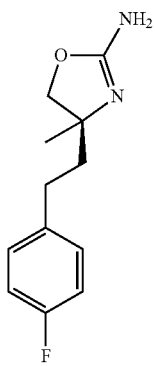 [SMILES: C[C@]1(CCc2ccc(F)cc2)COC(N)=N1]

The title compound, MS (ISP): 223.3 ((M+H)$^{+\cdot}$) was obtained in comparable yield analogous to the procedure described for Example 228 using 1-(2-bromo-ethyl)-4-fluorobenzene instead of 1-(2-bromo-ethyl)-2-chlorobenzene in step a).

Example 256

(S)-4-[2-(4-Chloro-phenyl)-ethyl]-4,5-dihydro-oxazol-2-ylamine

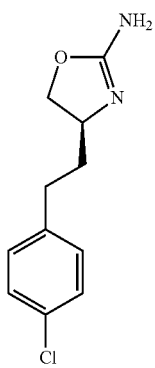 [SMILES: NC1=N[C@@H](CCc2ccc(Cl)cc2)CO1]

The title compound, MS (ISP): 225.3; 227.2 ((M+H)$^{+\cdot}$) was obtained in comparable yield analogous to the procedure described for Example 228 using (R)-(−)-2,5-dihydro-3,6-dimethoxy-2-isopropyl-pyrazine instead of (R)-(−)-2,5-dihydro-3,6-dimethoxy-2-isopropyl-5-methylpyrazine and 1-(2-bromo-ethyl)-4-chloro-benzene instead of 1-(2-bromo-ethyl)-2-chlorobenzene in step a).

Example 257

(S)-4-[1-(4-Chloro-phenyl)-cyclopropylmethyl]-4,5-dihydro-oxazol-2-ylamine

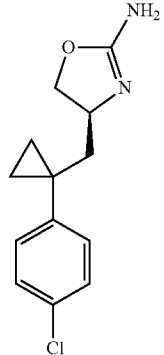 [SMILES: NC1=N[C@@H](CC2(c3ccc(Cl)cc3)CC2)CO1]

a) 1-Chloro-4-(1-iodomethyl-cyclopropyl)-benzene

To a stirred solution of triphenylphosphine (3.45 g, 13 mmol) and imidazole (0.90 g, 13 mmol) in dichloromethane (25 ml) under an argon atmosphere was added slowly iodine (3.33 g, 13 mmol) and [1-(4-chlorophenyl)-cyclopropyl]-methanol (2.00 g, 11 mmol). The mixture was stirred for 2 hours at room temperature, then dichloromethane (75 ml) was added and mixture was extracted with saturated sodium thiosulfate solution (100 ml) and hydrochloric acid (1N, 50 ml). The organic layer was dried over MgSO$_4$ and evaporated. The residue was suspended in ether and filtered to remove insoluble triphenylphosphine oxide. The ether was evaporated and the residue was purified by column chromatography (SiO$_2$, heptane/EtOAc=9:1) to yield a light yellow oil, (2.30 g, 72%); MS (EI): 292.0 (M$^{+\cdot}$).

b) (S)-4-[1-(4-Chloro-phenyl)-cyclopropylmethyl]-4,5-dihydro-oxazol-2-ylamine

The title compound, MS (ISP): 251.1; 253.1 ((M+H)$^{+\cdot}$) was obtained in comparable yield analogous to the procedure described for Example 228 using (R)-(−)-2,5-dihydro-3,6-dimethoxy-2-isopropyl-pyrazine instead of (R)-(−)-2,5-dihydro-3,6-dimethoxy-2-isopropyl-5-methylpyrazine and 1-chloro-4-(1-iodomethyl-cyclopropyl)-benzene instead of 1-(2-bromo-ethyl)-2-chlorobenzene in step a).

Example 258

(S)-4-[2-(3,4-Difluoro-phenyl)-ethyl]-4-methyl-4,5-dihydro-oxazol-2-ylamine

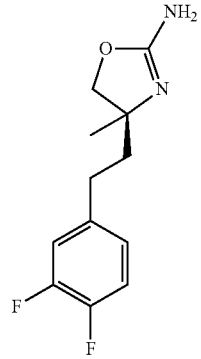 [SMILES: C[C@]1(CCc2ccc(F)c(F)c2)COC(N)=N1]

The title compound, MS (ISP): 241.1 ((M+H)+·) was obtained in comparable yield analogous to the procedure described for Example 228 using 1-(2-iodo-ethyl)-3,4-difluorobenzene instead of 1-(2-bromo-ethyl)-2-chlorobenzene in step a).

Example 259

(+)-(S)-4-(5-Fluoro-2-trifluoromethyl-phenyl)-4,5-dihydro-oxazol-2-ylamine

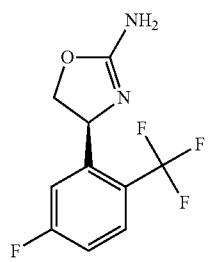 [SMILES: NC1=N[C@@H](c2cc(F)ccc2C(F)(F)F)CO1]

(RS)-(S)-4-(5-Fluoro-2-trifluoromethyl-phenyl)-4,5-dihydro-oxazol-2-ylamine (example 249) was separated by chiral HPLC (Chiralpak AD, iPrOH/heptane=5:95) to yield (+)-(S)-4-(5-fluoro-2-trifluoromethyl-phenyl)-4,5-dihydro-oxazol-2-ylamine (white solid; MS (ISP): 249.1 ([M+H]+). In analogy to example 252 and starting from the respective aldehyde was prepared:

Example 260

(RS)-4-(2,5-Dichloro-phenyl)-4,5-dihydro-oxazol-2-ylamine

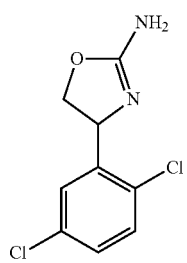 [SMILES: NC1=NC(c2cc(Cl)ccc2Cl)CO1]

From 2,5-dichlorobenzaldehyde. White solid. MS (ISP): 235.0 ([{37Cl}M+H]+), 233.0 ([{37Cl35Cl}M+H]+), 231.1 ([{35Cl}M+H]+)).

Example 261

(RS)-4-(2-Chloro-4,5-difluoro-phenyl)-4-methyl-4,5-dihydro-oxazol-2-ylamine

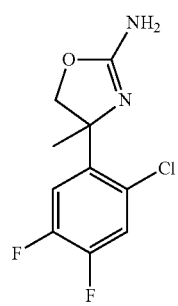 [SMILES: CC1(c2cc(F)c(F)cc2Cl)COC(N)=N1]

In analogy to example 206, the title compound was obtained starting from 2-chloro-4,5-difluoroacetophenone. White solid.
MS (ISP): 247.1 ([M+H]+)

Example 262

(RS)-4-(3,4-Difluoro-phenyl)-4-methyl-4,5-dihydro-oxazol-2-ylamine

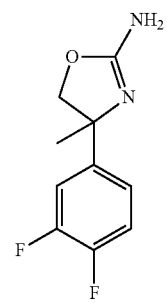

In analogy to example 206, the title compound was obtained starting from 3,4-difluoroacetophenone. White solid.
MS (ISP): 213.3 ([M+H]+)

Example 263

(RS)-4-(4-Chloro-3-methyl-phenyl)-4-methyl-4,5-dihydro-oxazol-2-ylamine

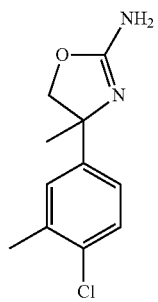

In analogy to example 206, the title compound was obtained starting from 4-chloro-3-methylacetophenone. White solid.
MS (ISP): 225.1 ([M+H]9

Examples 264 & 265

(−)-(R)-4-(2-Bromo-phenyl)-4,5-dihydro-oxazol-2-ylamine & (+)-(S)-4-(2-Bromo-phenyl)-4,5-dihydro-oxazol-2-ylamine

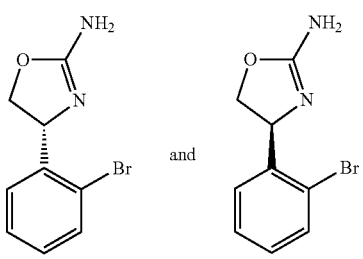 [SMILES: NC1=N[C@H](c2ccccc2Br)CO1 ; NC1=N[C@@H](c2ccccc2Br)CO1]

(RS)-4-(2-Bromo-phenyl)-4,5-dihydro-oxazol-2-ylamine (example 237) was separated by chiral HPLC (Chiralpak AD, iPrOH/heptane=5:95) to yield (−)-(R)-4-(2-bromo-phenyl)-4,5-dihydro-oxazol-2-ylamine (white solid; MS (ISP): 243.1

([{⁸¹Br}M+H]⁺), 241.1 ([{⁷⁹Br}M+H]⁺) and (+)-(S)-4-(2-bromo-phenyl)-4,5-dihydro-oxazol-2-ylamine (white solid; MS (ISP): 243.1 ([{⁸¹Br}M+H]⁺), 241.1 ([{⁷⁹Br}M+H]⁺).

Example 266

(S)-4-(3-Chloro-5-fluoro-phenyl)-4-methyl-4,5-dihydro-oxazol-2-ylamine

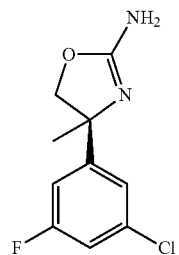

a) (RS)-4-(3-Chloro-5-fluoro-phenyl)-4-methyl-4,5-dihydro-oxazol-2-ylamine

In analogy to example 206, the title compound was obtained starting from 3'-chloro-5'-fluoroacetophenone. White solid.
MS (ISP): 229.1 ([M+H]⁺)

b) (S)-4-(3-Chloro-5-fluoro-phenyl)-4-methyl-dihydro-oxazol-2-ylamine (RS)-4-(3-Chloro-5-fluoro-phenyl)-4-methyl-4,5-dihydro-oxazol-2-ylamine was sepa-rated by chiral HPLC (Chiralpak AD, EtOH/heptane 15:850) to give (S)-4-(3-chloro-5-fluoro-phenyl)-4-methyl-4,5-dihydro-oxazol-2-ylamine. (+)-Enantiomer. White solid.
MS (ISP): 229.1 ([M+H]⁺)

Example 267

(S)-4-[2-(2-Chloro-phenyl)-ethyl]-4,5-dihydro-oxazol-2-ylamine

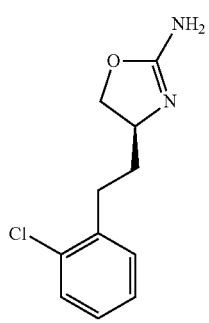 [SMILES: NC1=N[C@@H](CCc2ccccc2Cl)CO1]

The title compound, MS (ISP): 225.1; 227.1 ((M+H)⁺·) was obtained in comparable yield analogous to the procedure described for Example 228 using (R)-(−)-2,5-dihydro-3,6-dimethoxy-2-isopropyl-pyrazine instead of (R)-(−)-2,5-dihydro-3,6-dimethoxy-2-isopropyl-5-methylpyrazine and 1-(2-bromo-ethyl)-2-chloro-benzene instead of 1-(2-bromo-ethyl)-2-chlorobenzene in step a).

Example 268

(RS)-4-(4-Chloro-phenyl)-4-ethyl-4,5-dihydro-oxazol-2-ylamine

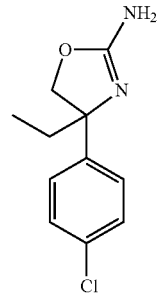

a) (RS)-2-Amino-2-(4-chloro-phenyl)-butyronitrile

A solution of 4'-chloropropiophenone (5 g) in MeOH (20 ml) was treated under an argon atmosphere and at r.t. with 7M NH₃ in MeOH (33.9 ml). Then, tetraisopropyl orthotitanate (10.54 ml) was added dropwise. The reaction mixture was stirred for 1 hr at r.t. Then, trimethylsilyl cyanide (3.72 ml) was added and stirring was continued at r.t. overnight. The reaction mixture was poured in ice and extracted with EtOAc. The organic layer was dried over MgSO₄, filtered and concentrated. The crude (RS)-2-amino-2-(4-chloro-phenyl)-butyronitrile (4.95 g) was used in the next reaction step without further purification.

b) (RS)-2-Amino-2-(4-chloro-phenyl)-butyric acid hydrochloride

A solution of (RS)-2-amino-2-(4-chloro-phenyl)-butyronitrile (4.9 g) in 5HCl (30 ml) was refluxed overnight, then cooled to r.t. and washed with EtOAc. The aqueous layer was concentrated. The crude (RS)-2-amino-2-(4-chloro-phenyl)-butyric acid hydrochloride (3.0 g) was used in the next reaction step without further purification.

c) (RS)-4-(4-Chloro-phenyl)-4-ethyl-4,5-dihydro-oxazol-2-ylamine

In analogy to example 206.b and c (RS)-2-amino-2-(4-chloro-phenyl)-butyric acid hydrochloride was converted to the title compound. White solid.
MS (ISP): 225.1 ([M+H]⁺)

Example 269

(RS)-4-Methyl-4-(2,3,4-trifluoro-phenyl)-4,5-dihydro-oxazol-2-ylamine

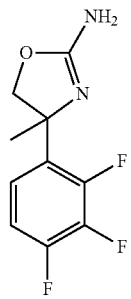

In analogy to example 206, the title compound was obtained starting from 2,3,4-trifluoroacetophenone. Off-white solid.
MS (ISP): 231.1 ([M+H]⁺)

Example 270

(S)-4-(5-Chloro-2-fluoro-phenyl)-4-methyl-4,5-dihydro-oxazol-2-ylamine

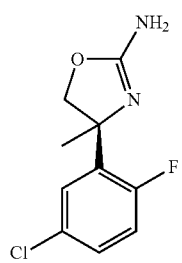

a) (S)-4-(5-Chloro-2-fluoro-phenyl)-4-methyl-4,5-dihydro-oxazol-2-ylamine

In analogy to example 206, the title compound was obtained starting from 5'-chloro-2'-fluoroacetophenone. White solid.

MS (ISP): 229.3 ([M+H]$^+$)

b) (RS)-4-(5-Chloro-2-fluoro-phenyl)-4-methyl-4,5-dihydro-oxazol-2-ylamine (RS)-4-(5-Chloro-2-fluoro-phenyl)-4-methyl-4,5-dihydro-oxazol-2-ylamine was separated by chiral HPLC (Chiralpak AD, EtOH/heptane 5:95) to give (S)-4-(5-chloro-2-fluoro-phenyl)-4-methyl-4,5-dihydro-oxazol-2-ylamine. (+)-Enantiomer. White solid.

MS (ISP): 229.1 ([M+H]$^+$)

Example 271

(RS)-4-Methyl-4-(4-chloro-2,5-difluoro-phenyl)-4,5-dihydro-oxazol-2-ylamine

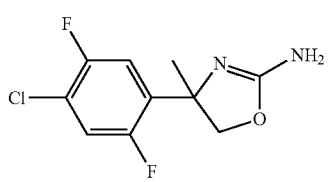 [SMILES: CC1(c2cc(F)c(Cl)cc2F)COC(N)=N1]

a) (RS)-4-(4-Chloro-2,5-difluoro-phenyl)-4-methyl-4,5-dihydro-oxazol-2-ylamine In analogy to example 147.a, but stirring the reaction mixture overnight instead of 3 hrs, the title compound was obtained starting from 4-chloro-2,5-difluoro-acetophenone. Off-white solid.

MS (ISP): 247.1 ([M+H]$^+$)

b) (RS)-4-(4-Chloro-2,5-difluoro-phenyl)-4-methyl-4,5-dihydro-oxazol-2-ylamine The title compound was obtained in analogy to example 206.b and 206.c. Off-white solid.

MS (ISP): 247.1 ([M+H]$^+$)

In analogy to example 252 and starting from the respective aldehyde was prepared:

Example 272

(RS)-4-(5-Chloro-2-methyl-phenyl)-4,5-dihydro-oxazol-2-ylamine

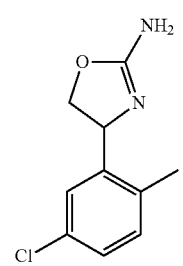

From 5-chloro-2-methylbenzaldehyde. White solid. MS (ISP): 213.1 ([{$^{37}$Cl}M+H]$^+$), 211.1 ([{$^{35}$Cl}M+H]$^+$)).

Example 273

(RS)-4-Methyl-4-(3,4,5-trifluoro-phenyl)-4,5-dihydro-oxazol-2-ylamine

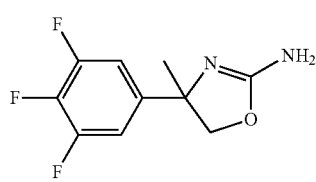 [SMILES: CC1(c2cc(F)c(F)c(F)c2)COC(N)=N1]

The title compound was obtained in analogy to example 268 starting from 3',4',5'-trifluoro-acetophenone. White solid.

MS (ISP): 231.3 ([M+H]$^+$)

Example 274

(RS)-4-(4-Chloro-2-fluoro-5-methyl-phenyl)-4-methyl-4,5-dihydro-oxazol-2-ylamine

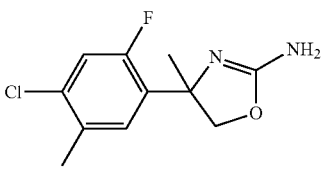 [SMILES: Cc1cc(C2(C)COC(N)=N2)c(F)cc1Cl]

The title compound was obtained in analogy to example 268 starting from 4-chloro-2-fluoro-5-methyl-acetophenone. White solid.

MS (ISP): 2434.1 ([M+H]$^+$)

Example 275

(S)-4-[1-(4-Chloro-phenyl)-cyclobutylmethyl]-4,5-dihydro-oxazol-2-ylamine

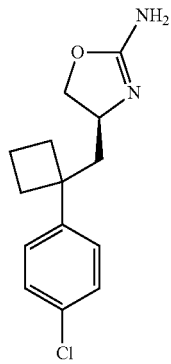 [SMILES: NC1=N[C@@H](CC2(c3ccc(Cl)cc3)CCC2)CO1]

a) 1-Chloro-4-(1-iodomethyl-cyclobutyl)-benzene

To a stirred solution of triphenylphosphine (4.91 g, 18.7 mmol) and imidazole (1.28 g, 18.7 mmol) in dichloromethane (40 ml) under an argon atmosphere was added slowly iodine (4.75 g, 18.7 mmol) and [1-(4-chlorophenyl)-cyclopropyl]-methanol (3.07 g, 15.6 mmol). The mixture was stirred for 2 hours at room temperature, then dichloromethane (100 ml) was added and mixture was extracted with saturated sodium thiosulfate solution (100 ml) and hydrochloric acid (1 N, 50 ml). The organic layer was dried over MgSO$_4$ and evaporated. The residue was suspended in ether and filtered to remove insoluble triphenylphosphine oxide. The ether was evaporated and the residue was purified by column chromatography (SiO$_2$, heptane/EtOAc=9:1) to yield a colourless oil, (2.50 g, 52%); MS (EI): 306.0 (M$^{+\cdot}$); 179.0 ((M–I)$^{+\cdot}$).

b) (S)-4-[1-(4-Chloro-phenyl)-cyclobutylmethyl]-4,5-dihydro-oxazol-2-ylamine The title compound, MS (ISP): 265.0; 267.1 ((M+H)$^{+\cdot}$) was obtained in comparable yield analogous to the procedure described for Example 228 using (R)-(–)-2,5-dihydro-3,6-dimethoxy-2-isopropyl-pyrazine instead of (R)-(–)-2,5-dihydro-3,6-dimethoxy-2-isopropyl-5-methylpyrazine and 1-chloro-4-(1-iodomethyl-cyclobutyl)-benzene instead of 1-(2-bromo-ethyl)-2-chlorobenzene in step a).

Example 276

(R)-4-(3-Chloro-4-fluoro-phenyl)-4-methyl-4,5-dihydro-oxazol-2-ylamine

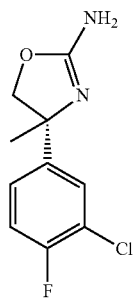

a) (R)-4-(3-Chloro-4-fluoro-phenyl)-4-methyl-4,5-dihydro-oxazol-2-ylamine

In analogy to example 206, the title compound was obtained starting from 3-chloro-4-fluoro-acetophenone. Viscous colorless oil.
MS (ISP): 229.4 ([M+H]$^+$)

b) ((R)-4-(3-Chloro-4-fluoro-phenyl)-4-methyl-4,5-dihydro-oxazol-2-ylamine (RS)-4-(3-Chloro-4-fluoro-phenyl)-4-methyl-4,5-dihydro-oxazol-2-ylamine was separated by chiral HPLC (Chiralpak AD, EtOH/heptane 1:9) to give (R)-4-(3-chloro-4-fluoro-phenyl)-4-methyl-4,5-dihydro-oxazol-2-ylamine. (–)-Enantiomer. Off-white solid.
MS (ISP): 229.1 ([M+H]$^+$)

Example 277

(R)-4-(3-Chloro-4-fluoro-phenyl)-4-methyl-4,5-dihydro-oxazol-2-ylamine

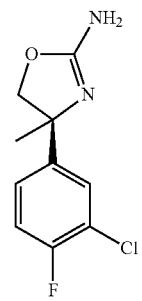

(RS)-4-(3-Chloro-4-fluoro-phenyl)-4-methyl-4,5-dihydro-oxazol-2-ylamine was separated by chiral HPLC (Chiralpak AD, EtOH/heptane 1:9) to give (S)-4-(3-chloro-4-fluoro-phenyl)-4-methyl-4,5-dihydro-oxazol-2-ylamine. (+)-Enantiomer. Off-white solid.
MS (ISP): 229.1 ([M+H]$^+$)

Examples 278 & 279

(–)-(R)-4-(5-Fluoro-2-methyl-phenyl)-4,5-dihydro-oxazol-2-ylamine & (+)-(S)-4-(5-Fluoro-2-methyl-phenyl)-4,5-dihydro-oxazol-2-ylamine

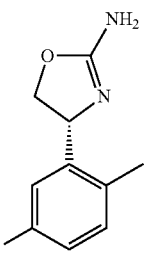 and 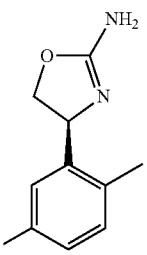

(RS)-4-(5-Fluoro-2-methyl-phenyl)-4,5-dihydro-oxazol-2-ylamine (example 250) was separated by chiral HPLC (Chiralpak AD, EtOH/heptane=10:90) to yield (–)-(R)-4-(5-fluoro-2-methyl-phenyl)-4,5-dihydro-oxazol-2-ylamine (white solid; MS (ISP): 195.1 ([M+H]$^+$), and (+)-(S)-4-(5-fluoro-2-methyl-phenyl)-4,5-dihydro-oxazol-2-ylamine (white solid; MS (ISP): 195.1 ([M+H]$^+$).

Example 280

(R)-4-(4-Chloro-3-methyl-phenyl)-4-methyl-4,5-dihydro-oxazol-2-ylamine

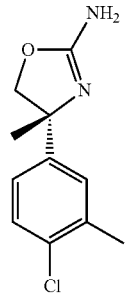

(RS)-4-(4-Chloro-3-methyl-phenyl)-4-methyl-4,5-dihydro-oxazol-2-ylamine (example 263) was separated by chiral HPLC (Chiralpak AD, EtOH/heptane=1:9) to give (R)-4-(4-chloro-3-methyl-phenyl)-4-methyl-4,5-dihydro-oxazol-2-ylamine. (−)-Enantiomer. White solid.
MS (ISP): 225.1 ([M+H]$^+$))

Example 281

(S)-4-(4-Chloro-3-methyl-phenyl)-4-methyl-4,5-dihydro-oxazol-2-ylamine

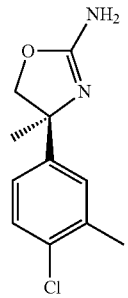

(RS)-4-(4-Chloro-3-methyl-phenyl)-4-methyl-4,5-dihydro-oxazol-2-ylamine (example 263) was separated by chiral HPLC (Chiralpak AD, EtOH/heptane=1:9) to give (S)-4-(4-chloro-3-methyl-phenyl)-4-methyl-4,5-dihydro-oxazol-2-ylamine. (+)-Enantiomer. White solid.
MS (ISP): 225.3 ([M+H]$^+$))

Example 282

(R)-4-(3,4-Difluoro-phenyl)-4-methyl-4,5-dihydro-oxazol-2-ylamine

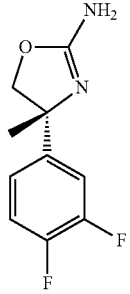

(RS)-4-(3,4-Difluoro-phenyl)-4-methyl-4,5-dihydro-oxazol-2-ylamine (example 262) was separated by chiral HPLC (Chiralpak AD, EtOH/heptane=1:9) to give (R)-4-(3,4-difluoro-phenyl)-4-methyl-4,5-dihydro-oxazol-2-ylamine. (−)-Enantiomer. White solid.
MS (ISP): 213.1 ([M+H]$^+$))

Example 283

(S)-4-(3,4-Difluoro-phenyl)-4-methyl-4,5-dihydro-oxazol-2-ylamine

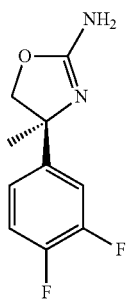

(RS)-4-(3,4-Difluoro-phenyl)-4-methyl-4,5-dihydro-oxazol-2-ylamine (example 262) was separated by chiral HPLC (Chiralpak AD, EtOH/heptane=1:9) to give (S)-4-(3,4-difluoro-phenyl)-4-methyl-4,5-dihydro-oxazol-2-ylamine. (+)-Enantiomer. White solid.
MS (ISP): 213.3 ([M+H]$^+$))

In analogy to example 87 were prepared:

Example 284

(S)-4-(3,4-Dichloro-phenoxymethyl)-4,5-dihydro-oxazol-2-ylamine

From tert-butyl (S)-4-(hydroxymethyl)-2,2-dimethyl-3-oxazolidinecarboxylate and 3,4-dichlorophenol. White solid.
MS (ISP): 265.0 ([{$^{37}$Cl}M+H]$^+$), 263.0 ([{$^{37}$Cl$^{35}$Cl}M+H]$^+$), 261.0 ([{$^{35}$Cl}M+H]$^+$)).

Example 285

(S)-4-(3,5-Dichloro-phenoxymethyl)-4,5-dihydro-oxazol-2-ylamine

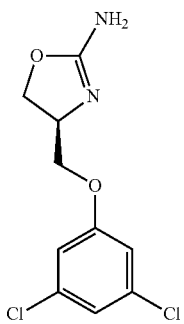 [SMILES: NC1=N[C@@H](COc2cc(Cl)cc(Cl)c2)CO1]

From tert-butyl (S)-4-(hydroxymethyl)-2,2-dimethyl-3-oxazolidinecarboxylate and 3,5-dichlorophenol. Courless oil. MS (ISP): 265.1 ([{$^{37}$Cl}M+H]$^+$), 263.1 ([{$^{37}$Cl$^{35}$Cl}M+H]$^+$), 261.1 ([{$^{35}$Cl}M+H]$^+$)).

Example 286

(S)-4-(3-Trifluoromethyl-phenoxymethyl)-4,5-dihydro-oxazol-2-ylamine

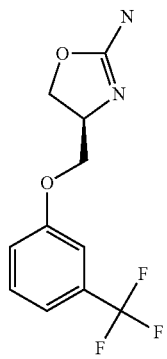 [SMILES: NC1=N[C@@H](COc2cccc(C(F)(F)F)c2)CO1]

From tert-butyl (S)-4-(hydroxymethyl)-2,2-dimethyl-3-oxazolidinecarboxylate and 3-(trifluoromethyl)phenol. Courless oil. MS (ISP): 261.0 ([M+H]9. In analogy to example 162 was prepared:

Example 287

(S)-4-[2-(3-Chloro-phenyl)-butyl]-4,5-dihydro-oxazol-2-ylamine

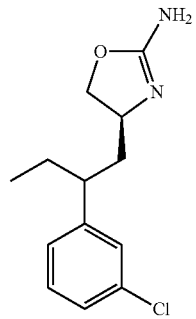 [SMILES: CCC(C[C@H]1COC(N)=N1)c1cccc(Cl)c1]

From (S)-4-(2,2-dibromo-vinyl)-2,2-dimethyl-oxazolidine-3-carboxylic acid tert-butyl ester by sequential treatment with 3-chlorophenyl boronic acid and diethylzinc. Mainly one epimer. Colourless oil. MS (ISP): 255.3 ([{$^{37}$Cl}M+H]$^+$), 253.3 ([{$^{35}$Cl}M+H]$^+$)).

Example 288

(S)-4-(3-Phenyl-propyl)-4,5-dihydro-oxazol-2-ylamine

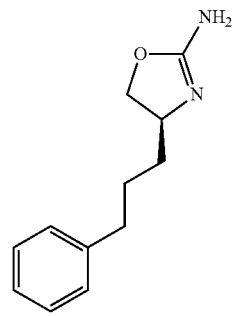 [SMILES: NC1=N[C@@H](CCCc2ccccc2)CO1]

The title compound, MS (ISP): 205.1 ((M+H)$^+$) was obtained in comparable yield analogous to the procedure described for Example 228 using (R)-(−)-2,5-dihydro-3,6-dimethoxy-2-isopropyl-pyrazine instead of (R)-(−)-2,5-dihydro-3,6-dimethoxy-2-isopropyl-5-methylpyrazine and (3-bromo-propyl)-benzene instead of 1-(2-bromo-ethyl)-2-chlorobenzene in step a).

Example 289

(S)-4-(4-Chloro-2,5-difluoro-phenyl)-4-methyl-4,5-dihydro-oxazol-2-ylamine

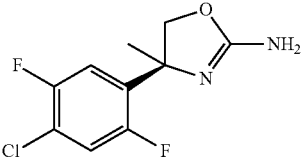

(RS)-4-(4-Chloro-2,5-difluoro-phenyl)-4-methyl-4,5-dihydro-oxazol-2-ylamine (example 271) was separated by chiral HPLC (Chiralpak AD, EtOH/heptane=5:95) to give the title compound. (+)-Enantiomer. White solid.

MS (ISP): 247.1 ([M+H]$^+$)

In analogy to example 252 and starting from the respective aldehyde were prepared:

Example 290

(RS)-4-(2-Fluoro-6-trifluoromethyl-phenyl)-4,5-dihydro-oxazol-2-ylamine

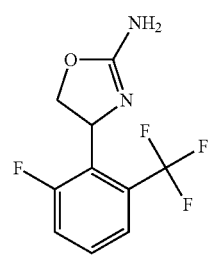 [SMILES: NC1=NC(c2c(F)cccc2C(F)(F)F)CO1]

From 2-fluoro-6-trifluoromethyl-benzaldehyde. White solid. MS (ISP): 248.9 ([M+H]9.

Example 291

(RS)-4-(4-Bromo-2-chloro-phenyl)-4,5-dihydro-oxazol-2-ylamine

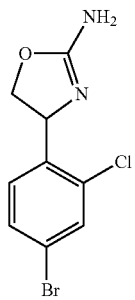

From 4-bromo-2-chloro-benzaldehyde. White solid. MS (ISP): 278.9 ([{$^{81}$Br$^{37}$Cl}M+H]$^+$), 276.9 ([{$^{81}$Br$^{35}$Cl or $^{79}$Br$^{37}$Cl}M+H]$^+$), 274.9 ([{$^{79}$Br$^{35}$Cl}M+H]$^+$).

Example 292

(S)-4-((S)-2-Phenyl-butyl)-4,5-dihydro-oxazol-2-ylamine

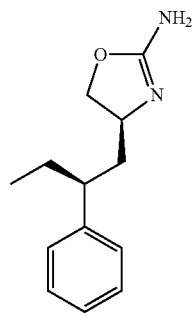 [SMILES: CC[C@@H](C[C@H]1COC(N)=N1)c1ccccc1]

a) ((R)-1-Iodomethyl-propyl)-benzene

To a solution of triphenylphosphine (15.4 g, 59 mmol) and imidazole (3.99 g, 59 mmol) in dichloromethane (150 ml) at room temperature was added portionwise iodine (14.9 g, 50 mmol) at such a rate that the temperature of the reaction mixture did not rise above 30° C. To the mixture was then added a solution of (R)-2-phenyl-butan-1-ol (7.34 g, 41 mmol, CAS 16460-75-6) in dichloromethane (50 ml) and the mixture was then stirred at room temperature overnight. The mixture was then concentrated in vacuo and the residue was resuspended in ether and the resulting crystals collected by filtration. The filtrate was concentrated in vacuo and the residue was triturated in heptane. The resulting crystals were removed by filtration and the filtrate was concentrated in vacuo. The residue was purified by column chromatography (SiO$_2$, heptane/EtOAc) to yield a colourless oil, (6.38 g, 60%).

b) (2R,5S)-2-Isopropyl-3,6-dimethoxy-5-((S)-2-phenyl-butyl)-2,5-dihydro-pyrazine A solution of (R)-(–)-2,5-dihydro-3,6-dimethoxy-2-isopropyl-5-methylpyrazine (4.25 g, 23.1 mmol) in tetrahydrofuran (30 ml) was cooled to –78° C., then n-butyllithium (1.6 M in hexane, 15.1 ml, 24.2 mmol) was added and the mixture was stirred for 1 hour. A solution of ((R)-1-iodomethyl-propyl)-benzene (6.30 g, 24.2 mmol) in tetrahydrofuran (30 ml) was added dropwise over 30 min and the mixture was stirred overnight while being allowed to warm slowly from –70° C. to room temperature. The reaction was quenched by addition of saturated aqueous ammonium chloride solution and the mixture was extracted with ether. The organic layer was separated, washed with saturated brine, then dried over Na$_2$SO$_4$ and concentrated in vacuo. The residue was purified by column chromatography (SiO$_2$, heptane/EtOAc) to yield a light yellow oil (4.69 g, 64%); MS (ISP): 317.0 ([M+H]$^+$).

c) (2S,4S)-2-Amino-4-phenyl-hexanoic acid methyl ester

To a solution of trifluoroacetic acid (3.4 ml) in water (440 ml) was added dropwise over 15 min a solution of (2R,5S)-2-isopropyl-3,6-dimethoxy-5-((S)-2-phenyl-butyl)-2,5-dihydro-pyrazine (4.69 g, 14.8 mmol) in acetonitrile (75 ml). The mixture was stirred overnight at room temperature then made basic by addition of saturated aqueous sodium carbonate solution and the mixture was extracted with ethyl acetate. The phases were separated and the organic phase was washed sequentially with water and with saturated brine, then dried over Na$_2$SO$_4$, filtered and concentrated in vacuo. The residue was purified by column chromatography (SiO$_2$, EtOAc/heptane) to yield a yellow oil (2.78 g, 85%); MS (ISP): 222.1 ([M+H]$^+$).

d) (2S,4S)-2-Amino-4-phenyl-hexan-1-ol

To a suspension of lithium aluminum hydride (121 mg, 3.18 mmol) in tetrahydrofuran (8 ml) was added a solution of (2S,4S)-2-amino-4-phenyl-hexanoic acid methyl ester (320 mg, 1.45 mmol) in tetrahydrofuran (10 ml) and the mixture was stirred for 16 hours. The reaction was quenched by dropwise addition of ethyl acetate, then acidified to pH 5 by addition of hydrochloric acid and then made basic by addition of saturated aqueous sodium bicarbonate solution. The mixture was taken up in ethyl acetate/tetrahydrofuran (1:1), the phases were separated and the organic phase was washed sequentially with water and with saturated brine. The organic phase was then dried over Na$_2$SO$_4$ and concentrated in vacuo. The residue was purified by chromatography (column: Isolute® Flash-NH$_2$ from Separtis; eluent: dichloromethane/MeOH) to yield a yellow oil, (116 mg, 42%); MS (ISP): 194.4 ([M+H]$^+$).

e) (S)-4-((S)-2-Phenyl-butyl)-4,5-dihydro-oxazol-2-ylamine

To a stirred, cooled (0° C.) solution of (2S,4S)-2-amino-4-phenyl-hexan-1-ol (270 mg, 1.40 mmol) and sodium acetate (229 mg, 2.70 mmol) in methanol (20 ml) was added dropwise a solution of cyanogen bromide (180 mg, 1.68 mmol) in methanol (2 ml) over 10 min. The mixture was then allowed to warm to r.t. and stirring was continued for 16 h. The mixture was concentrated in vacuo and the residue was taken up in ethyl acetate and washed sequentially with saturated aqueous sodium bicarbonate solution and with saturated brine. The organic phase was dried over sodium sulphate and concentrated in vacuo. The residue was purified by chromatography (column: Isolute® Flash-NH$_2$ from Separtis; eluent: heptane/EtOAc/MeOH) to yield a light yellow solid. MS (ISP): 219.3 ([M+H]$^+$).

Example 293

(S)-4-((R)-2-Phenyl-butyl)-4,5-dihydro-oxazol-2-ylamine

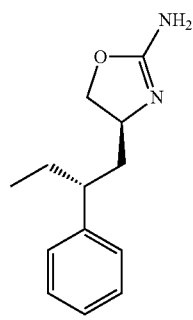 [SMILES: CC[C@H](C[C@H]1COC(N)=N1)c1ccccc1]

The title compound, MS (ISP): 219.4 ((M+H)$^{+\cdot}$) was obtained in comparable yield analogous to the procedure described for Example 292 starting from (S)-2-phenyl-butan-1-ol (CAS 33442-47-6). Colourless oil. MS (ISP): 219.4 ([M+H]$^+$).

Example 294

(RS)-4-(2,4-Dichloro-phenyl)-4-methyl-4,5-dihydro-oxazol-2-ylamine

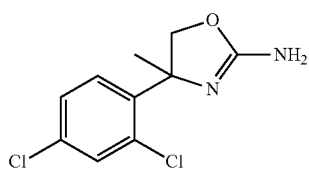

The title compound was obtained in analogy to example 268 starting from 2',4'-dichloro-acetophenone. Off-white viscous oil.

MS (ISP): 245.3 ([M+H]$^+$)

Examples 295 & 296

(−)-(R)-4-(2,4-Dichloro-phenyl)-4,5-dihydro-oxazol-2-ylamine & (+)-(S)-4-(2,4-Dichloro-phenyl)-4,5-dihydro-oxazol-2-ylamine

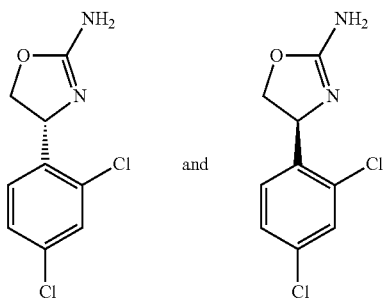 [SMILES: NC1=N[C@H](c2ccc(Cl)cc2Cl)CO1 ; "and" ; NC1=N[C@@H](c2ccc(Cl)cc2Cl)CO1]

(RS)-4-(2,4-Dichloro-phenyl)-4,5-dihydro-oxazol-2-ylamine (example 235) was separated by chiral HPLC (Chiralpak AD, EtOH/heptane=5:95) to yield (−)-(R)-4-(2,4-dichloro-phenyl)-4,5-dihydro-oxazol-2-ylamine (white solid; MS (ISP): 235.0 ([{$^{37}$Cl}M+H]$^+$), 233.0 ([{$^{37}$Cl$^{35}$Cl}M+H]$^+$), 231.1 ([{$^{35}$Cl}M+H]$^+$)) and (+)-(S)-4-(2,4-dichloro-phenyl)-4,5-dihydro-oxazol-2-ylamine (white solid; MS (ISP): 235.0 ([{$^{37}$Cl}M+H]$^+$), 233.0 ([{$^{37}$Cl$^{35}$Cl}M+H]$^+$), 231.1 ([{$^{35}$Cl}M+H]$^+$)).

Examples 297 & 298

(−)-(R)-4-(2,5-Dichloro-phenyl)-4,5-dihydro-oxazol-2-ylamine & (+)-(S)-4-(2,5-Dichloro-phenyl)-4,5-dihydro-oxazol-2-ylamine

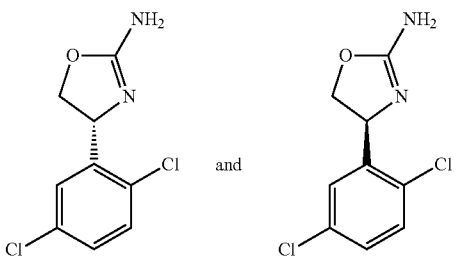 [SMILES: NC1=N[C@H](c2cc(Cl)ccc2Cl)CO1 ; "and" ; NC1=N[C@@H](c2cc(Cl)ccc2Cl)CO1]

(RS)-4-(2,5-Dichloro-phenyl)-4,5-dihydro-oxazol-2-ylamine (example 260) was separated by chiral HPLC (Chiralpak AD, EtOH/heptane=5:95) to yield (−)-(R)-4-(2,5-dichloro-phenyl)-4,5-dihydro-oxazol-2-ylamine (white solid; MS (ISP): 235.0 ([{$^{37}$Cl}M+H]$^+$), 233.0 ([{$^{37}$Cl$^{35}$Cl}M+H]$^+$), 231.1 ([{$^{35}$Cl}M+H]$^+$)) and (+)-(S)-4-(2,5-dichloro-phenyl)-4,5-dihydro-oxazol-2-ylamine (white solid; MS (ISP): 235.0 ([{$^{37}$Cl}M+H]$^+$), 233.0 ([{$^{37}$Cl$^{35}$Cl}M+H]$^+$), 231.1 ([{$^{35}$Cl}M+H]$^+$)).

Example 299

(RS)-4-(2,5-Dichloro-phenyl)-4-methyl-4,5-dihydro-oxazol-2-ylamine

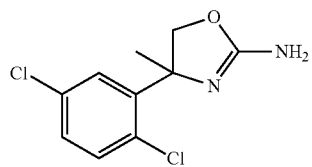

The title compound was obtained in analogy to example 271 starting from 2',5'-dichloro-acetophenone. Off-white viscous oil.

MS (ISP): 245.3 ([M+H]$^+$)

Examples 300 & 301

(−)-(R)-4-(2,3,4-Trifluoro-phenyl)-4,5-dihydro-oxazol-2-ylamine & (+)-(S)-4-(2,3,4-Trifluoro-phenyl)-4,5-dihydro-oxazol-2-ylamine

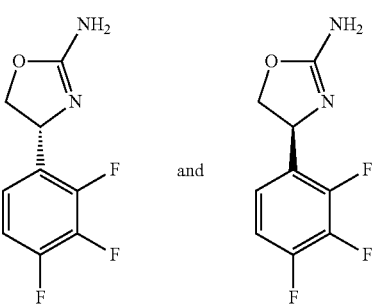 [SMILES: NC1=N[C@H](c2ccc(F)c(F)c2F)CO1 ; "and" ; NC1=N[C@@H](c2ccc(F)c(F)c2F)CO1]

(RS)-4-(2,3,4-Trifluoro-phenyl)-4,5-dihydro-oxazol-2-ylamine (example 17) was separated by chiral HPLC (Chiralpak AD, EtOH/heptane=5:95) to yield (−)-(R)-4-(2,3,4-trifluoro-phenyl)-4,5-dihydro-oxazol-2-ylamine (white solid; MS (ISP): 217.3 ([M+H]⁺)) and (+)-(S)-4-(2,3,4-trifluoro-phenyl)-4,5-dihydro-oxazol-2-ylamine (white solid; MS (ISP): 217.3 ([M+H]⁺)).

In analogy to example 252 and starting from the respective aldehyde was prepared:

Example 302

(RS)-4-(4-Bromo-2-trifluoromethyl-phenyl)-4,5-dihydro-oxazol-2-ylamine

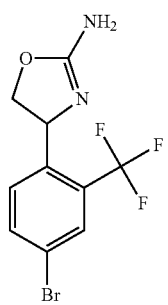 [SMILES: NC1=NC(c2ccc(Br)cc2C(F)(F)F)CO1]

From 4-bromo-2-trifluoromethyl-benzaldehyde. White solid. MS (ISP): 311.0 ([{⁸¹Br}M+H]⁺), 309.1 ([{⁷⁹Br}M+H]⁺).

Example 303

(S)-4-[2-(2-Chloro-6-fluoro-phenyl)-ethyl]-4,5-dihydro-oxazol-2-ylamine

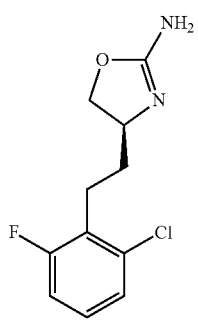 [SMILES: NC1=N[C@@H](CCc2c(F)cccc2Cl)CO1]

The title compound, MS (ISP): 243.0; 245.1 ([M+H]⁺) was obtained in comparable yield analogous to the procedure described for Example 228 using (R)-(−)-2,5-dihydro-3,6-dimethoxy-2-isopropyl-pyrazine instead of (R)-(−)-2,5-dihydro-3,6-dimethoxy-2-isopropyl-5-methylpyrazine and 2-chloro-6-fluoro-1-(2-iodo-ethyl)-benzene instead of 1-(2-bromo-ethyl)-2-chlorobenzene in step a).

Example 304

(S)-4-[2-(2,4-Dichloro-phenyl)-ethyl]-4-methyl-4,5-dihydro-oxazol-2-ylamine

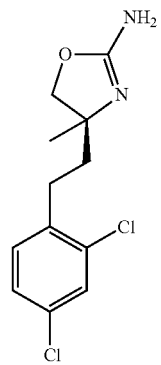 [SMILES: C[C@]1(CCc2ccc(Cl)cc2Cl)COC(N)=N1]

The title compound, MS (ISP): 273.1; 275.0 ([M+H]⁺˙) was obtained in comparable yield analogous to the procedure described for Example 228 using 2,4-dichloro-1-(2-iodo-ethyl)-benzene instead of 1-(2-bromo-ethyl)-2-chlorobenzene in step a).

Example 305

(R)-4-Methyl-4-(3,4,5-trifluoro-phenyl)-4,5-dihydro-oxazol-2-ylamine

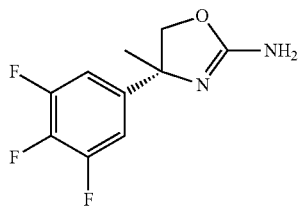 [SMILES: C[C@@]1(c2cc(F)c(F)c(F)c2)COC(N)=N1]

(RS)-4-Methyl-4-(3,4,5-trifluoro-phenyl)-4,5-dihydro-oxazol-2-ylamine (example 273) was separated by chiral HPLC (Chiralpak AD, EtOH/heptane=1:9) to give the title compound. (−)-Enantiomer. White solid.
MS (ISP): 231.1 ([M+H]⁺))

Example 306

(S)-4-Methyl-4-(3,4,5-trifluoro-phenyl)-4,5-dihydro-oxazol-2-ylamine

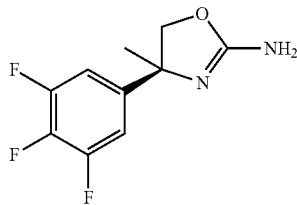 [SMILES: C[C@]1(c2cc(F)c(F)c(F)c2)COC(N)=N1]

(RS)-4-Methyl-4-(3,4,5-trifluoro-phenyl)-4,5-dihydro-oxazol-2-ylamine (example 273) was separated by chiral HPLC (Chiralpak AD, EtOH/heptane=1:9) to give the title compound. (+)-Enantiomer. White solid.
MS (ISP): 231.1 ([M+H]⁺))

Example 307

(R)-4-(4-Chloro-2-fluoro-5-methyl-phenyl)-4-methyl-4,5-dihydro-oxazol-2-ylamine

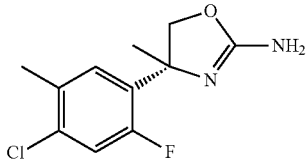 [SMILES: Cc1cc([C@]2(C)COC(N)=N2)c(F)cc1Cl]

(RS)-4-(4-Chloro-2-fluoro-5-methyl-phenyl)-4-m ethyl-4,5-dihydro-oxazol-2-ylamine (example 274) was separated by chiral HPLC (Chiralpak AD, EtOH/heptane=5:95) to give the title compound. (−)-Enantiomer. Waxy white solid.

MS (ISP): 243.3 ([M+H]$^+$)

Example 308

(S)-4-(4-Chloro-2-fluoro-5-methyl-phenyl)-4-methyl-4,5-dihydro-oxazol-2-ylamine

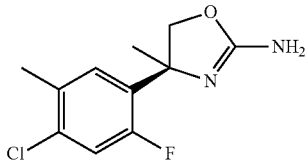 [SMILES: Cc1cc([C@@]2(C)COC(N)=N2)c(F)cc1Cl]

(RS)-4-(4-Chloro-2-fluoro-5-methyl-phenyl)-4-methyl-4,5-dihydro-oxazol-2-ylamine (example 274) was separated by chiral HPLC (Chiralpak AD, EtOH/heptane=5:95) to give the title compound. (+)-Enantiomer. Waxy white solid.

MS (ISP): 243.3 ([M+H]$^+$))

Example 309

(RS)-4-(4-Methoxy-phenyl)-4-methyl-4,5-dihydro-oxazol-2-ylamine

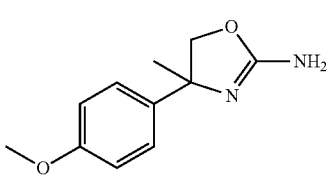

The title compound was obtained in analogy to example 271 starting from 4-methoxy-acetophenone. White solid.

MS (ISP): 206.9 ([M+H]$^+$)

In analogy to example 87 was prepared:

Example 310

(S)-4-(4-Bromo-phenoxymethyl)-4,5-dihydro-oxazol-2-ylamine

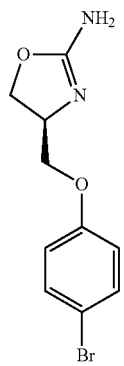

From tert-butyl (S)-4-(hydroxymethyl)-2,2-dimethyl-3-oxazolidinecarboxylate and 4-bromophenol. White solid. MS (ISP): 273.1 ([{$^{37}$Cl}M+H]$^+$), 271.1 ([{$^{35}$Cl}M+H]$^+$)).

Example 311

(RS)-4-(3-Chloro-2-fluoro-phenyl)-4-methyl-4,5-dihydro-oxazol-2-ylamine

The title compound was obtained in analogy to example 268 starting from 3-chloro-2-fluoro-acetophenone. White solid.

MS (ISP): 229.1 ([M+H]$^+$)

Example 312

(R)-4-(4-Chloro-phenyl)-4-ethyl-4,5-dihydro-oxazol-2-ylamine

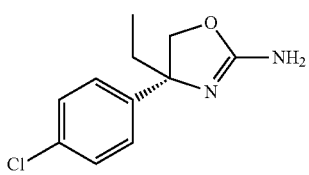

(RS)-4-(4-Chloro-phenyl)-4-ethyl-4,5-dihydro-oxazol-2-ylamine (example 268) was separated by chiral HPLC (Chiralpak AD, EtOH/heptane=5:95) to give the title compound. (−)-Enantiomer. White solid.

MS (ISP): 225.1 ([M+H]$^+$))

Example 313

(S)-4-(4-Chloro-phenyl)-4-ethyl-4,5-dihydro-oxazol-2-ylamine

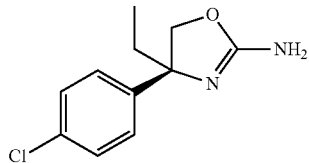

(RS)-4-(4-Chloro-phenyl)-4-ethyl-4,5-dihydro-oxazol-2-ylamine (example 268) was separated by chiral HPLC (Chiralpak AD, EtOH/heptane=5:95) to give the title compound. (+)-Enantiomer. White solid.
MS (ISP): 225.1 ([M+H])

Example 314

(+)-(S)-4-(5-Chloro-2-methyl-phenyl)-4,5-dihydro-oxazol-2-ylamine

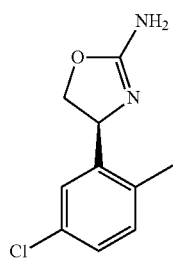

(RS)-4-(5-Chloro-2-methyl-phenyl)-4,5-dihydro-oxazol-2-ylamine (example 272) was separated by chiral HPLC (Chiralpak AD, EtOH/heptane=5:95) to yield (+)-(S)-4-(5-chloro-2-methyl-phenyl)-4,5-dihydro-oxazol-2-ylamine (white solid; MS (ISP): 213.1 ([$\{^{37}Cl\}$M+H]$^+$), 211.1 ([$\{^{35}Cl\}$M+H]$^+$)).

Examples 315 & 316

(−)-(R)-4-(4-Bromo-2-chloro-phenyl)-4,5-dihydro-oxazol-2-ylamine & (+)-(S)-4-(4-Bromo-2-chloro-phenyl)-4,5-dihydro-oxazol-2-ylamine

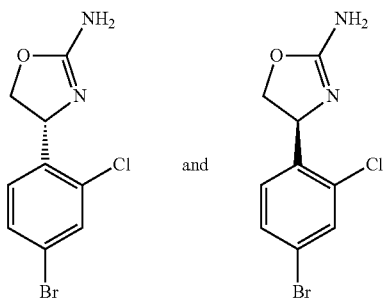 [SMILES: NC1=N[C@H](c2ccc(Br)cc2Cl)CO1 ; "and" ; NC1=N[C@@H](c2ccc(Br)cc2Cl)CO1]

(RS)-4-(4-Bromo-2-chloro-phenyl)-4,5-dihydro-oxazol-2-ylamine (example 291) was separated by chiral HPLC (Chiralpak AD, EtOH/heptane=5:95) to yield (−)-(R)-4-(4-bromo-2-chloro-phenyl)-4,5-dihydro-oxazol-2-ylamine (white solid; MS (ISP): 278.9 ([$\{^{81}Br^{37}Cl\}$M+H]$^+$), 276.9 ([$\{^{81}Br^{35}Cl$ or $^{79}Br^{37}Cl\}$M+H]$^+$), 274.9 ([$\{^{79}Br^{35}Cl\}$M+H]$^+$)) and (+)-(S)-4-(4-bromo-2-chloro-phenyl)-4,5-dihydro-oxazol-2-ylamine (white solid; MS (ISP): 278.9 ([$\{^{81}Br^{37}Cl\}$M+H]$^+$), 276.9 ([$\{^{81}Br^{35}Cl$ or $^{79}Br^{37}Cl\}$M+H]$^+$), 274.9 ([$\{^{79}Br^{35}Cl\}$M+H]$^+$)).

Example 317

(−)-(S)-4-(2-Fluoro-6-trifluoromethyl-phenyl)-4,5-dihydro-oxazol-2-ylamine

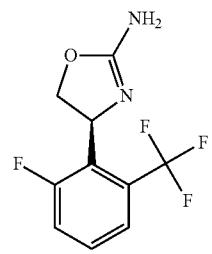 [SMILES: NC1=N[C@@H](c2c(F)cccc2C(F)(F)F)CO1]

(RS)-4-(2-Fluoro-6-trifluoromethyl-phenyl)-4,5-dihydro-oxazol-2-ylamine (example 290) was separated by chiral HPLC (Chiralpak AD, EtOH/heptane=5:95) to yield (−)-(S)-4-(2-fluoro-6-trifluoromethyl-phenyl)-4,5-dihydro-oxazol-2-ylamine (white solid; MS (ISP): 248.9 ([M+H]$^+$).

Example 318

(RS)-4-(2-Chloro-4-fluoro-phenyl)-4-methyl-4,5-dihydro-oxazol-2-ylamine

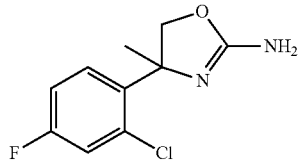

The title compound was obtained in analogy to example 206 starting from 2-chloro-4-fluoro-acetophenone. Off-white solid.
MS (ISP): 229.1 ([M+H]$^+$)

In analogy to example 87 was prepared:

Example 319

(S)-4-p-Tolyloxymethyl-4,5-dihydro-oxazol-2-ylamine

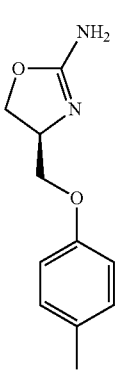

From tert-butyl (S)-4-(hydroxymethyl)-2,2-dimethyl-3-oxazolidinecarboxylate and 4-methyl-phenol. White solid. MS (ISP): 207.3 ([M+H]⁺).

Examples 320 & 321

(−)-(R)-4-(4-Bromo-3-fluoro-phenyl)-4,5-dihydro-oxazol-2-ylamine & (+)-(S)-4-(4-Bromo-3-fluoro-phenyl)-4,5-dihydro-oxazol-2-ylamine

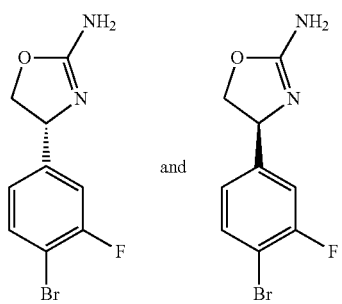 [SMILES: NC1=N[C@H](c2ccc(Br)c(F)c2)CO1 ; "and" ; NC1=N[C@@H](c2ccc(Br)c(F)c2)CO1]

(RS)-4-(4-Bromo-3-fluoro-phenyl)-4,5-dihydro-oxazol-2-ylamine (example 252) was separated by chiral HPLC (Chiralpak AD, EtOH/heptane=20:80) to yield (−)-(R)-4-(4-bromo-3-fluoro-phenyl)-4,5-dihydro-oxazol-2-ylamine (white solid; MS (ISP): 261.0 ([{⁸¹Br}M+H]⁺), 258.9 ([{⁷⁹Br}M+H]⁺)) and (+)-(S)-4-(4-bromo-3-fluoro-phenyl)-4,5-dihydro-oxazol-2-ylamine (white solid; MS (ISP): 261.0 ([{⁸¹Br}M+H]⁺), 258.9 ([{⁷⁹Br}M+H]⁺).

Example 322

(S)-4-[2-(2-Bromo-phenyl)-ethyl]-4,5-dihydro-oxazol-2-ylamine

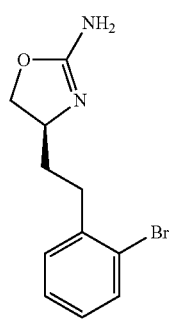 [SMILES: NC1=N[C@@H](CCc2ccccc2Br)CO1]

The title compound, MS (ISP): 191.3 ([M−Br+H]+); 269.1; 271.1 ([M+H]⁺) was obtained in comparable yield analogous to the procedure described for Example 228 using (R)-(−)-2,5-dihydro-3,6-dimethoxy-2-isopropyl-pyrazine instead of (R)-(−)-2,5-dihydro-3,6-dimethoxy-2-isopropyl-5-methylpyrazine and 2-bromo-1-(2-iodo-ethyl)-benzene instead of 1-(2-bromo-ethyl)-2-chlorobenzene in step a).

Example 323

(R)-4-Benzylsulfanylmethyl-4,5-dihydro-oxazol-2-ylamine

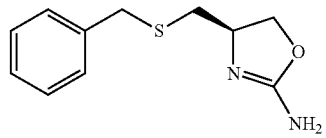

The title compound, MS (ISP): 223.2 ([M+H])⁺·) was obtained in comparable yield analogous to the procedure described for Example 195 using S-benzyl-L-cysteine instead of S-phenyl-L-cysteine in step a).

In analogy to example 87 was prepared:

Example 324

(S)-4-(4-Chloro-2-fluoro-phenoxymethyl)-4,5-dihydro-oxazol-2-ylamine

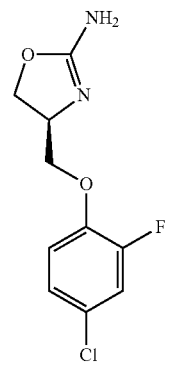 [SMILES: NC1=N[C@@H](COc2ccc(Cl)cc2F)CO1]

From tert-butyl (S)-4-(hydroxymethyl)-2,2-dimethyl-3-oxazolidinecarboxylate and 4-chloro-2-fluoro-phenol. White solid. MS (ISP): 247.2 ([{³⁷Cl}M+H]⁺), 245.2 ([{³⁵Cl}M+H]⁺)).

Example 325

((S)-4-Cyclohexyl-4,5-dihydro-oxazol-2-ylamine

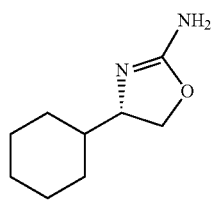 [SMILES: NC1=N[C@@H](C2CCCCC2)CO1]

The title compound was obtained in analogy to example 1.b starting from (S)-2-amino-2-cyclohexyl-ethanol. White solid.

MS (ISP): 169.1 ([M+H]⁺)

In analogy to example 252 and starting from the respective aldehyde was prepared:

Example 326

(RS)-4-(4-Bromo-3-chloro-phenyl)-4,5-dihydro-oxazol-2-ylamine

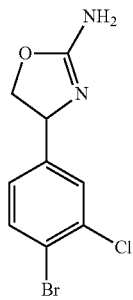

From 4-bromo-3-chloro-benzaldehyde. White solid. MS (ISP): 278.9 ([{$^{81}$Br$^{37}$Cl}M+H]$^+$), 277.0 ([{$^{81}$Br$^{35}$Cl or $^{79}$Br$^{37}$Cl}M+H]$^+$), 274.9 ([{$^{79}$Br$^{35}$Cl}M+H]$^+$)).

Example 327

(RS)-4-(3,4-Dichloro-phenyl)-4-ethyl-4,5-dihydro-oxazol-2-ylamine

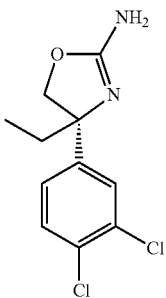 [SMILES: CC[C@@]1(c2ccc(Cl)c(Cl)c2)COC(N)=N1]

a) (S)-4-(3,4-Dichloro-phenyl)-4-ethyl-4,5-dihydro-oxazol-2-ylamine

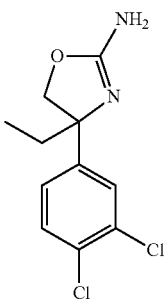 [SMILES: CCC1(c2ccc(Cl)c(Cl)c2)COC(N)=N1]

In analogy to example 206, the title compound was obtained starting from 3,4-dichloropropiophenone. White solid.

b) (R)-4-(3,4-Dichloro-phenyl)-4-ethyl-4,5-dihydro-oxazol-2-ylamine (S)-4-(3,4-Dichloro-phenyl)-4-ethyl-4,5-dihydro-oxazol-2-ylamine was separated by chiral HPLC (Chiralpak AD, EtOH/heptane 1:9) to give the title compound. (−)-Enantiomer. Off-white solid.

MS (ISP): 259.0 ([M+H]$^+$)

Example 328

(S)-4-(3,4-Dichloro-phenyl)-4-ethyl-4,5-dihydro-oxazol-2-ylamine

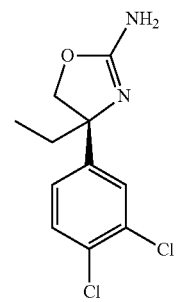 [SMILES: CC[C@]1(c2ccc(Cl)c(Cl)c2)COC(N)=N1]

(RS)-4-(3,4-Dichloro-phenyl)-4-ethyl-4,5-dihydro-oxazol-2-ylamine was separated by chiral HPLC (Chiralpak AD, EtOH/heptane 1:9) to give the title compound. (+)-Enantiomer. Off-white solid.

MS (ISP): 258.8 ([M+H]$^+$)

Examples 329 & 330

(−)-(R)-4-(4-Bromo-3-chloro-phenyl)-4,5-dihydro-oxazol-2-ylamine & (+)-(S)-4-(4-Bromo-3-chloro-phenyl)-4,5-dihydro-oxazol-2-ylamine

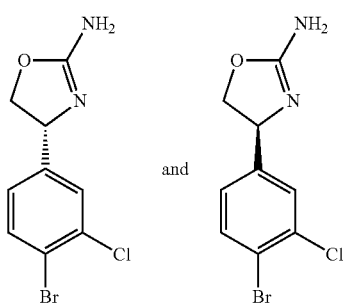 [SMILES: NC1=N[C@H](c2ccc(Br)c(Cl)c2)CO1 ; "and" ; NC1=N[C@@H](c2ccc(Br)c(Cl)c2)CO1]

(RS)-4-(4-Bromo-3-chloro-phenyl)-4,5-dihydro-oxazol-2-ylamine (example 326) was separated by chiral HPLC (Chiralpak AD, EtOH/heptane=20:80) to yield (−)-(R)-4-(4-bromo-3-chloro-phenyl)-4,5-dihydro-oxazol-2-ylamine (white solid; MS (ISP): 278.9 ([{$^{81}$Br$^{37}$Cl}M+H]$^+$), 277.0 ([{$^{81}$Br$^{35}$Cl or $^{79}$Br$^{7}$Cl}M+H]$^+$), 274.9 ([{$^{79}$Br$^{35}$Cl}M+H]$^+$)) and (+)-(S)-4-(4-bromo-3-chloro-phenyl)-4,5-dihydro-oxazol-2-ylamine (white solid; MS (ISP): 278.9 ([{$^{81}$Br$^{37}$Cl}M+H]$^+$), 277.0 ([{$^{81}$Br$^{35}$Cl or $^{79}$Br$^{37}$Cl}M+H]$^+$), 274.9 ([{$^{79}$Br$^{35}$Cl}M+H]$^+$)).

Example 331

(RS)-4-(2,3-Dichloro-phenyl)-4-methyl-4,5-dihydro-oxazol-2-ylamine

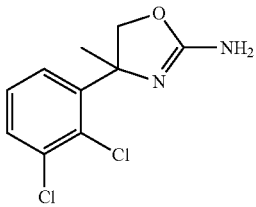

The title compound was obtained in analogy to example 271 starting from 2,3-dichloro-acetophenone. White solid.
MS (ISP): 245.3 ([M+H]$^+$)

Example 332

(S)-4-(2-Cyclohexyl-ethyl)-4,5-dihydro-oxazol-2-ylamine

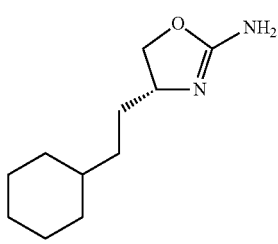 [SMILES: NC1=N[C@H](CCC2CCCCC2)CO1]

The title compound was obtained in analogy to example 1 starting from (+)-ethyl-(S)-2 amino-4-cyclohexylbutyrate. Off-white solid.
MS (ISP): 197.1 ([M+H]$^+$)

Example 333

(S)-4-[2-(2,5-Dichloro-phenyl)-ethyl]-4,5-dihydro-oxazol-2-ylamine

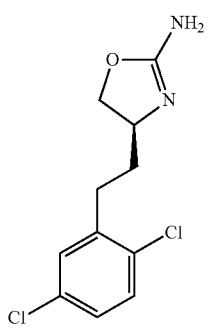 [SMILES: NC1=N[C@@H](CCc2cc(Cl)ccc2Cl)CO1]

The title compound, MS (ISP): 258.9; 261.0 ([M+H]$^+$) was obtained in comparable yield analogous to the procedure described for Example 228 using (R)-(−)-2,5-dihydro-3,6-dimethoxy-2-isopropyl-pyrazine instead of (R)-(−)-2,5-dihydro-3,6-dimethoxy-2-isopropyl-5-methylpyrazine and 1-(2-bromo-ethyl)-2,5-dichloro-benzene instead of 1-(2-bromo-ethyl)-2-chlorobenzene in step a).

In analogy to example 163 were prepared:

Example 334

(S)-4-[2-(2,4-Difluoro-phenyl)-butyl]-4,5-dihydro-oxazol-2-ylamine

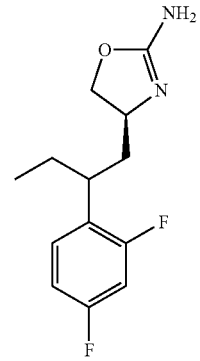 [SMILES: CCC(C[C@H]1COC(N)=N1)c1ccc(F)cc1F]

From (S)-4-(2,2-dibromo-vinyl)-2,2-dimethyl-oxazolidine-3-carboxylic acid tert-butyl ester by sequential treatment with 2,4-difluorophenyl boronic acid and diethylzinc. Mainly one epimer. Colourless oil. MS (ISP): 255.1 ([M+H]$^+$).

Example 335

(S)-4-[2-(2,3,4-Trifluoro-phenyl)-butyl]-4,5-dihydro-oxazol-2-ylamine

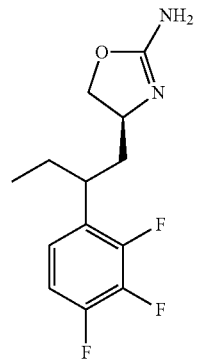 [SMILES: CCC(C[C@H]1COC(N)=N1)c1ccc(F)c(F)c1F]

From (S)-4-(2,2-dibromo-vinyl)-2,2-dimethyl-oxazolidine-3-carboxylic acid tert-butyl ester by sequential treatment with 2,3,4-trifluorophenyl boronic acid and diethylzinc. Mainly one epimer. Colourless oil. MS (ISP): 273.1 ([M+H]$^+$).

Example 336

(S)-4-[2-(3,4,5-Trifluoro-phenyl)-butyl]-4,5-dihydro-oxazol-2-ylamine

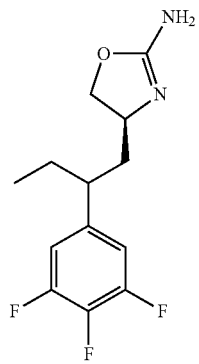 [SMILES: CCC(C[C@H]1COC(N)=N1)c1cc(F)c(F)c(F)c1]

From (S)-4-(2,2-dibromo-vinyl)-2,2-dimethyl-oxazolidine-3-carboxylic acid tert-butyl ester by sequential treatment with 3,4,5-trifluorophenyl boronic acid and diethylzinc. Mainly one epimer. Colourless oil. MS (ISP): 273.1 ([M+H]$^+$).

In analogy to example 252 and starting from the respective aldehyde was prepared:

Example 337

(RS)-4-(4-Fluoro-2-methyl-phenyl)-4,5-dihydro-oxazol-2-ylamine

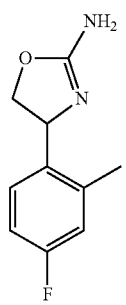

From 4-fluoro-2-methyl-benzaldehyde. White solid. MS (ISP): 195.1 ([M+H]$^+$)

Examples 338 & 339

(+)-(S)-4-(4-Bromo-2-trifluoromethyl-phenyl)-4,5-dihydro-oxazol-2-ylamine & (−)-(R)-4-(4-Bromo-2-trifluoromethyl-phenyl)-4,5-dihydro-oxazol-2-ylamine

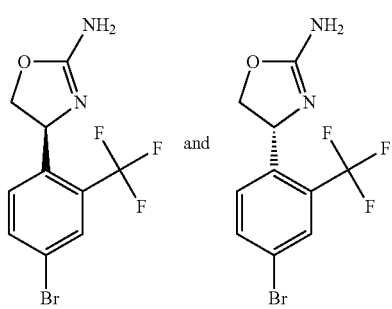 [SMILES: NC1=N[C@@H](c2ccc(Br)cc2C(F)(F)F)CO1 ; NC1=N[C@H](c2ccc(Br)cc2C(F)(F)F)CO1]

(RS)-4-(4-Bromo-2-trifluoromethyl-phenyl)-4,5-dihydro-oxazol-2-ylamine (example 302) was separated by chiral HPLC (Chiralpak AD, EtOH/heptane=20:80) to yield (−)-(R)-4-(4-bromo-2-trifluoromethyl-phenyl)-4,5-dihydro-oxazol-2-ylamine (colourless viscous oil; MS (ISP): 311.0 ([{$^{81}$Br}M+H]$^+$), 309.1 ([{$^{79}$Br}M+H]$^+$)) and (+)-(S)-4-(4-bromo-2-trifluoromethyl-phenyl)-4,5-dihydro-oxazol-2-ylamine (colourless viscous oil; MS (ISP): 311.0 ([{$^{81}$Br}M+H]$^+$), 309.1 ([{$^{79}$Br}M+H]$^+$)).

In analogy to example 163 was prepared:

Example 340

(S)-4-[2-(3-Fluoro-phenyl)-butyl]-4,5-dihydro-oxazol-2-ylamine

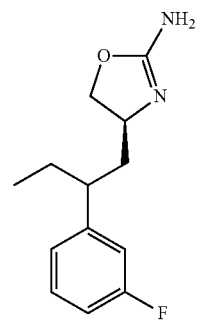 [SMILES: CCC(C[C@H]1COC(N)=N1)c1cccc(F)c1]

From (S)-4-(2,2-dibromo-vinyl)-2,2-dimethyl-oxazolidine-3-carboxylic acid tert-butyl ester by sequential treatment with 3-fluorophenyl boronic acid and diethylzinc. Mainly one epimer. Colourless oil. MS (ISP): 237.3 ([M+H]$^+$).

Example 341

(+)-(S)-4-(5-Chloro-2-trifluoromethyl-phenyl)-4,5-dihydro-oxazol-2-ylamine

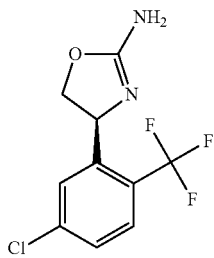 [SMILES: NC1=N[C@@H](c2cc(Cl)ccc2C(F)(F)F)CO1]

(RS)-4-(5-Chloro-2-trifluoromethyl-phenyl)-4,5-dihydro-oxazol-2-ylamine (example 225) was separated by chiral HPLC (Chiralpak AD, EtOH/heptane=20:80) to yield (−)-(S)-4-(5-chloro-2-trifluoromethyl-phenyl)-4,5-dihydro-oxazol-2-ylamine (off-white solid; MS (ISP): 267.1 ([{$^{37}$Cl}M+H]$^+$), 265.0 ([{$^{35}$Cl}M+H]$^+$).

Example 342

(S)-4-(1-Phenyl-cyclopropylmethyl)-4,5-dihydro-oxazol-2-ylamine

The title compound, MS (ISP): 217.1 ([M+H]+·) was obtained in comparable yield analogous to the procedure described for Example 257 using (1-phenyl-cyclopropyl)-methanol instead of [1-(4-chlorophenyl)-cyclopropyl]-methanol in step a).

In analogy to example 87 was prepared:

Example 343

(S)-4-(3-Chloro-phenoxymethyl)-4,5-dihydro-oxazol-2-ylamine

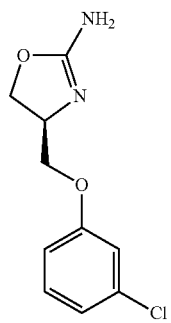 [SMILES: NC1=N[C@@H](COc2cccc(Cl)c2)CO1]

From tert-butyl (S)-4-(hydroxymethyl)-2,2-dimethyl-3-oxazolidinecarboxylate and 3-chloro-phenol. Colourless oil. MS (ISP): 229.2 ([{$^{37}$Cl}M+H]$^+$), 227.2 ([{$^{35}$Cl}M+H]$^+$)).

Example 344

(RS)-4-(4-Chloro-2-ethyl-phenyl)-4,5-dihydro-oxazol-2-ylamine

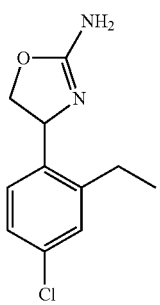

a) 4-Chloro-2-ethyl-benzaldehyde

The title compound was obtained starting from 4-chloro-2-fluoro-benzaldehyde by sequential treatment with N-butylaminine/p-toluenesulphonic acid and ethylmagnesium chloride/manganese(II) chloride according to the procedures described in *Synthesis* 1999, 2138-2144 and WO 2007/085557. Yellow oil.

b) (RS)-4-(4-Chloro-2-ethyl-phenyl)-4,5-dihydro-oxazol-2-ylamine

In analogy to example 252, the title compound was obtained starting from 4-chloro-2-ethyl-benzaldehyde. Light yellow solid. MS (ISP): 227.1 ([{$^{37}$Cl}M+H]$^+$), 225.1 ([{$^{35}$Cl}M+H]$^+$)).

Examples 345

(−)-(R)-4-Methyl-4-(2,3,6-trifluoro-phenyl)-4,5-dihydro-oxazol-2-ylamine

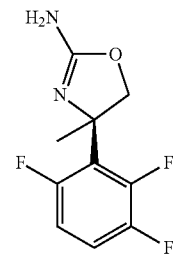 [SMILES: C[C@@]1(c2c(F)ccc(F)c2F)COC(N)=N1]

a) (RS)-4-Methyl-4-(2,3,6-trifluoro-phenyl)-4,5-dihydro-oxazol-2-ylamine

In analogy to example 206, the title compound was obtained starting from 1-(2,3,6-trifluoro-phenyl)-ethanone. White solid. MS (ISP): 231.3 ([M+H]$^+$)

a) (−)-(R)-4-Methyl-4-(2,3,6-trifluoro-phenyl)-4,5-dihydro-oxazol-2-ylamine (RS)-4-Methyl-4-(2,3,6-trifluoro-phenyl)-4,5-dihydro-oxazol-2-ylamine was separated by chiral HPLC (Chiralpak AD, iPrOH/heptane=5:95) to yield (−)-(R)-4-methyl-4-(2,3,6-trifluoro-phenyl)-4,5-dihydro-oxazol-2-ylamine (white solid; MS (ISP): 231.1 ([M+H]$^+$).

Examples 346

(+)-(S)-4-Methyl-4-(2,3,6-trifluoro-phenyl)-4,5-dihydro-oxazol-2-ylamine

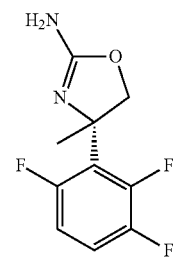 [SMILES: C[C@]1(c2c(F)ccc(F)c2F)COC(N)=N1]

(RS)-4-Methyl-4-(2,3,6-trifluoro-phenyl)-4,5-dihydro-oxazol-2-ylamine (Example 345.a) was separated by chiral HPLC (Chiralpak AD, iPrOH/heptane=5:95) to yield (+)-(S)-4-methyl-4-(2,3,6-trifluoro-phenyl)-4,5-dihydro-oxazol-2-ylamine (white solid; MS (ISP): 231.1 ([M+H]$^+$).

Examples 347 & 348

(−)-(R)-4-(4-Fluoro-2-methyl-phenyl)-4,5-dihydro-oxazol-2-ylamine & (+)-(S)-4-(4-Fluoro-2-methyl-phenyl)-4,5-dihydro-oxazol-2-ylamine

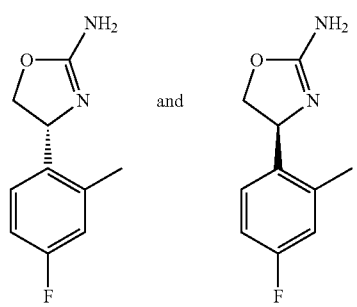

(RS)-4-(4-Fluoro-2-methyl-phenyl)-4,5-dihydro-oxazol-2-ylamine (example 337) was separated by chiral HPLC (Chiralpak AD, EtOH/heptane=10:90) to yield (−)-(R)-4-(4-fluoro-2-methyl-phenyl)-4,5-dihydro-oxazol-2-ylamine (white solid; MS (ISP): 195.1 ([M+H]$^+$) and (+)-(S)-4-(4-fluoro-2-methyl-phenyl)-4,5-dihydro-oxazol-2-ylamine (white solid; MS (ISP): 195.1 ([M+H]$^+$).

In analogy to example 252 and starting from the respective aldehyde was prepared:

Example 349

(RS)-4-(4-Bromo-2-fluoro-phenyl)-4,5-dihydro-oxazol-2-ylamine

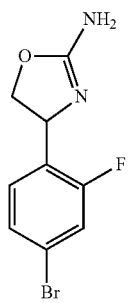

From 4-bromo-2-fluoro-benzaldehyde. White solid. MS (ISP): 261.0 ([$^{81}$Br]M+H]$^+$), 258.9 ([$^{79}$Br]M+H]$^+$)).

In analogy to example 1 was prepared:

Example 350

(S)-4-Benzyloxymethyl-4,5-dihydro-oxazol-2-ylamine

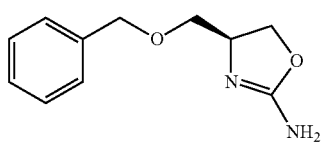

From O-benzyl-L-serine methyl ester. Colourless oil. MS (ISP): 206.9 ([M+H]$^+$)

In analogy to example 252 and starting from the respective aldehyde was prepared:

Example 351

(RS)-4-(3-Chloro-4-methyl-phenyl)-4,5-dihydro-oxazol-2-ylamine

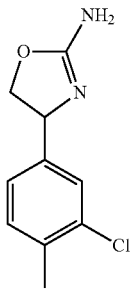

From 3-chloro-4-methyl-benzaldehyde. White solid. MS (ISP): 213.1 ([$^{37}$Cl]M+H]$^+$), 211.0 ([$^{35}$Cl]M+H]$^+$)).

Example 352

(+)-(R)-4-(5-Chloro-2-trifluoromethyl-phenyl)-4,5-dihydro-oxazol-2-ylamine

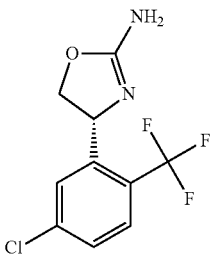 [SMILES: NC1=N[C@H](c2cc(Cl)ccc2C(F)(F)F)CO1]

(RS)-4-(5-Chloro-2-trifluoromethyl-phenyl)-4,5-dihydro-oxazol-2-ylamine (example 225) was separated by chiral HPLC (Chiralpak AD, EtOH/heptane=20:80) to yield (+)-(R)-4-(5-chloro-2-trifluoromethyl-phenyl)-4,5-dihydro-oxazol-2-ylamine (off-white solid; MS (ISP): 267.1 ([$^{37}$Cl]M+H]$^+$), 265.0 ([$^{35}$Cl]M+H]$^+$).

In analogy to example 87 were prepared:

Example 353

(S)-4-(2,4-Difluoro-phenoxymethyl)-4,5-dihydro-oxazol-2-ylamine

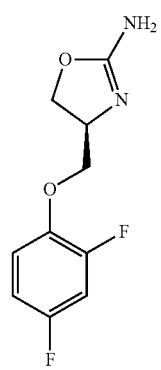 [SMILES: NC1=N[C@@H](COc2ccc(F)cc2F)CO1]

From tert-butyl (S)-4-(hydroxymethyl)-2,2-dimethyl-3-oxazolidinecarboxylate and 2,4-difluorophenol. Colourless oil. MS (ISP): 229.2 ([M+H]$^+$).

Example 354

(S)-4-(2-Fluoro-phenoxymethyl)-4,5-dihydro-oxazol-2-ylamine

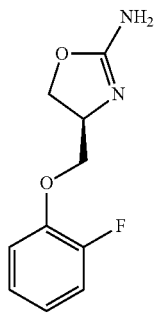 [SMILES: NC1=N[C@@H](COc2ccccc2F)CO1]

From tert-butyl (S)-4-(hydroxymethyl)-2,2-dimethyl-3-oxazolidinecarboxylate and 2,4-difluorophenol. Colourless oil. MS (ISP): 211.1 ([M+H]$^+$).
In analogy to example 162 were prepared:

Example 355

(S)-4-[2-(3-Chloro-2-fluoro-phenyl)-butyl]-4,5-dihydro-oxazol-2-ylamine

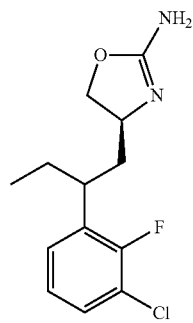 [SMILES: CCC(C[C@H]1COC(N)=N1)c1cccc(Cl)c1F]

From (S)-4-(2,2-dibromo-vinyl)-2,2-dimethyl-oxazolidine-3-carboxylic acid tert-butyl ester by sequential treatment with 3-chloro-2-fluorophenyl boronic acid and diethylzinc. Mainly one epimer. Colourless oil. MS (ISP): 273.2 ([{$^{37}$Cl}M+H]$^+$), 271.3 ([{$^{35}$Cl}M+H]$^+$)).

Example 356

(S)-4-[2-(3-Chloro-4-fluoro-phenyl)-butyl]-4,5-dihydro-oxazol-2-ylamine

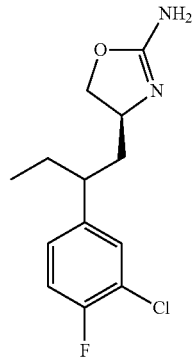

From (S)-4-(2,2-dibromo-vinyl)-2,2-dimethyl-oxazolidine-3-carboxylic acid tert-butyl ester by sequential treatment with 3-chloro-4-fluorophenyl boronic acid and diethylzinc. Mainly one epimer. Colourless oil. MS (ISP): 273.1 ([{$^{37}$Cl}M+H]$^+$), 271.1 ([{$^{35}$Cl}M+H]$^+$)).

Example 357

(S)-4-[2-(3-Chloro-5-fluoro-phenyl)-butyl]-4,5-dihydro-oxazol-2-ylamine

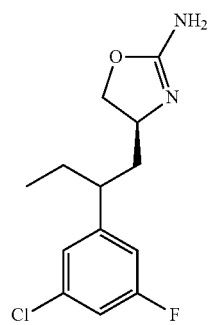 [SMILES: CCC(C[C@H]1COC(N)=N1)c1cc(F)cc(Cl)c1]

From (S)-4-(2,2-dibromo-vinyl)-2,2-dimethyl-oxazolidine-3-carboxylic acid tert-butyl ester by sequential treatment with 3-chloro-5-fluorophenyl boronic acid and diethylzinc. Mainly one epimer. Colourless oil. MS (ISP): 273.3 ([{$^{37}$Cl}M+H]$^+$), 271.3 ([{$^{35}$Cl}M+H]$^+$)).

Example 358

(S)-4-[2-(5-Chloro-2-fluoro-phenyl)-butyl]-4,5-dihydro-oxazol-2-ylamine

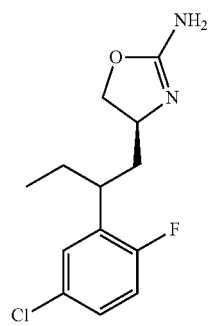 [SMILES: CCC(C[C@H]1COC(N)=N1)c1cc(Cl)ccc1F]

From (S)-4-(2,2-dibromo-vinyl)-2,2-dimethyl-oxazolidine-3-carboxylic acid tert-butyl ester by sequential treatment with 5-chloro-2-fluorophenyl boronic acid and diethylzinc. Mainly one epimer. Colourless oil. MS (ISP): 273.1 ([{$^{37}$Cl}M+H]$^+$), 271.1 ([{$^{35}$Cl}M+H]$^+$)).

In analogy to example 344 was prepared:

Example 359

(RS)-4-(4-Chloro-2-cyclopropyl-phenyl)-4,5-dihydro-oxazol-2-ylamine

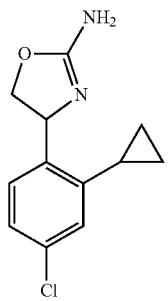 [SMILES: NC1=NC(c2ccc(Cl)cc2C2CC2)CO1]

Starting from 4-chloro-2-fluoro-benzaldehyde. White solid. MS (ISP): 239.1 ([{$^{37}$Cl}M+H]$^+$), 237.1 ([{$^{35}$Cl}M+H]$^+$)).

In analogy to example 1 were prepared:

Example 360

(S)-4-Cyclohexylmethyl-4,5-dihydro-oxazol-2-ylamine

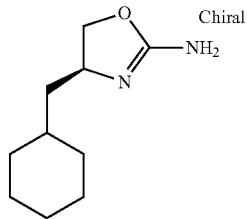 [SMILES: NC1=N[C@@H](CC2CCCCC2)CO1]

From (S)-2-amino-3-cyclohexyl-propan-1-ol. White amorphous solid.
MS (ISP): 183.2 ([M+H]$^+$)

Example 361

(R)-4-(3-Phenyl-propyl)-4,5-dihydro-oxazol-2-ylamine

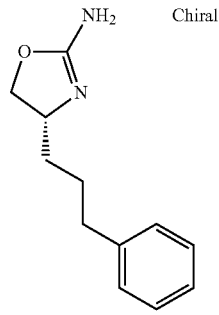 [SMILES: NC1=N[C@H](CCCc2ccccc2)CO1]

From D-2-amino-5-phenyl-pentanoic acid. Light yellow amorphous solid.
MS (ISP): 205.3 ([M+H]$^+$)

Example 362

(S)-4-[(Benzyl-ethyl-amino)-methyl]-4,5-dihydro-oxazol-2-ylamine

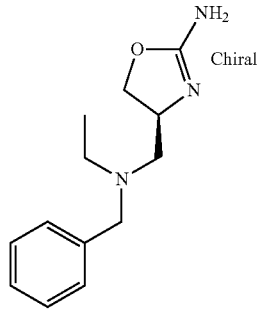 [SMILES: CCN(Cc1ccccc1)C[C@H]1COC(N)=N1]

a) (S)-4-(Benzylamino-methyl)-2,2-dimethyl-oxazolidine-3-carboxylic acid tert-butyl ester To a stirred solution of tert-butyl (R)-(−)-4-formyl-2,2-dimethyl-3-oxazolinecarboxylate (2.0 g) at r.t. in methanol (20 ml) under an argon atmosphere was added benzylamine (0.935 g) and the mixture was stirred overnight at 60° C. Then at room temperature NaBH$_4$ (0.495 g) was added and the mixture was stirred for additional 4 h. This was taken up in dichloromethane and aqueouos sodium bicarbonate solution. The aqueous phase was back extracted with dichloromethane. The combined organics were dried over MgSO$_4$, filtered and concentrated. The crude product was purified by column chromatography (column: Isolute® Flash-NH$_2$ from Separtis; eluent: heptane/ethyl acetate=1:1) to give (S)-4-(benzylamino-methyl)-2,2-dimethyl-oxazolidine-3-carboxylic acid tert-butyl ester (1.72 g, 61%) as colourless oil. MS (ISP): 321.1 ([M+H]$^+$)

b) (S)-4-[(Benzyl-ethyl-amino)-methyl]-2,2-dimethyl-oxazolidine-3-carboxylic acid tert-butyl ester To a stirred solution of (S)-4-(benzylamino-methyl)-2,2-dimethyl-oxazolidine-3-carboxylic acid tert-butyl ester (800 mg) at r.t. in methanol (10 ml) under an argon atmosphere were added acetaldehyde (0.70 ml), ZnCl2 (1.36 g) and NaBH$_3$CN (0.47 g). The mixture was warmed to 50° C. and stirring at that temperature was continued for 17 h. The mixture was cooled to r.t. and partitioned between ammonium chloride solution and dichloromethane. The combined organic layers were dried over MgSO$_4$, filtered and concentrated. The residue was purified by column chromatography (column: Isolute® Flash-NH$_2$ from Separtis; eluent: heptane/ethyl acetate=1:1) to give (S)-4-[(benzyl-ethyl-amino)-methyl]-2,2-dimethyl-oxazolidine-3-carboxylic acid tert-butyl ester (160 mg, 18%) as colorless oil. MS (ISP): 293.5 ([M-tBu+H]$^+$)

c) (S)-4-[(Benzyl-ethyl-amino)-methyl]-4,5-dihydro-oxazol-2-ylamine

To a stirred solution of (S)-4-(benzylamino-methyl)-2,2-dimethyl-oxazolidine-3-carboxylic acid tert-butyl ester (155 mg) in ethanol (2 ml) under an argon atmosphere was added HCl solution (5 M in ethanol; 2.0 ml). The mixture was stirred at 60° C. for 2 hours and concentrated. The residue was taken up in EtOAc and washed with 1N NaOH. The aqueous layer was back extracted with EtOAc. The combined organics were washed with brine, dried over MgSO$_4$ and concentrated. The residue was dissolved in methanol (2 ml) and sodium acetate (79 mg) was added. Under ice cooling cyanogen bromide (51 mg) was added and stirring was continued for 18 h. The mixture was directly adsorbed on silica gel and purified by column chromatography (Isolute® SPE flash NH₂ column, aminopropyl-functionalized silica; gradient: CH₂Cl₂-> CH₂Cl₂/MeOH 9:1) to provide (R)-4-[(ethyl-phenyl-amino)-methyl]-4,5-dihydro-oxazol-2-ylamine (25 mg, 22%) as colourless oil. MS (ISP): 234.3 ([M+H]⁺)

Examples 363 & 364

(−)-(R)-4-(4-Chloro-2-ethyl-phenyl)-4,5-dihydro-oxazol-2-ylamine & (+)-(S)-4-(4-Chloro-2-ethyl-phenyl)-4,5-dihydro-oxazol-2-ylamine

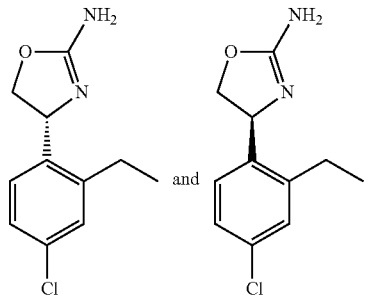

(RS)-4-(4-Chloro-2-ethyl-phenyl)-4,5-dihydro-oxazol-2-ylamine (example 344) was separated by chiral HPLC (Chiralpak AD, EtOH/heptane=10:90) to yield (−)-(R)-4-(4-chloro-2-ethyl-phenyl)-4,5-dihydro-oxazol-2-ylamine (white solid; MS (ISP): 227.1 ([{³⁷Cl}M+H]⁺), 225.1 ([{³⁵Cl}M+H]⁺)) and (+)-(S)-4-(4-chloro-2-ethyl-phenyl)-4,5-dihydro-oxazol-2-ylamine (white solid; MS (ISP): 227.1 ([{³⁷Cl}M+H]⁺), 225.1 ([{³⁵Cl}M+H]⁺)).

In analogy to example 252 and starting from the respective aldehyde was prepared:

Example 365

(RS)-4-(3-Fluoro-2-methyl-phenyl)-4,5-dihydro-oxazol-2-ylamine

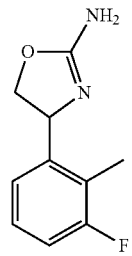

From 3-fluoro-2-methyl-benzaldehyde. Light yellow solid. MS (ISP): 195.3 ([M+H]⁺)).

Examples 366 & 367

(−)-(R)-4-(4-Bromo-2-fluoro-phenyl)-4,5-dihydro-oxazol-2-ylamine & (+)-(S)-4-(4-Bromo-2-fluoro-phenyl)-4,5-dihydro-oxazol-2-ylamine

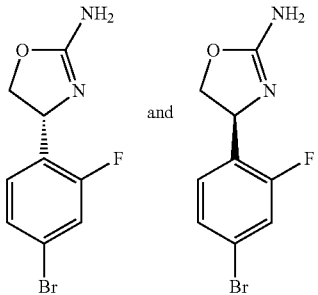 [SMILES: NC1=N[C@H](c2ccc(Br)cc2F)CO1 ; NC1=N[C@@H](c2ccc(Br)cc2F)CO1]

(RS)-4-(4-Bromo-2-fluoro-phenyl)-4,5-dihydro-oxazol-2-ylamine (example 349) was separated by chiral HPLC (Chiralpak AD, EtOH/heptane=10:90) to yield (−)-(R)-4-(4-bromo-2-fluoro-phenyl)-4,5-dihydro-oxazol-2-ylamine (white solid; MS (ISP): 261.0 ([{⁸¹Br}M+H]⁺), 258.9 ([{⁷⁹Br}M+H]⁺)) and (+)-(S)-4-(4-bromo-2-fluoro-phenyl)-4,5-dihydro-oxazol-2-ylamine (white solid; MS (ISP): 261.0 ([{⁸¹Br}M+H]⁺), 258.9 ([{⁷⁹Br}M+H]⁺)).

Examples 368 & 369

(−)-(R)-4-(4-Chloro-2-cyclopropyl-phenyl)-4,5-dihydro-oxazol-2-ylamine & (+)-(S)-4-(4-Chloro-2-cyclopropyl-phenyl)-4,5-dihydro-oxazol-2-ylamine

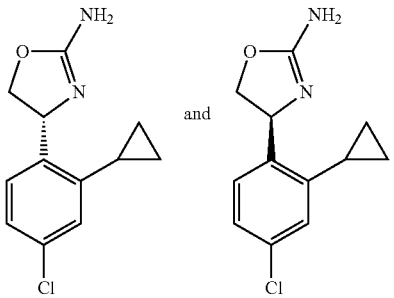 [SMILES: NC1=N[C@H](c2ccc(Cl)cc2C2CC2)CO1 ; NC1=N[C@@H](c2ccc(Cl)cc2C2CC2)CO1]

(RS)-4-(4-Chloro-2-cyclopropyl-phenyl)-4,5-dihydro-oxazol-2-ylamine (example 359) was separated by chiral HPLC (Chiralpak AD, EtOH/heptane=10:90) to yield (−)-(R)-4-(4-chloro-2-cyclopropyl-phenyl)-4,5-dihydro-oxazol-2-ylamine (white solid; MS (ISP): 239.1 ([{³⁷Cl}M+H]⁺), 237.1 ([{³⁵Cl}M+H]⁺)) and (+)-(S)-4-(4-chloro-2-cyclopropyl-phenyl)-4,5-dihydro-oxazol-2-ylamine (white solid; MS (ISP): 239.1 ([{³⁷Cl}M+H]⁺), 237.1 ([{³⁵Cl}M+H]⁺)).

In analogy to example 87 was prepared:

Example 370

(R)-4-(4-Chloro-phenylsulfanylmethyl)-4,5-dihydro-oxazol-2-ylamine

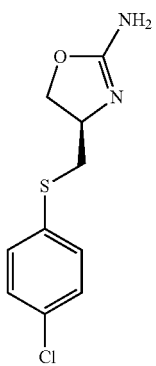 [SMILES: NC1=N[C@@H](CSc2ccc(Cl)cc2)CO1]

From tert-butyl (S)-4-(hydroxymethyl)-2,2-dimethyl-3-oxazolidinecarboxylate and 4-chloro-thiophenol. White crystals. MS (ISP): 245.2 ([{³⁷Cl}M+H]⁺), 243.2 ([{³⁵Cl}M+H]⁺)).

In analogy to example 252 and starting from the respective aldehyde was prepared:

Example 371

(RS)-4-(3-Fluoro-2-trifluoromethyl-phenyl)-4,5-dihydro-oxazol-2-ylamine

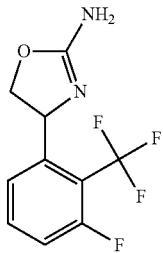 [SMILES: NC1=NC(c2cccc(F)c2C(F)(F)F)CO1]

From 3-fluoro-2-(trifluoromethyl)-benzaldehyde. Yellow solid. MS (ISP): 249.3 ([M+H]$^+$)).

In analogy to example 332 was prepared:

Example 372

(R)-4-(2-Cyclohexyl-ethyl)-4,5-dihydro-oxazol-2-ylamine

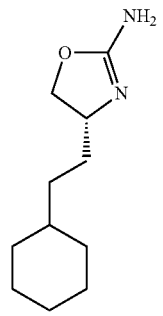 [SMILES: NC1=N[C@H](CCC2CCCCC2)CO1]

Starting from (+)-ethyl-(S)-2 amino-4-cyclohexylbutyrate. White crystals. MS (ISP): 197.2 ([M+H]$^+$)).

Examples 373 & 374

(−)-(R)-4-(3-Chloro-4-methyl-phenyl)-4,5-dihydro-oxazol-2-ylamine & (+)-(S)-4-(3-Chloro-4-methyl-phenyl)-4,5-dihydro-oxazol-2-ylamine

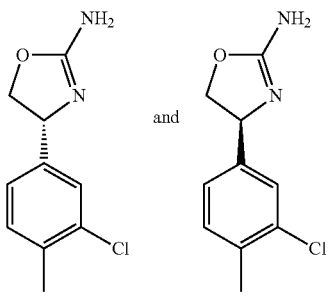

(RS)-4-(3-Chloro-4-methyl-phenyl)-4,5-dihydro-oxazol-2-ylamine (example 351) was separated by chiral HPLC (Chiralpak AD, EtOH/heptane=20:80) to yield (−)-(R)-4-(3-chloro-4-methyl-phenyl)-4,5-dihydro-oxazol-2-ylamine (white solid; MS (ISP): 213.1 ([{$^{37}$Cl}M+H]$^+$), 211.0 ([{$^{35}$Cl}M+H]$^+$)) and (+)-(S)-4-(3-chloro-4-methyl-phenyl)-4,5-dihydro-oxazol-2-ylamine (white solid; MS (ISP): 213.1 ([{$^{37}$Cl}M+H]$^+$), 211.0 ([{$^{35}$Cl}M+H]$^+$)).

Example 375

(S)-4-[2-(3-Chloro-phenyl)-5,5,5-trifluoro-pentyl]-4,5-dihydro-oxazol-2-ylamine

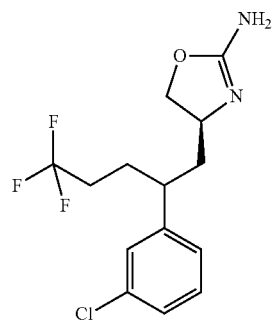 [SMILES: NC1=N[C@@H](CC(CCC(F)(F)F)c2cccc(Cl)c2)CO1]

a) rac-2-(3-Chloro-phenyl)-5,5,5-trifluoro-pentanoic acid

To a stirred solution of m-chlorophenylacetic acid (2.38 g, 14 mmol) in tetrahydrofuran (85 ml) was added at −78° C. lithium diisopropylamide solution (31 ml 1M in THF, 31 mmol). After stirring the mixture for 20 min 1-iodo-3,3,3-trifluoropropane (4.38 g, 20 mmol) was added and the mixture was allowed to warm to room temperature overnight. Water (5 ml) was added followed by 2N hydrochloric acid (10 ml). The reaction mixture was extracted twice with ethyl acetate. The combined organic layers were dried over MgSO$_4$ and evaporated and the residue was purified by column chromatography (SiO$_2$, heptane/EtOAc=9:1) to yield a colourless oil, (1.75 g, 47%); MS (EI): 264.9 (M$^{+\cdot}$).

b) rac-2-(3-Chloro-phenyl)-5,5,5-trifluoro-pentan-1-ol

To a stirred solution of 2-(3-chloro-phenyl)-5,5,5-trifluoro-pentanoic acid (1.75 g, 7 mmol) in tetrahydrofuran (40 ml) under an argon atmosphere was added slowly lithium aluminum hydride (0.4 g, 11 mmol) and the mixture was stirred for 17 hours at room temperature. For work-up water (1.5 ml) and 2N sodium hydroxide solution (0.5 ml) were added and the mixture was stirred for 30 min. After filtration the solvent was evaporated and the residue was purified by column chromatography (SiO$_2$, heptane/EtOAc=1:1 to yield a colourless oil, (1.25 g, 75%); MS (EI): 311.0 ((M+OAc)$^{+\cdot}$).

c) rac-1-Chloro-3-(4,4,4-trifluoro-1-iodomethyl-butyl)-benzene

To a stirred solution of triphenylphosphine (1.56 g, 6.0 mmol) and imidazole (0.41 g, 6.0 mmol) in dichloromethane (16 ml) under an argon atmosphere was added slowly iodine (1.51 g, 6.0 mmol) and 2-(3-chloro-phenyl)-5,5,5-trifluoro-pentan-1-ol (1.26 g, 5.0 mmol). The mixture was stirred for 2 hours at room temperature, then dichloromethane (50 ml) was added and mixture was extracted with saturated sodium thiosulfate solution (50 ml) and hydrochloric acid (1N, 25 ml). The organic layer was dried over MgSO$_4$ and evaporated. The residue was suspended in ether and filtered to remove insoluble triphenylphosphine oxide. The ether was evaporated and the residue was purified by column chromatography (SiO$_2$, heptane/EtOAc=9:1) to yield a light yellow liquid, (1.73 g, 96%); (EI): 235.0 ((M–I)$^+$·).

d) (S)-4-[2-(3-Chloro-phenyl)-5,5,5-trifluoro-pentyl]-4,5-dihydro-oxazol-2-ylamine The title compound, MS (ISP): 321.1 ((M+H)$^+$·) was obtained in comparable yield analogous to the procedure described for Example 228 using (R)-(–)-2,5-dihydro-3,6-dimethoxy-2-isopropyl-pyrazine instead of (R)-(–)-2,5-dihydro-3,6-dimethoxy-2-isopropyl-5-methylpyrazine and rac-1-chloro-3-(4,4,4-trifluoro-1-iodomethyl-butyl)-benzene instead of 1-(2-bromo-ethyl)-2-chlorobenzene in step a).

Analagously to Example 1 there were prepared:

Example 376

(R)-4-((R)-1-Benzyloxy-ethyl)-4,5-dihydro-oxazol-2-ylamine

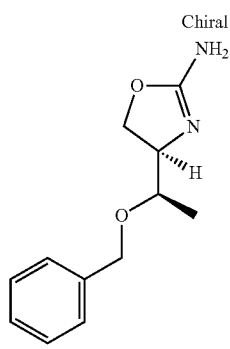 [SMILES: C[C@@H](OCc1ccccc1)[C@H]1COC(N)=N1]

From O-Benzyl-L-threonine. White solid. MS (ISP): 221.4 ([M+H]$^+$).

Example 377

(S)-4-(4-Chloro-benzyloxymethyl)-4,5-dihydro-oxazol-2-ylamine

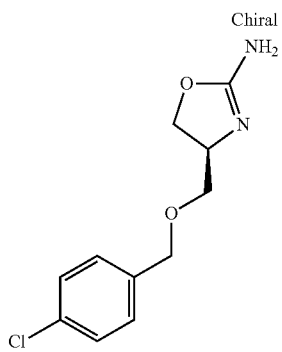 [SMILES: NC1=N[C@@H](COCc2ccc(Cl)cc2)CO1]

From O-p-chlorobenzyl-L-serine. Light yellow oil. MS (ISP): 241.2; 243.3 ([M+H]$^+$).

Example 378

(R)-4-[(Dimethyl-phenyl-silanyl)-methyl]-4,5-dihydro-oxazol-2-ylamine

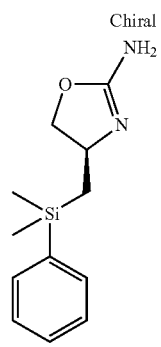 [SMILES: C[Si](C)(C[C@H]1COC(N)=N1)c1ccccc1]

The title compound, MS (ISP): 158.2 ([M–Ph+H]$^+$·), 235.1 ([M+H]$^+$·) was obtained in comparable yield analogous to the procedure described for Example 228 using (R)-(–)-2,5-dihydro-3,6-dimethoxy-2-isopropyl-pyrazine instead of (R)-(–)-2,5-dihydro-3,6-dimethoxy-2-isopropyl-5-methylpyrazine and chloromethyl dimethyl phenylsilane instead of 1-(2-bromo-ethyl)-2-chlorobenzene in step a).

Examples A-G

Additionally the following known compounds were prepared as TAAR1 ligands using procedures analogous to those describe above:

A: (S)-4-Phenyl-4,5-dihydro-oxazol-2-ylamine (CAS 165035-65-4)
B: (R)-4-Phenyl-4,5-dihydro-oxazol-2-ylamine (CAS 165035-66-5)
C: (S)-4-Benzyl-4,5-dihydro-oxazol-2-ylamine (CAS 856899-65-5)
D: (RS)-4-Phenethyl-4,5-dihydro-oxazol-2-ylamine (CAS 103522-08-3)
E: 4,4-Diphenyl-4,5-dihydro-oxazol-2-ylamine (CAS 132798-69-7)
F: (RS)-4-Benzyloxymethyl-4,5-dihydro-oxazol-2-ylamine (CAS 103521-92-2)
G: (RS)-4-Cyclohexyl-4,5-dihydro-oxazol-2-ylamine (CAS 63204-74-0)

The invention claimed is:
1. A compound which is selected from the group consisting of
(S)-4-(2-fluoro-4-trifluoromethyl-phenyl)-4-methyl-4,5-dihydro-oxazol-2-ylamine,
(RS)- 4-(4-fluoro-2-trifluoromethyl-phenyl)-4,5-dihydro-oxazol-2-ylamine,
(RS)-4-(5-chloro-2-trifluoromethyl-phenyl)-4,5-dihydro-oxazol-2-ylamine,
(RS)-4-(4-chloro-2-trifluoromethyl-phenyl)-4,5-dihydro-oxazol-2-ylamine,
(RS)-4-(4,5-dichloro-2-trifluoromethyl-phenyl)-4,5-dihydro-oxazol-2-ylamine,
(+)-(S)-4-(4-chloro-2-trifluoromethyl-phenyl)-4,5-dihydro-oxazol-2-ylamine,
(+)-(S)-4-(4,5-dichloro-2-trifluoromethyl-phenyl)-4,5-dihydro-oxazol-2-ylamine,
(–)-(R)-4-(4,5-dichloro-2-trifluoromethyl-phenyl)-4,5-dihydro-oxazol-2-ylamine,

(+)-(S)-4-(4-fluoro-2-trifluoromethyl-phenyl)-4,5-dihydro-oxazol-2-ylamine,
(RS)-4-(5-fluoro-2-trifluoromethyl-phenyl)-4,5-dihydro-oxazol-2-ylamine,
(RS)-4-(5-fluoro-2-methyl-phenyl)-4,5-dihydro-oxazol-2-ylamine,
(+)-(S)-4-(5-fluoro-2-trifluoromethyl-phenyl)-4,5-dihydro-oxazol-2-ylamine,
(RS)-4-(4-chloro-3-methyl-phenyl)-4-methyl-4,5-dihydro-oxazol-2-ylamine,
(RS)-4-(5-chloro-2-methyl-phenyl)-4,5-dihydro-oxazol-2-ylamine,
(RS)-4-(4-chloro-2-fluoro-5-methyl-phenyl)-4-methyl-4,5-dihydro-oxazol-2-ylamine,
(S)-4-(4-chloro-3-methyl-phenyl)-4-methyl-4,5-dihydro-oxazol-2-ylamine,
(RS)-4-(4-bromo-2-trifluoromethyl-phenyl)-4,5-dihydro-oxazol-2-ylamine,
(S)-4-(4-chloro-2-fluoro-5-methyl-phenyl)-4-methyl-4,5-dihydro-oxazol-2-ylamine,
(+)-(S)-4-(5-chloro-2-methyl-phenyl)-4,5-dihydro-oxazol-2-ylamine,
(RS)-4-(4-fluoro-2-methyl-phenyl)-4,5-dihydro-oxazol-2-ylamine,
(+)-(S)-4-(4-bromo-2-trifluoromethyl-phenyl)-4,5-dihydro-oxazol-2-ylamine,
(+)-(S)-4-(5-chloro-2-trifluoromethyl-phenyl)-4,5-dihydro-oxazol-2-ylamine,
(RS)-4-(4-chloro-2-ethyl-phenyl)-4,5-dihydro-oxazol-2-ylamine,
(+)-(S)-4-(4-fluoro-2-methyl-phenyl)-4,5-dihydro-oxazol-2-ylamine,
(RS)-4-(3-chloro-4-methyl-phenyl)-4,5-dihydro-oxazol-2-ylamine,
(RS)-4-(4-chloro-2-cyclopropyl-phenyl)-4,5-dihydro-oxazol-2-ylamine,
(S)-4-(4-chloro-2-ethyl-phenyl)-4,5-dihydro-oxazol-2-ylamine,
(RS)-4-(3-fluoro-2-methyl-phenyl)-4,5-dihydro-oxazol-2-ylamine,
(S)-4-(4-chloro-2-cyclopropyl-phenyl)-4,5-dihydro-oxazol-2-ylamine,
(RS)-4-(3-fluoro-2-trifluoromethyl-phenyl)-4,5-dihydro-oxazol-2-ylamine, and
(S)-4-(3-chloro-4-methyl-phenyl)-4,5-dihydro-oxazol-2-ylamine.

2. A pharmaceutical composition comprising a compound or a pharmaceutically suitable acid addition salt thereof and a pharmaceutically acceptable carrier, wherein the compound is selected from the group consisting of
(S)-4-(2-fluoro-4-trifluoromethyl-phenyl)-4-methyl-4,5-dihydro-oxazol-2-ylamine,
(RS)- 4-(4-fluoro-2-trifluoromethyl-phenyl)-4,5-dihydro-oxazol-2-ylamine,
(RS)-4-(5-chloro-2-trifluoromethyl-phenyl)-4,5-dihydro-oxazol-2-ylamine,
(RS)-4-(4-chloro-2-trifluoromethyl-phenyl)-4,5-dihydro-oxazol-2-ylamine,
(RS)-4-(4,5-dichloro-2-trifluoromethyl-phenyl)-4,5-dihydro-oxazol-2-ylamine,
(+)-(S)-4-(4-chloro-2-trifluoromethyl-phenyl)-4,5-dihydro-oxazol-2-ylamine,
(+)-(S)-4-(4,5-dichloro-2-trifluoromethyl-phenyl)-4,5-dihydro-oxazol-2-ylamine,
(−)-(R)-4-(4,5-dichloro-2-trifluoromethyl-phenyl)-4,5-dihydro-oxazol-2-ylamine,
(+)-(S)-4-(4-fluoro-2-trifluoromethyl-phenyl)-4,5-dihydro-oxazol-2-ylamine,
(RS)-4-(5-fluoro-2-trifluoromethyl-phenyl)-4,5-dihydro-oxazol-2-ylamine,
(RS)-4-(5-fluoro-2-methyl-phenyl)-4,5-dihydro-oxazol-2-ylamine,
(+)-(S)-4-(5-fluoro-2-trifluoromethyl-phenyl)-4,5-dihydro-oxazol-2-ylamine,
(RS)-4-(4-chloro-3-methyl-phenyl)-4-methyl-4,5-dihydro-oxazol-2-ylamine,
(RS)-4-(5-chloro-2-methyl-phenyl)-4,5-dihydro-oxazol-2-ylamine,
(RS)-4-(4-chloro-2-fluoro-5-methyl-phenyl)-4-methyl-4,5-dihydro-oxazol-2-ylamine,
(S)-4-(4-chloro-3-methyl-phenyl)-4-methyl-4,5-dihydro-oxazol-2-ylamine,
(RS)-4-(4-bromo-2-trifluoromethyl-phenyl)-4,5-dihydro-oxazol-2-ylamine,
(S)-4-(4-chloro-2-fluoro-5-methyl-phenyl)-4-methyl-4,5-dihydro-oxazol-2-ylamine,
(+)-(S)-4-(5-chloro-2-methyl-phenyl)-4,5-dihydro-oxazol-2-ylamine,
(RS)-4-(4-fluoro-2-methyl-phenyl)-4,5-dihydro-oxazol-2-ylamine,
(+)-(S)-4-(4-bromo-2-trifluoromethyl-phenyl)-4,5-dihydro-oxazol-2-ylamine,
(+)-(S)-4-(5-chloro-2-trifluoromethyl-phenyl)-4,5-dihydro-oxazol-2-ylamine,
(RS)-4-(4-chloro-2-ethyl-phenyl)-4,5-dihydro-oxazol-2-ylamine,
(+)-(S)-4-(4-fluoro-2-methyl-phenyl)-4,5-dihydro-oxazol-2-ylamine,
(RS)-4-(3-chloro-4-methyl-phenyl)-4,5-dihydro-oxazol-2-ylamine,
(RS)-4-(4-chloro-2-cyclopropyl-phenyl)-4,5-dihydro-oxazol-2-ylamine,
(S)-4-(4-chloro-2-ethyl-phenyl)-4,5-dihydro-oxazol-2-ylamine,
(RS)-4-(3-fluoro-2-methyl-phenyl)-4,5-dihydro-oxazol-2-ylamine,
(S)-4-(4-chloro-2-cyclopropyl-phenyl)-4,5-dihydro-oxazol-2-ylamine,
(RS)-4-(3-fluoro-2-trifluoromethyl-phenyl)-4,5-dihydro-oxazol-2-ylamine, and
(S)-4-(3-chloro-4-methyl-phenyl)-4,5-dihydro-oxazol-2-ylamine
or a pharmaceutically suitable acid addition salt thereof.

* * * * *